(12) United States Patent
Shitara et al.

(10) Patent No.: US 8,492,526 B2
(45) Date of Patent: *Jul. 23, 2013

(54) EFFECTOR FUNCTION ENHANCED RECOMBINANT ANTIBODY COMPOSITION

(75) Inventors: Kenya Shitara, Tokyo (JP); Rinpei Niwa, Tokyo (JP); Akito Natsume, Tokyo (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/166,487

(22) Filed: Jun. 22, 2011

(65) Prior Publication Data

US 2012/0022238 A1  Jan. 26, 2012

Related U.S. Application Data

(63) Continuation of application No. 12/019,160, filed on Jan. 24, 2008, now Pat. No. 7,994,290.

(30) Foreign Application Priority Data

Jan. 24, 2007 (JP) .................................. 2007-013640

(51) Int. Cl.
*C07K 16/00* (2006.01)

(52) U.S. Cl.
USPC .................................... 530/387.1; 424/130.1

(58) Field of Classification Search
None
See application file for complete search history.

(56) References Cited

U.S. PATENT DOCUMENTS

| 6,737,056 | B1 | 5/2004 | Presta |
| 2007/0148165 | A1 | 6/2007 | Shitara et al. |

FOREIGN PATENT DOCUMENTS

| WO | 2005/070963 | A1 | 8/2005 |
| WO | 2006/105338 | A2 | 5/2006 |
| WO | 2006/088494 | A2 | 8/2006 |

OTHER PUBLICATIONS

Ole H. Brekke et al., "Human IgG3 Can Adopt the Disulfide Bond Pattern Characteristic for IgG1 Without Resembling it in Complement Mediated Cell Lysis", Molecular Immunology, 1993, 30(16):1419-1425.
Stephen M. Canfield et al., "The Binding Affinity of Human IgG for its High Affinity Fc Receptor is Determined by Multiple Amino Acids in the $C_H2$ Domain and Is Modulated by the Hinge Region", J. Exp. Med., 1991, 173:1483-1491.
European Patent Office, Office Action issued in EP Patent Application No. 08703820.4 on May 6, 2011 (in the name of Kyowa Hakko Kirin Co., Ltd.).
European Patent Office, Extended European Search Report issued in EP Patent Application No. 08703820.4 on Jul. 23, 2010 (in the name of Kyowa Hakko Kirin Co., Ltd.).
Esohe E. Idusogie, "Engineered Antibodies with Increased Activity to Recruit Complement", Journal of Immunology, 2001, 166(4): 2571-2575.
A. Morgan et al., "The N-terminal end of the $C_H2$ domain of chimeric human IgG1 anti-HLA-DR is necessary for C1q, FcγRI and FcγRIII binding", Immunology, 1995, 86:319-324.
Akito Natsume, "Engineered Antibodies of IgG1/IgG3 Mixed Isotype wuth Enhanced Cytotoxic Activities", Cancer Research, 2008, 68(10): 3863-3872.
Rinpei Niwa, "IgG subclass-independent improvement of antibody-dependent cellular cytotoxicity by fucose removal from $ASN^{297}$-linked oliogosaccharides", Journal of Immunological Methods, 2005, 306(102): 151-160.
International Bureau, International Search Report issued in International Application No. PCT/JP2008/050993 on Mar. 18, 2008 (in the name of Kyowa Hakko Kogyo Co., Ltd.).
Mitsuo Satoh et al., "The oligosaccharide structure of antibody affects its effector function", Molecular Medicine, 2003, 40(9):1024-1032.
Verne N. Schumaker et al., "Ultracentrifuge Studies of the Binding of IgG of Different Subclasses to the C1q Subunit of the First Component of Complement", Biochemistry, 1976, 15(23):5175-5181.
Mi-Hua Tao et al., "Structural Features of Human Immunoglobulin G that Determine Isotype-specific Differences in Complement Activation", J. Exp. Med., 1993, 178: 661-667.
John E. Thommesen et al., "Lysine 322 in the human IgG3 $C_H2$ domain is crucial for antibody dependent complement activation", Molecular Immunology, 2000, 37: 995-1004.
E. Van Loghem et al., "Staphylococcal Protein A and Human IgG Subclasses and Allotypes", Scandinavian Journal of Immunology, 1982, 15:275-278.
Naoko Yamane-Ohnuki et al., "Establishment of FUT8 Knockout Chinese Hamster Ovary Cells: an Ideal Host Cell Line for Producing Completely Defucosylated Antibodies With Enhanced Antibody-Dependent Cellular Cytotoxicity", Biotechnology and Bioengineering, 2004, 87(5): 614-622.
Edelman et al., "The Covalent Structure of an Entire gammaG Immunoglobin Molecule," Proceedings of the National Academy of Sciences of the United States of America, 1969, pp. 78-85, vol. 63, No. 1.
Japanese Patent Office, Communication dated Nov. 15, 2011, issued in corresponding Japanese Patent Application No. 2008-555104.

*Primary Examiner* — Laura B Goddard
*Assistant Examiner* — Meera Natarajan
(74) *Attorney, Agent, or Firm* — Sughrue Mion, PLLC

(57) ABSTRACT

Disclosed are a recombinant antibody composition which is a human IgG1 antibody, comprises a CH2 domain in which amino acids at positions 276 and 339 indicated by the EU index as in Kabat, et al. are replaced by other amino acids and has more improved complement-dependent cytotoxic activity than an antibody comprising a CH2 domain before the amino acids are replaced; a DNA encoding the antibody molecule or a heavy chain constant region of the antibody molecule contained in the recombinant antibody composition; a transformant obtainable by introducing the DNA into a host cell; a process for producing the recombinant antibody composition using the transformant; and a medicament comprising the recombinant antibody composition as an active ingredient.

7 Claims, 29 Drawing Sheets

● : N-Acetylglucosamine (GlcNAc)

☐ : Mannose

■ : Galactose

☆ : Fucose

Pmo: Promoter
VL: Light chain variable region gene
Ck: Human light chain constant region
VH: Heavy chain variable region gene
CH1: CH1 domain gene
hinge: Hinge domain gene
CH2: CH2 domain gene
CH3: CH3 domain gene ☐ Cγ1: Human IgG1 heavy chain constant region gene
■ Cγ3: Human IgG3 light chain constant region gene FIG. 8
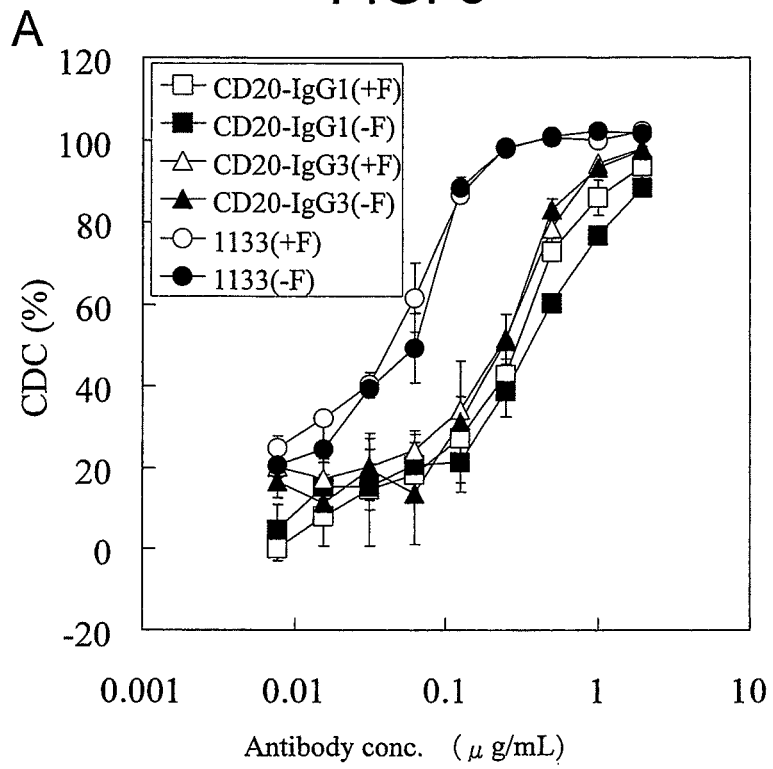
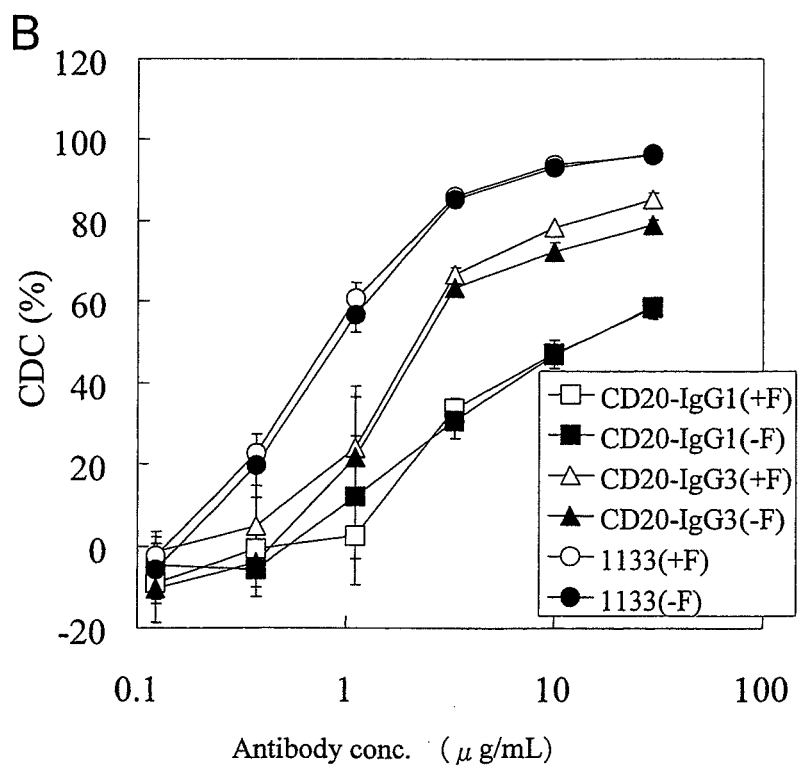

FIG. 11
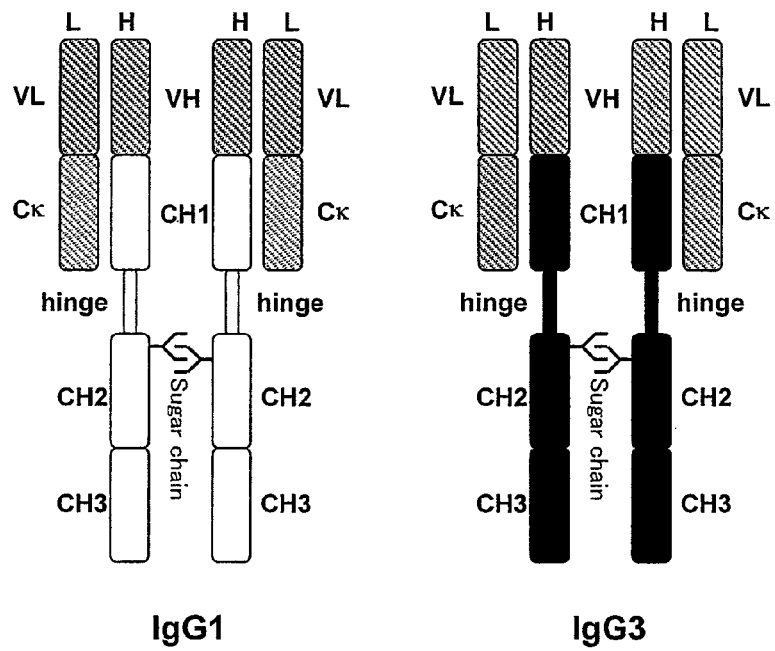
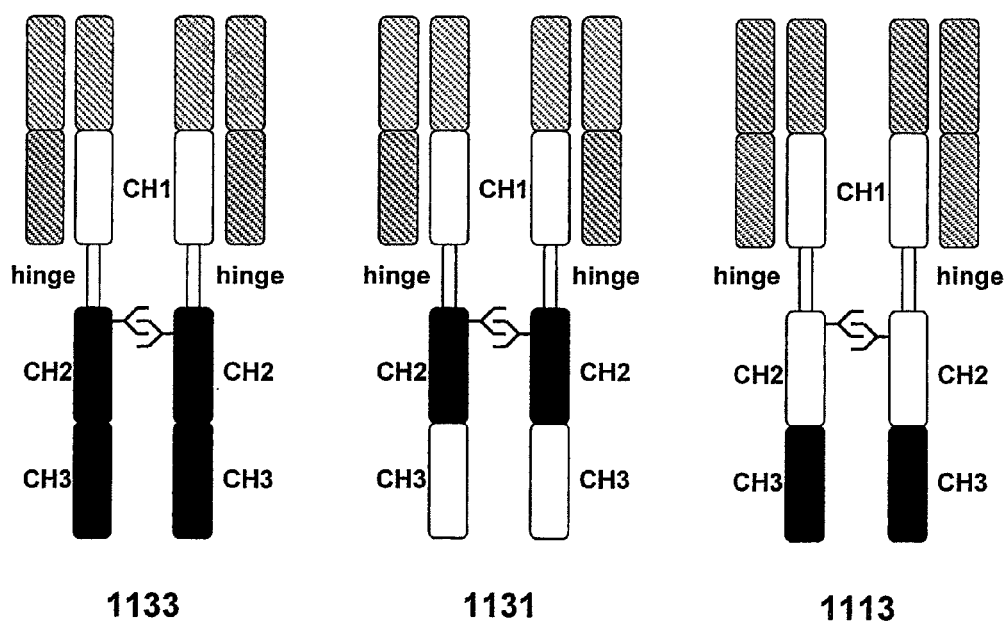

Pmo: Promoter
VL: Light chain variable region gene
Ck: Human light chain constant region
VH: Heavy chain variable region gene
CH1: CH1 domain gene
hinge: Hinge domain gene
CH2: CH2 domain gene
CH3: CH3 domain gene ☐ Cγ1: Human IgG1 heavy chain constant region gene
■ Cγ3: Human IgG3 light chain constant region gene Pmo: Promoter
VL: Light chain variable region gene
Ck: Human light chain constant region
VH: Heavy chain variable region gene
CH1: CH1 domain gene
hinge: Hinge domain gene
CH2: CH2 domain gene
CH3: CH3 domain gene Cγ1: Human IgG1 heavy chain constant region gene
Cγ3: Human IgG3 light chain constant region gene

FIG. 18

```
         231       240       250       260       270       280       290
IgG1    APELLGGPSVFLFPPKPKDTLMISRTPEVTCVVVDVSHEDPEVKFNWYVDGVEVHNAKTK
                                                       * *
IgG3    APELLGGPSVFLFPPKPKDTLMISRTPEVTCVVVDVSHEDPEVQFKWYVDGVEVHNAKTK 291       300       310       320       330       340
IgG1    PREEQYNSTYRVVSVLTVLHQDWLNGKEYKCKVSNKALPAPIEKTISKAK
             *  *                                      *
IgG3    PREEQFNSTFRVVSVLTVLHQDWLNGKEYKCKVSNKALPAPIEKTISKTK
```

EFFECTOR FUNCTION ENHANCED RECOMBINANT ANTIBODY COMPOSITION

CROSS-REFERENCE TO RELATED APPLICATIONS

This is a continuation application of U.S. patent application Ser. No. 12/019,160, filed Jan. 24, 2008 (now U.S. Pat. No. 7,994,290), which claims priority of Japanese Patent Application No. 2007-013640, filed Jan. 24, 2007, the disclosures of which are incorporated herein by reference in their entirety.

BACKGROUND OF THE INVENTION

1. Field of the Invention

The present invention relates to a recombinant antibody composition which is a human IgG1 antibody, comprises a CH2 domain in which amino acids at positions 276 and 339 indicated by the EU index as in Kabat, et al. are replaced by other amino acids and has more improved complement-dependent cytotoxic activity than an antibody comprising a CH2 domain before the amino acids are replaced; a DNA encoding the antibody molecule or a heavy chain constant region of the antibody molecule contained in the recombinant antibody composition; a transformant obtainable by introducing the DNA into a host cell; a process for producing the recombinant antibody composition using the transformant; and a medicament comprising the recombinant antibody composition as an active ingredient.

2. Brief Description of the Background Art

Since antibodies are protein molecules having high binding activity and binding specificity to a target molecule (antigen) and high stability in blood, applications thereof to diagnostic, preventive and therapeutic agents for various human diseases have been attempted (Non-patent Document 1). Although antibodies are generally produced by administering (immunizing) an antigen to a non-human animal, antibodies obtained from a non-human animal have an amino acid sequence specific to the species and side effects are caused due to that the antibodies are recognized as foreign substances in the human body. Accordingly, human chimeric antibodies or humanized antibodies have been prepared from antibodies of animals other than human (non-human animals) using gene recombination techniques (Non-patent Documents 2 to 5).

The human chimeric antibodies and humanized antibodies have resolved problems possessed by non-human animal antibodies such as mouse antibodies, such as the high immunogenicity, low effector function and short blood half-life, and applications of monoclonal antibodies to pharmaceutical preparations were made possible by using them (Non-patent Documents 6 to 9). In the Unites States, for example, a plurality of humanized antibodies have already been approved as an antibody for cancer treatment, and are on the market (Non-patent Document 10).

These human chimeric antibodies and humanized antibodies actually show effects to a certain degree at clinical level, but therapeutic antibodies having higher effects are in demand. For example, in the case of single administration of RITUXAN™ (Non-patent Document 11) (manufactured by IDEC/Roche/Genentech) which is a human chimeric antibody to CD20, it has been reported that its response ratio for recurrent low malignancy non-Hodgkin lymphoma patients in the phase III clinical test is no more than 48% (complete remission 6%, partial remission 42%), and its average duration of response is 12 months (Non-patent Document 12). In the case of combination use of RITUXAN™ and chemotherapy (CHOP: Cyclophosphamide, Doxorubicin, Vincristine), it has been reported that its response ratio for recurrent low malignancy and follicular non-Hodgkin lymphoma patients by the phase II clinical test is 95% (complete remission 55%, partial remission 45%), but side effects due to CHOP were found (Non-patent Document 13). In the case of single administration of HERCEPTIN™ (manufactured by Genentech) which is a humanized antibody to HER2, it has been reported that its response ratio for metastatic breast cancer patients in the phase III clinical test is only 15%, and its average duration of response is 9.1 months (Non-patent Document 14).

The human antibody molecule is also called immunoglobulin (hereinafter referred to as Ig) and classified into isotypes of IgA1, IgA2, IgD, IgE, IgG1, IgG2, IgG3, IgG4 and IgM based on its molecular structure. IgG1, IgG2, IgG3 and IgG4 having relatively high homology in amino acid sequences are genetically called IgG. Human IgG is mainly used as a therapeutic antibody.

An antibody molecule comprises two kinds of polypeptides, i.e., a heavy chain (hereinafter referred to as H chain) and a light chain (hereinafter referred to as L chain). A human IgG antibody molecule comprises two H chains and two L chains. Also, an H chain comprises an H chain variable region (hereinafter referred to as VH) and an H chain constant region (hereinafter referred to as CH), and an L chain comprises an L chain variable region (hereinafter referred to as VL) and an L chain constant region (hereinafter referred to as CL). The H chain constant region comprises four domains which are respectively called CH1, hinge, CH2 and CH3 domains from the domain close to VH located at the heavy chain N-terminal in this order. Also, the CH2 domain and CH3 domain in combination are called Fc.

An antibody binds to an antigen via an antigen-biding region (hereinafter referred to as Fv) comprising VH and VL and binds to an effector molecule in the immune system such as a receptor or a complement via the H chain constant region. Under the mediation of the binding to the effector molecule in the immune system, the antibody induces an effector activity such as a complement-dependent cell-mediated cytotoxic activity (hereinafter referred to as CDC activity), an antibody-dependent cellular cytotoxic activity (hereinafter referred to as ADCC activity) or a phagocytic activity so as to eliminate the antigen or cells (a pathogen or tumor cells) expressing the antigen.

To induce the ADCC activity or phagocytic activity, it is important that the antibody binds to a member of the Fc gamma receptor (hereinafter referred to as FcγR) family expressed on the surface of various leukocytes such as natural killer cells (hereinafter referred to as NK cells), monocytes, macrophages or granulocytes. The FcγR family includes activated FcγR and regulated FcγR. FcγRI, FcγRIIa, FcγRIIIa and FcγRIIIb belong to the activated FcγR, and FcγRIIb belongs to the regulated FcγR. A human IgG antibody strongly binds to such a receptor and consequently induces the ADCC activity or phagocytic activity of leukocytes.

The ADCC activity is a reaction in which leukocytes such as NK cells mainly lyse targets cell under the mediation of an antibody. The antibody binds to an antigen on the surface of the target cells via Fv and binds to FcγRIIIa on the surface of NK cells via Fc. As a result, the NK cells release cytotoxic molecules such as perforin or granzyme and thus lyse the target cells (Non-patent Documents 15 and 16).

The CDC activity is a reaction in which a group of serum proteins called complements lyses target cells under the mediation of an antibody. The complements are classified into C1 to C9 proteins, and they are subjected to chain reaction to thereby induce the CDC activity. Each of the complement proteins is activated by reacting with a specific complement protein and then reacts with the subsequent complement protein. These chain reactions start with the binding of the first complement component C1 to the Fc of an antibody, which has been bonded via Fv to an antigen on the surface of target cells, via C1q that is one of the proteins constituting C1. Finally, complexes of C5 to C9 are polymerized together to form a hole in the cell membrane of the target cells, which results in the lysis of the target cells (Non-patent Documents 15 and 16).

Four human IgG isotypes (IgG1, IgG2, IgG3 and IgG4) are highly homologous with each other in the amino acid sequence in the H chain constant region except for the hinges showing a wide variety. However, these isotypes induce an effector activity of different strengths (Non-patent Document 17). In general, the ADCC activity decreases in the following order: IgG1>IgG3>IgG4≧IgG2 (Non-patent Documents 18 and 19), while the CDC activity decreases in the following order: IgG3≧IgG1>>IgG2≈IgG4. As discussed above, the binding of an antibody to C1q is important in inducing the CDC activity. The biding constants (Ka) in the binding of C1q to a monomeric antibody molecule in human IgG isotypes, i.e., IgG1, IgG2, IgG3 and IgG4 are $1.2 \times 10^4$, $0.64 \times 10^4$, $2.9 \times 10^4$ and $0.44 \times 10^4$, respectively (Non-patent Document 20), reflecting the difference in CDC activity among these isotypes.

Concerning the drug effect mechanisms of clinically employed antibody drugs, the importance of ADCC and CDC activities has particularly attracted public attention. It is reported that RITUXAN™ as described above, which is a human chimeric antibody of the IgG1 isotype, shows ADCC and CDC activities in vitro (Non-patent Document 21). Relating to the clinical effects of RITUXAN™, it is reported that RITUXAN™ shows high therapeutic effects on a patient showing a genotype with high ADCC activity (Non-patent Document 22), that complement components in blood are quickly consumed following the administration thereof (Non-patent Document 23), that the expression of CD59, which is a CDC activity regulator, shows an increase in cancer cells of a patient suffering from recurrence after the administration thereof (Non-patent Document 24), and the like. These reports indicate that RITUXAN™ actually exerts the effector function in the body of a patient. It is also reported that HERCEPTIN™ as described above, which is a humanized antibody of the IgG1 subclass, shows the ADCC activity in vitro (Non-patent Document 25).

Although human IgG1 and human IgG3 are isotypes having excellent ADCC and CDC activities, it is known that human IgG3 antibody has a shorter half life in the blood than other human IgG isotypes and thus quickly disappears from the blood after the administration (Non-patent Document 26). It is also known that human IgG3 has no protein A-binding activity, differing from other human IgG isotypes (Non-patent Document 27). In producing an antibody on an industrial scale, a purification process using protein A is predominant and other processes using, for example, protein G have some problems such as a high purification cost.

It is known that protein A binds to a human IgG antibody molecule (Non-patent Document 28). When indicated by the EU index as in Kabat, et al. (Non-patent Document 29), it is pointed out as the results of X-ray crystallographic analysis that a loop comprising the amino acids at positions 252 to 254, a loop consisting of the amino acids at positions 308 to 312, and a loop comprising the amino acids at positions 433 to 436 are important (Non-patent Document 28). As the results of nuclear magnetic resonance (NMR) analysis, it is further indicated that Ile253, Ser254, His310, Gln311, His433, His 435 and His436 are particularly important in the Fc of IgG1 (Non-patent Document 30). Furthermore, Kim, et al. found that the protein A-binding activity was attenuated by replacing His435 of a human IgG1 with Arg435 derived from IgG3 (Non-patent Document 31). Hereinafter, the positions of the amino acids in the amino acid sequence of an antibody molecule are represented based on the EU index as in Kabat, et al. (Non-patent Document 29).

Based on the above it can be said that human IgG1 antibody is the most suitable isotype as an antibody drug, since it has higher ADCC and CDC activities than other isotypes, can be purified using protein A, shows a long half life in blood and has a merit from the viewpoint of production cost. Although a human IgG1 antibody has been employed as drugs in practice as described above, the drug effects exhibited by the existing antibody drugs are still insufficient. Thus, there has been required an antibody drug having improved effects. In order to satisfy this requirement, studies have been made on an antibody having enhanced effector activities. As discussed above, an effector activity of an antibody reflects the binding activity of the H chain constant region to an effector molecule in the immune system. Accordingly, the effector activity of the antibody can be enhanced by enhancing the binding activity of the H chain constant region to the effector molecule in the immune system.

In order to analyze the effector activities of human antibodies, studies have been made on antibodies comprising two kinds of human isotype amino acid sequences which are prepared by partly swapping the amino acid sequences in the heavy chain constant region between two kinds of human isotype antibodies having different effector activity (Patent Document 1 and Non-patent Documents 32 and 33). In late 1980's, Morrison, et al. indicated that antibody molecules, which were prepared by swapping the individual domains (CH1, CH2, CH3 and hinge) in the heavy chain constant region between IgG1 having a high effector activity and IgG4 having a low effector activity, or between IgG2 having a low effector activity and IgG3 having a high effector activity, could be expressed as recombinant proteins (Patent Document 1). As the results of the subsequent analysis on these antibody molecules, they have clarified that the C-terminal side of the CH2 domain is important in the CDC activity of IgG1 and the CH2 domain is important in the CDC activity of IgG3 (Non-patent Document 32); the CH2 domain and hinge are important in the binding of IgG1 and IgG3 to FcγRI (Non-patent Document 33); and the like.

As described above, the CH2 domain is important in the CDC activity. The amino acid sequences of human IgG1 antibody and human IgG3 antibody having high CDC activity have been analyzed. Concerning the amino acid sequences of CH2, it is known that Leu235 (Non-patent Document 34), Asp270, Lys322, Pro329 and Pro331 (Non-patent Document 35) are important in the CDC activity of human IgG1; and Gly233, Leu234, Leu235, Gly236 (Non-patent Document 36) and Lys322 (Non-patent Document 37) are important in the CDC activity of human IgG3. Brekke, et al. analyzed various antibody molecules prepared by transplanting amino acid residues being common to the CH2 domain amino acid sequences of human IgG1 antibody and human IgG3 antibody having high CDC activity or several amino acid residues being different from a human IgG4 antibody having very low CDC activity into a human IgG4 antibody. As a result, they found that the CDC activity of human IgG4 antibody was enhanced by swapping Ser331 in human IgG4 by Pro331 which is common to a human IgG1 and a human IgG3 (Non-patent Document 38).

Moreover, attempts have been made to enhance the CDC activity by swapping a part of the amino acid sequence of the heavy chain constant region of human IgG3 antibody, which is the human IgG isotype having the highest CDC activity, by an amino acid sequence originating in another human IgG isotype. Concerning the hinge lengths of each IgG isotypes, IgG1 has 15 amino acid residues, IgG2 has 12 amino acid residues, IgG3 has 62 amino acid residues and IgG4 has 12 amino acid residues. Thus, the human IgG has a structural characteristic of having a longer hinge than other IgG3 isotypes (Non-patent Document 1). The hinge of human IgG3 antibody consisting of 62 amino acids is encoded by four exons on a gene. Michaelsen, et al. reported that the CDC activity of human IgG3 antibody having a hinge that was shortened to 15 amino acid residues by deleting three exons in the N-terminal side among these four exons was higher than IgG3 and IgG1 (Non-patent Document 39). Norderhang, et al. reported that the CDC activity is further increased by swapping the amino acid sequences of the hinge shortened in the above and the amino acid sequences of the hinge of IgG4. Further, Brekke, et al. reported that when the hinge of human IgG3 antibody was swapped by the hinge of human IgG1 antibody, the CDC activity of the resultant antibody was higher than IgG3 and similar to IgG1 or more (Non-patent Document 41).

On the other hand, studies have been made on an antibody prepared by replacing the amino acid sequence of the heavy chain constant region of human IgG1 antibody by an artificial amino acid sequence which is not present in the nature to thereby increase the C1q-binding activity and thus enhance the CDC activity (Non-patent Document 42 and Patent Documents 2 to 5). As described above, the CDC activity is induced by the binding of C1q, which is one of the proteins constituting complement protein C1, to the Fc of an antibody molecule. Idusogie, et al. reported that by replacing Lys326 or Glu333 in the CH2 domain of RITUXAN™ (a human IgG1 chimeric antibody) as described above with an other amino acid, the CDC activity was enhanced twice at most (Non-patent Document 42, Patent Document 2). Furthermore, Idusogie, et al. indicated that by replacing Lys326 or Glu333 in IgG2 with an other amino acid, the CDC activity of IgG2, which inherently corresponds to a several hundredth part of the CDC activity of IgG1, was increased to about one over twenty-five of IgG1 (Patent Documents 3 to 5).

However, such an antibody prepared through the replacement of an amino acid sequence which is not present in the nature has a risk that it is recognized as a foreign matter in the human body and thus induces a side effect similar to the non-human animal antibody as discussed above. On the other hand, the amino acid sequence of an antibody prepared by swapping amino acid sequences between human isotypes is a combination of amino acid sequences of antibodies inherently carried by humans.

In the therapeutic effects of a therapeutic antibody, the ADCC and phagocytic activities induced by the biding of the Fc region of the antibody to FcγR and the CDC activity mediated by the biding of the antibody to C1q are both important. However, the bindings of the antibody to C1q and to the FcγR are both mediated by the Fc and, therefore, it is feared that an amino acid modification aiming to enhance the CDC activity might damage the ADCC activity. In practice, Idusogie, et al. reported that an antibody in which the CDC activity was enhanced by replacing the Fc of human IgG1 antibody with an artificial amino acid sequence showed a serious lowering in the ADCC activity (Non-patent Document 42).

As a procedure for enhancing an effector activity of an antibody other than the replacement in an amino acid sequence, regulation of a sugar chain attached to the constant region of the antibody may be cited. It is known that the ADCC activity of human IgG antibody changes based on the structure of a complex-type N-glycoside-linked sugar chain attached asparagine at position 297 in the Fc (FIG. 1 shows a model view thereof) (Patent Document 6). It is also reported that the ADCC activity of the antibody changes depending on the amounts of galactose and N-acetylglucosamine contained in this sugar chain (Non-patent Documents 43 to 46). However, the ADCC activity is mostly affected by fucose binding to N-acetylglucosamine in the reducing terminal through α1,6-bond in the sugar chain. Namely, an IgG antibody having complex-type N-glycoside-linked sugar chains in which fucose is not bound to N-acetylglucosamine in the reducing terminal in the sugar chains shows remarkably higher ADCC and FcγRIIIa-binding activities than an IgG antibody having complex-type N-glycoside-linked sugar chain in which fucose is bound to N-acetylglucosamine in the reducing terminal in the sugar chains (Non-patent Documents 47, 48 and 49 and Patent Document 7). Although antibody molecules having no fucose in sugar chains exist in vivo as a natural-type, α1,6-fucosyltransferase gene-knockout cells have been known as cells capable of specifically producing an antibody composition having complex-type N-glycoside-linked sugar chains in which fucose is not bound to N-acetylglucosamine in the reducing terminal in the sugar chains (Patent Documents 7 and 8)

Non-patent Document 1: *Monoclonal Antibodies: Principles and Applications*, Wiley-Liss, Inc. (1995)
Non-patent Document 2: *Nature*, 312, 643 (1984)
Non-patent Document 3: *Proc. Natl. Acad. Sci. USA*, 81, 6851 (1984)
Non-patent Document 4: *Nature*, 321, 522 (1986)
Non-patent Document 5: *Nature*, 332, 323 (1988)
Non-patent Document 6: *Immunol. Today*, 21, 364 (2000)
Non-patent Document 7: *Immunol. Today*, 21, 403 (2000)
Non-patent Document 8: *Ann. Allergy Asthma Immunol.*, 81, 105 (1998)
Non-patent Document 9: *Nature Biotechnol.*, 16, 1015 (1998)
Non-patent Document 10: *Nature Reviews Cancer*, 1, 119 (2001)
Non-patent Document 11: *Curr. Opin. Oncol.*, 10, 548 (1998)
Non-patent Document 12: *J. Clin. Oncol.*, 16, 2825 (1998)
Non-patent Document 13: *J. Clin. Oncol.*, 17, 268 (1999)
Non-patent Document 14: *J. Clin. Oncol.*, 17, 2639 (1999)
Non-patent Document 15: *Chemical Immunology*, 65, 88 (1997)
Non-patent Document 16: *Immunol. Today*, 20, 576 (1999)
Non-patent Document 17: *Monoclonal Antibodies: Principles and Applications*, Wiley-Liss, Inc. (1995)
Non-patent Document 18: *Nature*, 332, 323 (1988)
Non-patent Document 19: *Journal of Experimental Medicine*, 166, 1351 (1987)
Non-patent Document 20: *Biochemistry*, 15, 5175 (1976)
Non-patent Document 21: *Oncogene*, 22, 7359 (2003)
Non-patent Document 22: *Blood*, 99, 754 (2002)
Non-patent Document 23: *J. Immunol.*, 172, 3280 (2004)
Non-patent Document 24: *J. Clin. Oncol.*, 21, 1466 (2003)
Non-patent Document 25: *Cancer Immunol. Immunother.*, 37, 255 (1993)
Non-patent Document 26: *Cancer Res.*, 58, 3905 (1998)

Non-patent Document 27: *Scand. J. Immunol.*, 15, 275 (1982)
Non-patent Document 28: *Biochemistry*, 20, 2361 (1981)
Non-patent Document 29: *Sequence of Proteins of Immunological Interest*, Fifth Edition (1991)
Non-patent Document 30: *FEBS Lett.*, 328, 49 (1993)
Non-patent Document 31: *Eur. J. Immunol.*, 29, 2819 (1999)
Non-patent Document 32: *Journal of Experimental Medicine*, 173, 1025 (1991)
Non-patent Document 33: *Journal of Experimental Medicine*, 173, 1483 (1991)
Non-patent Document 34: *Immunology*, 86, 319 (1995)
Non-patent Document 35: *J. Immunol.*, 164, 4178 (2000)
Non-patent Document 36: *Mol. Immunol.*, 34, 1019 (1997)
Non-patent Document 37: *Mol. Immunol.*, 37, 995 (2000)
Non-patent Document 38: *Eur. J. Immunol.*, 24, 2542 (1994)
Non-patent Document 39: *Scand. J. Immunol.*, 32, 517 (1990)
Non-patent Document 40: *Eur. J. Immunol.*, 21, 2379 (1991)
Non-patent Document 41: *Mol. Immunol.*, 30, 1419 (1993)
Non-patent Document 42: *J. Immunol.*, 166, 2571 (2001)
Non-patent Document 43: *Human Antib Hybrid*, 5, 143 (1994)
Non-patent Document 44: *Hum Antib Hybrid*, 6, 82 (1995)
Non-patent Document 45: *Nat. Biotechnol.*, 17, 176 (1999)
Non-patent Document 46: *Biotechnol. Bioeng.*, 74, 288 (2001)
Non-patent Document 47: *Clin. Cancer. Res.*, 10, 6248 (2004)
Non-patent Document 48: *J. Biol. Chem.*, 277, 26733 (2002)
Non-patent Document 49: *J. Biol. Chem.*, 278, 3466 (2003)
Patent Document 1: US2003/0158389A1
Patent Document 2: WO00/42072
Patent Document 3: US2004/0132101 A1
Patent Document 4: US2005/0054832 A1
Patent Document 5: WO00/61739
Patent Document 6: WO02/31140
Patent Document 7: WO03/85107

SUMMARY OF THE INVENTION

An object of the present invention is to provide an antibody having enhanced effector functions such as CDC activity and ADCC activity and has improved therapeutic effect without losing other effector functions and having antigenicity. Furthermore, it is to provide an antibody which can be produced as a medicine, for example, which has protein-A binding activity.

The present invention provides a recombinant antibody composition which is a human IgG1 antibody, comprises a CH2 domain in which amino acids at positions 276 and 339 indicated by the EU index as in Kabat, et al. are replaced by other amino acids and has more improved complement-dependent cytotoxic activity than an antibody comprising a CH2 domain before the amino acids are replaced; a DNA encoding the antibody molecule or a heavy chain constant region of the antibody molecule contained in the recombinant antibody composition; a transformant obtainable by introducing the DNA into a host cell; a process for producing the recombinant antibody composition using the transformant; and a medicament comprising the recombinant antibody composition as an active ingredient.

BRIEF DESCRIPTION OF THE DRAWINGS

FIG. 8 shows the CDC activity of anti-CD20 human IgG1 antibody, anti-CD20 human IgG3 antibody and 1133-type anti-CD20 chimeric isotype antibody to ST 486 cell (A) or Raji cell (B). The abscissa shows an antibody concentration, and the ordinate shows the CDC activity in each antibody concentration. In the graph, □ shows CD20-IgG1(+F), ■ shows CD20-IgG1(−F), Δ shows CD20-IgG3(+F), ▲ shows CD20-IgG3(−F), shows 1133(+F) and ● shows 1133(−F).

FIG. 11 is a schematic illustration showing domain structures of a human IgG1 antibody, a human IgG3 antibody, a 1133-type chimeric isotype, a 1131-type chimeric isotype and a 1113-type chimeric isotype.

FIG. 18 is a schematic illustration showing comparison of the amino acid sequences of CH domains of human IgG1 antibody (SEQ ID NO: 55) and human IgG3 antibody (SEQ ID NO: 56). The position of each amino acid sequence is based on the EU index as in Kabat, et al. In the graph, * shows positions in which amino acid sequences are different between the human IgG1 antibody and the human IgG3 antibody.

DETAILED DESCRIPTION OF THE INVENTION

Figure 1:
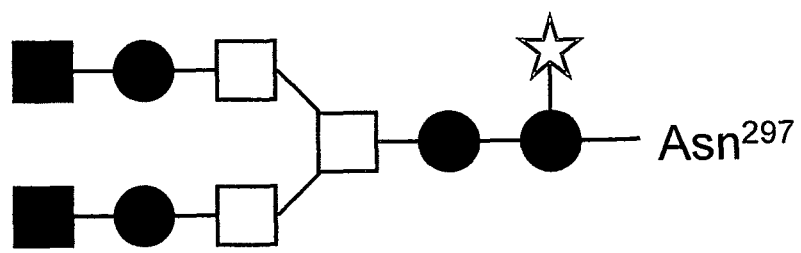
FIG. 1 is a schematic illustration showing structure of a complex-type N-linked sugar chain bound to asparagine at position 297 in the heavy chain of an IgG antibody.

Preferably, the present invention relates to the following (1) to (24):

(1) A recombinant antibody composition which is a human IgG1 antibody, comprises a CH2 domain in which amino acids at positions 276 and 339 indicated by the EU index as in Kabat, et al. are replaced by other amino acids and has more improved complement-dependent cytotoxic activity than an antibody comprising a CH2 domain before the amino acids are replaced.

(2) The recombinant antibody composition according to the above (1), which is a human IgG1 antibody, wherein the amino acids at positions 276 and 339 indicated by the EU index as in Kabat, et al. are replaced by lysine and threonine, respectively.
(3) The recombinant antibody composition according to the above (1) or (2), wherein a polypeptide contained in a CH3 domain in the Fc region is a polypeptide comprising amino acids corresponding to the same positions in a human IgG3 antibody indicated by the EU index.
(4) The recombinant antibody composition according to any one of the above (1) to (3), comprising a human IgG1 antibody molecule having complex-type N-glycoside-linked sugar chains in the Fc region, wherein the ratio of sugar chains in which fucose is not bound to N-acetylglucosamine in the reducing terminal of the sugar chains among the total complex-type N-glycoside-linked sugar chains which bind to the Fc region contained in the composition is 20% or more.
(5) The recombinant antibody composition according to any one of the above (1) to (3), comprising a human IgG1 antibody molecule having complex-type N-glycoside-linked sugar chains in the Fc region, wherein the complex-type N-glycoside-linked sugar chains bound to the Fc region of the antibody are sugar chains in which fucose is not bound to N-acetylglucosamine in the reducing terminal in the sugar chains.
(6) A DNA encoding an antibody molecule contained in the recombinant antibody composition described in any one of the above (1) to (3).
(7) A DNA encoding a heavy chain constant region of an antibody molecule contained in the recombinant antibody composition described in any one of the above (1) to (3).
(8) A transformant obtainable by introducing the DNA described in the above (6) into a host cell.
(9) The transformant according to the above (8), wherein the host cell is a cell resistant to a lectin which recognizes a sugar chain structure in which 1-position of fucose is bound to 6-position of N-acetylglucosamine in the reducing terminal through α-bond in the N-glycoside-linked sugar chain.
(10) The transformant according to the above (8), wherein when a gene encoding an antibody molecule is introduced into the host cell, the host cell is capable of producing an antibody composition comprising an antibody molecule having complex-type N-glycoside-linked sugar chains in the Fc region, wherein the ratio of sugar chains in which fucose is not bound to N-acetylglucosamine in the reducing terminal of the sugar chains among the total complex-type N-glycoside-linked sugar chains which bind to the Fc region contained in the composition is 20% or more.
(11) The transformant according to the above (10), wherein the sugar chains in which fucose is not bound are sugar chains in which 1-position of fucose is bound to 6-position of N-acetylglucosamine in the reducing terminal through α-bond in the complex-type N-glycoside-linked sugar chain.
(12) The transformant according to the above (8), wherein the host cell is a cell in which a genome is modified so as to have decreased or deleted activity of an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in the complex-type N-glycoside-linked sugar chain.
(13) The transformant according to the above (8), wherein the host cell is a cell in which all of alleles on a genome encoding an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in the complex-type N-glycoside-linked sugar chain are knocked out.
(14) The transformant according to the above (12) or (13), wherein the enzyme relating to the synthesis of an intracellular sugar nucleotide, GDP-fucose is an enzyme selected from GDP-mannose 4,6-dehydratase (GMD) and GDP-4-keto-6-deoxy-D-mannose-3,5- epimerase (Fx).
(15) The transformant according to the above (14), wherein the GDP-mannose 4,6-dehydratase is a protein encoded by a DNA selected from the group consisting of the following (a) and (b):
(a) a DNA comprising the nucleotide sequence represented by SEQ ID NO:18;
(b) a DNA which hybridizes with the DNA consisting of the nucleotide sequence represented by SEQ ID NO:18 under stringent conditions and encodes a protein having GDP-mannose 4,6-dehydratase activity.
(16) The transformant according to the above (14), wherein the GDP-mannose 4,6-dehydratase is a protein selected from the group consisting of the following (a) to (c):
(a) a protein comprising the amino acid sequence represented by SEQ ID NO:19;
(b) a protein consisting of an amino acid sequence in which one or more amino acid(s) is/are deleted, substituted, inserted and/or added in the amino acid sequence represented by SEQ ID NO:19 and having GDP-mannose 4,6-dehydratase activity;
(c) a protein consisting of an amino acid sequence which has 80% or more homology with the amino acid sequence represented by SEQ ID NO:19 and having GDP-mannose 4,6-dehydratase activity.
(17) The transformant according to the above (14), wherein the GDP-4-keto-6-deoxy-D-mannose-3,5-epimerase is a protein encoded by a DNA selected from the group consisting of the following (a) and (b):
(a) a DNA comprising the nucleotide sequence represented by SEQ ID NO:20;
(b) a DNA which hybridizes with the DNA consisting of the nucleotide sequence represented by SEQ ID NO:20 under stringent conditions and encodes a protein having GDP-4-keto-6-deoxy-D-mannose-3,5-epimerase activity.
(18) The transformant according to the above (14), wherein the GDP-4-keto-6-deoxy-D-mannose-3,5-epimerase is a protein selected from the group consisting of the following (a) to (c):
(a) a protein comprising the amino acid sequence represented by SEQ ID NO:21;
(b) a protein consisting of an amino acid sequence in which one or more amino acid(s) is/are deleted, substituted, inserted and/or added in the amino acid sequence represented by SEQ ID NO:21 and having GDP-4-keto-6-deoxy-D-mannose-3,5-epimerase activity;
(c) a protein consisting of an amino acid sequence which has 80% or more homology with the amino acid sequence represented by SEQ ID NO:21 and has GDP-4-keto-6-deoxy-D-mannose-3,5-epimerase activity.
(19) The transformant according to the above (12) or (13), wherein the enzyme relating to the modification of a sugar chain in which 1-position of fucose is bound to 6-position of N-acetylglucosamine in the reducing terminal through α-bond in the complex-type N-glycoside-linked sugar chain is α1,6-fucosyltransferase.

(20) The transformant according to (19), wherein the α1,6-fucosyltransferase is a protein encoded by a DNA selected from the group consisting of the following (a) to (d):
(a) a DNA comprising the nucleotide sequence represented by SEQ ID NO:22;
(b) a DNA comprising the nucleotide sequence represented by SEQ ID NO:23;
(c) a DNA which hybridizes with the DNA consisting of the nucleotide sequence represented by SEQ ID NO:22 under stringent conditions and encodes a protein having α1,6-fucosyltransferase activity;
(d) a DNA which hybridizes with the DNA consisting of the nucleotide sequence represented by SEQ ID NO:23 under stringent conditions and encodes a protein having α-1,6-fucosyltransferase activity.
(21) The transformant according to the above (19), wherein the α1,6-fucosyltransferase is a protein selected from the group consisting of the following (a) to (f):
(a) a protein comprising the amino acid sequence represented by SEQ ID NO:24;
(b) a protein comprising the amino acid sequence represented by SEQ ID NO:25;
(c) a protein consisting of an amino acid sequence in which one or more amino acid(s) is/are deleted, substituted, inserted and/or added in the amino acid sequence represented by SEQ ID NO:24 and having α1,6-fucosyltransferase activity;
(d) a protein consisting of an amino acid sequence in which one or more amino acid(s) is/are deleted, substituted, inserted and/or added in the amino acid sequence represented by SEQ ID NO:25 and having α1,6-fucosyltransferase activity;
(e) a protein consisting of an amino acid sequence which has 80% or more homology with the amino acid sequence represented by SEQ ID NO:24 and having α1,6-fucosyltransferase activity;
(f) a protein consisting of an amino acid sequence which has 80% or more homology with the amino acid sequence represented by SEQ ID NO:25 and having α1,6-fucosyltransferase activity.
(22) The transformant according to any one of the above (8) to (21), wherein the host cell is a cell selected from the group consisting of the following (a) to (i):
(a) a CHO cell derived from a Chinese hamster ovary tissue;
(b) a rat myeloma cell line, YB2/3HL.P2.G11.16Ag.20 cell;
(c) a mouse myeloma cell line, NS0 cell;
(d) a mouse myeloma cell line, SP2/0-Ag14 cell;
(e) a BHK cell derived from a syrian hamster kidney tissue;
(f) an antibody-producing hybridoma cell;
(g) a human leukemia cell line, Namalwa cell;
(h) an embryonic stem cell;
(i) a fertilized egg cell.
(23) A process for producing a recombinant antibody composition, which comprises culturing the transformant described in any one of the above (8) to (22) in a medium to form and accumulate the antibody composition in the culture; and recovering and purifying the antibody composition from the culture.
(24) A pharmaceutical composition comprising the recombinant antibody composition described in any one of the above (1) to (5) as an active ingredient.

The present invention is described below in detail.

An antibody molecule is also referred to as an immunoglobulin (hereinafter referred to as Ig), and a human antibody is classified into isotypes of IgA1, IgA2, IgD, IgE, IgG1, IgG2, IgG3, IgG4 and IgM. IgG1, IgG2, IgG3 and IgG4 which have relatively high homology in amino acid sequences are generically referred to as IgG.

An antibody molecule is constituted by polypeptides called a heavy chain (also referred to as H chain) and a light chain (also referred to as L chain). Also, the H chain is constituted by regions of an H chain variable region (also referred to as VH) and an H chain constant region (also referred to as CH) from its N-terminal, and the L chain is constituted by regions of an L chain variable region (also referred to as VL) and an L chain constant region (also referred to as CL) from its N-terminal. CH is further constituted by domains of a CH1 domain, a hinge domain, a CH2 domain and a CH3 domain. The domain means a functional constitution unit constituting each polypeptide in the antibody molecule. Also, the CH2 domain and the CH3 domain in combination are called Fc region.

The CH1 domain, the hinge domain, the CH2 domain, the CH3 domain and the Fc region in the present invention are defined by positions of amino acid residues from the N-terminal indicated by the EU index as in Kabat, et al. [*Sequence of Proteins of Immunological Interest,* 5th Edition (1991)]. Specifically, CH1 is defined as the amino acid sequence of positions 118 to 215 indicated by the EU index, the hinge is defined as the amino acid sequence of positions 216 to 230 indicated by the EU index, CH2 is defined as the amino acid sequence of positions 231 to 340 indicated by the EU index, and CH3 is defined as the amino acid sequence of positions 341 to 447 indicated by the EU index (the number of an amino acid residue shown below is based on the EU index).

The recombinant antibody composition of the present invention includes recombinant antibody composition which is a human IgG1 antibody, comprises a CH2 domain in which amino acids at positions 276 and 339 indicated by the EU index as in Kabat, et al. are replaced by other amino acids and has more improved complement-dependent cytotoxic activity than an antibody comprising a CH2 domain before the amino acids are replaced.

The other amino acids may be any amino acid, so long as they are amino acids which increase the CDC activity in comparison with the antibody comprising a CH2 domain before the amino acid substitutions. Preferably, the amino acid at position 276 is an amino acid selected from aspartic acid, leucine, serine or lysine, and the amino acid at position 339 is an amino acid selected from aspartic acid, phenylalanine, isoleucine, lysine, asparagine, serine, tryptophan, tyrosine and threonine.

The other amino acids are more preferably amino acids corresponding to the CH2 domain of the IgG3 antibody.

The other amino acids are most preferably lysine as the amino acid at position 276 and threonine as the amino acid at position 339.

Furthermore, the recombinant antibody composition of the present invention includes the recombinant antibody composition, wherein a polypeptide contained in a CH3 domain in the Fc region is a polypeptide comprising amino acids corresponding to the same positions in a human IgG3 antibody indicated by the EU index.

Specific examples include a recombinant antibody composition in which the polypeptide comprising a CH3 domain in the Fc region is a polypeptide selected from the following (a) to (h):
(a) in the EU index, positions 341 to 447 are derived from human IgG1;
(b) in the EU index, positions 341 to 356 are derived from human IgG3, and positions 357 to 447 are derived from human IgG1;

(c) in the EU index, positions 341 to 358 are derived from human IgG3, and positions 359 to 447 are derived from human IgG1;
(d) in the EU index, positions 341 to 384 are derived from human IgG3, and positions 385 to 447 are derived from human IgG1;
(e) in the EU index, positions 341 to 392 are derived from human IgG3, and positions 393 to 447 are derived from human IgG1;
(f) in the EU index, positions 341 to 397 are derived from human IgG3, and positions 398 to 447 are derived from human IgG1;
(g) in the EU index, positions 341 to 422 are derived from human IgG3, and positions 423 to 447 are derived from human IgG1;
(h) in the EU index, positions 341 to 434 and positions 436 to 447 are derived from human IgG3, and position 435 is derived from human IgG1.

The amino acid sequence of the CL region in the recombinant antibody composition of the present invention may be either an amino acid sequence of a human antibody or an amino acid sequence of a non-human animal, and is preferably Cκ or Cλ in an amino acid sequence of a human antibody.

In the present invention, a chimeric isotype means a heavy chain constant region comprising amino acid sequences of two or more kinds of human isotypes in which a part of an amino acid sequence of a human isotype heavy chain constant region is swapped for an amino acid sequence of a corresponding part in a different human isotype. Hereinafter, a chimeric isotype recombinant antibody means a recombinant antibody in which the heavy chain constant region is s chimeric isotype.

Also, the recombinant antibody composition of the present invention may be any recombinant antibody composition, so long as it is an antibody having Fc and binding activity to a target molecule or a fusion protein having Fc having binding activity to a target molecule.

The antibody having binding activity to a target molecule includes a human chimeric antibody, a humanized antibody and a human antibody.

The fusion protein having Fc and having binding activity to a target molecule includes a fusion protein of a molecule having binding activity to a target molecule with Fc, a fusion protein of an antibody having binding activity to a target molecule with Fc, a fusion protein of an antibody fragment having binding activity to a target molecule with Fc, and the like.

Specific examples of the Fc fusion protein include an Fc fusion protein in which a receptor or a ligand is fused with the Fc region, an Fc fusion protein in which plural Fc regions are fused with the Fc region of an antibody, and the like.

The antibody fragment having binding activity to a target molecule includes Fab, Fab', F(ab')$_2$, scFv, diabody, dsFv, a peptide comprising CDR, and the like.

A Fab is an antibody fragment having a molecular weight of about 50,000 and having antigen binding activity, in which about a half of the N-terminal side of H chain and the entire L chain, among fragments obtained by treating IgG antibody with a protease, papain (cleaving an amino acid residue at the 224th position of the H chain), are bound together through a disulfide bond (S—S bond).

A F(ab')$_2$ is an antibody fragment having antigen binding activity and having a molecular weight of about 100,000 which is somewhat larger than one in which Fab are bound via an S—S bond in the hinge region, among fragments obtained by treating IgG with a protease, pepsin (by cleaving the H chain at the 234th amino acid residue).

A Fab' is an antibody fragment having a molecular weight of about 50,000 and having antigen binding activity, which is obtained by cleaving an S—S bond in the hinge region of the F(ab')$_2$.

An scFv is a VH-P-VL or VL-P-VH polypeptide in which one chain VH and one chain VL are linked using an appropriate peptide linker (P) having 12 or more residues and is an antibody fragment having antigen binding activity.

A diabody is an antibody fragment in which scFvs having the same or different antigen binding specificity forms a dimer, and has divalent antigen binding activity to the same antigen or two specific antigen binding activities to different antigens.

A dsFv is obtained by binding polypeptides in which one amino acid residue of each of VH and VL is substituted with a cysteine residue via an S—S bond between the cysteine residues.

A peptide comprising CDR is constituted by including at least one region or more of CDRs of VH or VL. A peptide comprising plural CDRs can be produced by binding directly or via an appropriate peptide linker.

A human chimeric antibody is an antibody which comprises VH and VL of an antibody derived from an animal other than a human (non-human animal), and CH and CL of a human antibody. The non-human animal may be any animal such as a mouse, a rat, a hamster or a rabbit, so long as a hybridoma can be prepared therefrom.

A hybridoma is a cell producing a monoclonal antibody having desired immunospecificity which is obtained by cell fusion of a B cell obtained by immunizing a non-human animal with an antigen, with a myeloma cell derived from a mouse or the like. Accordingly, a variable region constituting an antibody produced by a hybridoma comprises an amino acid sequence of a non-human animal antibody.

The human chimeric antibody can be produced by obtaining cDNAs encoding VH and VL from a monoclonal antibody-producing hybridoma derived from a non-human animal, inserting them into an expression vector for animal cell comprising DNAs encoding CH and CL of human antibody to thereby construct a human chimeric antibody expression vector, and then introducing the vector into an animal cell to express the antibody.

As the CH of the human chimeric antibody, any CH can be used, so long as it belongs to human immunoglobulin (hIg), and those belonging to the hIgG class are preferred, and any one of the subclasses belonging to the hIgG class, such as γ1 (IgG1), γ2 (IgG2), γ3 (IgG3) and γ4 (IgG4), can be used. As the CL of the human chimeric antibody, any CL can be used, so long as it belongs to the hIg class, and those belonging to the κ class (Cκ) or λ class (Cλ) can be used.

A humanized antibody is an antibody in which amino acid sequences of CDRs of VH and VL of a non-human animal antibody are grafted into appropriate positions of VH and VL of a human antibody. The region other than CDRs of VH and VL is referred to as a framework region (hereinafter referred to FR).

The humanized antibody can be produced by constructing cDNA encoding amino acid sequences of CDRs in VH of a non-human animal and an amino acid sequence of VH comprising an amino acid sequence of FR in VH of a human antibody and a cDNA encoding amino acid sequences of CDRs in VL of a non-human animal and an amino acid sequence of VL comprising an amino acid sequence of FR in VL of a human antibody; inserting them into an expression vector for animal cell comprising DNAs encoding CH and CL of a human antibody to thereby construct a humanized antibody expression vector; and then introducing the expression vector into an animal cell to express the humanized antibody.

As the CH of the humanized antibody, any CH can be used, so long as it belongs to the hIg, and those of the hIgG class are preferred and any one of the subclasses belonging to the hIgG class, such as γ1 (IgG1), γ2 (IgG2), γ3 (IgG3) and γ4 (IgG4), can be used. As the CL of the human CDR-grafted antibody, any CL can be used, so long as it belongs to the hIg class, and those belonging to Cκ or Cλ can be used.

A human antibody is originally an antibody naturally existing in the human body, but it also includes antibodies obtained from a human antibody phage library or a human antibody-producing transgenic animal, which is prepared based on the recent advance in genetic engineering, cell engineering and developmental engineering techniques.

The antibody existing in the human body can be prepared, for example by isolating a human peripheral blood lymphocyte, immortalizing it by infecting with EB virus or the like and then cloning it to thereby obtain lymphocytes capable of producing the antibody, culturing the lymphocytes thus obtained, and purifying the antibody from the culture.

The human antibody phage library is a library in which antibody fragments such as Fab and scFv are expressed on the phage surface by inserting a gene encoding an antibody prepared from a human B cell into a phage gene. A phage expressing an antibody fragment having the desired antigen binding activity can be recovered from the library, using its activity to bind to an antigen-immobilized substrate as the index. The antibody fragment can be converted further into a human antibody molecule comprising two full H chains and two full L chains by genetic engineering techniques.

A human antibody-producing transgenic animal is an animal in which a human antibody gene is integrated into cells. Specifically, a human antibody-producing transgenic animal can be prepared by introducing a gene encoding a human antibody into a mouse ES cell, grafting the ES cell into an early stage embryo of other mouse and then developing it. A human antibody is prepared from the human antibody-producing transgenic non-human animal by obtaining a human antibody-producing hybridoma by a hybridoma preparation method usually carried out in non-human mammals, culturing the obtained hybridoma and forming and accumulating the human antibody in the culture.

The amino acid sequence of CL in the recombinant antibody composition of the present invention may be either an amino acid sequence of a human antibody or an amino acid sequence from a non-human animal, but it is preferably Cκ or Cλ of an amino acid sequence of a human antibody.

In the recombinant antibody composition of the present invention, the amino acid sequences of VH and VL may be any of amino acid sequences of VH and VL in a human antibody, amino acid sequences of VH and VL in a non-human animal antibody or amino acid sequences of a humanized antibody in which CDRs of a non-human animal are grafted to the framework of a human antibody. Specific examples include amino acid sequences of VH and VL of a non-human animal antibody produced by a hybridoma, amino acid sequences of VH and VL of a humanized antibody, amino acid sequences of VH and VL of a human antibody, and the like.

The recombinant antibody composition of the present invention includes antibodies having any specificity, and is preferably an antibody which recognizes a tumor-related antigen, an antibody which recognizes an allergy- or inflammation-related antigen, an antibody which recognizes cardiovascular disease-related antigen, an antibody which recognizes an autoimmune disease-related antigen or an antibody which recognizes a viral or bacterial infection-related antigen, and more preferably an antibody which recognizes a tumor-related antigen.

The tumor-related antigen includes CD1a, CD2, CD3, CD4, CD5, CD6, CD7, CD9, CD10, CD13, CD19, CD20, CD21, CD22, CD25, CD28, CD30, CD32, CD33, CD38, CD40, CD40 ligand (CD40L), CD44, CD45, CD46, CD47, CD52, CD54, CD55, CD55, CD59, CD63, CD64, CD66b, CD69, CD70, CD74, CD80, CD89, CD95, CD105, CD134, CD137, CD138, CD147, CD158, CD160, CD162, CD164, CD200, CD227, adrenomedullin, angiopoietin related protein 4 (ARP4), aurora, B7-H1, B7-DC, integlin, bone marrow stromal antigen 2 (BST2), CA125, CA19.9, cadherin, cc-chemokine receptor (CCR) 4, CCR7, carcinoembryonic antigen (CEA), cysteine-rich fibroblast growth factor receptor-1 (CFR-1), c-Met, c-Myc, collagen, CTA, connective tissue growth factor (CTGF), CTLA-4, cytokeratin-18, DF3, E-catherin, epidermal growth facter receptor (EGFR), EGFRvIII, EGFR2 (HER2), EGFR3 (HER3), EGFR4 (HER4), endoglin, epithelial cell adhesion molecule (EpCAM), endothelial protein C receptor (EPCR), ephrin, ephrin receptor (Eph), EphA2, endotheliase-2 (ET2), FAM3D, fibroblast activating protein (FAP), Fc receptor homolog 1 (FcRH1), ferritin, fibroblast growth factor-8 (FGF-8), FGF8 receptor, basic FGF (bFGF), bFGF receptor, FGF receptor (FGFR) 3, FGFR4, FLT1, FLT3, folate receptor, Frizzled homologue 10 (FZD10), frizzled receptor 4 (FZD-4), G250, G-CSF receptor, ganglioside (such as GD2, GD3, GM2 and GM3), globo H, gp75, gp88, GPR-9-6, heparanase I, hepatocyte growth factor (HGF), HGF receptor, HLA antigen (such as HLA-DR), HM1.24, human milk fat globule (HMFG), hRS7, heat shock protein 90 (hsp90), idiotype epitope, insulin-like growth factor (IGF), IGF receptor (IGFR), interleukin (such as IL-6 and IL-15), interleukin receptor (such as IL-6R and IL-15R), integrin, immune receptor translocation associated-4 (IRTA-4), kallikrein 1, KDR, KIR2DL1, KIR2DL2/3, KS1/4, lamp-1, lamp-2, laminin-5, Lewis y, sialyl Lewis x, lymphotoxin-beta receptor (LTBR), LUNX, melanoma-associated chondroitin sulfate proteoglycan (MCSP), mesothelin, MICA, Mullerian inhibiting substance-type II receptor (MISIIR), mucin, neural cell adhesion molecule (NCAM), Nec1-5, Notch1, osteopontin, platelet-derived growth factor (PDGF), PDGF receptor, platelet factor-4 (PF-4), phosphatidylserine, Prostate Specific Antigen (PSA), prostate stem cell antigen (PSCA), prostate specific membrane antigen (PSMA), Parathyroid hormone related protein/peptide (PTHrP), receptor activator of NF-kappaB ligand (RANKL), receptor for hyaluronic acid mediated motility (RHAMM), ROBOT, SART3, semaphorin 4B (SEMA4B), secretory leukocyte protease inhibitor (SLPI), SM5-1, sphingosine-1-phosphate, tumor-associated glycoprotein-72 (TAG-72), transferrin receptor (TfR), TGF-beta, Thy-1, Tie-1, Tie2 receptor, T cell immunoglobulin domain and mucin domain 1 (TIM-1), human tissue factor (hTF), Tn antigen, tumor necrosis factor (TNF), Thomsen-Friedenreich antigen (TF antigen), TNF receptor, tumor necrosis factor-related apoptosis-inducing ligand (TRAIL), TRAIL receptor (such as DR4 and DR5), trkC, TROP-2, TWEAK receptor Fn14, -type IV collagenase, urokinase receptor, vascular endothelial growth factor (VEGF), VEGF receptor (VEGFR1, VEGFR2, VEGFR3), vimentin, VLA-4 and the like.

The antibody which recognizes a tumor-related antigen includes anti-GD2 antibody [*Anticancer Res.*, 13, 331 (1993)], anti-GD3 antibody [*Cancer Immunol. Immunother.*, 36, 260 (1993)], anti-GM2 antibody [*Cancer Res.*, 54, 1511 (1994)], anti-HER2 antibody [*Proc. Natl. Acad. Sci. USA*, 89, 4285 (1992)], anti-CD52 antibody [*Proc. Natl. Acad. Sci. USA*, 89, 4285 (1992)], anti-MAGE antibody [*British J. Cancer*, 83, 493 (2000)], anti-HM1.24 antibody [*Molecular Immunol.*, 36, 387 (1999)], anti-parathyroid hormone-related protein (PTHrP) antibody [*Cancer*, 88, 2909 (2000)], anti-basic fibroblast growth factor antibody, anti-fibroblast growth factor 8 antibody [*Proc. Natl. Acad. Sci. USA*, 86, 9911 (1989)], anti-basic fibroblast growth factor receptor antibody, anti-fibroblast growth factor 8 receptor antibody [*J. Biol. Chem.*, 265, 16455 (1990)], anti-insulin-like growth factor antibody [*J. Neurosci. Res.*, 40, 647 (1995)], anti-insulin-like growth factor receptor antibody [*J. Neurosci. Res.*, 40, 647 (1995)], anti-PMSA antibody [*J. Urology*, 160, 2396 (1998)], anti-vascular endothelial cell growth factor antibody [*Cancer Res.*, 57, 4593 (1997)], anti-vascular endothelial cell growth factor receptor antibody [*Oncogene*, 19, 2138 (2000)], anti-CD20 antibody [*Curr. Opin. Oncol.*, 10, 548 (1998)], anti-Her2 antibody, anti-CD10 antibody, and the like.

The antibody which recognizes an allergy- or inflammation-related antigen includes anti-interleukin 6 antibody [*Immunol. Rev.*, 127, 5 (1992)], anti-interleukin 6 receptor antibody [*Molecular Immunol.*, 31, 371 (1994)], anti-interleukin 5 antibody [*Immunol. Rev.*, 127, 5 (1992)], anti-interleukin 5 receptor antibody, anti-interleukin 4 antibody [*Cytokine*, 3, 562 (1991)], anti-interleukin 4 receptor antibody [*J. Immunol. Meth.*, 217, 41 (1998)], anti-tumor necrosis factor antibody [*Hybridoma*, 13, 183 (1994)], anti-tumor necrosis factor receptor antibody [*Molecular Pharmacol.*, 58, 237 (2000)], anti-CCR4 antibody [*Nature*, 400, 776 (1999)], anti-chemokine antibody [Peri et al., *J. Immuno. Meth.*, 174, 249-257 (1994)], anti-chemokine receptor antibody [*J. Exp. Med.*, 186, 1373 (1997)] or the like. The antibody which recognizes a cardiovascular disease-related antigen includes anti-GpIIb/IIIa antibody [*J. Immunol.*, 152, 2968 (1994)], anti-platelet-derived growth factor antibody [*Science*, 253, 1129 (1991)], anti-platelet-derived growth factor receptor antibody [*J. Biol. Chem.*, 272, 17400 (1997)], anti-blood coagulation factor antibody [*Circulation*, 101, 1158 (2000)] and the like.

The antibody which recognizes virus- or bacterial infection-related antigen includes anti-gp120 antibody [*Structure*, 8, 385 (2000)], anti-CD4 antibody [*J. Rheumatology*, 25, 2065 (1998)], anti-CCR5 antibody, anti-verotoxin antibody [*J. Clin. Microbiol.*, 37, 396 (1999)], and the like.

Furthermore, the present invention relates to a recombinant antibody composition having binding activity to protein A.

To have binding activity to protein A means that the recombinant antibody composition can be purified by using the protein A.

The binding activity to protein A can be measured by ELISA, surface plasmon resonance or the like. Specifically, the antibody composition is allowed to react with protein A solid-phased on a plate and then is further allowed to react with an antibody which recognizes the variously labeled antibodies, and the binding activity can be measured by determining the antibody composition bound to protein A.

The protein A binding activity similar to that of the IgG1 antibody means that when the binding activity or affinity of the antibody of the present invention or the IgG1 antibody to protein A is measured, the binding activity or activity having affinity is substantially similar to that of the IgG1 antibody.

Also, the antibody composition is allowed to react with protein A bound to a carrier such as sepharose at high pH conditions such as a pH of about 5 to 8, followed by washing, and then the binding activity can be measured by determining the antibody composition eluted at low pH conditions such as a pH of about 2 to 5.

The antibody molecule has Fc, and N-glycoside-linked sugar chains are bound to its region. Accordingly, two sugar chains are bound per one antibody molecule.

The N-glycoside-linked sugar chain include a complex-type sugar chain in which the non-reducing terminal side of the core structure comprises one or plurality of parallel side chains of galactose-N-acetylglucosamine (hereinafter referred to as "Gal-GlcNAc") and the non-reducing terminal side of Gal-GlcNAc further comprises a structure of sialic acid, bisecting N-acetylglucosamine or the like.

In the present invention, the complex-type N-glycoside-linked sugar chain is represented by the following formula:

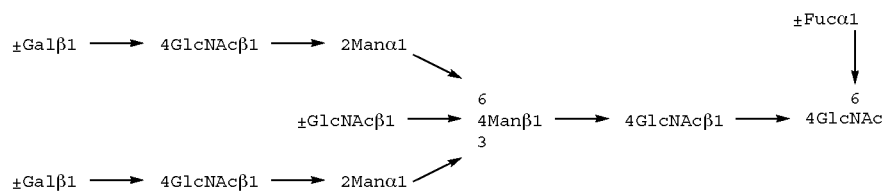

Among the recombinant antibody compositions of the present invention, the recombinant antibody composition comprising an antibody molecule having the N-glycoside-linked sugar chains in Fc may comprise an antibody molecule having the same sugar chain structure or an antibody molecule having different sugar chain structures, so long as it has the above sugar chain structure. That is, the recombinant antibody composition of the present invention means a composition comprising a recombinant antibody molecule having the same or different sugar chain structure(s).

Furthermore, among the recombinant antibodies of the present invention, the antibody composition comprising an antibody molecule having complex-type N-glycoside-linked sugar chains in Fc, wherein the ratio of sugar chains in which fucose is not bound to N-acetylglucosamine in the reducing terminal of the sugar chains among the total complex-type N-glycoside-linked sugar chains which bind to Fc contained in the composition, has high ADCC activity in addition to CDC activity.

As the ratio of the ratio of sugar chains in which fucose is not bound to N-acetylglucosamine in the reducing terminal of the antibody, antibodies having any ratio are included, so long as the ADCC activity as well as the CDC activity are increased. The ratio is preferably 20% or more, more preferably 51% to 100%, still more preferably 80% to 100%, particularly preferably 90% to 99% and most preferably 100%.

In the present invention, the sugar chain in which fucose is not bound may have any sugar chain structure in the non-reducing terminal, so long as fucose is not bound to N-acetylglucosamine in the reducing terminal in the above formula.

In the present invention, the case where fucose is not bound to N-acetylglucosamine in the reducing terminal in the sugar chain means that fucose is not substantially bound. An antibody composition in which fucose is not substantially bound specifically refers to an antibody composition in which fucose is not substantially detected, i.e., the content of fucose is below the detection limit, when subjected to the sugar chain analysis described in the following item 4. A recombinant antibody composition in which fucose is not bound to N-acetylglucosamine in the reducing terminals of all sugar chains has highest ADCC activity.

The ratio of antibody molecules having sugar chains in which fucose is not bound to N-acetylglucosamine in the reducing terminal in the sugar chains contained in the composition which comprises an antibody molecule having complex-type N-glycoside-linked sugar chains in Fc can be determined by releasing the sugar chains from the antibody molecule using a known method such as hydrazinolysis or enzyme digestion [*Biochemical Experimentation Methods 23—Method for Studying Glycoprotein Sugar Chain* (Japan Scientific Societies Press), edited by Reiko Takahashi (1989)], carrying out fluorescence labeling or radioisotope labeling of the released sugar chains and then separating the labeled sugar chains by chromatography. Also, the released sugar chains can be determined by analyzing it with the HPAED-PAD method [*J. Liq. Chromatogr.*, 6, 1577 (1983)].

The transformant producing the recombinant antibody composition of the present invention can be obtained by introducing, into an animal cell, a recombinant antibody composition expression vector into which DNAs encoding a variable region and a constant region of an antibody molecule are inserted.

The recombinant antibody expression vector is constructed as described below.

Each of the above DNAs encoding CH and CL is introduced into a vector for expression of recombinant antibody to produce a recombinant antibody composition expression vector for animal cell.

The vector for expression of recombinant antibody includes pAGE107 (Japanese Published Unexamined Patent Application No. 22979/91; Miyaji H. et al., *Cytotechnology*, 3, 133-140 (1990)), pAGE103 (Mizukami T. and Itoh S., *J. Biochem.*, 101, 1307-1310 (1987)), pHSG274 (Brady G. et al., Gene, 27, 223-232 (1984)), pKCR (O'Hare K. et al., *Proc. Natl. Acad. Sci. USA.*, 78, 1527-1531 (1981)), pSG1βd2-4 (Miyaji H. et al., *Cytotechnology*, 4, 173-180 (1990)) and the like. The promoter and enhancer used as the vector for expression of recombinant antibody include SV40 early promoter and enhancer (Mizukami T. and Itoh S., *J. Biochem.*, 101, 1307-1310 (1987)), LTR promoter and enhancer of Moloney mouse leukemia virus (Kuwana Y. et al., *Biochem. Biophys. Res. Commun.*, 149, 960-968 (1987)), immunoglobulin H chain promoter (Mason J. O. et al., *Cell*, 41, 479-487 (1985)) and enhancer (Gillies S. D. et al., *Cell*, 33, 717-728 (1983)) and the like.

The vector for expression of recombinant antibody composition may be either of a-type in which genes encoding the H chain and L chain exist on separate vectors or of a-type in which both genes exist on the same vector (tandem-type). In respect of easiness of construction of a recombinant antibody composition expression vector, easiness of introduction into animal cells, and balance between the expression amounts of the H and L chains of an antibody in animal cells, a tandem-type of the vector for expression of recombinant antibody composition is more preferred (Shitara K. et al., *J. Immunol. Methods*, 167, 271-278 (1994)). The tandem-type vector for expression of recombinant antibody composition includes pKANTEX93 (WO97/10354), pEE18 (Bentley K. J. et al., *Hybridoma*, 17, 559-567 (1998)) and the like.

cDNAs encoding VH and VL of antibodies for various antigens are cloned into the upstream of DNAs encoding CH and CL of the constructed vector for expression of recombinant antibody composition to thereby construct a recombinant antibody composition expression vector.

A method for introducing the expression vector into a host cell includes electroporation (Japanese Published Unexamined Patent Application No. 257891-90; Miyaji H. et al., *Cytotechnology*, 3, 133-140 (1990)) and the like.

The host cell producing the recombinant antibody composition of the present invention may be any host cell which is generally used in production of a recombinant protein, such as an animal cell, a plant cell or a microorganism.

The host cell producing the recombinant antibody composition of the present invention includes a CHO cell derived from a Chinese hamster ovary tissue, a rat myeloma cell line YB2/3HL.P2.G11.16Ag.20 cell, a mouse myeloma cell line NS0 cell, a mouse myeloma SP2/0-Ag14 cell, a BHK cell derived from a syrian hamster kidney tissue, a human leukemia cell line Namalwa cell, a hybridoma cell produced by using a myeloma cell and any B cell, a hybridoma cell produced by a B cell obtained by immunizing with an antigen a transgenic non-human animal produced by using an embryonic stem cell or a fertilized egg cell and any myeloma cell; a hybridoma cell produced by the above myeloma cell and a B cell obtained by immunizing a transgenic non-human animal produced by using an embryonic stem cell or a fertilized egg cell; and the like, with an antigen.

The host cell capable of expressing a recombinant antibody composition having high ADCC activity as well as CDC activity includes a host cell resistant to a lectin which recognizes a sugar chain structure in which 1-position of fucose is bound to 6-position of N-acetylglucosamine in the reducing terminal through α-bond in the complex-type N-glycoside-linked sugar chain, such as a host cell capable of producing an antibody composition comprising an antibody molecule having complex-type N-glycoside-linked sugar chains in the Fc region, wherein the ratio of sugar chains in which fucose is not bound to N-acetylglucosamine in the reducing terminal of the sugar chains among the total complex-type N-glycoside-linked sugar chains which bind to the Fc region contained in the composition is 20% or more. Examples include cells in which activity of at least one protein described below is decreased or deleted, and the like:

(a) an enzyme relating to synthesis of an intracellular sugar nucleotide, GDP-fucose;
(b) an enzyme relating to the modification of a sugar chain in which 1-position of fucose is bound to 6-position of N-acetylglucosamine in the reducing terminal through α-bond in a complex-type N-glycoside-linked sugar chain;
(c) a protein relating to transport of an intracellular sugar nucleotide, GDP-fucose, to the Golgi body.

The above host cell is preferably a host cell in which a gene encoding α1,6-fucosyltransferase in the host cell is knocked out (WO02/31140, WO03/85107).

The enzyme relating to synthesis of an intracellular sugar nucleotide, GDP-fucose may be any enzyme, so long as it is an enzyme relating to the synthesis of the intracellular sugar nucleotide, GDP-fucose, as a supply source of fucose to a sugar chain. The enzyme relating to synthesis of an intracellular sugar nucleotide, GDP-fucose includes an enzyme which has influence on the synthesis of the intracellular sugar nucleotide, GDP-fucose, and the like.

The intracellular sugar nucleotide, GDP-fucose, is supplied by a de novo synthesis pathway or a salvage synthesis pathway. Thus, all enzymes relating to the synthesis pathways are included in the enzyme relating to synthesis of an intracellular sugar nucleotide, GDP-fucose.

The enzyme relating to the de novo synthesis pathway of an intracellular sugar nucleotide, GDP-fucose includes GDP-mannose 4,6-dehydratase (hereinafter referred to as "GMD"), GDP-keto-6-deoxymannose-3,5-epimerase, 4,6-reductase (hereinafter referred to as "Fx") and the like.

The enzyme relating to the salvage synthesis pathway of an intracellular sugar nucleotide, GDP-fucose includes GDP-beta-L-fucose pyrophosphorylase (hereinafter referred to as "GFPP"), fucokinase and the like.

As the enzyme which has influence on the synthesis of an intracellular sugar nucleotide, GDP-fucose, an enzyme which has influence on the activity of the enzyme relating to the synthesis pathway of the intracellular sugar nucleotide, GDP-fucose described above, and an enzyme which has influence on the structure of substances as the substrate of the enzyme are also included.

The GDP-mannose 4,6-dehydratase includes:
(a) a DNA comprising the nucleotide sequence represented by SEQ ID NO:18;
(b) a DNA which hybridizes with the DNA consisting of the nucleotide sequence represented by SEQ ID NO:18 under stringent conditions and encodes a protein having GDP-mannose 4,6-dehydratase activity,
and the like.

The GDP-mannose 4,6-dehydratase includes:
(a) a protein comprising the amino acid sequence represented by SEQ ID NO:19;
(b) a protein consisting of an amino acid sequence in which one or more amino acid(s) is/are deleted, substituted, inserted and/or added in the amino acid sequence represented by SEQ ID NO:19 and having GDP-mannose 4,6-dehydratase activity;
(c) a protein consisting of an amino acid sequence which has 80% or more homology with the amino acid sequence represented by SEQ ID NO:19 and having GDP-mannose 4,6-dehydratase activity;
and the like.

The GDP-4-keto-6-deoxy-D-mannose-3,5-epimerase includes:
(a) a DNA comprising the nucleotide sequence represented by SEQ ID NO:20;
(b) a DNA which hybridizes with the DNA consisting of the nucleotide sequence represented by SEQ ID NO:20 under stringent conditions and encodes a protein having GDP-4-keto-6-deoxy-D-mannose-3,5-epimerase activity; and the like.

The GDP-4-keto-6-deoxy-D-mannose-3,5-epimerase includes:
(a) a protein comprising the amino acid sequence represented by SEQ ID NO:21;
(b) a protein consisting of an amino acid sequence in which one or more amino acid(s) is/are deleted, substituted, inserted and/or added in the amino acid sequence represented by SEQ ID NO:21 and having GDP-4-keto-6-deoxy-D-mannose-3,5-epimerase activity;
(c) a protein consisting of an amino acid sequence which has 80% or more homology with the amino acid sequence represented by SEQ ID NO:21 and has GDP-4-keto-6-deoxy-D-mannose-3,5-epimerase activity;
and the like.

The enzyme relating to the modification of a sugar chain in which 1-position of fucose is bound to 6-position of N-acetylglucosamine in the reducing terminal through α-bond in a complex-type N-glycoside-linked sugar chain includes any enzyme, so long as it is an enzyme relating to the reaction of binding of 1-position of fucose to 6-position of N-acetylglucosamine in the reducing terminal through α-bond in the complex-type N-glycoside-linked sugar chain. The enzyme relating to the reaction of binding of 1-position of fucose to 6-position of N-acetylglucosamine in the reducing terminal through α-bond in the complex-type N-glycoside-linked sugar chain includes an enzyme which has influence on the reaction of binding of 1-position of fucose to 6-position of N-acetylglucosamine in the reducing terminal through α-bond in the complex-type N-glycoside-linked sugar chain. Examples include α1,6-fucosyltransferase, α-L-fucosidase and the like.

Also, the enzyme relating to the reaction of binding of 1-position of fucose to 6-position of N-acetylglucosamine in the reducing terminal through α-bond in the complex-type N-glycoside-linked sugar chain includes an enzyme which has influence on the activity of the enzyme relating to the reaction of binding of 1-position of fucose to 6-position of N-acetylglucosamine in the reducing terminal through α-bond in the complex-type N-glycoside-linked sugar chain and an enzyme which has influence on the structure of substances as the substrate of the enzyme.

In the present invention, the α1,6-fucosyltransferase is a protein encoded by a DNA of the following (a), (b), (c) or (d):
(a) a DNA comprising the nucleotide sequence represented by SEQ ID NO:22;
(b) a DNA comprising the nucleotide sequence represented by SEQ ID NO:23;
(c) a DNA which hybridizes with the DNA consisting of the nucleotide sequence represented by SEQ ID NO:22 under stringent conditions and encodes a protein having α1,6-fucosyltransferase activity;
(d) a DNA which hybridizes with the DNA consisting of the nucleotide sequence represented by SEQ ID NO:23 under stringent conditions and encodes a protein having α-1,6-fucosyltransferase activity, or
(e) a protein comprising the amino acid sequence represented by SEQ ID NO:24;
(f) a protein comprising the amino acid sequence represented by SEQ ID NO:25;
(g) a protein consisting of an amino acid sequence in which one or more amino acid(s) is/are deleted, substituted, inserted and/or added in the amino acid sequence represented by SEQ ID NO:24 and having α1,6-fucosyltransferase activity;
(h) a protein consisting of an amino acid sequence in which one or more amino acid(s) is/are deleted, substituted, inserted and/or added in the amino acid sequence represented by SEQ ID NO:25 and having α1,6-fucosyltransferase activity;
(i) a protein consisting of an amino acid sequence which has 80% or more homology with the amino acid sequence represented by SEQ ID NO:24 and having α1,6-fucosyltransferase activity;
(j) a protein consisting of an amino acid sequence which has 80% or more homology with the amino acid sequence represented by SEQ ID NO:25 and having α1,6-fucosyltransferase activity;
and the like.

The protein relating to transport of an intracellular sugar nucleotide, GDP-fucose, to the Golgi body may be any protein, so long as it is a protein relating to the transport of the intracellular sugar nucleotide, GDP-fucose, to the Golgi body, or a protein which has an influence on the reaction for the transport of the intracellular sugar nucleotide, GDP-fucose, to the Golgi body. The protein relating to the transport of the intracellular sugar nucleotide, GDP-fucose, to the Golgi body includes a GDP-fucose transporter and the like.

Also, the protein which has an influence on the reaction for the transport of the intracellular sugar nucleotide, GDP-fucose, to the Golgi body include a protein which has an influence on the activity of the above protein relating to the transport of the intracellular sugar nucleotide, GDP-fucose, to the Golgi body or has influence on the expression thereof.

The DNA encoding the amino acid sequence of the enzyme relating to synthesis of an intracellular sugar nucleotide, GDP-fucose includes a DNA comprising the nucleotide sequence represented by SEQ ID NO:18 or 20; a DNA which hybridizes with the DNA consisting of the nucleotide sequence represented by SEQ ID NO:18 or 20 under stringent conditions and encodes a protein having activity of the enzyme relating to synthesis of an intracellular sugar nucleotide, GDP-fucose; and the like.

The DNA encoding the amino acid sequence of the α1,6-fucosyltransferase includes a DNA comprising the nucleotide sequence represented by SEQ ID NO:22 or 23; a DNA which hybridizes with the DNA consisting of the nucleotide sequence represented by SEQ ID NO:22 or 23 under stringent conditions and encodes a protein having α1,6-fucosyltransferase activity; and the like.

In the present invention, the DNA which hybridizes under stringent conditions refers to a DNA which is obtained by colony hybridization, plaque hybridization, Southern hybridization or the like using, for example, a DNA consisting of the nucleotide sequence represented by any one of the above SEQ ID NOs or a fragment thereof as a probe. A specific example of such DNA is a DNA which can be identified by performing hybridization at 65° C. in the presence of 0.7 to 1.0 M sodium chloride using a filter with colony- or plaque-derived DNA immobilized thereon, and then washing the filter at 65° C. with a 0.1 to 2-fold concentration SSC solution (1-fold concentration SSC solution: 150 mM sodium chloride and 15 mM sodium citrate). Hybridization can be carried out according to the methods described in *Molecular Cloning, A Laboratory Manual*, Second Edition, Cold Spring Harbor Lab. Press (1989) (hereinafter referred to as "*Molecular Cloning*, Second Edition"), *Current Protocols in Molecular Biology*, John Wiley & Sons (1987-1997) (hereinafter referred to as "*Current Protocols in Molecular Biology*"); *DNA Cloning* 1: *Core Techniques, A Practical Approach*, Second Edition, Oxford University (1995); and the like. Specifically, the DNA capable of hybridization under stringent conditions includes DNA having at least 60% or more homology, preferably 70% or more homology, more preferably 80% or more homology, further preferably 90% or more homology, particularly preferably 95% or more homology, most preferably 98% or more homology to the nucleotide sequence represented by any one of the above SEQ ID NOs.

In the present invention, the protein consisting of an amino acid sequence wherein one or more amino acid residue(s) is/are deleted, substituted, inserted and/or added in the amino acid sequence represented by any one of the above SEQ ID NOs and having the above activity can be obtained, for example, by introducing a site-directed mutation into DNA encoding the protein having the amino acid sequence represented by any one of the above SEQ ID NOs by site-directed mutagenesis described in *Molecular Cloning*, Second Edition, *Current Protocols in Molecular Biology* (1987-1997), *Nucleic Acids Research*, 10, 6487 (1982), *Proc. Natl. Acad. Sci., USA*, 79, 6409 (1982), *Gene*, 34, 315 (1985), *Nucleic Acids Research*, 13, 4431 (1985), *Proc. Natl. Acad. Sci. USA*, 82, 488 (1985), or the like. The number of amino acid residues which are deleted, substituted, inserted and/or added is one or more, and is not specifically limited, but it is within the range where deletion, substitution, insertion or addition is possible by known methods such as the above site-directed mutagenesis. The suitable number is 1 to dozens, preferably 1 to 20, more preferably 1 to 10, further preferably 1 to 5.

Also, in the present invention, in order for the protein to have above activity, it is preferred to have at least 80% or more homology, preferably 85% or more homology, more preferably 90% or more homology, further preferably 95% or more homology, particularly preferably 97% or more homology, most preferably 99% or more homology to the amino acid sequence represented by any one of the above SEQ ID NOs, when calculated by use of analysis software such as BLAST [*J. Mol. Biol.*, 215, 403 (1990)] or FASTA [*Methods in Enzymology*, 183, 63 (1990)].

The method for obtaining a cell in which the above enzyme activity is decreased or deleted may by any method, so long as it is a method for decreasing or deleting the objective enzyme activity. Examples include:
(a) gene disruption targeting at a gene encoding the enzyme;
(b) introduction of a dominant-negative mutant of a gene encoding the enzyme;
(c) introduction of a mutation into the enzyme;
(d) suppression of transcription or translation of a gene encoding the enzyme;
(e) selection of a cell line resistant to a lectin which recognizes a sugar chain structure in which 1-position of fucose is bound to 6-position of N-acetylglucosamine in the reducing terminal through α-bond in a N-glycoside-linked sugar chain; and the like.

As the lectin which recognizes a sugar chain structure in which 1-position of fucose is bound to 6-position of N-acetylglucosamine in the reducing terminal through α-bond in a N-glycoside-linked sugar chain, any lectin capable of recognizing the sugar chain structure can be used. Specific examples include lentil lectin LCA (lentil agglutinin derived from *Lens culinaris*), pea lectin PSA (pea lectin derived from *Pisum sativum*), broad bean lectin VFA (agglutinin derived from *Vicia faba*), *Aleuria aurantia* lectin AAL (lectin derived from *Aleuria aurantia*) and the like.

The "cell resistant to a lectin" refers to a cell in which growth is not inhibited by the presence of a lectin at an effective concentration. The "effective concentration" is a concentration higher than the concentration that does not allow the normal growth of a cell prior to the genome modification (hereinafter referred to also as parent cell line), preferably equal to the concentration that does not allow the normal growth of a cell prior to the genome modification, more preferably 2 to 5 times, further preferably 10 times, most preferably 20 or more times the concentration that does not allow the normal growth of a cell prior to the modification of the genomic gene.

The effective concentration of lectin that does not inhibit growth may be appropriately determined according to each cell line. It is usually 10 µg/ml to 10 mg/ml, preferably 0.5 mg/ml to 2.0 mg/ml.

Processes for producing the recombinant antibody composition of the present invention are described below in detail.

1. Process for Producing Recombinant Antibody Composition

The recombinant antibody composition of the present invention can be obtained, for example, by expressing it in a host cell using the methods described in *Molecular Cloning*, Second Edition; *Current Protocols in Molecular Biology*; *Antibodies, A Laboratory manual*, Cold Spring Harbor Laboratory (1988) (hereinafter referred to as *Antibodies*); *Monoclonal Antibodies: principles and practice*, Third Edition, Acad. Press (1993) (hereinafter referred to as *Monoclonal Antibodies*); *Antibody Engineering, A Practical Approach*, IRL Press at Oxford University Press, 1996 (hereinafter referred to as *Antibody Engineering*); and the like, for example, in the following manner.

(1) Construction of a Recombinant Antibody Composition Expression Vector of the Present Invention A recombinant antibody composition expression vector of the present invention is an expression vector for animal cell into which genes encoding H chain and L chain constant regions of an antibody molecule contained in the recombinant antibody composition of the present invention are introduced. The vector for expression of the recombinant antibody composition can be constructed by cloning each of the genes encoding H chain and L chain constant regions of an antibody molecule contained in the recombinant antibody composition into a vector for expression of animal cell.

The gene encoding the H chain constant region of an antibody molecule contained in the recombinant antibody composition of the present invention can be produced by cloning genes encoding the H chain constant regions of IgG1 antibody and then ligating gene fragments encoding desired amino acid sequences. Also, the total DNA can be synthesized by using synthetic DNAs and synthesis using PCR can also be carried out (*Molecular Cloning*, Second Edition). Furthermore, it can be produced by combining these techniques.

The expression vector for animal cell may by any vector, so long as the above gene encoding the constant region of an antibody molecule can be introduced and expressed. Examples include pKANTEX93 [*Mol. Immunol.*, 37, 1035 (2000)], pAGE107 [*Cytotechnology*, 3, 133 (1990), pAGE103 [*J. Biochem.*, 101, 1307 (1987)], pHSG274 [*Gene*, 27, 223 (1984)], pKCR [*Proc. Natl. Acad. Sci. U.S.A.*, 78, 1527 (1981)], pSG113d2-4 [*Cytotechnology*, 4, 173 (1990)] and the like. The promoter and enhancer used for the expression vector for animal cell include SV40 early promoter and enhancer [*J. Biochem.*, 101, 1307 (1987)], LTR of Moloney mouse leukemia virus [*Biochem. Biophys. Res. Commun.*, 149, 960 (1987)], immunoglobulin H chain promoter [*Cell*, 41, 479 (1985)] and ehnancer [*Cell*, 33, 717 (1983)] and the like.

The vector for expression of the recombinant antibody composition of the present invention may be either of a-type in which genes encoding the H chain and L chain of antibody exist on separate vectors or of a-type in which both genes exist on the same vector (hereinafter referred to as tandem-type). In respect of easiness of construction of a recombinant antibody composition expression vector of the present invention, easiness of introduction into animal cells, and balance between the expression amounts of the H and L chains of antibody in animal cells, a tandem-type of the vector for expression of humanized antibody is more preferred (*J. Immunol. Methods*, 167, 271 (1994)).

The constructed recombinant antibody composition expression vector of the present invention can be used for expression of a human chimeric antibody, a humanized antibody and a human antibody in animal cells.

(2) Obtaining of cDNA Encoding V Region of Non-Human Animal Antibody cDNAs encoding an H chain variable region (hereinafter referred to as "VH") and an L chain variable region (hereinafter referred to as "VL") of a non-human animal antibody such as a mouse antibody can be obtained in the following manner.

A cDNA is synthesized by using as a probe mRNA extracted from a hybridoma cell which produces any antibody. The synthesized cDNA is cloned into a vector such as a phage or a plasmid to obtain a cDNA library. Each of a recombinant phage or recombinant plasmid comprising a cDNA encoding VH and a recombinant phage or recombinant plasmid comprising a cDNA encoding the L chain V region is isolated from the library by using cDNA encoding C region or V region of a known mouse antibody as the probe. Full length nucleotide sequences of VH and VL of the mouse antibody of interest on the recombinant phage or recombinant plasmid are determined, and full length amino acid sequences of VH and VL are deduced from the nucleotide sequences.

Hybridoma cells producing any non-human animal-derived antibody can be obtained by immunizing a non-human animal with an antigen bound to the antibody, preparing hybridomas from antibody-producing cells of the immunized animal and myeloma cells according to a known method [*Molecular Cloning*, Second Edition; *Current Protocols in Molecular Biology; Antibodies, A Laboratory manual*, Cold Spring Harbor Laboratory (1988) (hereinafter referred to as *Antibodies*); *Monoclonal Antibodies: principles and practice*, Third Edition, Acad. Press (1993) (hereinafter referred to as *Monoclonal Antibodies*), *Antibody Engineering, A Practical Approach*, IRL Press at Oxford University Press (1996) (hereinafter referred to as *Antibody Engineering*)], selecting cloned hybridomas, culturing the selected hybridomas and purifying cells from the culture supernatant.

As the non-human animal, any animal can be used so long as hybridoma cells can be prepared from the animal. Suitable animals include mouse, rat, hamster and rabbit.

The methods for preparing total RNA from a hybridoma cell include the guanidine thiocyanate-cesium trifluoroacetate method [*Methods in Enzymol.*, 154, 3 (1987)], and the methods for preparing mRNA from the total RNA include the oligo (dT) immobilized cellulose column method [*Molecular Cloning, A Laboratory Manual*, Cold Spring Harbor Lab. Press (1989)]. Examples of the kits for preparing mRNA from a hybridoma cell include Fast Track mRNA Isolation Kit (manufactured by Invitrogen) and Quick Prep mRNA Purification Kit (manufactured by Pharmacia).

The methods for synthesizing the cDNA and preparing the cDNA library include conventional methods [*Molecular Cloning, A Laboratory Manual*, Cold Spring Harbor Lab. Press (1989), *Current Protocols in Molecular Biology*, Supplement 1-34], or methods using commercially available kits such as SuperScript™ Plasmid System for cDNA Synthesis and Plasmid Cloning (manufactured by GIBCO BRL) and ZAP-cDNA Synthesis Kit (manufactured by Stratagene).

In preparing the cDNA library, the vector for integrating the cDNA synthesized using the mRNA extracted from a hybridoma cell as a template may be any vector so long as the cDNA can be integrated. Examples of suitable vectors include ZAP Express [*Strategies*, 5, 58 (1992)], pBluescript II SK(+) [*Nucleic Acids Research*, 17, 9494 (1989)], λZAP II (manufactured by STRATAGENE), λgt10, λgt11 [*DNA Cloning: A Practical Approach*, I, 49 (1985)], Lambda BlueMid (manufactured by Clontech), λExCell, pT7T3 18U (manufactured by Pharmacia), pcD2 [*Mol. Cell. Biol.*, 3, 280 (1983)], pUC18 [*Gene*, 33, 103 (1985)] and the like.

As *Escherichia coli* for introducing the cDNA library constructed with a phage or plasmid vector, any *Escherichia coli* can be used so long as the cDNA library can be introduced, expressed and maintained. Examples of suitable *Escherichia coli* include XL1-Blue MRF' [*Strategies*, 5, 81 (1992)], C600 [*Genetics*, 39, 440 (1954)], Y1088, Y1090 [*Science*, 222, 778 (1983)], NM522 [*J. Mol. Biol.*, 166, 1 (1983)], K802 [*J. Mol. Biol.*, 16, 118 (1966)], JM105 [*Gene*, 38, 275 (1985)] and the like.

The methods for selecting the cDNA clones encoding VH and VL of a non-human animal-derived antibody from the cDNA library include colony hybridization or plaque hybridization [*Molecular Cloning, A Laboratory Manual*, Cold Spring Harbor Laboratory Press New York (1989)] using an isotope- or fluorescence-labeled probe. It is also possible to prepare the cDNAs encoding VH and VL by preparing primers and carrying out PCR [*Molecular Cloning, A Laboratory Manual*, Cold Spring Harbor Laboratory Press New York (1989), *Current Protocols in Molecular Biology*, Supplement 1-34] using the cDNA or cDNA library as a template.

The nucleotide sequences of the cDNAs selected by the above methods can be determined by cleaving the cDNAs with appropriate restriction enzymes, cloning the fragments into a plasmid such as pBluescript SK(-) (manufactured by STRATAGENE), and then analyzing the sequences by generally employed nucleotide sequence analyzing methods such as the dideoxy method of Sanger, et al. [*Proc. Natl. Acad. Sci. USA*, 74, 5463 (1977)] or by use of nucleotide sequence analyzers such as ABI PRISM 377 DNA Sequencer (manufactured by Applied Biosystems).

The full length of amino acid sequences of VH and VL are deduced from the determined nucleotide sequences and compared with the full length of amino acid sequences of VH and VL of a known antibody [*Sequences of Proteins of Immunological Interest*, US Dept. Health and Human Services (1991)], whereby it can be confirmed that the obtained cDNAs encode amino acid sequences which completely comprise VH and VL of the antibody including secretory signal sequences.

Further, when the amino acid sequence of an antibody variable region or the nucleotide sequence of DNA encoding the variable region is already known, the DNA can be obtained by the following methods.

When the amino acid sequence is known, the DNA can be obtained by designing a DNA sequence encoding the variable region taking into consideration the frequency of codon usage [*Sequences of Proteins of Immunological Interest*, US Dept. Health and Human Services (1991)], synthesizing several synthetic DNAs constituting approximately 100-nucleotides based on the designed DNA sequence, and carrying out PCR using the synthetic DNAs. When the nucleotide sequence is known, the DNA can be obtained by synthesizing several synthetic DNAs constituting approximately 100-nucleotides based on the nucleotide sequence information and carrying out PCR using the synthetic DNAs.

(3) Analysis of the Amino Acid Sequence of the V Region of an Antibody from a Non-Human Animal By comparing the full length of amino acid sequences of VH and VL of the antibody including secretory signal sequences with the amino acid sequences of VH and VL of a known antibody [*Sequences of Proteins of Immunological Interest*, US Dept. Health and Human Services (1991)], it is possible to deduce the length of the secretory signal sequences and the N-terminal amino acid sequences and further to know the subgroup to which the antibody belongs. In addition, the amino acid sequences of CDRs of VH and VL can be deduced in a similar manner.

(4) Construction of a Human Chimeric Antibody Expression Vector

A human chimeric antibody expression vector can be constructed by inserting the cDNAs encoding VH and VL of an antibody of a non-human animal into sites upstream of the genes encoding CH and CL of a human antibody in the vector for expression of recombinant antibody composition described in the above 1 (1). For example, a human chimeric antibody expression vector can be constructed by ligating the cDNAs encoding VH and VL of an antibody of a non-human animal respectively to synthetic DNAs comprising the 3'-terminal nucleotide sequences of VH and VL of an antibody of a non-human animal and the 5'-terminal nucleotide sequences of CH and CL of a human antibody and also having recognition sequences for appropriate restriction enzymes at both ends, and inserting them into sites upstream of the genes encoding CH and CL of a human antibody in the vector for expression of recombinant antibody composition described in the above 1 (1) so as to express them in an appropriate form.

(5) Construction of cDNA Encoding V Region of a Humanized Antibody cDNAs encoding VH and VL of a humanized antibody can be constructed in the following manner. First, amino acid sequences of FRs of VH and VL of a human antibody for grafting CDRs of VH and VL of a non-human animal-derived antibody are selected. The amino acid sequences of FRs of VH and VL of a human antibody may be any of those from human antibodies. Suitable sequences include the amino acid sequences of FRs of VHs and VLs of human antibodies registered at databases such as Protein Data Bank, and the amino acid sequences common to subgroups of FRs of VHs and VLs of human antibodies [*Sequences of Proteins of Immunological Interest*, US Dept. Health and Human Services (1991)]. In order to prepare a humanized antibody having a sufficient activity, it is preferred to select amino acid sequences having a homology of as high as possible (at least 60% or more) with the amino acid sequences of FRs of VH and VL of the desired non-human animal-derived antibody.

Next, the amino acid sequences of CDRs of VH and VL of the desired non-human animal-derived antibody are grafted to the selected amino acid sequences of FRs of VH and VL of a human antibody to design amino acid sequences of VH and VL of a humanized antibody. The designed amino acid sequences are converted into DNA sequences taking into consideration the frequency of codon usage in the nucleotide sequences of antibody genes [*Sequences of Proteins of Immunological Interest*, US Dept. Health and Human Services (1991)], and DNA sequences encoding the amino acid sequences of VH and VL of the humanized antibody are designed. Several synthetic DNAs constituting approximately 100-nucleotides are synthesized based on the designed DNA sequences, and PCR is carried out using the synthetic DNAs. It is preferred to design 4 to 6 synthetic DNAs for each of the H chain and the L chain in view of the reaction efficiency of PCR and the lengths of DNAs that can be synthesized.

Cloning into the vector for expression of the recombinant antibody composition of the present invention constructed in the above 1 (1) can be easily carried out by introducing recognition sequences for appropriate restriction enzymes to the 5'-terminals of synthetic DNAs present on both ends. After the PCR, the amplification products are cloned into a plasmid such as pBluescript SK(-) (manufactured by STRATAGENE) and the nucleotide sequences are determined by the method described in the above 1 (2) to obtain a plasmid carrying DNA sequences encoding the amino acid sequences of VH and VL of the desired humanized antibody.

(6) Modification of the Amino Acid Sequence of V Region of a Humanized Antibody

It is known that a humanized antibody prepared merely by grafting CDRs of VH and VL of a non-human animal-derived antibody to FRs of VH and VL of a human antibody has a lower antigen-binding activity compared with the original non-human animal-derived antibody [*BIO/TECHNOLOGY*, 9, 266 (1991)]. This is probably because in VH and VL of the original non-human animal-derived antibody, not only CDRs but also some of the amino acid residues in FRs are involved directly or indirectly in the antigen-binding activity, and such amino acid residues are replaced by amino acid residues of FRs of VH and VL of the human antibody by CDR grafting. In order to solve this problem, attempts have been made in the preparation of a humanized antibody to raise the lowered antigen-binding activity by identifying the amino acid residues in the amino acid sequences of FRs of VH and VL of a human antibody which are directly relating to the binding to an antigen or which are indirectly relating to it through interaction with amino acid residues in CDRs or maintenance of the three-dimensional structure of antibody, and modifying such amino acid residues to those derived from the original non-human animal-derived antibody [*BIO/TECHNOLOGY,* 9, 266 (1991)].

In the preparation of a humanized antibody, it is most important to efficiently identify the amino acid residues in FR which are relating to the antigen-binding activity. For the efficient identification, construction and analyses of the three-dimensional structures of antibodies have been carried out by X ray crystallography [*J. Mol. Biol.,* 112, 535 (1977)], computer modeling [*Protein Engineering,* 7, 1501 (1994)], and the like Although these studies on the three-dimensional structures of antibodies have provided much information useful for the preparation of humanized antibodies, there is no established method for preparing a humanized antibody that is adaptable to any-type of antibody. That is, at present, it is still necessary to make trial-and-error approaches, e.g., preparation of several modifications for each antibody and examination of each modification for the correlation with the antigen-binding activity.

Modification of the amino acid residues in FRs of VH and VL of a human antibody can be achieved by PCR as described in the above 1 (5) using synthetic DNAs for modification. The nucleotide sequence of the PCR amplification product is determined by the method described in the above 1 (2) to confirm that the desired modification has been achieved.

(7) Construction of a Humanized Antibody Expression Vector

A humanized antibody expression vector can be constructed by inserting the cDNAs encoding VH and VL of the humanized antibody constructed in the above 1 (5) and (6) into sites upstream of the genes encoding CH and CL of a human antibody in the vector for expression of the recombinant antibody composition of the present invention described in the above 1 (1). For example, a humanized antibody expression vector can be constructed by introducing recognition sequences for appropriate restriction enzymes to the 5'-terminals of synthetic DNAs present on both ends among the synthetic DNAs used for constructing VH and VL of the humanized antibody in the above 1 (5) and (6), and inserting them into sites upstream of the genes encoding CH and CL of a human antibody in the vector for expression of the recombinant antibody of the present invention described in the above 1 (1) so as to express them in an appropriate form.

(8) Stable Production of a Humanized Antibody

Transformants capable of stably producing a human chimeric antibody or a humanized antibody can be obtained by introducing the human chimeric antibody or humanized antibody expression vectors described in the above 1 (4) and (7) into appropriate animal cells.

Introduction of the humanized antibody expression vector into an animal cell can be carried out by electroporation [Japanese Published Unexamined Patent Application No. 257891/90; *Cytotechnology,* 3, 133 (1990)], and the like As the animal cell for introducing the human chimeric antibody or humanized antibody expression vector, any animal cell capable of producing a human chimeric antibody or a humanized antibody can be used.

Examples of the animal cells include mouse myeloma cell lines NS0 and SP2/0, Chinese hamster ovary cells CHO/dhfr-- and CHO/DG44, rat myeloma cell lines YB2/0 and IR983F, Syrian hamster kidney-derived BHK cell, and human myeloma cell line Namalwa. Chinese hamster ovary cell CHO/DG44 and rat myeloma cell line YB2/0 are preferred.

After the introduction of the human chimeric antibody or humanized antibody expression vector, the transformant capable of stably producing the human chimeric antibody or the humanized antibody can be selected using a medium for animal cell culture containing an agent such as G418 sulfate (hereinafter referred to as G418; manufactured by SIGMA) according to the method described in Japanese Published Unexamined Patent Application No. 257891/90. Examples of the media for animal cell culture include RPMI1640 medium (manufactured by Nissui Pharmaceutical Co., Ltd.), GIT medium (manufactured by Nihon Pharmaceutical Co., Ltd.), EX-CELL 302 medium (manufactured by JRH), IMDM medium (manufactured by GIBCO BRL), Hybridoma-SFM medium (manufactured by GIBCO BRL), and media prepared by adding various additives such as fetal calf serum (hereinafter referred to as FCS) to these media. By culturing the obtained transformant in the medium, the human chimeric antibody or the humanized antibody can be formed and accumulated in the culture supernatant. The amount and the antigen-binding activity of the human chimeric antibody or the humanized antibody produced in the culture supernatant can be measured by enzyme-linked immunosorbent assay [hereinafter referred to as ELISA; *Antibodies: A Laboratory Manual,* Cold Spring Harbor Laboratory, Chapter 14 (1998); *Monoclonal Antibodies: Principles and Practice,* Academic Press Limited (1996)] or the like. The amount of the human chimeric antibody or the humanized antibody to be produced by the transformant can be increased by utilizing a DHFR gene amplification system or the like according to the method described in Japanese Published Unexamined Patent Application No. 257891/90.

The human chimeric antibody or the humanized antibody can be purified from the culture supernatant of the transformant using a protein A column [*Antibodies: A Laboratory Manual,* Cold Spring Harbor Laboratory, Chapter 8 (1988); *Monoclonal Antibodies: Principles and Practice,* Academic Press Limited (1996)]. In addition, purification methods generally employed for the purification of proteins can also be used. For example, the purification can be carried out by combinations of gel filtration, ion exchange chromatography, ultrafiltration and the like. The molecular weight of the H chain, L chain or whole antibody molecule of the purified human chimeric antibody or humanized antibody can be measured by SDS-denatured polyacrylamide gel electrophoresis [hereinafter referred to as SDS-PAGE; *Nature,* 227, 680 (1970)], Western blotting [*Antibodies: A Laboratory Manual,* Cold Spring Harbor Laboratory, Chapter 12 (1988); *Monoclonal Antibodies: Principles and Practice,* Academic Press Limited (1996)], and the like Shown above is the method for producing the antibody composition using an animal cell as the host. The antibody composition can also be produced using yeast, an insect cell, a plant cell, an animal individual or a plant individual by similar methods.

Accordingly, when the host cell is capable of expressing an antibody molecule, the antibody composition of the present invention can be produced by introducing a gene encoding an antibody into the host cell which expresses an antibody molecule, culturing the cell, and purifying the desired antibody composition from the culture.

When yeast is used as the host cell, YEP13 (ATCC 37115), YEp24 (ATCC 37051), YCp50 (ATCC 37419), and the like can be used as the expression vector.

As the promoter, any promoters capable of expressing in yeast strains can be used. Suitable promoters include promoters of genes of the glycolytic pathway such as hexosekinase, PHO5 promoter, PGK promoter, GAP promoter, ADH promoter, gal 1 promoter, gal 10 promoter, heat shock protein promoter, MFα1 promoter and CUP 1 promoter.

Examples of suitable host cells are microorganisms belonging to the genera *Saccharomyces, Schizosaccharomyces, Kluyveromyces, Trichosporon* and *Schwanniomyces*, and specifically, *Saccharomyces cerevisiae, Schizosaccharomyces pombe, Kluyveromyces lactis, Trichosporon pullulans, Schwanniomyces alluvius* and the like.

Introduction of the recombinant vector can be carried out by any of the methods for introducing DNA into yeast, for example, electroporation [*Methods Enzymol.,* 194, 182 (1990)], the spheroplast method [*Proc. Natl. Acad. Sci. USA,* 84, 1929 (1978)], the lithium acetate method [*J. Bacteriology,* 153, 163 (1983)] and the method described in *Proc. Natl. Acad. Sci. USA,* 75, 1929 (1978).

When an animal cell is used as the host cell, pcDNAI, pcDM8 (commercially available from Funakoshi Co., Ltd.), pAGE107 [Japanese Published Unexamined Patent Application No. 22979/91; *Cytotechnology,* 3, 133 (1990)], pAS3-3 (Japanese Published Unexamined Patent Application No. 227075/90), pCDM8 [*Nature,* 329, 840 (1987)], pcDNAI/Amp (manufactured by Invitrogen Corp.), pREP4 (manufactured by Invitrogen Corp.), pAGE103 [*J. Biochemistry,* 101, 1307 (1987)], pAGE210, and the like can be used as the expression vector.

As the promoter, any promoters capable of expressing in animal cells can be used. Suitable promoters include the promoter of IE (immediate early) gene of cytomegalovirus (CMV), SV40 early promoter, the promoter of a retrovirus, metallothionein promoter, heat shock promoter, SRα promoter, and the like. The enhancer of IE gene of human CMV may be used in combination with the promoter.

Examples of suitable host cells are human-derived Namalwa cells, monkey-derived COS cells, Chinese hamster-derived CHO cells, HBT5637 (Japanese Published Unexamined Patent Application No. 299/88), rat myeloma cells, mouse myeloma cells, cells derived from Syrian hamster kidney, embryonic stem cells, fertilized egg cells and the like.

When an insect cell is used as the host cell, the protein can be expressed by the methods described in *Current Protocols in Molecular Biology; Baculovirus Expression Vectors, A Laboratory Manual,* W. H. Freeman and Company, New York (1992); Bio/Technology, 6, 47 (1988), and the like.

That is, the expression vector and a baculovirus are cotransfected into insect cells to obtain a recombinant virus in the culture supernatant of the insect cells, and then insect cells are infected with the recombinant virus, whereby the protein can be expressed.

The gene introducing vectors useful in this method include pVL1392, pVL1393, pBlueBacIII (products of Invitrogen Corp.) and the like.

An example of the baculovirus is *Autographa californica* nuclear polyhedrosis virus, which is a virus infecting insects belonging to the family Barathra.

Examples of the insect cells are *Spodoptera frugiperda* ovarian cells Sf9 and Sf21 [*Current Protocols in Molecular Biology; Baculovirus Expression Vectors, A Laboratory Manual,* W.H. Freeman and Company, New York (1992)] and *Trichoplusia ni* ovarian cell High 5 (manufactured by Invitrogen Corp.).

Cotransfection of the above expression vector and the above baculovirus into insect cells for the preparation of the recombinant virus can be carried out by the calcium phosphate method (Japanese Published Unexamined Patent Application No. 227075/90), lipofection [*Proc. Natl. Acad. Sci. USA,* 84, 7413 (1987)], and the like.

When a plant cell is used as the host cell, Ti plasmid, tobacco mosaic virus vector, and the like can be used as the expression vector.

As the promoter, any promoters capable of expressing in plant cells can be used. Suitable promoters include 35S promoter of cauliflower mosaic virus (CaMV), rice actin 1 promoter, and the like.

Examples of suitable host cells are cells of plants such as tobacco, potato, tomato, carrot, soybean, rape, alfalfa, rice, wheat and barley.

Introduction of the recombinant vector can be carried out by any of the methods for introducing DNA into plant cells, for example, the method using *Agrobacterium* (Japanese Published Unexamined Patent Application Nos. 140885/84 and 70080/85, WO94/00977), electroporation (Japanese Published Unexamined Patent Application No. 251887/85) and the method using particle gun (gene gun) (Japanese Patent Nos. 2606856 and 2517813).

Introduction of the recombinant vector can be carried out by any of the methods for introducing DNA into animal cells, for example, electroporation [*Cytotechnology,* 3, 133 (1990)], the calcium phosphate method (Japanese Published Unexamined Patent Application No. 227075/90), lipofection [*Proc. Natl. Acad. Sci. USA,* 84, 7413 (1987)], the injection method (*Manipulating the Mouse Embryo, A Laboratory Manual*), the method using particle gun (gene gun) (Japanese Patent Nos. 2606856 and 2517813), the DEAE-dextran method [*Biomanual Series 4—Methods of Gene Transfer, Expression and Analysis* (Yodosha), edited by Takashi Yokota and Kenichi Arai (1994)] and the virus vector method (*Manipulating the Mouse Embryo, A Laboratory Manual*).

Expression of the gene encoding the antibody can be carried out not only by direct expression but also by secretory production, expression of a fusion protein of the Fc region and another protein, and the like according to the methods described in *Molecular Cloning,* Second Edition.

The antibody composition can be produced by culturing the transformant obtained as above in a medium, allowing the antibody molecules to form and accumulate in the culture, and recovering them from the culture. Culturing of the transformant in a medium can be carried out by conventional methods for culturing the host cell.

For the culturing of the transformant obtained by using a eucaryote such as yeast as the host, any of natural media and synthetic media can be used insofar as it is a medium suitable for efficient culturing of the transformant which contains carbon sources, nitrogen sources, inorganic salts, and the like which can be assimilated by the host used.

As the carbon sources, any carbon sources that can be assimilated by the microorganisms can be used. Examples of suitable carbon sources include carbohydrates such as glucose, fructose, sucrose, molasses containing them, starch and starch hydrolyzate; organic acids such as acetic acid and propionic acid; and alcohols such as ethanol and propanol.

As the nitrogen sources, ammonia, ammonium salts of organic or inorganic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various fermented microbial cells and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate, calcium carbonate and the like.

Culturing is usually carried out under aerobic conditions, for example, by shaking culture or submerged spinner culture under aeration. The culturing temperature is preferably 15 to 40° C., and the culturing period is usually 16 hours to 7 days. The pH is maintained at 3.0 to 9. during the culturing. The pH adjustment is carried out by using an organic or inorganic acid, an alkali solution, urea, calcium carbonate, ammonia, and the like If necessary, antibiotics such as ampicillin and tetracycline may be added to the medium during the culturing.

When a microorganism transformed with a recombinant vector using an inducible promoter is cultured, an inducer may be added to the medium, if necessary. For example, in the case of a microorganism transformed with a recombinant vector using lac promoter, isopropyl-β-D-thiogalactopyranoside or the like may be added to the medium; and in the case of a microorganism transformed with a recombinant vector using trp promoter, indoleacrylic acid or the like may be added.

For the culturing of the transformant obtained by using an animal cell as the host, generally employed media such as RPMI1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)], 199 medium [*Proceeding of the Society for the Biological Medicine*, 73, 1 (1950)] and Whitten's medium [*Developmental Engineering Experimentation Manual—Preparation of Transgenic Mice* (Kodansha), edited by Motoya Katsuki (1987)], media prepared by adding fetal calf serum or the like to these media, and the like can be used as the medium.

Culturing is usually carried out under conditions of pH 6.0 to 8.0 at 30 to 40° C. for 1 to 7 days in the presence of 5% $CO_2$.

If necessary, antibiotics such as kanamycin and penicillin may be added to the medium during the culturing.

For the culturing of the transformant obtained by using an insect cell as the host, generally employed media such as TNM-FH medium (manufactured by Pharmingen, Inc.), Sf-900 II SFM medium (manufactured by Life Technologies, Inc.), ExCell 400 and ExCell 405 (manufactured by JRH Biosciences, Inc.) and Grace's Insect Medium [*Nature*, 195, 788 (1962)] can be used as the medium.

Culturing is usually carried out under conditions of pH 6.0 to 7.0 at 25 to 30° C. for 1 to 5 days.

If necessary, antibiotics such as gentamicin may be added to the medium during the culturing.

The transformant obtained by using a plant cell as the host may be cultured in the form of cells as such or after differentiation into plant cells or plant organs. For the culturing of such transformant, generally employed media such as Murashige-Skoog (MS) medium and White medium, media prepared by adding phytohormones such as auxin and cytokinin to these media, and the like can be used as the medium.

Culturing is usually carried out under conditions of pH 5.0 to 9.0 at 20 to 40° C. for 3 to 60 days.

If necessary, antibiotics such as kanamycin and hygromycin may be added to the medium during the culturing.

As described above, the antibody composition can be produced by culturing, according to a conventional culturing method, the transformant derived from an animal cell or a plant cell and carrying an expression vector into which DNA encoding the antibody molecule has been integrated, allowing the antibody composition to form and accumulate, and recovering the antibody composition from the culture.

Expression of the gene encoding the antibody can be carried out not only by direct expression but also by secretory production, fusion protein expression, and the like according to the methods described in *Molecular Cloning*, Second Edition.

The antibody composition may be produced by intracellular expression in host cells, may be produced by extracellular secretion from host cells or may be produced on outer membranes of host cells. A desirable production method can be adopted by changing the kind of the host cells used or the structure of the antibody molecule to be produced.

When the antibody composition is produced in host cells or on outer membranes of host cells, it is possible to force the antibody composition to be secreted outside the host cells by applying the method of Paulson, et al. [*J. Biol. Chem.*, 264, 17619 (1989)], the method of Lowe, et al. [*Proc. Natl. Acad. Sci. USA*, 86, 8227 (1989); *Genes Develop.*, 4, 1288 (1990)], or the methods described in Japanese Published Unexamined Patent Application No. 336963/93, WO94/23021, and the like That is, it is possible to force the desired antibody molecule to be secreted outside the host cells by inserting DNA encoding the antibody molecule and DNA encoding a signal peptide suitable for the expression of the antibody molecule into an expression vector, introducing the expression vector into the host cells, and then expressing the antibody molecule by use of recombinant DNA techniques.

It is also possible to increase the amount of the antibody composition to be produced by utilizing a gene amplification system using a dihydrofolate reductase gene or the like according to the method described in Japanese Published Unexamined Patent Application No. 227075/90.

Further, the antibody composition can be produced using an animal individual into which a gene is introduced (non-human transgenic animal) or a plant individual into which a gene is introduced (transgenic plant) constructed by redifferentiating the animal or plant cells into which genes are introduced.

When the transformant is an animal individual or plant individual, the antibody composition can be produced by rearing or cultivating the animal or plant in a usual manner, allowing the antibody composition to form and accumulate therein, and collecting the antibody composition from the animal individual or plant individual.

Production of the antibody composition using an animal individual can be carried out, for example, by producing the desired antibody composition in an animal constructed by introducing the gene according to known methods [*American Journal of Clinical Nutrition*, 63, 639S (1996); *American Journal of Clinical Nutrition*, 63, 627S (1996); *Bio/Technology*, 9, 830 (1991)].

In the case of an animal individual, the antibody composition can be produced, for example, by raising a non-human transgenic animal into which DNA encoding the antibody molecule is introduced, allowing the antibody composition to form and accumulate in the animal, and collecting the antibody composition from the animal. The places where the antibody composition is formed and accumulated include milk (Japanese Published Unexamined Patent Application No. 309192/88), egg or the like of the animal. As the promoter in this process, any promoters capable of expressing in an animal can be used. Preferred promoters include mammary gland cell-specific promoters such as a casein promoter, β casein promoter, β lactoglobulin promoter and whey acidic protein promoter.

Production of the antibody composition using a plant individual can be carried out, for example, by cultivating a transgenic plant into which DNA encoding the antibody molecule is introduced according to known methods [*Soshiki Baiyo (Tissue Culture)*, 20 (1994); *Soshiki Baiyo (Tissue Culture)*, 21 (1995); *Trends in Biotechnology*, 15, 45 (1997)], allowing the antibody composition to form and accumulate in the plant, and collecting the antibody composition from the plant.

When the antibody composition produced by the transformant into which the gene encoding the antibody molecule is introduced is expressed in a soluble form in cells, the cells are recovered by centrifugation after the completion of culturing and suspended in an aqueous buffer, followed by disruption using a sonicator, French press, Manton Gaulin homogenizer, Dynomill or the like to obtain a cell-free extract. A purified preparation of the antibody composition can be obtained by centrifuging the cell-free extract to obtain the supernatant and then subjecting the supernatant to ordinary means for isolating and purifying enzymes, e.g., extraction with a solvent, salting-out with ammonium sulfate, and the like, desalting, precipitation with an organic solvent, anion exchange chromatography using resins such as diethylaminoethyl (DEAE)-Sepharose and DIAION HPA-75 (manufactured by Mitsubishi Chemical Corporation), cation exchange chromatography using resins such as S-Sepharose FF (manufactured by Pharmacia), hydrophobic chromatography using resins such as butyl Sepharose and phenyl Sepharose, gel filtration using a molecular sieve, affinity chromatography, chromatofocusing, and electrophoresis such as isoelectric focusing, alone or in combination.

When the antibody composition is referred to as an insoluble body in cells, the cells are similarly recovered and disrupted, followed by centrifugation to recover the insoluble body of the antibody composition as a precipitate fraction. The recovered insoluble body of the antibody composition is solubilized with a protein-denaturing agent. The solubilized antibody solution is diluted or dialyzed, whereby the antibody composition is renatured to have normal three-dimensional structure. Then, a purified preparation of the antibody composition can be obtained by the same isolation and purification methods as described above.

When the antibody composition is extracellularly secreted, the antibody composition or its derivative can be recovered in the culture supernatant. That is, the culture is treated by the same means as above, e.g., centrifugation, to obtain the culture supernatant. A purified preparation of the antibody composition can be obtained from the culture supernatant by using the same isolation and purification methods as described above.

2. Preparation of Recombinant Antibody Composition-Producing Cell of the Present Invention The cell producing the antibody composition having high ADCC activity as well as high CDC activity among the recombinant antibody compositions of the present invention can be produced by preparing a host cell used for the production of the recombinant antibody composition of the present invention by the following techniques and then introducing the human chimeric antibody or humanized antibody expression vector described in the above 1 (4) and (7) into the host cell.

Specifically, a cell in which an enzyme relating to the modification of the N-glycoside-linked sugar chain bound to Fc of an antibody molecule, that is, an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in the complex-type N-glycoside-linked sugar chain is inactivated is selected, or a cell obtained by various artificial techniques described below can be used as a host cell. The details are described below.

(1) Gene Disruption Technique Targeting at a Gene Encoding an Enzyme

The host cell used for the production of the cell producing the antibody having high ADCC activity (hereinafter referred to as high ADCC activity antibody) can be prepared by a gene disruption technique targeting a gene encoding an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in a complex-type N-glycoside-linked sugar chain. Examples of the enzymes relating to the synthesis of an intracellular sugar nucleotide, GDP-fucose include GDP-mannose 4,6-dehydratase (hereinafter referred to as GMD) and GDP-4-keto-6-deoxy-D-mannose-3,5-epimerase (hereinafter referred to as Fx).

Examples of the enzymes relating to the modification of a sugar chain in which 1-position of fucose is bound to 6-position of N-acetylglucosamine in the reducing terminal through α-bond in a complex-type N-glycoside-linked sugar chain include α1,6-fucosyltransferase, α-L-fucosidase, and the like. The gene as used herein includes DNA and RNA.

The method of gene disruption may be any method capable of disrupting the gene encoding the enzyme. Useful methods include the antisense method, the ribozyme method, the homologous recombination method, the RNA-DNA oligonucleotide method (hereinafter referred to as the RDO method), the RNA interference method (hereinafter referred to as the RNAi method), the method using a retrovirus and the method using a transposon, and the like. These methods are specifically described below.

(a) Preparation of the Host Cell for the Production of the High ADCC Activity Antibody-Producing Cell by the Antisense Method or the Ribozyme Method The host cell used for the production of the high ADCC activity antibody-producing cell can be prepared by the antisense method or the ribozyme method described in *Cell Technology*, 12, 239 (1993); *BIO/TECHNOLOGY*, 17, 1097 (1999); *Hum. Mol. Genet.*, 5, 1083 (1995); *Cell Technology*, 13, 255 (1994); *Proc. Natl. Acad. Sci. U.S.A.*, 96, 1886 (1999); and the like targeting at a gene encoding an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in a complex-type N-glycoside-linked sugar chain, for example, in the following manner.

A cDNA or a genomic DNA encoding an enzyme relating to the synthesis of the intracellular sugar nucleotide, GDP-fucose or an enzyme relating to the modification of a sugar chain in which 1-position of fucose is bound to 6-position of N-acetylglucosamine in the reducing terminal through α-bond in a complex-type N-glycoside-linked sugar chain is prepared. The nucleotide sequence of the prepared cDNA or genomic DNA is determined. Based on the determined DNA sequence, an antisense gene or a ribozyme of appropriate length is designed which comprises a DNA moiety encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain, non-translated regions or introns.

In order to express the antisense gene or ribozyme in a cell, a recombinant vector is prepared by inserting a fragment or full-length of the prepared DNA into a site downstream of a promoter in an appropriate expression vector.

A transformant can be obtained by introducing the recombinant vector into a host cell suited for the expression vector.

The host cell used for the production of the recombinant antibody composition of the present invention comprising an antibody molecule having complex-type N-glycoside-linked sugar chains in the Fc region, wherein the ratio of sugar chains in which fucose is not bound to N-acetylglucosamine in the reducing terminal of the sugar chains among the total complex-type N-glycoside-linked sugar chains which bind to the Fc region contained in the composition is 20% or more can be obtained by selecting a transformant using, as an index, the activity of the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain. The host cell used for the production of the high ADCC activity antibody-producing cell can also be obtained by selecting a transformant using, as an index, the sugar chain structure of a glycoprotein on the cell membrane or the sugar chain structure of the produced antibody molecule.

As the host cell used for the production of the high ADCC activity antibody-producing cell, any yeast, animal cell, insect cell, plant cell, or the like can be used so long as it has a gene encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain. Examples of the host cells include those described in the above 1.

The expression vectors that can be employed are those capable of autonomous replication or integration into the chromosome in the above host cells and comprising a promoter at a position appropriate for the transcription of the designed antisense gene or ribozyme. Examples of the expression vectors include those described in the above 1.

Introduction of a gene into various host cells can be carried out by the methods suitable for introducing a recombinant vector into various host cells described in the above 1.

Selection of a transformant using, as an index, the activity of an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in a complex-type N-glycoside-linked sugar chain can be carried out, for example, by the following methods.

Methods for Selecting a Transformant

A cell in which the activity of an enzyme relating to the synthesis of the intracellular sugar nucleotide, GDP-fucose or an enzyme relating to the modification of a sugar chain in which 1-position of fucose is bound to 6-position of N-acetylglucosamine in the reducing terminal through α-bond in a complex-type N-glycoside-linked sugar chain is deleted can be selected by measuring the activity of the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain using biochemical methods or genetic engineering techniques described in *Shin Seikagaku Jikken Koza (New Lectures on Experiments in Biochemistry) 3—Saccharides I, Glycoprotein* (Tokyo Kagaku Dojin), edited by The Japanese Biochemical Society (1988); *Cell Technology, Extra Edition, Experimental Protocol Series, Glycobiology Experimental Protocol, Glycoprotein, Glycolipid and Proteoglycan* (Shujunsha), edited by Naoyuki Taniguchi, Akemi Suzuki, Kiyoshi Furukawa and Kazuyuki Sugawara (1996); *Molecular Cloning*, Second Edition; *Current Protocols in Molecular Biology*; and the like. An example of the biochemical methods is a method in which the enzyme activity is evaluated using an enzyme-specific substrate. Examples of the genetic engineering techniques include Northern analysis and RT-PCR in which the amount of mRNA for a gene encoding the enzyme is measured.

Selection of a transformant using, as an index, the sugar chain structure of a glycoprotein on the cell membrane can be carried out, for example, by the method described in 2(5) below. Selection of a transformant using, as an index, the sugar chain structure of a produced antibody molecule can be carried out, for example, by the methods described in 4 or 5 below.

Preparation of a cDNA encoding an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in a complex-type N-glycoside-linked sugar chain can be carried out, for example, by the following method.

Preparation Method of cDNA

Total RNA or mRNA is prepared from a various host cell tissue or cell.

A cDNA library is prepared from the obtained total RNA or mRNA.

Degenerative primers are prepared based on the amino acid sequence of an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in a complex-type N-glycoside-linked sugar chain, and a gene fragment encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain is obtained by PCR using the prepared cDNA library as a template.

A DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain can be obtained by screening the cDNA library using the obtained gene fragment as a probe.

As the mRNA of a human or non-human animal tissue or cell, commercially available one (for example, manufactured by Clontech) may be used, or it may be prepared from a human or non-human animal tissue or cell in the following manner.

The methods for preparing total RNA from a human or non-human animal tissue or cell include the guanidine thiocyanate-cesium trifluoroacetate method [*Methods in Enzymology*, 154, 3 (1987)], the acidic guanidine thiocyanate-phenol-chloroform (AGPC) method [*Analytical Biochemistry*, 162, 156 (1987); *Experimental Medicine*, 9, 1937 (1991)] and the like.

The methods for preparing mRNA as poly(A)+RNA from the total RNA include the oligo (dT) immobilized cellulose column method (*Molecular Cloning*, Second Edition).

It is also possible to prepare mRNA by using a commercially available kit such as Fast Track mRNA Isolation Kit (manufactured by Invitrogen) or Quick Prep mRNA Purification Kit (manufactured by Pharmacia).

A cDNA library is prepared from the obtained mRNA of a human or non-human animal tissue or cell. The methods for preparing the cDNA library include the methods described in *Molecular Cloning*, Second Edition; *Current Protocols in Molecular Biology; A Laboratory Manual*, 2nd Ed. (1989); and the like, and methods using commercially available kits such as SuperScript Plasmid System for cDNA Synthesis and Plasmid Cloning (manufactured by Life Technologies) and ZAP-cDNA Synthesis Kit (manufactured by STRATAGENE).

As the cloning vector for preparing the cDNA library, any vectors, e.g. phage vectors and plasmid vectors, can be used so long as they are autonomously replicable in *Escherichia coli* K12. Examples of suitable vectors include ZAP Express [manufactured by STRATAGENE; *Strategies*, 5, 58 (1992)], pBluescript II SK(+) [*Nucleic Acids Research*, 17, 9494 (1989)], λZAP II (manufactured by STRATAGENE), λgt10, λgt11 [*DNA Cloning, A Practical Approach*, 1, 49 (1985)], λTriplEx (manufactured by Clontech), λExCell (manufactured by Pharmacia), pT7T318U (manufactured by Pharmacia), pcD2 [*Mol. Cell. Biol.*, 3, 280 (1983)], pUC18 [*Gene*, 33, 103 (1985)], and the like.

Any microorganism can be used as the host microorganism for preparing the cDNA library, but *Escherichia coli* is preferably used. Examples of suitable host microorganisms are *Escherichia coli* XL1-Blue MRF' [manufactured by STRATAGENE; *Strategies*, 5, 81 (1992)], *Escherichia coli* C600 [*Genetics*, 39, 440 (1954)], *Escherichia coli* Y1088 [*Science*, 222, 778 (1983)], *Escherichia coli* Y1090 [*Science*, 222, 778 (1983)], *Escherichia coli* NM522 [*J. Mol. Biol.*, 166, 1 (1983)], *Escherichia coli* K802 [*J. Mol. Biol.*, 16, 118 (1966)], *Escherichia coli* JM105 [*Gene*, 38, 275 (1985)], and the like.

The cDNA library may be used as such in the following analysis. Alternatively, in order to efficiently obtain full-length cDNAs by decreasing the ratio of partial cDNAs, a cDNA library prepared using the oligo-cap method developed by Sugano, et al. [*Gene*, 138, 171 (1994); *Gene*, 200, 149 (1997); *Protein, Nucleic Acid and Enzyme*, 41, 603 (1996); *Experimental Medicine*, 11, 2491 (1993); *cDNA Cloning* (Yodosha) (1996); *Methods for Preparing Gene Libraries* (Yodosha) (1994)] may be used in the following analysis.

Degenerative primers specific for the 5'-terminal and 3'-terminal nucleotide sequences of a nucleotide sequence presumed to encode the amino acid sequence of an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in a complex-type N-glycoside-linked sugar chain are prepared based on the amino acid sequence of the enzyme. A gene fragment encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain can be obtained by DNA amplification by PCR [*PCR Protocols*, Academic Press (1990)] using the prepared cDNA library as a template.

It can be confirmed that the obtained gene fragment is a DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain by analyzing the nucleotide sequence by generally employed nucleotide sequence analyzing methods such as the dideoxy method of Sanger, et al. [*Proc. Natl. Acad. Sci. U.S.A.*, 74, 5463 (1977)] or by use of nucleotide sequence analyzers such as ABI PRISM 377 DNA Sequencer (manufactured by Applied Biosystems).

A DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain can be obtained from the cDNA or cDNA library synthesized from the mRNA contained in a human or non-human animal tissue or cell by colony hybridization or plaque hybridization (*Molecular Cloning*, Second Edition) using the above gene fragment as a probe.

A cDNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain can also be obtained by amplification by PCR using the cDNA or cDNA library synthesized from the mRNA contained in a human or non-human animal tissue or cell as a template and using the primers used for obtaining the gene fragment encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain.

The nucleotide sequence of the DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain can be determined by generally employed nucleotide sequence analyzing methods such as the dideoxy method of Sanger, et al. [*Proc. Natl. Acad. Sci. U.S.A.*, 74, 5463 (1977)] or by use of nucleotide sequence analyzers such as ABI PRISM 377 DNA Sequencer (manufactured by Applied Biosystems).

By carrying out a search of nucleotide sequence databases such as GenBank, EMBL or DDBJ using a homology search program such as BLAST based on the determined nucleotide sequence of the cDNA, it can be confirmed that the obtained DNA is a gene encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain among the genes in the nucleotide sequence database.

Examples of the nucleotide sequences of the genes encoding the enzyme relating to the synthesis of an intracellular sugar nucleotide, GDP-fucose obtained by the above methods include the nucleotide sequences represented by SEQ ID NO:18 or 20.

Examples of the nucleotide sequences of the genes encoding the enzyme relating to the modification of a sugar chain in which 1-position of fucose is bound to 6-position of N-acetylglucosamine in the reducing terminal through α-bond in a complex-type N-glycoside-linked sugar chain obtained by the above methods include the nucleotide sequence represented by SEQ ID NO:22 or 23.

The cDNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain can also be obtained by chemical synthesis with a DNA synthesizer such as DNA Synthesizer Model 392 (manufactured by Perkin Elmer) utilizing the phosphoamidite method based on the determined nucleotide sequence of the desired DNA.

Preparation of a genomic DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain can be carried out, for example, by the following method.

Method for Preparing Genomic DNA

The genomic DNA can be prepared by known methods described in *Molecular Cloning*, Second Edition, *Current Protocols in Molecular Biology*, and the like In addition, the genomic DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain can also be obtained by using a kit such as Genomic DNA Library Screening System (manufactured by Genome Systems) or Universal GenomeWalker™ Kits (manufactured by CLONTECH).

The nucleotide sequence of the DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain can be determined by generally employed nucleotide analyzing methods such as the dideoxy method of Sanger, et al. [*Proc. Natl. Acad. Sci. U.S.A.*, 74, 5463 (1977)] or by use of nucleotide sequence analyzers such as ABI PRISM 377 DNA Sequencer (manufactured by Applied Biosystems).

By carrying out a search of nucleotide sequence databases such as GenBank, EMBL or DDBJ using a homology search program such as BLAST based on the determined nucleotide sequence of the genomic DNA, it can be confirmed that the obtained DNA is a gene encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain among the genes in the nucleotide sequence database.

The genomic DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain can also be obtained by chemical synthesis with a DNA synthesizer such as DNA Synthesizer Model 392 (manufactured by Perkin Elmer) utilizing the phosphoamidite method based on the determined nucleotide sequence of the DNA.

Examples of the nucleotide sequences of the genomic DNAs encoding the enzyme relating to the synthesis of an intracellular sugar nucleotide, GDP-fucose obtained by the above methods include the nucleotide sequences represented by SEQ ID NOs:26, 27, 28 and 29.

An example of the nucleotide sequence of the genomic DNA encoding the enzyme relating to the modification of a sugar chain in which 1-position of fucose is bound to 6-position of N-acetylglucosamine in the reducing terminal through α-bond in a complex-type N-glycoside-linked sugar chain obtained by the above methods is the nucleotide sequence represented by SEQ ID NO:30.

The host cell used for the production of the antibody composition of the present invention can also be obtained without using an expression vector by directly introducing into a host cell an antisense oligonucleotide or ribozyme designed based on the nucleotide sequence encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain.

The antisense oligonucleotide or ribozyme can be prepared by known methods or by using a DNA synthesizer. Specifically, based on the sequence information on an oligonucleotide having a sequence corresponding to 5 to 150, preferably 5 to 60, more preferably 10 to 40 continuous nucleotides in the nucleotide sequence of the cDNA and genomic DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain, an oligonucleotide corresponding to the sequence complementary to the above oligonucleotide (antisense oligonucleotide) or a ribozyme comprising the oligonucleotide sequence can be synthesized.

The oligonucleotide includes oligo RNA and derivatives of the oligonucleotide (hereinafter referred to as oligonucleotide derivatives).

The oligonucleotide derivatives include an oligonucleotide derivative wherein the phosphodiester bond in the oligonucleotide is converted to a phosophorothioate bond, an oligonucleotide derivative wherein the phosphodiester bond in the oligonucleotide is converted to an N3'-P5' phosphoamidate bond, an oligonucleotide derivative wherein the ribose-phosphodiester bond in the oligonucleotide is converted to a peptide-nucleic acid bond, an oligonucleotide derivative wherein the uracil in the oligonucleotide is substituted with C-5 propynyluracil, an oligonucleotide derivative wherein the uracil in the oligonucleotide is substituted with C-5 thiazolyluracil, an oligonucleotide derivative wherein the cytosine in the oligonucleotide is substituted with C-5 propynylcytosine, an oligonucleotide derivative wherein the cytosine in the oligonucleotide is substituted with phenoxazine-modified cytosine, an oligonucleotide derivative wherein the ribose in the oligonucleotide is substituted with 2'-O-propylribose, and an oligonucleotide derivative wherein the ribose in the oligonucleotide is substituted with 2'-methoxyethoxyribose [*Cell Technology*, 16, 1463 (1997)].

(b) Preparation of the Host Cell for the Production of High ADCC Activity Antibody-Producing Cell by the Homologous Recombination Method The host cell used for the production of the high ADCC activity antibody-producing cell can be prepared by modifying a target gene on the chromosome by the homologous recombination method targeting a gene encoding an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in a complex-type N-glycoside-linked sugar chain.

Modification of the target gene on the chromosome can be carried out by using the methods described in *Manipulating the Mouse Embryo, A Laboratory Manual*, Second Edition, Cold Spring Harbor Laboratory Press (1994) (hereinafter referred to as "*Manipulating the Mouse Embryo, A Laboratory Manual*"; *Gene Targeting, A Practical Approach*, IRL Press at Oxford University Press (1993); *Biomanual Series* 8, *Gene Targeting, Preparation of Mutant Mice Using ES Cells*, Yodosha (1995) (hereinafter referred to as *Preparation of Mutant Mice Using ES Cells*); and the like, for example, in the following manner.

A genomic DNA encoding an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in a complex-type N-glycoside-linked sugar chain is prepared.

Based on the nucleotide sequence of the genomic DNA, a target vector is prepared for homologous recombination of a target gene to be modified (e.g., the structural gene or promoter gene for the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain).

The host cell used for the production of the high ADCC activity antibody-producing cell can be prepared by introducing the prepared target vector into a host cell and selecting a cell in which homologous recombination occurred between the target gene on the chromosome and the target vector.

As the host cell, any yeast, animal cell, insect cell, plant cell, or the like can be used so long as it has a gene encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain. Examples of the host cells include those described in the above 1.

The genomic DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain can be prepared by the methods for preparing a genomic DNA described in the above 1 (1) (a).

Examples of the nucleotide sequences of the genomic DNAs encoding the enzyme relating to the synthesis of the intracellular sugar nucleotide, GDP-fucose obtained by the above methods include the nucleotide sequences represented by SEQ ID NOs:26, 27, 28 and 29.

An example of the nucleotide sequence of the genomic DNA encoding the enzyme relating to the modification of a sugar chain in which 1-position of fucose is bound to 6-position of N-acetylglucosamine in the reducing terminal through α-bond in a complex-type N-glycoside-linked sugar chain obtained by the above methods is the nucleotide sequence represented by SEQ ID NO:30.

The target vector for use in the homologous recombination of the target gene on the chromosome can be prepared according to the methods described in *Gene Targeting, A Practical Approach*, IRL Press at Oxford University Press (1993); *Biomanual Series* 8, *Gene Targeting, Preparation of Mutant Mice Using ES Cells*, Yodosha (1995); and the like The target vector may be either a replacement-type or an insertion-type.

Introduction of the target vector into various host cells can be carried out by the methods suitable for introducing a recombinant vector into various host cells described in the above 1.

The methods for efficiently selecting a homologous recombinant include positive selection, promoter selection, negative selection and polyA selection described in *Gene Targeting, A Practical Approach*, IRL Press at Oxford University Press (1993); *Biomanual Series* 8, *Gene Targeting, Preparation of Mutant Mice Using ES Cells*, Yodosha (1995); and the like The methods for selecting the desired homologous recombinant from the selected cell lines include Southern hybridization (Molecular Cloning, Second Edition) and PCR [*PCR Protocols*, Academic Press (1990)] with the genomic DNA.

(c) Preparation of the Host Cell for the High Adcc Activity Antibody-Producing Cell by the RDO Method The host cell used for the production of the high ADCC activity antibody-producing cell can be prepared by the RDO method targeting a gene encoding an enzyme relating to the synthesis of the intracellular sugar nucleotide, GDP-fucose or an enzyme relating to the modification of a sugar chain in which 1-position of fucose is bound to 6-position of N-acetylglucosamine in the reducing terminal through α-bond in a complex-type N-glycoside-linked sugar chain, for example, in the following manner.

A cDNA or a genomic DNA encoding an enzyme relating to the synthesis of the intracellular sugar nucleotide, GDP-fucose or an enzyme relating to the modification of a sugar chain in which 1-position of fucose is bound to 6-position of N-acetylglucosamine in the reducing terminal through α-bond in a complex-type N-glycoside-linked sugar chain is prepared by the methods described in the above 1 (1) (a). The nucleotide sequence of the prepared cDNA or genomic DNA is determined. Based on the determined DNA sequence, an RDO construct of appropriate length which comprises a part encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain, a part of its non-translated region or a part of introns is designed and synthesized.

The host cell can be obtained by introducing the synthesized RDO into a host cell and then selecting a transformant in which a mutation occurred in the target enzyme, that is, the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain.

As the host cell, any yeast, animal cell, insect cell, plant cell, or the like can be used so long as it has a gene encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain. Examples of the host cells include those described in the above 1.

Introduction of the RDO into various host cells can be carried out by the methods suitable for introducing a recombinant vector into various host cells described in the above 1.

The cDNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain can be prepared by the methods for preparing a cDNA described in the above 2 (1) (a) or the like.

The genomic DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain can be prepared by the methods for preparing a genomic DNA described in the above 2 (1) (b) or the like.

After DNA is cleaved with appropriate restriction enzymes, the nucleotide sequence of the DNA can be determined by subcloning the DNA fragments into a plasmid such as pBluescript SK(−) (manufactured by Stratagene), subjecting the clones to the reaction generally used as a method for analyzing a nucleotide sequence such as the dideoxy method of Sanger et al. [*Proc. Natl. Acad. Sci., USA*, 74, 5463 (1977)] or the like, and then analyzing the clones by using an automatic nucleotide sequence analyzer such as ABI PRISM 377 DNA Sequencer (manufactured by Applied Biosystems) or the like.

The RDO can be prepared by conventional methods or by using a DNA synthesizer. The methods for selecting a cell in which a mutation occurred by introducing the RDO into the host cell, in the gene encoding the enzyme, that is, the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain include the methods for directly detecting mutations in chromosomal genes described in *Molecular Cloning*, Second Edition, *Current Protocols in Molecular Biology*, and the like.

For the selection of the transformant, the following methods can also be employed: the method using, as an index, the activity of the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain described in the above 2 (1) (a); the method using, as an index, the sugar chain structure of a glycoprotein on the cell membrane described in 2 (5) below; and the method using, as an index, the sugar chain structure of a produced antibody molecule described in 4 or 5 below.

The RDO can be designed according to the descriptions in *Science*, 273, 1386 (1996); *Nature Medicine*, 4, 285 (1998); *Hepatology*, 25, 1462 (1997); *Gene Therapy*, 5, 1960 (1999); *Gene Therapy*, 5, 1960 (1999); *J. Mol. Med.*, 75, 829 (1997); *Proc. Natl. Acad. Sci. USA*, 96, 8774 (1999); *Proc. Natl. Acad. Sci. USA*, 96, 8768 (1999); *Nuc. Acids Res.*, 27, 1323 (1999); *Invest. Dermatol.*, 111, 1172 (1998); *Nature Biotech.*, 16, 1343 (1998); *Nature Biotech.*, 18, 43 (2000); *Nature Biotech.*, 18, 555 (2000); and the like.

(d) Preparation of the Host Cell for the Production of the High ADCC Activity Antibody-Producing Cell by the RNAi Method The host cell used for the production of the high ADCC activity antibody-producing cell can be prepared by the RNAi method targeting a gene encoding an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in a complex-type N-glycoside-linked sugar chain, for example, in the following manner.

A cDNA encoding an enzyme relating to the synthesis of the intracellular sugar nucleotide, GDP-fucose or an enzyme relating to the modification of a sugar chain in which 1-position of fucose is bound to 6-position of N-acetylglucosamine in the reducing terminal through α-bond in a complex-type N-glycoside-linked sugar chain is prepared by the methods described in the above 2 (1) (a). The nucleotide sequence of the prepared cDNA is determined. Based on the determined cDNA sequence, an RNAi gene of appropriate length is designed which comprises a part encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain, or a part of non-translated regions.

In order to express the RNAi gene in a cell, a recombinant vector is prepared by inserting a fragment or full-length of the prepared cDNA into a site downstream of a promoter in an appropriate expression vector. The recombinant vector is introduced into a host cell suited for the expression vector to obtain a transformant. The host cell used for the preparation of the high ADCC activity antibody-producing cell can be obtained by selecting a transformant using, as an index, the activity of the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain, or the sugar chain structure of a produced antibody molecule or a glycoprotein on the cell membrane.

As the host cell, any yeast, animal cell, insect cell, plant cell, or the like can be used so long as it has a gene encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain. Examples of the host cells include those described in the above 1.

The expression vectors that can be employed are those capable of autonomous replication or integration into the chromosome in the above host cells and comprising a promoter at a position appropriate for the transcription of the designed RNAi gene. Examples of the expression vectors include those described in the above 1.

Introduction of a gene into various host cells can be carried out by the methods suitable for introducing a recombinant vector into various host cells described in the above 1.

The methods for selecting the transformant using, as an index, the activity of the enzyme relating to the synthesis of an intracellular sugar nucleotide, GDP-fucose or the activity of the enzyme relating to the modification of a sugar chain in which 1-position of fucose is bound to 6-position of N-acetylglucosamine in the reducing terminal through α-bond in a complex-type N-glycoside-linked sugar chain include the methods described in the above 2 (1) (a).

The methods for selecting the transformant using, as an index, the sugar chain structure of a glycoprotein on the cell membrane include the method described in 2 (5). The methods for selecting the transformant using, as an index, the sugar chain structure of a produced antibody molecule include the methods described in 4 or 5 below.

The methods for preparing cDNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain include the methods for preparing a cDNA described in the above 2 (1) (a), and the like.

The host cell used for the production of the high CDC activity and high ADCC activity antibody-producing cell can also be obtained, without using an expression vector, by directly introducing into a host cell the RNAi gene designed based on the nucleotide sequence encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain.

The RNAi gene can be prepared by known methods or by using a DNA synthesizer. The RNAi gene construct can be designed according to the descriptions in *Nature*, 391, 806 (1998); *Proc. Natl. Acad. Sci. USA*, 95, 15502 (1998); *Nature*, 395, 54 (1998); *Proc. Natl. Acad. Sci. USA*, 96, 5049 (1999); *Cell*, 95, 1017 (1998); *Proc. Natl. Acad. Sci. USA*, 96, 1451 (1999); *Proc. Natl. Acad. Sci. USA*, 95, 13959 (1998); *Nature Cell Biol.*, 2, 70 (2000); and the like.

(e) Preparation of the Host Cell for the Production of the High ADCC Activity Antibody-Producing Cell by the Method Using a Transposon The host cell used for the production of the high ADCC activity antibody-producing cell can be prepared by using the transposon system described in *Nature Genet.*, 25, 35 (2000), and the like, and then selecting a mutant using, as an index, the activity of the enzyme relating to the synthesis of an intracellular sugar nucleotide, GDP-fucose or the activity of the enzyme relating to the modification of a sugar chain in which 1-position of fucose is bound to 6-position of N-acetylglucosamine in the reducing terminal through α-bond in a complex-type N-glycoside-linked sugar chain, or the sugar chain structure of a produced antibody molecule or a glycoprotein on the cell membrane.

The transposon system is a system for inducing a mutation by random insertion of an exogenous gene into the chromosome, wherein usually an exogenous gene inserted into a transposon is used as a vector for inducing a mutation and a transposase expression vector for randomly inserting the gene into the chromosome is introduced into the cell at the same time.

Any transposase can be used so long as it is suitable for the sequence of the transposon to be used.

As the exogenous gene, any gene can be used so long as it can induce a mutation in the DNA of a host cell.

As the host cell, any yeast, animal cell, insect cell, plant cell, or the like can be used so long as it has a gene encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain. Examples of the host cells include those described in the above 1. Introduction of the gene into various host cells can be carried out by the methods suitable for introducing a recombinant vector into various host cells described in the above 1.

The methods for selecting the mutant using, as an index, the activity of the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain include the methods described in the above 2 (1) (a).

The methods for selecting the mutant using, as an index, the sugar chain structure of a glycoprotein on the cell membrane include the method described in 2 (5). The methods for selecting the mutant using, as an index, the sugar chain structure of a produced antibody molecule include the methods described in 4 or 5 below.

(2) Technique of Introducing a Dominant-Negative Mutant of a Gene Encoding an Enzyme The host cell used for the production of the high ADCC activity antibody-producing cell can be prepared by using the technique of introducing a dominant-negative mutant of a target gene, i.e., a gene encoding an enzyme relating to the synthesis of the intracellular sugar nucleotide, GDP-fucose or an enzyme relating to the modification of a sugar chain in which 1-position of fucose is bound to 6-position of N-acetylglucosamine in the reducing terminal through α-bond in a complex-type N-glycoside-linked sugar chain. Examples of the enzymes relating to the synthesis of the intracellular sugar nucleotide, GDP-fucose include GMD and Fx. Examples of the enzymes relating to the modification of a sugar chain in which 1-position of fucose is bound to 6-position of N-acetylglucosamine in the reducing terminal through α-bond in a complex-type N-glycoside-linked sugar chain include α1,6-fucosyltransferase and α-L-fucosidase.

These enzymes have substrate specificity and catalyze specific reactions. By disrupting the active center of such enzymes having substrate specificity and catalytic activity, their dominant-negative mutants can be prepared. Preparation of a dominant-negative mutant is described in detail below, using GMD as an example among the target enzymes.

As a result of the analysis of the three-dimensional structure of GMD derived from *Escherichia coli*, it has been revealed that four amino acids (threonine at position 133, glutamic acid at position 135, tyrosine at position 157 and lysine at position 161) have an important function for the enzyme activity (*Structure*, 8, 2, 2000). That is, the mutants prepared by substituting the above four amino acids by other amino acids based on the three-dimensional structure information all showed significantly decreased enzyme activity. On the other hand, little change was observed in the ability of the mutants to bind to the GMD coenzyme NADP or the substrate GDP-mannose. Accordingly, a dominant-negative mutant can be prepared by substituting the four amino acids which are responsible for the enzyme activity of GMD. On the basis of the result of preparation of a dominant-negative mutant of GMD derived from *Escherichia coli*, dominant-negative mutants can be prepared by performing homology comparison and three-dimensional structure prediction using the amino acid sequence information. For example, in the case of GMD derived from CHO cell (SEQ ID NO:19), a dominant-negative mutant can be prepared by substituting threonine at position 155, glutamic acid at position 157, tyrosine at position 179 and lysine at position 183 by other amino acids. Preparation of such a gene carrying introduced amino acid substitutions can be carried out by site-directed mutagenesis described in *Molecular Cloning*, Second Edition, *Current Protocols in Molecular Biology*, and the like.

The host cell used for the production of the high ADCC activity antibody-producing cell can be prepared according to the method of gene introduction described in *Molecular Cloning*, Second Edition, *Current Protocols in Molecular Biology, Manipulating the Mouse Embryo*, Second Edition, and the like using a gene encoding a dominant-negative mutant of a target enzyme (hereinafter abbreviated as dominant-negative mutant gene) prepared as above, for example, in the following manner.

A dominant-negative mutant gene encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain is prepared.

Based on the full-length DNA of the prepared dominant-negative mutant gene, a DNA fragment of appropriate length containing a region encoding the protein is prepared according to need.

A recombinant vector is prepared by inserting the DNA fragment or full-length DNA into a site downstream of a promoter in an appropriate expression vector. The recombinant vector is introduced into a host cell suited for the expression vector to obtain a transformant.

The host cell used for the preparation of the high ADCC activity antibody-producing cell can be obtained by selecting a transformant using, as an index, the activity of the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain, or the sugar chain structure of a produced antibody molecule or a glycoprotein on the cell membrane.

As the host cell, any yeast, animal cell, insect cell, plant cell, or the like can be used so long as it has a gene encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain. Examples of the host cells include those described in the above 1.

The expression vectors that can be employed are those capable of autonomous replication or integration into the chromosome in the above host cells and comprising a promoter at a position appropriate for the transcription of the DNA encoding the desired dominant-negative mutant. Examples of the expression vectors include those described in the above 1.

Introduction of a gene into various host cells can be carried out by the methods suitable for introducing a recombinant vector into various host cells described in the above 1.

The methods for selecting the transformant using, as an index, the activity of the enzyme relating to the synthesis of an intracellular sugar nucleotide, GDP-fucose or the activity of the enzyme relating to the modification of a sugar chain in which 1-position of fucose is bound to 6-position of N-acetylglucosamine in the reducing terminal through α-bond in a complex-type N-glycoside-linked sugar chain include the methods described in 2 (1) (a) below.

The methods for selecting the transformant using, as an index, the sugar chain structure of a glycoprotein on the cell membrane include the method described in 2 (5) below. The methods for selecting the transformant using, as an index, the sugar chain structure of a produced antibody molecule include the methods described in 4 or 5 below.

(3) Technique of Introducing a Mutation into an Enzyme

The host cell used for the preparation of the high ADCC activity antibody-producing cell can be prepared by introducing a mutation into a gene encoding an enzyme relating to the synthesis of the intracellular sugar nucleotide, GDP-fucose or an enzyme relating to the modification of a sugar chain in which 1-position of fucose is bound to 6-position of N-acetylglucosamine in the reducing terminal through α-bond in a complex-type N-glycoside-linked sugar chain, and then selecting a desired cell line in which the mutation occurred in the enzyme.

Examples of the enzymes relating to the synthesis of the intracellular sugar nucleotide, GDP-fucose include GMD, Fx, and the like. Examples of the enzymes relating to the modification of a sugar chain in which 1-position of fucose is bound to 6-position of N-acetylglucosamine in the reducing terminal through α-bond in a complex-type N-glycoside-linked sugar chain include α1,6-fucosyltransferase, α-L-fucosidase, and the like.

The methods for introducing a mutation into the enzyme include: 1) a method in which a desired cell line is selected from mutants obtained by subjecting a parent cell line to mutagenesis or by spontaneous mutation using, as an index, the activity of the enzyme relating to the synthesis of an intracellular sugar nucleotide, GDP-fucose or the activity of the enzyme relating to the modification of a sugar chain in which 1-position of fucose is bound to 6-position of N-acetylglucosamine in the reducing terminal through α-bond in a complex-type N-glycoside-linked sugar chain; 2) a method in which a desired cell line is selected from mutants obtained by subjecting a parent cell line to mutagenesis or by spontaneous mutation using, as an index, the sugar chain structure of a produced antibody molecule; and 3) a method in which a desired cell line is selected from mutants obtained by subjecting a parent cell line to mutagenesis or by spontaneous mutation using, as an index, the sugar chain structure of a glycoprotein on the cell membrane.

Mutagenesis may be carried out by any method capable of inducing a point mutation, a deletion mutation or a frameshift mutation in DNA of a cell of a parent cell line.

Suitable methods include treatment with ethyl nitrosourea, nitrosoguanidine, benzopyrene or an acridine dye and irradiation. Various alkylating agents and carcinogens are also useful as mutagens. A mutagen is allowed to act on a cell by the methods described in *Soshiki Baiyo no Gijutsu* (*Tissue Culture Techniques*), Third Edition (Asakura Shoten), edited by The Japanese Tissue Culture Association (1996); *Nature Genet.*, 24, 314 (2000); and the like.

Examples of the mutants generated by spontaneous mutation include spontaneous mutants obtained by continuing subculture under usual cell culture conditions without any particular treatment for mutagenesis.

The methods for measuring the activity of the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex-type N-glycoside-linked sugar chain include the methods described in the above 1 (1) (a). The methods for determining the sugar chain structure of a produced antibody molecule include the methods described in 4 or 5 below. The methods for determining the sugar chain structure of a glycoprotein on the cell membrane include the method described in the above 2 (5).

(4) Technique of Suppressing Transcription or Translation of a Gene Encoding an Enzyme The host cell used for the preparation of the high ADCC activity antibody-producing cell can be prepared by suppressing transcription or translation of a target gene, i.e., a target gene encoding an enzyme relating to the synthesis of the intracellular sugar nucleotide, GDP-fucose or an enzyme relating to the modification of a sugar chain in which 1-position of fucose is bound to 6-position of N-acetylglucosamine in the reducing terminal through α-bond in a complex-type N-glycoside-linked sugar chain using the antisense RNA/DNA technique [*Bioscience and Industry*, 50, 322 (1992); *Chemistry*, 46, 681 (1991); *Biotechnology*, 9, 358 (1992); *Trends in Biotechnology*, 10, 87 (1992); *Trends in Biotechnology*, 10, 152 (1992); Cell Technology, 16, 1463 (1997)], the triple helix technique [*Trends in Biotechnology*, 10, 132 (1992)], and the like.

Examples of the enzymes relating to the synthesis of the intracellular sugar nucleotide, GDP-fucose include GMD, Fx, and the like. Examples of the enzymes relating to the modification of a sugar chain in which 1-position of fucose is bound to 6-position of N-acetylglucosamine in the reducing terminal through α-bond in a complex-type N-glycoside-linked sugar chain include α1,6-fucosyltransferase, α-L-fucosidase, and the like.

The methods for measuring the activity of the enzyme relating to the synthesis of an intracellular sugar nucleotide, GDP-fucose or the activity of the enzyme relating to the modification of a sugar chain in which 1-position of fucose is bound to 6-position of N-acetylglucosamine in the reducing terminal through α-bond in a complex-type N-glycoside-linked sugar chain include the methods described in the above 2 (1) (a).

The methods for determining the sugar chain structure of a glycoprotein on the cell membrane include the method described in the above 2 (5). The methods for determining the sugar chain structure of a produced antibody molecule include the methods described in 4 or 5 below.

(5) Technique of Selecting a Cell Line Resistant to a Lectin which Recognizes a Sugar Chain Structure in which 1-Position of Fucose is Bound to 6-position of N-Acetylglucosamine in the Reducing Terminal Through α-Bond in a N-Glycoside-Linked Sugar Chain The host cell used for the preparation of the high ADCC activity antibody-producing cell can be prepared by selecting a cell line resistant to a lectin which recognizes a sugar chain structure in which 1-position of fucose is bound to 6-position of N-acetylglucosamine in the reducing terminal through α-bond in a N-glycoside-linked sugar chain.

Selection of a cell line resistant to a lectin which recognizes a sugar chain structure in which 1-position of fucose is bound to 6-position of N-acetylglucosamine in the reducing terminal through α-bond in a N-glycoside-linked sugar chain can be carried out, for example, by the method using a lectin described in *Somatic Cell Mol. Genet.*, 12, 51 (1986), and the like.

As the lectin, any lectin can be used so long as it recognizes a sugar chain structure in which 1-position of fucose is bound to 6-position of N-acetylglucosamine in the reducing terminal through α-bond in a N-glycoside-linked sugar chain. Specific examples include lentil lectin LCA (lentil agglutinin derived from *Lens culinaris*), pea lectin PSA (pea lectin derived from *Pisum sativum*), broad bean lectin VFA (agglutinin derived from *Vicia faba*) and *Aleuria aurantia* lectin AAL (lectin derived from *Aleuria aurantia*).

Specifically, the cell line resistant to a lectin which recognizes a sugar chain structure in which 1-position of fucose is bound to 6-position of N-acetylglucosamine in the reducing terminal through α-bond in a N-glycoside-linked sugar chain can be selected by culturing cells in a medium containing the above lectin at a concentration of 1 µg/ml to 1 mg/ml for one day to 2 weeks, preferably one day to one week, subculturing surviving cells or picking up a colony and transferring it into a culture vessel, and subsequently continuing the culturing using the medium containing the lectin.

3. Evaluation of the Activity of the Antibody Composition

The protein amount, antigen-binding activity or cytotoxic activity of the purified antibody composition can be measured using the known methods described in *Monoclonal Antibodies, Antibody Engineering*, or the like.

Specifically, when the antibody composition is a human chimeric antibody or a humanized antibody, the binding activity to an antigen or the binding activity to cultured cell line which is antigen-positive can be measured by ELISA, the fluorescent antibody technique [*Cancer Immunol. Immunother.*, 36, 373 (1993)], and the like. The cytotoxic activity to cultured cell line which is antigen-positive can be evaluated by measuring CDC activity, ADCC activity, or the like [*Cancer Immunol. Immunother.*, 36, 373 (1993)].

The method for measuring ADCC activity includes a method in which a target cell labeled with a radioisotope, a fluorescent substance, a dye or the like is allowed to contact with an antibody and an effector cell, and then the activity of the labeled substance released from the injured target cell is measured; a method in which a target cell is allowed to contact with an antibody and an effector cell, and then the biological activity of an enzyme released from the injured target cell is measured; and the like.

The method for measuring CDC activity includes a method in which a target cell labeled with a radioisotope, a fluorescent substance, a dye or the like is allowed to contact with an antibody and a biological specimen such as serum containing a complement component, and then the activity of the labeled substance released from the injured target cell is measured; a method in which a target cell is allowed to contact with an antibody and a biological specimen such as serum containing a complement component, and then the biological activity of an enzyme released from the injured target cell is measured; and the like.

The safety and therapeutic effect of the antibody composition in human can be evaluated using an appropriate animal model of a species relatively close to human, e.g., cynomolgus monkey.

4. Analysis of Sugar Chains in the Antibody Composition

The sugar chain structure of the antibody molecule expressed in various cells can be analyzed according to general methods of analyzing the sugar chain structure of glycoprotein. For example, a sugar chain bound to an IgG molecule consists of neutral sugars such as galactose, mannose and fucose, amino sugars such as N-acetylglucosamine, and acidic sugars such as sialic acid, and can be analyzed by techniques such as sugar composition analysis and sugar chain structure analysis using two-dimensional sugar chain mapping.

(1) Analysis of Neutral Sugar and Amino Sugar Compositions

The sugar chain composition of an antibody composition can be analyzed by carrying out acid hydrolysis of sugar chains with trifluoroacetic acid or the like to release neutral sugars or amino sugars and analyzing the composition ratio.

Specifically, the analysis can be carried out by a method using a carbohydrate analysis device manufactured by Dionex. BioLC is a device for analyzing the sugar composition by HPAEC-PAD (high performance anion-exchange chromatography-pulsed amperometric detection) [*J. Liq. Chromatogr.*, 6, 1577 (1983)].

The composition ratio can also be analyzed by the fluorescence labeling method using 2-aminopyridine. Specifically, the composition ratio can be calculated by fluorescence labeling an acid-hydrolyzed sample by 2-aminopyridylation according to a known method [*Agric. Biol. Chem.*, 55(1), 283-284 (1991)] and then analyzing the composition by HPLC.

(2) Analysis of Sugar Chain Structure

The sugar chain structure of an antibody composition can be analyzed by two-dimensional sugar chain mapping [*Anal. Biochem.*, 171, 73 (1988); *Seibutsukagaku Jikkenho (Biochemical Experimentation Methods)* 23—*Totanpakushitsu Tosa Kenkyuho (Methods of Studies on Glycoprotein Sugar Chains)*, Gakkai Shuppan Center, edited by Reiko Takahashi (1989)]. The two-dimensional sugar chain mapping is a method of deducing a sugar chain structure, for example, by plotting the retention time or elution position of a sugar chain by reversed phase chromatography as the X axis and the retention time or elution position of the sugar chain by normal phase chromatography as the Y axis, respectively, and comparing them with the results of known sugar chains.

Specifically, a sugar chain is released from an antibody by hydrazinolysis of the antibody and subjected to fluorescence labeling with 2-aminopyridine (hereinafter referred to as PA) [*J. Biochem.*, 95, 197 (1984)]. After being separated from an excess PA-treating reagent by gel filtration, the sugar chain is subjected to reversed phase chromatography. Then, each peak of the fractionated sugar chain is subjected to normal phase chromatography. The sugar chain structure can be deduced by plotting the obtained results on a two-dimensional sugar chain map and comparing them with the spots of a sugar chain standard (manufactured by Takara Shuzo Co., Ltd.) or those in the literature [*Anal. Biochem.*, 171, 73 (1988)].

The structure deduced by the two-dimensional sugar chain mapping can be confirmed by carrying out mass spectrometry, e.g., MALDI-TOF-MS, of each sugar chain.

5. Method for Determining the Sugar Chain Structure of an Antibody Molecule

An antibody composition comprises an antibody molecule having different sugar chain structures binding to the Fc region of antibody. Among the antibody compositions of the present invention, the recombinant antibody composition comprising an antibody molecule having complex type N-glycoside-linked sugar chains in the Fc region, in which the ratio of sugar chains in which fucose is not bound to the N-acetylglucosamine in the reducing terminal to the total complex-type N-glycoside-linked sugar chains bound to the Fc region contained in the composition is 20% or more, shows high ADCC activity. Such an antibody composition can be determined using the method for analyzing the sugar chain structure of an antibody molecule described in the above 4. Further, it can also be determined by immunoassays using lectins.

Determination of the sugar chain structure of an antibody molecule by immunoassays using lectins can be made according to the immunoassays such as Western staining, RIA (radioimmunoassay), VIA (viroimmunoassay), EIA (enzymeimmunoassay), FIA (fluoroimmunoassay) and MIA (metalloimmunoassay) described in the literature [*Monoclonal Antibodies: Principles and Applications*, Wiley-Liss, Inc. (1995); *Enzyme Immunoassay*, 3rd Ed., Igaku Shoin (1987); *Enzyme Antibody Technique*, Revised Edition, Gakusai Kikaku (1985); and the like], for example, in the following manner.

A lectin recognizing the sugar chain structure of an antibody molecule constituting an antibody composition is labeled, and the labeled lectin is subjected to reaction with a sample antibody composition, followed by measurement of the amount of a complex of the labeled lectin with the antibody molecule.

Examples of lectins useful for determining the sugar chain structure of an antibody molecule include WGA (wheat-germ agglutinin derived from *T. vulgaris*), ConA (concanavalin A derived from *C. ensiformis*), RIC (toxin derived from *R. communis*), L-PHA (leukoagglutinin derived from *P. vulgaris*), LCA (lentil agglutinin derived from *L. culinaris*), PSA (pea lectin derived from *P. sativum*), AAL (*Aleuria aurantia* lectin), ACL (*Amaranthus caudatus* lectin), BPL (*Bauhinia purpurea* lectin), DSL (*Datura stramonium* lectin), DBA (*Dolichos biflorus* agglutinin), EBL (Elderberry balk lectin), ECL (*Erythrina cristagalli* lectin), EEL (*Euonymus europaeus* lectin), GNL (*Galanthus nivalis* lectin), GSL (*Griffonia simplicifolia* lectin), HPA (*Helix pomatia* agglutinin), HHL (*Hippeastrum hybrid* lectin), Jacalin, LTL (*Lotus tetragonolobus* lectin), LEL (*Lycopersicon esculentum* lectin), MAL (*Maackia amurensis* lectin), MPL (*Madura pomifera* lectin), NPL (*Narcissus pseudonarcissus* lectin), PNA (peanut agglutinin), E-PHA (*Phaseolus vulgaris* erythroagglutinin), PTL (*Psophocarpus tetragonolobus* lectin), RCA (*Ricinus communis* agglutinin), STL (*Solanum tuberosum* lectin), SJA (*Sophora japonica* agglutinin), SBA (soybean agglutinin), UEA (*Ulex europaeus* agglutinin), VVL (*Vicia villosa* lectin) and WFA (*Wisteria floribunda* agglutinin)

It is preferred to use lectins specifically recognizing a sugar chain structure wherein fucose is bound to the N-acetylglucosamine in the reducing terminal in complex-type N-glycoside-linked sugar chains. Examples of such lectins include lentil lectin LCA (lentil agglutinin derived from *Lens culinaris*), pea lectin PSA (pea lectin derived from *Pisum sativum*), broad bean lectin VFA (agglutinin derived from *Vicia faba*) and *Aleuria aurantia* lectin AAL (lectin derived from *Aleuria aurantia*).

6. Utilization of the Recombinant Antibody Composition of the Present Invention

Since the recombinant antibody composition of the present invention has higher CDC activity than an IgG1 antibody and an IgG3 antibody, it has more excellent property in therapeutic effects than conventional antibody compositions. Also, among the antibody compositions of the present invention, since the recombinant antibody composition comprising an antibody molecule having complex-type N-glycoside-linked sugar chains in the Fc region, wherein the ratio of sugar chains in which fucose is not bound to N-acetylglucosamine in the reducing terminal of the sugar chains among the total complex-type N-glycoside-linked sugar chains which bind to the Fc region contained in the composition is 20% or more has higher CDC activity and higher ADCC activity than an IgG1 antibody and an IgG3 antibody, it has more excellent property in therapeutic effects than conventional antibody compositions. Furthermore, among the recombinant antibody compositions of the present invention, the recombinant antibody composition comprising an antibody molecule having complex-type N-glycoside-linked sugar chains in the Fc region, wherein the ratio of sugar chains in which fucose is not bound to N-acetylglucosamine in the reducing terminal of the sugar chains among the total complex-type N-glycoside-linked sugar chains which bind to the Fc region contained in the composition is 100% is more preferred.

A medicament comprising the recombinant antibody composition of the present invention may be administered alone as a therapeutic agent. However, it is preferably mixed with one or more pharmaceutically acceptable carriers and provided as a pharmaceutical preparation produced by an arbitrary method well known in the technical field of pharmaceutics.

It is desirable to administer the medicament by the route that is most effective for the treatment. Suitable administration routes include oral administration and parenteral administration such as intraoral administration, intratracheal administration, intrarectal administration, subcutaneous administration, intramuscular administration and intravenous administration. In the case of an antibody preparation, intravenous administration is preferable.

The medicament may be in the form of spray, capsules, tablets, granules, syrup, emulsion, suppository, injection, ointment, tape, and the like.

The preparations suitable for oral administration include emulsions, syrups, capsules, tablets, powders and granules.

Liquid preparations such as emulsions and syrups can be prepared using, as additives, water, sugars (e.g., sucrose, sorbitol and fructose), glycols (e.g., polyethylene glycol and propylene glycol), oils (e.g., sesame oil, olive oil and soybean oil), antiseptics (e.g., p-hydroxybenzoates), flavors (e.g., strawberry flavor and peppermint), and the like.

Capsules, tablets, powders, granules, and the like can be prepared using, as additives, excipients (e.g., lactose, glucose, sucrose and mannitol), disintegrating agents (e.g., starch and sodium alginate), lubricants (e.g., magnesium stearate and talc), binders (e.g., polyvinyl alcohol, hydroxypropyl cellulose and gelatin), surfactants (e.g., fatty acid esters), plasticizers (e.g., glycerin), and the like.

The pharmaceutical preparations suitable for parenteral administration include injections, suppositories and sprays.

Injections can be prepared using carriers comprising a salt solution, a glucose solution, or a mixture thereof, and the like It is also possible to prepare powder injections by freeze-drying the antibody composition according to a conventional method and adding sodium chloride thereto.

Suppositories can be prepared using carriers such as cacao butter, hydrogenated fat and carboxylic acid.

The antibody composition may be administered as such in the form of spray, or sprays may be prepared using carriers which do not stimulate the oral or airway mucous membrane of a recipient and which can disperse the antibody composition as fine particles to facilitate absorption thereof.

Suitable carriers include lactose and glycerin. It is also possible to prepare aerosols, dry powders, and the like according to the properties of the antibody composition and the carriers used. In preparing these parenteral preparations, the above-mentioned additives for the oral preparations may also be added.

The dose and administration frequency will vary depending on the desired therapeutic effect, the administration route, the period of treatment, the patient's age, body weight, and the like. However, an appropriate dose of the active ingredient for an adult person is generally 10 µg/kg to 20 mg/kg per day.

The anti-tumor effect of the antibody composition against various tumor cells can be examined by in vitro tests such as CDC activity measurement and ADCC activity measurement and in vivo tests such as anti-tumor experiments using tumor systems in experimental animals (e.g., mice).

The CDC activity and ADCC activity measurements and anti-tumor experiments can be carried out according to the methods described in the literature [*Cancer Immunology Immunotherapy*, 36, 373 (1993); *Cancer Research*, 54, 1511 (1994); and the like].

The present invention provides a recombinant antibody composition which is a human IgG1 antibody, comprises a CH2 domain in which amino acids at positions 276 and 339 indicated by the EU index as in Kabat, et al. are replaced by other amino acids and has more improved complement-dependent cytotoxic activity than an antibody comprising a CH2 domain before the amino acids are replaced; a DNA encoding the antibody molecule or a heavy chain constant region of the antibody molecule contained in the recombinant antibody composition; a transformant obtainable by introducing the DNA into a host cell; a process for producing the recombinant antibody composition using the transformant; and a medicament comprising the recombinant antibody composition as an active ingredient.

The present invention is described below based on Examples; however, the present invention is not limited thereto.

EXAMPLE 1

Preparation of Anti-CD20 Human IgG1 Antibody, Anti-CD20 Human IgG3 Antibody and Anti-CD20 Chimeric Isotype Antibody Using Animal Cells 1. Production of Expression Vector for Anti-CD20 Human IgG3 Chimeric Antibody cDNA was synthesized from human lymph node-derived poly A+ RNA (manufactured by BD Biosciences Clontech) using cDNA Synthesis Kit (manufactured by Amersham Pharmacia Biotech) in accordance with the instructions attached thereto. PCR was carried out using 100 ng of cDNA as the template, and using KOD plus (manufactured by TOYOBO) and human IgG constant region-specific synthetic DNA primers (manufactured by FASMAC) comprising the amino acid sequences represented by SEQ ID NOs:1 and 2 in accordance with the attached instructions of KOD plus. PCR was carried out using GeneAmp PCR System 9700 (manufactured by Applied Biosystems) after thermal denaturation at 94° C. for 1 minute, followed by 30 cycles consisting of reactions at 94° C. for 15 seconds, at 62° C. for 30 seconds and at 68° C. for 90 seconds. After further carrying out reaction at 68° C. for 7 minutes, 2.5 U of Taq DNA polymerase (manufactured by Takara Shuzo) was added thereto and allowed to react at 68° C. for 7 minutes in order to add adenine to the 3'-terminal. The reaction solution was subjected to electrophoresis using 1% agarose gel, and an amplified fragment of about 1.1 kbp considered to be a gene of the heavy chain constant region of IgG3 was recovered by using QIAquick Gel Extraction Kit (manufactured by Qiagen). A ligation reaction with a plasmid pCRII-TOPO vector (manufactured by Invitrogen) was carried out by adding Ligation High solution (manufactured by TOYOBO), and *Escherichia coli* DH5α (manufactured by TOYOBO) was transformed using the reaction solution. Each plasmid DNA was prepared from the thus obtained transformant clones and allowed to react using Big Dye Terminator Cycle Sequencing Kit v3.1 (manufactured by Applied Biosystems) in accordance with the instructions attached thereto, and then the nucleotide sequence of the DNA inserted into the plasmid was analyzed by a DNA sequencer ABI PRISM 3700 DNA Analyzer of the same company to confirm that this sequence is a nucleotide sequence encoding the same amino acid sequence of the heavy chain constant region of a conventionally known human IgG3 (GenBank accession No. AAH33178).

Figure 2:
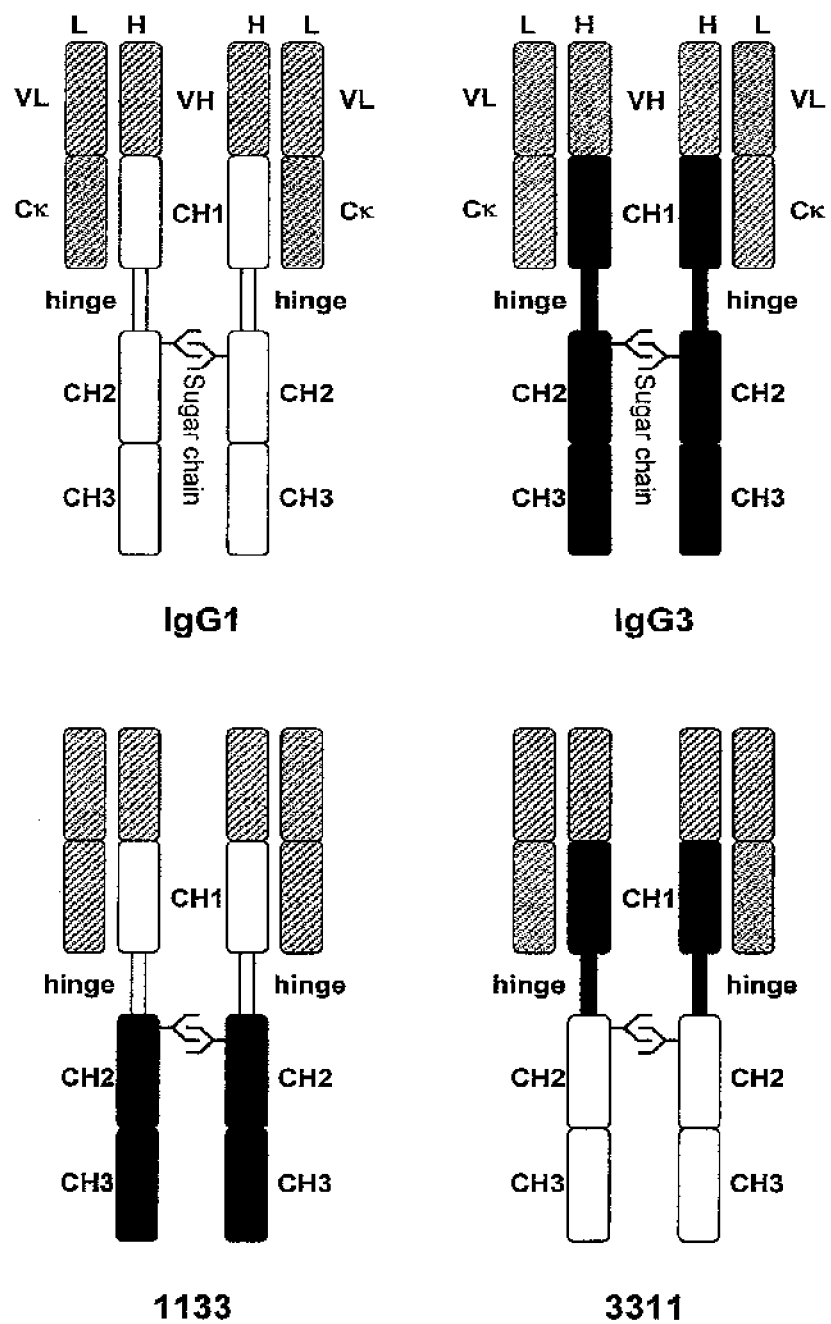
FIG. 2 is a schematic illustration showing domain structures of human IgG1 antibody, human IgG3 antibody, 1133-type chimeric isotype and 3311-type chimeric isotype.

A gene fragment of 1.13 kbp in the heavy chain constant region of IgG3 was purified from the above-described plasmid into which the gene of the heavy chain constant region of human IgG3 was inserted, by treatment with restriction enzymes ApaI and NruI (both manufactured by Takara Shuzo). Stable animal cell expression vector for anti-CD20 human IgG1 chimeric antibody (described in WO03/055993), pKANTEX2B8P, which comprises a variable region identical to the mouse-derived variable region of an anti-CD20 human IgG1 antibody RITUXAN™, human κ-type light chain constant region and human IgG1 heavy chain constant region, was digested with ApaI and NruI. Expression vector for anti-CD20 human IgG3 antibody, pKANTEX2B8γ3 (FIG. 2) was constructed by cleaving the IgG1 constant region gene, purifying the remaining fragment of about 12.6 kbp and ligating it with the above-described IgG3 constant region gene fragment using the Ligation High solution. The amino acid sequences of the heavy chain variable region, the light chain variable region and the light chain constant region of the anti-CD20 human IgG3 antibody encoded by pKANTEX2B8γ3 were identical to the amino acid sequences of the heavy chain variable region, the light chain variable region and the light chain constant region of the anti-CD20 human IgG1 chimeric antibody encoded by pKANTEX2B8P.

2. Production of Anti-CD20 Chimeric Isotype Antibody Expression Vector

Figure 3:
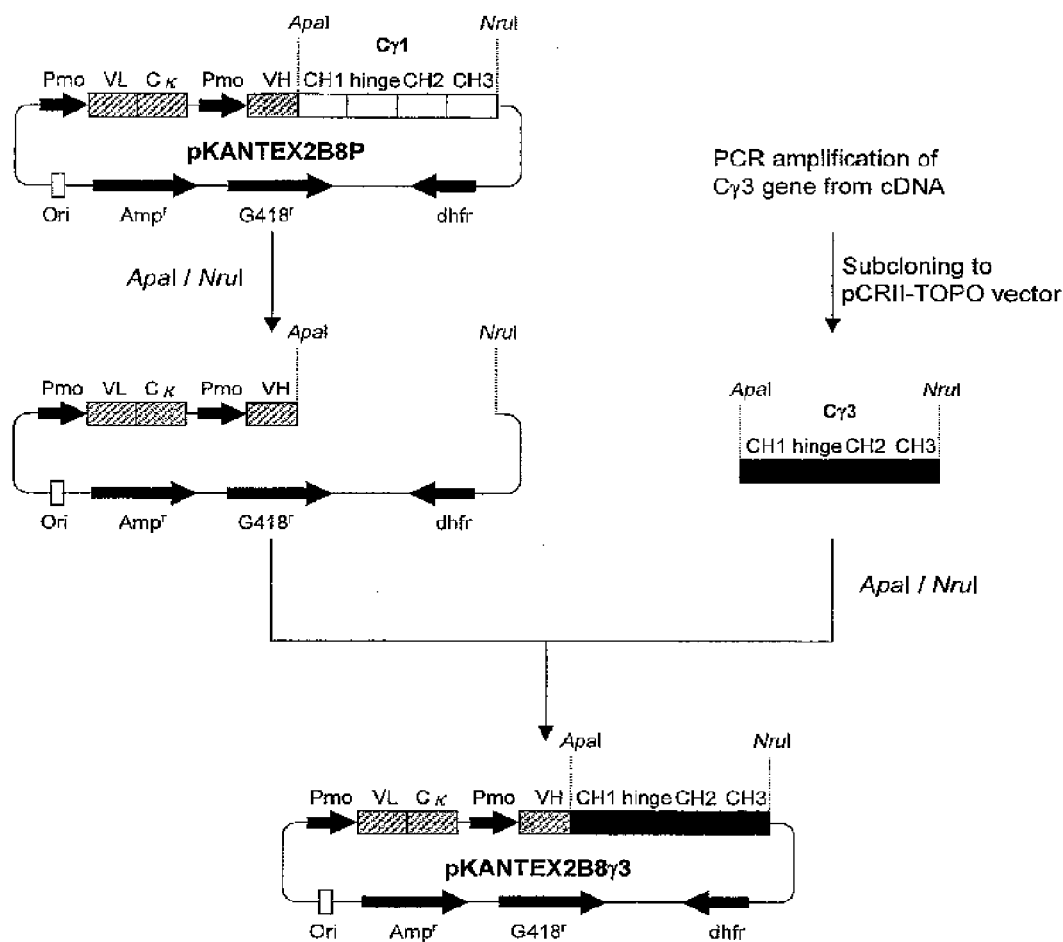
FIG. 3 shows construction steps of a plasmid pKANTEX2B8γ3.

An anti-CD20 chimeric isotype antibody, wherein the amino acid sequences of the heavy chain variable region, the light chain variable region and the light chain constant region are identical to the amino acid sequences of the heavy chain variable region, the light chain variable region and the light chain constant region of the anti-CD20 human IgG1 antibody encoded by pKANTEX2B8P and the amino acid sequence of the heavy chain constant region comprises the amino acid sequence of the heavy chain constant region of an anti-CD20 human IgG1 antibody encoded by pKANTEX2B8P and the amino acid sequence of the heavy chain constant region of an anti-CD20 human IgG3 antibody encoded by pKANTEX2B8γ3 was prepared in accordance with the following procedure. The anti-CD20 chimeric isotype antibody having a heavy chain constant region in which the CH1 and hinge are constituted by the amino acid sequences from a human IgG1 antibody, and the Fc region is constituted by the amino acid sequence from a human IgG3 antibody, is called 1133-type anti-CD20 chimeric isotype antibody, and the anti-CD20 chimeric isotype antibody having a heavy chain constant region wherein the CH1 and hinge are constituted by the amino acid sequences from a human IgG3 antibody, and the Fc regions is constituted by the amino acid sequence from a human IgG1 antibody, is called 3311-type anti-CD20 chimeric isotype antibody. As a result of search using amino acid sequence database, it was found that the amino acid sequences of heavy chain constant regions of these anti-CD20 chimeric isotype antibodies are novel amino acid sequences. Subclasses from which each domain of the 1133-type anti-CD20 chimeric isotype antibody and the 3311-type anti-CD20 chimeric antibody was derived, and corresponding amino acid sequences of heavy chain constant regions are shown in Table 1. Schematic illustration of these anti-CD20 antibodies is shown in FIG. 3.

TABLE 1

| Structural name | CH1 | Hinge | CH2 | CH3 | Amino acid sequence |
|---|---|---|---|---|---|
| 1133 | IgG1 | IgG1 | IgG3 | IgG3 | SEQ ID NO: 3 |
| 3311 | IgG3 | IgG3 | IgG1 | IgG1 | SEQ ID NO: 4 |

Figure 4:
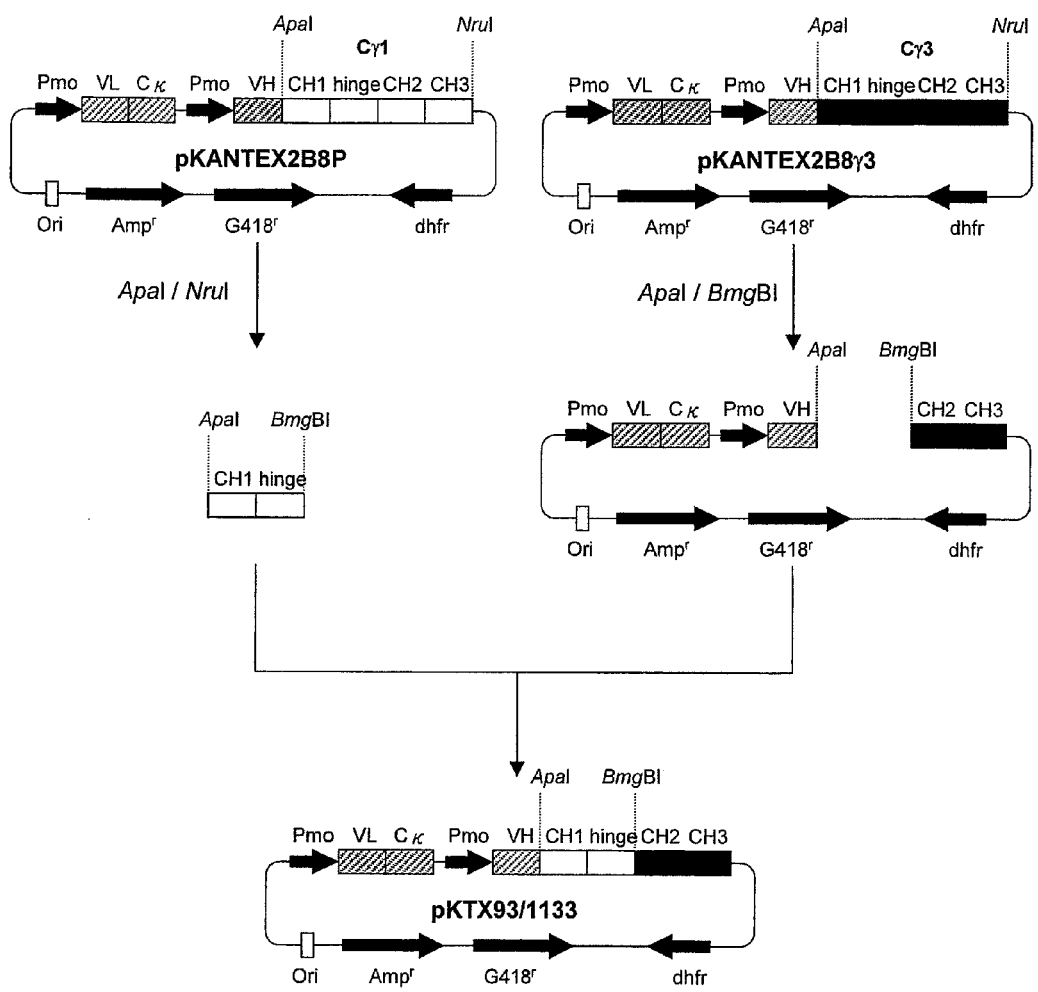
FIG. 4 shows construction steps of a plasmid pKTX93/1133.

(1) Construction of Expression Vector Encoding 1133-Type Anti-CD20 Chimeric Isotype Antibody The expression vector encoding the 1133-type anti-CD20 chimeric isotype antibody, pKTX93/113 was constructed in the following manner (FIG. 4). A DNA fragment of about 430 bp encoding CH1 and hinge of human IgG1 antibody was cleaved and purified from the expression vector for anti-CD20 human IgG1 antibody, pKANTEX2B8P, using restriction enzymes ApaI (manufactured by Takara Shuzo) and BmgBI (manufactured by New England Biolabs). On the other hand, a DNA fragment of about 13 kbp was cleaved and purified from the expression vector for anti-CD20 human IgG3 antibody, pKANTEX2B8γ3, described in the item 1 of this Example by the similar treatment with restriction enzymes. After mixing these purified DNA preparations, a ligation reaction was carried out using Ligation High solution (manufactured by TOYOBO), and *Escherichia coli* XL1-BLUE MRF' (manufactured by Stratagene) was transformed using the reaction solution. Each plasmid DNA was prepared from the thus obtained transformant clones and allowed to react using Big Dye Terminator Cycle Sequencing Kit v3.1 (manufactured by Applied Biosystems) in accordance with the instructions attached thereto, and then the nucleotide sequence of the DNA inserted into the plasmid was analyzed by a DNA sequencer ABI PRISM 3700 DNA Analyzer of the same company to confirm that the plasmid pKTX93/1133 shown in FIG. 4 was obtained.

Figure 5:
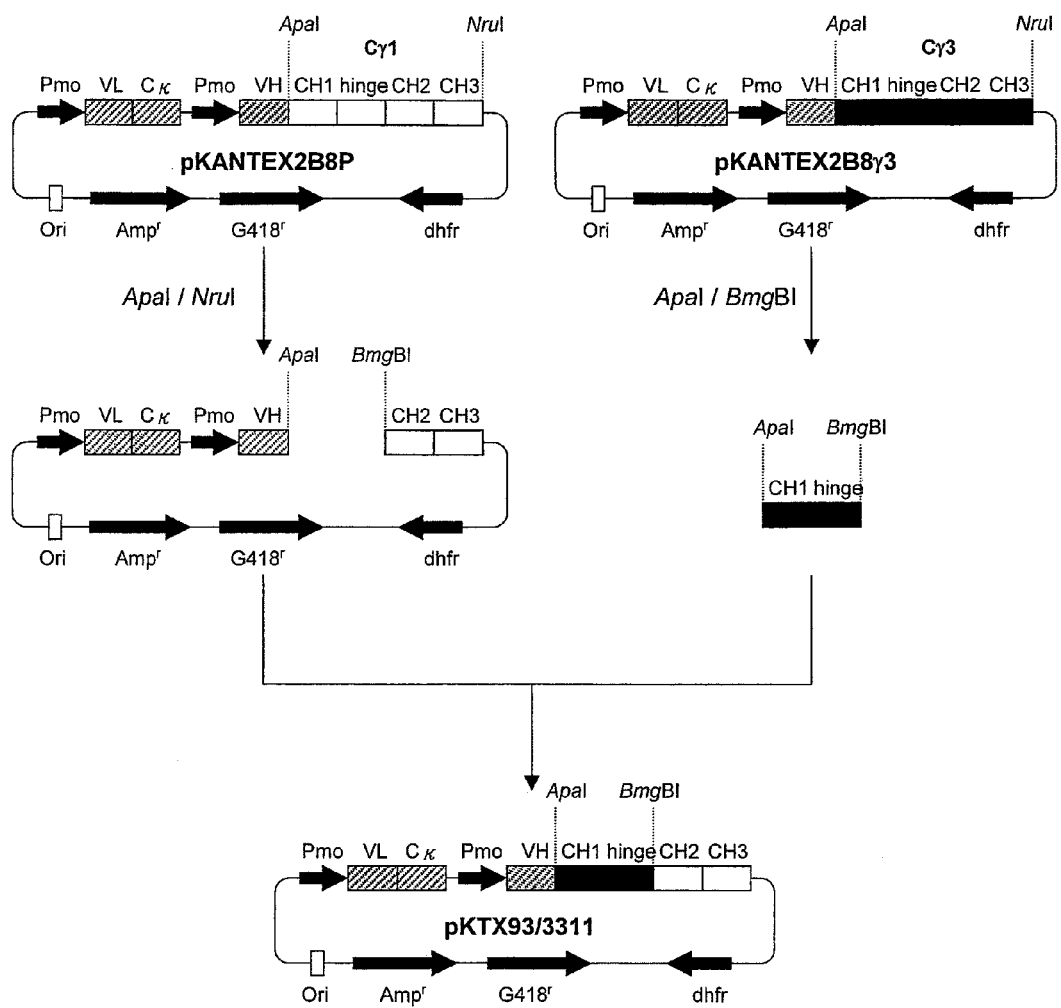
FIG. 5 shows construction steps of a plasmid pKTX93/3311.

(2) Construction of Expression Vector Encoding the 3311-Type Anti-Cd20 Chimeric Isotype Antibody The expression vector encoding the 3311-type anti-CD20 chimeric isotype antibody, pKTX93/3311, was constructed in the following manner (FIG. 5). A DNA fragment of about 570 bp encoding CH1 and hinge of human IgG3 antibody was cleaved and purified from the expression vector for anti-CD20 human IgG3 chimeric antibody, pKANTEX2B8γ3, described in the item 1 of this Example using restriction enzymes ApaI (manufactured by Takara Shuzo) and BmgBI (manufactured by New England Biolabs). On the other hand, a DNA fragment of about 13 kbp was cleaved and purified from the expression vector for anti-CD20 human IgG1 antibody, pKANTEX2B8P, by the similar treatment with restriction enzymes. After mixing these purified DNA preparations, a ligation reaction was carried out using Ligation High solution (manufactured by TOYOBO), and *Escherichia coli* XL1-BLUE MRF' (manufactured by Stratagene) was transformed using the reaction solution. Each plasmid DNA was prepared from the thus obtained transformant clones and allowed to react using Big Dye Terminator Cycle Sequencing Kit v3.1 (manufactured by Applied Biosystems) in accordance with the instructions attached thereto, and then the nucleotide sequence of the DNA inserted into the plasmid was analyzed by a DNA sequencer ABI PRISM 3700 DNA Analyzer of the same company to confirm that the plasmid pKTX93/3311 shown in FIG. 5 was obtained.

3. Stable Expression of Various Anti-CD20 Antibodies in Animal Cells

Cells for stably producing an anti-CD20 human IgG3 antibody or anti-CD20 chimeric isotype antibody, in which the expression vector for anti-CD20 human IgG3 antibody, pKTX93/1133, and expression vectors for anti-CD20 chimeric isotype antibody, pKTX93/1133 and pKTX93/3311, prepared in the items 1 and 2 of this Example, were introduced into a CHO/DG44 cell [*Somatic Cell Mol. Genet.*, 12, 555 (1986)] and the CHO/DG44 cell in which α1,6-fucosyltransferase gene was knocked out (hereinafter referred to as CHO/FUT8$^{-/-}$) [*Biotechnol. Bioeng.*, 87, 614 (2004)] as host cells were prepared in the following manner. The CHO/DG44 cell is a host cell widely used in the production of recombinant protein. The CHO/FUT8$^{-/-}$ is a host cell in which FUT8 of the CHO/DG44 cell is knocked out on the genome. In addition, the expression vector for anti-CD20 human IgG1 antibody, pKANTEX2B8P, was introduced into the CHO/FUT8$^{-/-}$ cell alone, and a cell capable of stably producing an anti-CD20 human IgG1 antibody was prepared in the same manner.

After introducing 8 μg of each expression vector into 1.6×10$^6$ cells of the CHO/DG44 cell or CHO/FUT8$^{-/-}$ cell by the electroporation method [*Cytotechnology*, 3, 133 (1990)], the cells were suspended in 40 ml of IMDM-(10) [IMDM medium (manufactured by GIBCO-BRL) containing 10% of dialyzed fetal bovine serum (dFBS)] and dispensed at 100 μl/well into a 96-well microplate (manufactured by Sumitomo Bakelite). After culturing at 37° C. for 24 hours in a 5% CO$_2$ incubator, the cells were cultured for 1 to 2 weeks in the IMDM-(10) containing G418 at concentration of 500 μg/ml. After the culturing, culture supernatant was recovered from each well, and the amount of the anti-CD20 chimeric isotype antibody in the culture supernatant was measured by the ELISA which is described later in the item 4 of this Example. Regarding the transformants of wells in which expression of the anti-CD20 chimeric isotype antibody was found in the culture supernatants, in order to increase the antibody expression amount using the dhfr gene amplification system, the cells were suspended in the IMDM-(10) medium containing G418 at concentration of 500 μg/ml and methotrexate at concentration of 50 nM (hereinafter referred to as MTX: manufactured by SIGMA) as an inhibitor of dihydrofolate reductase which was the dhfr gene product and cultured at 37° C. for about 1 week in a 5% CO$_2$ incubator to thereby obtain transformants having resistance to 50 nM of MTX. Subsequently, the MTX concentration was successively raised to 100 nM and then to 200 nM to finally obtain transformants which can proliferate in the IMDM-(10) medium containing G418 at concentration of 500 μg/ml and 200 nM MTX and also can express the antibodies encoded by the respective expression vectors at high level.

4. Measurement of Antibody Concentration in Culture Supernatant (ELISA)

Goat anti-human IgG (H & L) antibody (manufactured by American Qualex) was diluted to 1 μg/ml with phosphate buffered saline (hereinafter referred to as PBS), dispensed at 50 μl/well into a 96-well plate for ELISA (manufactured by Greiner) and allowed to stand at room temperature for 1 hour for adsorption. After the reaction, the plate was washed with PBS, and 1% bovine serum albumin (hereinafter referred to as BSA; manufactured by Proliant Inc)-containing PBS (hereinafter referred to as 1% BSA-PBS) was added thereto at 100 μl/well and allowed to react at room temperature for 1 hour to block the remaining active groups. After removing 1% BSA-PBS, culture supernatants to be measured were added at 50 μl/well and allowed to react at room temperature for 2 hours. After the reaction, each well was washed with 0.05% Tween 20-containing PBS (hereinafter referred to as Tween-PBS), and then a peroxidase-labeled goat anti-human IgG (Fc) antibody solution (manufactured by American Qualex) diluted 500-fold with PBS was added at 50 μl/well as the secondary antibody solution and allowed to react at room temperature for 1 hour. After washing with Tween-PBS, ABTS substrate solution [a solution prepared by dissolving 0.55 g of ammonium 2,2'-azino-bis(3-ethylbenzothiazoline-6-sulfonate) in 1 liter of 0.1 M citrate buffer (pH 4.2) and adding 1 μl/ml of hydrogen peroxide just before the use] was added at 50 μl/well for color development, and the absorbance at 415 nm (hereinafter referred to as OD415) was measured.

5. Purification of Various Anti-CD20 Antibodies

Each of the transformants capable of expressing various anti-CD20 antibodies obtained in the item 3 of this Example was suspended in IMDM-FCS(10) containing 200 nM of MTX to a density of 1×10$^5$ cells/ml, and then dispensed at 100 ml into triple flasks (manufactured by Nalgenunc) and cultured at 37° C. for 2 days in a 5% CO$_2$ incubator. Culture supernatant was removed from each flask, the inside of the flask was washed with 50 ml of PBS, and then 100 ml of EXCELL 301 medium (manufactured by JRH Biosciences) was added to the flask to continue the culturing at 37° C. for 5 days in the 5% CO$_2$ incubator. This culture supernatant was recovered, centrifuged at 3000 rpm and 4° C. for 5 minutes, and then the supernatant was recovered and subjected to filtration sterilization using a 0.22 um PES Membrane (manufactured by Iwaki). The various anti-CD20 antibodies were purified from the thus sterilized culture supernatants using a column packed with Prosep-A (Protein-A binding resin: manufactured by Millipore) or Prosep-G (Protein-G binding resin: manufactured by Millipore) in accordance with the instructions attached thereto. The IgG1 anti-CD20 antibody was purified by protein A, but since the IgG3 anti-CD20 antibody was not purified by protein A, purification was carried out by using protein G. Regarding the anti-CD20 chimeric isotype antibodies, the 3311-type was purified by protein A. On the other hand, the 1133-type was not purified with protein A, but could be purified by protein G.

The expression vector and host cell of each antibody and names of the purified antibody samples are shown in Table 2. In this connection, in the table, the samples having (+F) in the name indicate an antibody sample produced using CHO/DG44 as the host cell in which fucose is bound to sugar chains linked to Fc, and samples having (−F) in the name indicate antibody samples produced using CHO/FUT8$^{-/-}$ as the host cell in which fucose is not bound to sugar chains linked to Fc.

TABLE 2

| Expression vector | Host cell | Purified antibody (name) |
| --- | --- | --- |
| pKANTEX2B8 | CHO/FUT8$^{-/-}$ | CD20-IgG1(−F) |
| pKANTEX2B8γ3 | CHO/DG44 | CD20-IgG3(+F) |
| pKANTEX2B8γ3 | CHO/FUT8$^{-/-}$ | CD20-IgG3(−F) |
| pKTX93/1133 | CHO/DG44 | 1133(+F) |
| pKTX93/1133 | CHO/FUT8$^{-/-}$ | 1133(−F) |
| pKTX93/3311 | CHO/DG44 | 3311(+F) |
| pKTX93/3311 | CHO/FUT8$^{-/-}$ | 3311(−F) |

6. Evaluation of the Purification Degree of Various Anti-CD20 Antibody Samples Purified by SDS-PAGE In order to evaluate the purification degree of the purified samples of various anti-CD20 antibodies obtained in the item 5 of this Example, SDS-polyacrylamide gel electrophoresis (hereinafter referred to as SDS-PAGE) was carried out in accordance with a conventionally known method [*Nature*, 227, 680 (1970)], using about 1 µg of each of the purified samples of various anti-CD20 antibodies. As a comparative control of the electrophoresis degree, the same operation was also carried out for an anti-CD20 human IgG1 antibody RITUXAN™. Hereinafter, RITUXAN™ is referred to as CD20-IgG1(+F).

As a result, 1133(+F) and 1133(–F) showed an electrophoresis pattern similar to that of the human IgG1 antibody CD20-IgG1(+F), and 3311(+F) and 3311(–F) showed an electrophoresis pattern similar to that of the human IgG3 antibody CD20-IgG3(+F). In the case of CD20-IgG1(+F), CD20-IgG1(–F), 1133(+F) and 1133(–F), the band of the H chain was found at about 50 kilodaltons (hereinafter referred to as kDa), and that of the L chain was found at about 24 kDa, and in the case of CD20-IgG3(+F), CD20-IgG3(–F), 3311(+F) and 3311(–F), the band of the H chain was found at about 54 kDa, and that of the L chain was found at about 24 kDa, so that it was confirmed that each of the prepared anti-CD20 antibodies is constituted by the desired H chain and L chain.

Based on the above results, it was confirmed that the desired IgG molecules constituted by H chain and L chain are contained at a sufficient ratio in the purified samples of respective anti-CD20 antibodies obtained in the item 5 of this Example.

EXAMPLE 2

Activity Evaluation of Various Anti-CD20 Antibodies

Comparison of various activities was carried out for the purified samples of various anti-CD20 antibodies obtained in the item 5 of Example 1 in the following manner.

1. Measurement of Binding Activity of Various Anti-Cd20 Antibodies to Cd20-Positive Cell Binding activity of the various anti-CD20 antibody purification samples obtained in the item 5 of Example 1 to CD20-positive cells was measured in a competitive inhibition system with biotinylated RITUXAN™, by fluorescent antibody technique using a flow cytometer. As negative controls, an anti-Her2 human IgG1 antibody HERCEPTIN™ [Proc. Natl. Acad. Sci. U.S.A., 89, 4285 (1992)] and an anti-CCR4 human IgG1 antibody KM3060 [Cancer Res., 64, 2127 (2004)] were used.

A CD20-positive Burkitt lymphoma-derived cell line Daudi cell (ATCC: CCL-213) was dispensed at $5\times10^5$ cells per well into a 96-well U-plate (manufactured by Falcon), and then a buffer for FACS [0.2 mg/ml human IgG (manufactured by Sigma), 0.02% EDTA, 0.05% $NaN_3$, 1% BSA] containing 10 µg/ml or 1 µg/ml of the respective CD20 antibodies obtained in the item 5 of Example 1, or the negative controls anti-Her2 antibody HERCEPTIN™ [Proc. Natl. Acad. Sci. U.S.A., 89, 4285 (1992)] and anti-CCR4 antibody KM3060 (WO02/31140), and containing 0.5 µg/ml of biotin-labeled anti-CD20 chimeric antibody RITUXAN™ [prepared by biotinylating RITUXAN™ using EZ-Link Sulfo-NHS-LC-Biotin (manufactured by Pierce)], was added thereto at 50 µl/well. After reaction at 4° C. for 60 minutes under shade, the cells were washed twice with the buffer for FACS, and then the PE-labeled streptoavidin diluted 200-fold with the buffer for FACS was added thereto at 50 µl/well. After reaction at 4° C. for 60 minutes under shade, the cells were washed twice with the buffer for FACS and suspended in 1 ml of the buffer for FACS, and then the fluorescence intensity was measured with a flow cytometer EPICS-XL (manufactured by Coulter).

Figure 6:
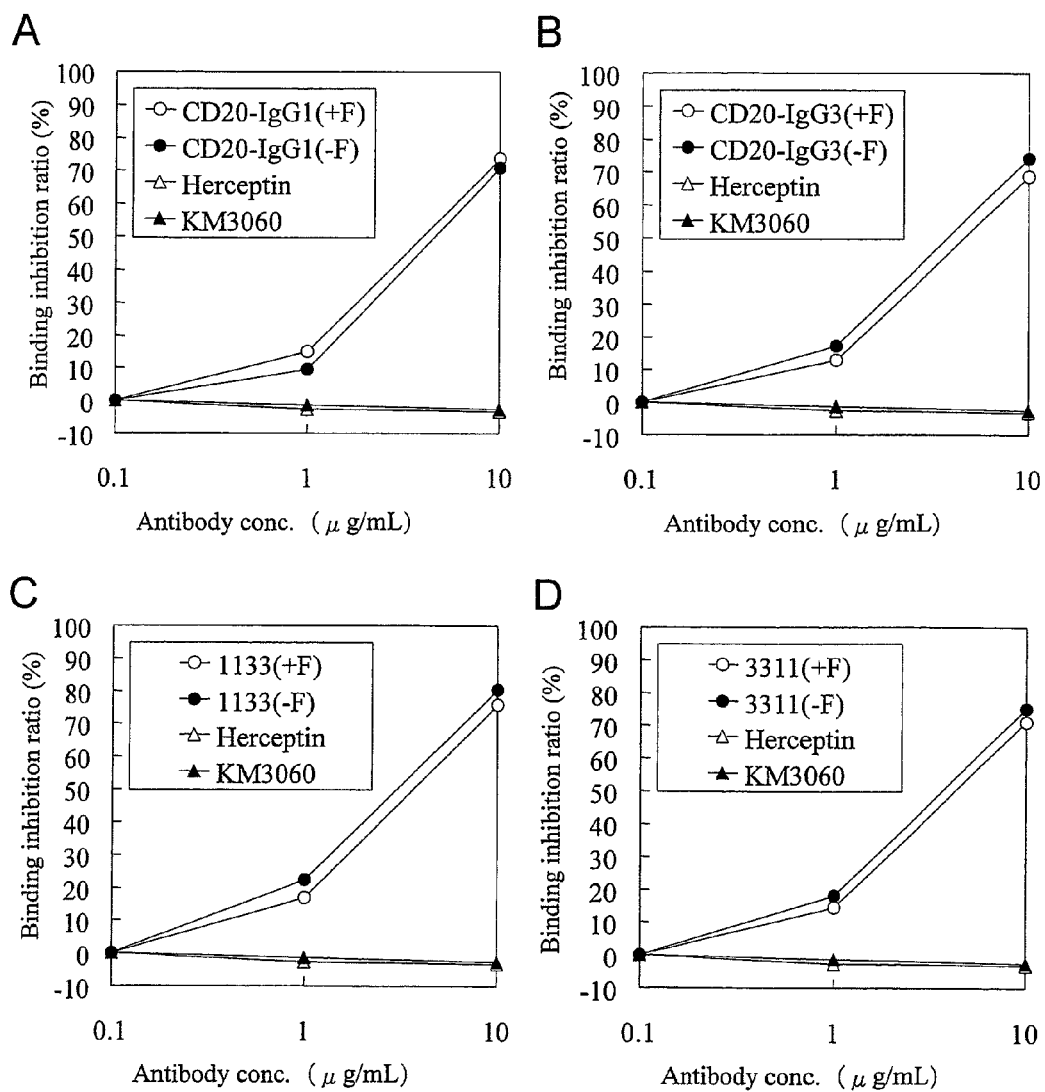
FIG. 6 shows the binding activity of anti-CD20 human IgG1 antibody, anti-CD20 human IgG3 antibody, 1133-type anti-CD20 chimeric isotype antibody and 3311-type anti-CD20 chimeric isotype antibody with an anti-CD20 antibody CD20-IgG1(+F) in a competitive inhibition assay to Daudi cell. The abscissa shows a sample concentration, and the ordinate shows a binding inhibition ratio at each sample concentration. In the graphs, Δ and ▲ are common to graphs A to H and show a negative control anti-Her2 antibody HERCEPTIN™ (Δ) and an anti-CCR4 antibody KM3060 (▲). Regarding ○ and ● in the graphs, the corresponding sample is different in each graph, and graph A shows CD20-IgG1(+F) (○) and CD20-IgG1(−F) (●), graph B shows CD20-IgG3(+F) (○) and CD20-IgG3(−F) (●), graph C shows 1133(+F) (○) and 1133(−F) (●), and graph D shows 3311(+F) (○) and 3311(−F) (●).

The results are shown in FIG. 6. The negative controls anti-Her2 antibody HERCEPTIN™ and anti-CCR4 antibody KM3060 did not inhibit binding of the biotin-labeled RITUXAN™ to the CD20-positive cell Daudi, but all of the anti-CD20 chimeric isotype antibodies, anti-CD20 human IgG1 antibodies and anti-CD20 human IgG3 antibodies concentration dependently inhibited the binding and the degree was almost the same. Also, in all of the anti-CD20 antibodies, the antibody sample produced by CHO/DG44 as a host cell and the antibody sample produced by CHO/FUT8$^{-/-}$ as a host cell have similar binding inhibition activity, and the presence or absence of fucose in the sugar chains bound to the antibody did not have influence on the binding inhibition activity. Based on these results, it was shown that antigen-binding of the anti-CD20 chimeric isotype antibodies is CD20-specific, that the antigen-binding activity of the anti-CD20 chimeric isotype antibodies is similar to that of the anti-CD20 human IgG1 chimeric antibody, and the presence or absence of fucose in the sugar chains bound to the Fc did not have influence on the antigen-binding activity.

2. Measurement of CDC Activity of Various Anti-CD20 Antibodies to Daudi Cell

In vitro CDC activity of the purified samples of various anti-CD20 antibodies obtained in the item 5 of Example 1 was measured using a CD20-positive Daudi cell.

The reaction was carried out in a 96-well flat-bottomed plate (manufactured by Sumitomo Bakelite), and a human complement dilution medium [prepared by diluting a human complement (manufactured by SIGMA) 6-fold with RPMI 1640 medium (manufactured by GIBCO BRL) containing 10% FBS (manufactured by JRH)] containing $5\times10^4$ cells of the Daudi cell and containing 0.3 µg/ml of the purified antibody sample was dispensed at 150 µl into respective reaction wells. In addition, a reaction well containing no anti-CD20 chimeric isotype antibody (0% reaction well) was prepared as a control in case CDC was not induced, and a reaction well containing no Daudi cell (100% reaction well) as a control in case CDC was induced. After culturing at 37° C. for 2 hours in an atmosphere of 5% $CO_2$, WST-1 reagent (manufactured by ROCHE) was added at 15 µl into respective reaction wells and allowed to react at 37° C. for 4 hours in an atmosphere of 5% $CO_2$. After completion of the reaction, OD450 in each well was measured, and the CDC activity (%) was calculated from the absorbance of each well using the following formula:

CDC activity (%)=100×{1−(reaction well absorbance−100% reaction well absorbance)/(0% reaction well absorbance−100% reaction well absorbance)}

Figure 7:
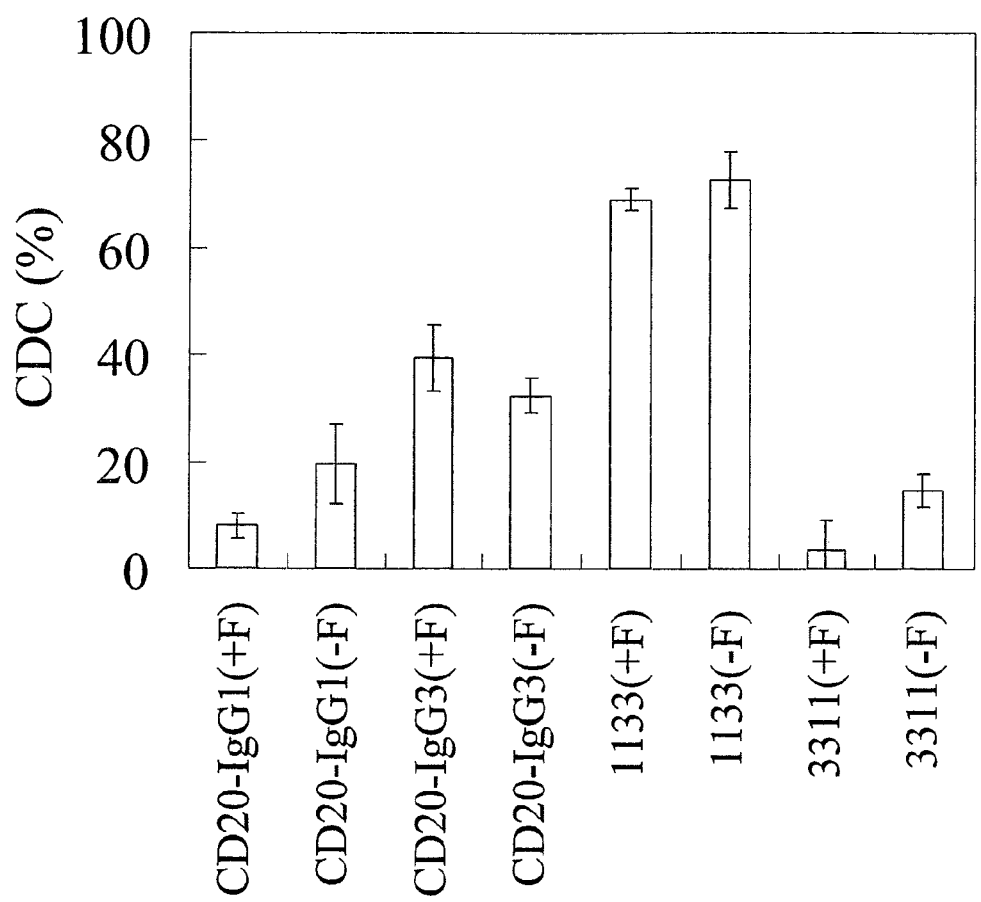
FIG. 7 shows the CDC activity of anti-CD20 human IgG1 antibody, anti-CD20 human IgG3 antibody and 1133-type anti-CD20 chimeric isotype antibody and 3311-type anti-CD20 chimeric isotype antibody to Daudi cell. The abscissa shows sample names, and the ordinate shows the CDC activity. The graph shows the CDC activity of each sample at a concentration of 0.3 μg/ml.

The results are shown in FIG. 7. As is shown in FIG. 7, the CDC activity of the anti-CD20 human IgG3 antibody was higher than that of the anti-CD20 human IgG1 antibody, so that it was confirmed that the CDC activity of IgG3 is higher than that of IgG1. However, the CDC activity of the 1133-type anti-CD20 chimeric isotype antibody is remarkably higher than that of the anti-CD20 human IgG3 antibody. On the other hand, the CDC activity of the 3311-type anti-CD20 chimeric isotype antibody was low similarly to that of the anti-CD20 human IgG1 antibody. Also, in all of the anti-CD20 antibodies, the antibody samples produced by CHO/DG44 as the host cell and the antibody samples produced by CHO/FUT8$^{-/-}$ as the host cell showed almost the same CDC activity, and the presence or absence of the fucose in the sugar chains bound to the antibody had no influence on the CDC activity. Furthermore, similar results were found in an antibody concentration of 1 µg/ml. Based on these results, it was found that the CDC activity of the 1133-type anti-CD20 chimeric isotype antibody is higher than that of the anti-CD20 human IgG1 antibody and the anti-CD20 human IgG3 antibody, and that the presence or absence of the fucose in the sugar chains bound to Fc has no influence on the CDC activity.

3. CDC Activity Measurement of 1133-Type Anti-CD20 Chimeric Isotype Antibody

In order to further fully evaluate CDC activity of the 1133-type anti-CD20 chimeric isotype antibodies which showed particularly high CDC activity in the item 2 of this Example, measurement of CDC activity was carried out in the same manner as in the item 2 of this Example using a CD20-positive Burkitt lymphoma-derived cell line ST 486 cell (ATCC: CRL-1647) or Burkitt lymphoma-derived cell line Raji cell (ATCC: CCL-86).

The results are shown in FIG. 8. As is shown in FIG. 8, in each of the ST 486 cell line (FIG. 8A) and Raji cell line (FIG. 8B), the CDC activity of the anti-CD20 human IgG3 antibody was higher than that of the anti-CD20 human IgG1 antibody, and the 113-type anti-CD20 chimeric isotype antibody showed higher CDC activity than the anti-CD20 human IgG1 antibody and the anti-CD20 human IgG3 antibody. In addition, in all of these anti-CD20 antibodies, the antibody samples produced by CHO/DG44 as the host cell and the antibody samples produced by CHO/FUT8$^{-/-}$ as the host cell showed almost the same CDC activity and it was shown that the presence or absence of the fucose in the sugar chains bound to the antibody ha no influence on the CDC activity.

4. Measurement of ADCC Activity of Various Anti-CD20 Antibodies to Cd20-Positive Cell Line In vitro ADCC activity of the purified samples of various anti-CD20 antibodies obtained in the item 5 of Example 1 was measured in the following manner using a CD20-positive Daudi cell as the target cell. Cytotox 96 Kit (manufactured by Promega) was used in the measurement.

(1) Preparation of Human Effector Cell Suspension

From a healthy volunteer, 50 ml of peripheral blood was collected and gently mixed with 0.2 ml of heparin sodium (manufactured by Takeda Pharmaceutical). A monocyte fraction was separated from this using Lymphoprep (manufactured by Daiichi Pure Chemicals) in accordance with the instructions attached thereto and then washed by centrifugation once with RPMI 1640 medium and once with 10% FBS-RPMI 1640 medium, and the cell was used as the effector cell.

(2) Measurement of ADCC Activity

The reaction was carried out in a 96-well flat-bottomed plate (manufactured by Falcon), and 10% FBS-RPMI 1640 medium containing $2\times10^5$ cells of the effector cell and $1\times10^4$ cells of the Daudi cell or ST 486 cell and containing each anti-CD20 antibody at varied concentration was dispensed at 200 µl into each reaction well. In addition, a medium well without the effector cell, target cell and antibody, an effector well containing the effector cell alone, a target well containing the target cell alone, an NK well containing the effector cell and target cell without antibody, a 100% reaction well containing the target cell alone and to which 20 µl of the Lysis buffer attached to the kit was added 3 hours and 15 minutes after commencement of the reaction, and a 100% reaction control well without the effector cell, target cell and antibody and to which 20 µl of the Lysis buffer attached to the kit was added 3 hours and 15 minutes after commencement of the reactions, were respectively prepared as subjective wells necessary for calculating ADCC activity. After carrying out reaction at 37° C. for 4 hours under an atmosphere of 5% $CO_2$ in each reaction well, the reaction plate was centrifuged to recover 50 µl of supernatant from each well. The supernatants of wells were respectively transferred to the wells of a 96-well U-bottom plate (manufactured by Sumitomo Bakelite), and a coloring substrate solution (prepared by dissolving one ampoule of the substrate attached to the kit in 12 ml of the assay buffer attached to the kit) was added at 50 µl into each well. The coloring reaction was carried out at 37° C. for 30 minutes, the reaction termination solution attached to the kit was added at 50 µl to each well, and then OD450 was measured to calculate the ADCC activity (%) from the absorbance of each well using the following formula.

$$\text{ADCC activity } (\%)=100\times(S-E-T)/(\text{Max}-T)$$

Figure 9:
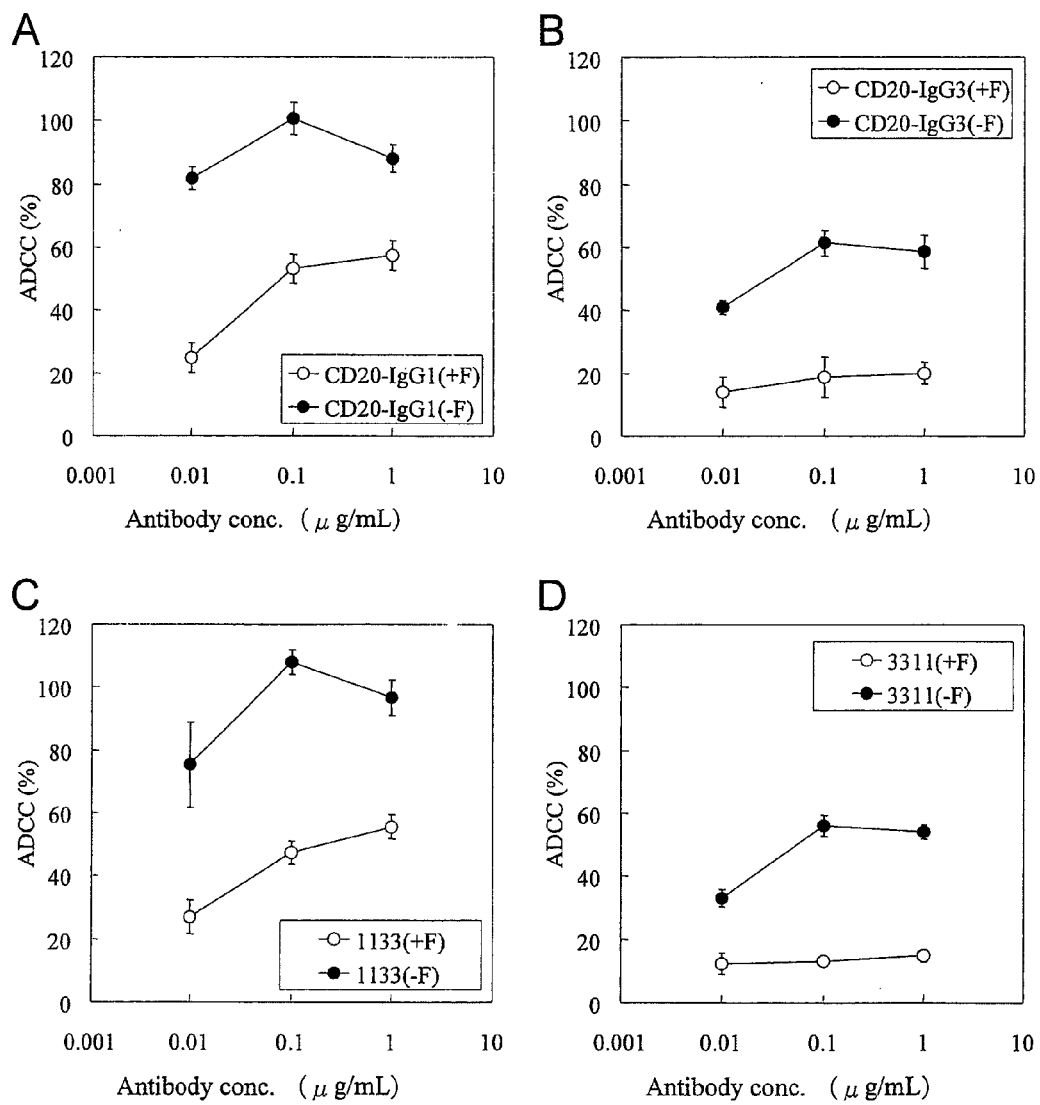
FIG. 9 shows the ADCC activity of anti-CD20 human IgG1 antibody, anti-CD20 human IgG3 antibody, 1133-type anti-CD20 chimeric isotype antibody and 3311-type anti-CD20 chimeric isotype antibody to Daudi cell. The abscissa shows an antibody concentration, and the ordinate shows the ADCC activity at each antibody concentration. Regarding ○ and ● in the graphs, the corresponding sample is different in each graph, and graph A shows CD20-IgG1(+F) (○) and CD20-IgG1(−F) (●), graph B shows CD20-IgG3(+F) (○) and CD20-IgG3(−F) (●), graph C shows 1133(+F) (○) and 1133(−F) (●), and graph D shows 3311(+F) (○) and 3311(−F) (●).

S=sample reaction well absorbance—medium well absorbance
E=effector well absorbance—medium well absorbance
T=target well absorbance—medium well absorbance
Max=100% reaction well—100% reaction control well The results are shown in FIG. 9. As is shown in FIG. 9, in all of the anti-CD20 antibodies, the antibody samples produced from CHO/FUT8$^{-/-}$ showed higher ADCC activity than the antibody samples produced from CHO/DG44. From this result, it was found that, also in the case of all of the anti-CD20 chimeric isotype antibodies prepared in this Example, the ADCC activity is increased in the antibody composition in which fucose is not bound to the N-acetylglucosamine existing in the reducing terminal in the complex-type N-glycoside-linked sugar chain bound to the Fc of the antibody, in comparison with the antibody composition in which fucose is bound to the N-acetylglucosamine existing in the reducing terminal of the complex-type N-glycoside-linked sugar chain bound to the Fc of the antibody. Also, it was confirmed that the anti-CD20 human IgG1 antibodies show higher ADCC activity than that of the anti-CD20 human IgG3 antibodies, that is, ADCC activity of IgG1 is higher than that of IgG3. Also, the 1133-type anti-CD20 chimeric isotype antibodies maintained high ADCC activity similar to the level of anti-CD20 human IgG1 chimeric antibodies. In addition, it was found that ADCC activity of the 3311-type anti-CD20 chimeric isotype antibodies is low similarly to the level of anti-CD20 human IgG3 antibodies.

5. Measurement of the Binding Activity of Various Anti-CD20 Antibodies to Recombinant Fcγ Receptor IIIa In order to analyze the ADCC activity enhancing mechanism by the 1133-type anti-CD20 chimeric isotype antibody confirmed in the item 4 of this Example, the binding activity of the purified samples of the various anti-CD20 antibodies obtained in the item 5 of Example 1 to Fcγ receptor Ma (hereinafter referred to as FcγRIIIa) which is one of Fc receptor family expressing on the surface of NK cell was measured in accordance with a conventionally known method [*Clin. Cancer Res.*, 10, 6248 (2004)].

Figure 10:
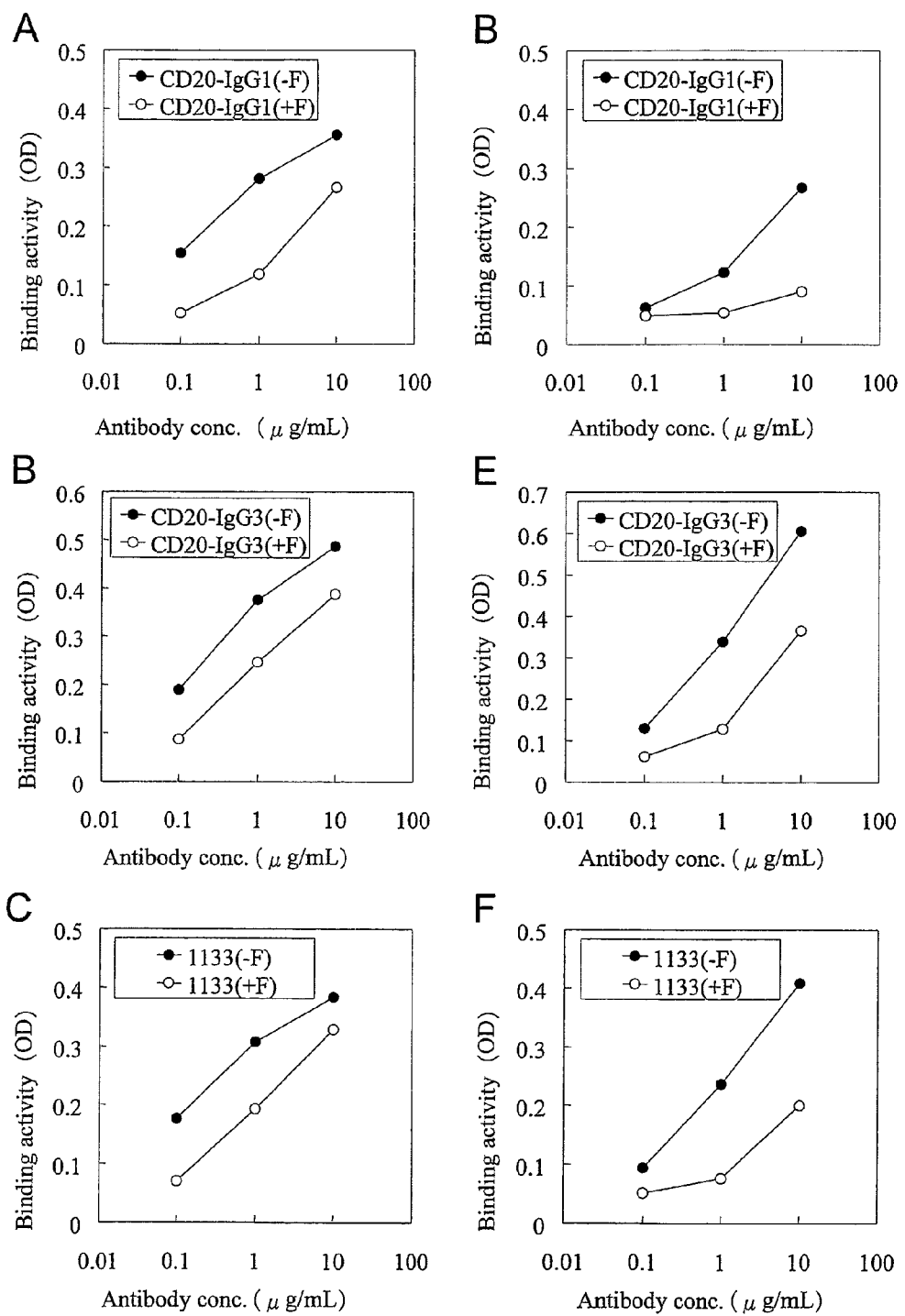
FIG. 10 shows the binding activity of anti-CD20 human IgG1 antibody, anti-CD20 human IgG3 antibody and 1133-type anti-CD20 chimeric isotype antibody to soluble human FcγRIIa (valine-type) (A to C) or soluble human FcγRIIa (phenylalanine-type) (D to F) in ELISA in the absence of the antigen CD20. The abscissa shows an antibody concentration, and the ordinate shows absorbance at each antibody concentration. Graphs A and D show binding activity of CD20-IgG1(−F) (●) and CD20-IgG1(+F) (O), graphs B and E show that of CD20-IgG3(−F) (●) and CD20-IgG3(+F) (○), and graphs C and F show that of 1133(−F) (●) and 1133(+F) (○) to the soluble human FcγRIIa (valine-type) (A to C) or the soluble human FcγRIIa (phenylalanine-type) (D to F).

The results are shown in FIG. 10. As is shown in FIG. 10, the anti-CD20 antibodies produced by CHO/FUT8$^{-/-}$ showed higher binding activity for FcγRIIIa than that of the anti-CD20 antibodies produced by CHO/DG44. Based on this result, it was found that the increase of ADCC activity of antibody, due to the presence or absence of the fucose binding to the N-acetylglucosamine existing in the reducing terminal in the complex-type N-glycoside-linked sugar chain which is bound to Fc of the 1133-type anti-CD20 chimeric isotype antibody, is caused by increase of the binding activity of the Fc region to the Fc receptor.

Based on the above, the 1133-type anti-CD20 chimeric isotype antibody having the same heavy chain variable region, light chain variable region and light chain constant region as the anti-CD20 human IgG1 chimeric antibody RITUXAN™, in which CH1 and the hinge of the heavy chain constant region are the amino acid sequences of human IgG1 antibody and Fc is the amino acid sequence of human IgG3 antibody, has CDC activity that exceeds anti-CD20 human IgG1 antibody and anti-CD20 human IgG3 chimeric antibody and also has ADCC activity substantially equivalent to that of the anti-CD20 human IgG1 antibody. In addition, it was shown that the activity of binding Fc to an Fc receptor is increased and the ADCC activity is improved similarly to the case of the anti-CD20 human IgG1 antibody by removing fucose binding to the N-acetylglucosamine in the reducing terminal in the complex-type N-glycoside-linked sugar chain bound to the Fc.

Relationship between structures and activities of each of the prepared chimeric isotype antibodies is shown in Table 3 based on the results obtained in the above. In the table, ADCC activity and CDC activity were expressed in descending order as +++, ++ and +.

TABLE 3

| Purified antibody (name) | CH1 | Hinge | CH2 | CH3 | ADCC | CDC | Protein A |
|---|---|---|---|---|---|---|---|
| CD20-IgG1(+F) | IgG1 | IgG1 | IgG1 | IgG1 | ++ | + | + |
| CD20-IgG1(−F) | IgG1 | IgG1 | IgG1 | IgG1 | +++ | + | + |
| CD20-IgG3(+F) | IgG3 | IgG3 | IgG3 | IgG3 | + | ++ | − |
| CD20-IgG3(−F) | IgG3 | IgG3 | IgG3 | IgG3 | ++ | ++ | − |
| 1133(+F) | IgG1 | IgG1 | IgG3 | IgG3 | ++ | +++ | − |
| 1133(−F) | IgG1 | IgG1 | IgG3 | IgG3 | +++ | +++ | − |
| 3311(+F) | IgG3 | IgG3 | IgG1 | IgG1 | + | + | + |
| 3311(−F) | IgG3 | IgG3 | IgG1 | IgG1 | ++ | + | + |

Based on the above, it was shown that 1133-type chimeric isotype antibody molecule having a heavy chain constant region in which CH1 and the hinge are amino acid sequences of human IgG1 antibody and CH2 and CH3 are amino acid sequences of human IgG3 antibody has CDC activity higher than that of the human IgG1 antibody and human IgG3 antibody and maintains high ADCC activity substantially equivalent to that of the human IgG1 antibody.

According to the above results, it was found that the CDC activity of an anti-CD20 human IgG1 antibody is remarkably enhanced by swapping the Fc among the heavy chain constant region of an anti-CD20 human IgG1 antibody with the amino acid sequence of an anti-CD20 human IgG3 antibody.

EXAMPLE 3

Production of 1131-Type Anti-CD20 Chimeric Isotype Antibody and 1113-Type Anti-CD20 Chimeric Antibody Using Animal Cell 1. Production of Expression Vector for 1131-Type Anti-CD20 Chimeric Isotype Antibody and Expression Vector for 1113-Type Anti-CD20 Chimeric Isotype Antibody Next, in order to examine which domain of the Fc region should be swapped with the amino acid sequence of human IgG3 antibody to enhance the CDC activity, the chimeric isotype antibody in which each of the CH2 domain or CH3 domain of the 1133-type was replaced with each of the amino acid sequence of human IgG1 antibody was prepared. The CDC activity was measured to compare which domain was important for enhancing the CDC activity. An anti-CD20 chimeric isotype antibody having a heavy constant region in which CH1, the hinge and CH3 are a human IgG1 antibody and only CH2 domain is a human IgG3 antibody is referred to as 1131-type, and an anti-CD20 chimeric isotype antibody having a heavy chain constant region in which CH1, the hinge and CH2 are a human IgG1 antibody and only CH3 domain is a human IgG antibody is referred to as 1113-type. In all of anti-CD20 chimeric isotype antibodies, the amino acid sequences of the heavy chain variable region, the light chain variable region and the light chain constant region are the same as the amino acid sequences of the heavy chain variable region, the light chain variable region and the light chain constant region, respectively, of an anti-CD20 human IgG1 antibody encoded by pKANTEX2B8P. Domain structures of heavy chain constant region and amino acid sequences of the anti-CD20 chimeric isotype antibodies are shown in Table 4. All of these chimeric isotype antibodies have a novel heavy chain constant region. In addition, a schematic illustration of each chimeric isotype is shown in FIG. 11.

TABLE 4

| Structure name | CH1 | Hinge | CH2 | CH3 | Amino acid sequence |
|---|---|---|---|---|---|
| 1113 | IgG1 | IgG1 | IgG1 | IgG3 | SEQ ID NO: 5 |
| 1131 | IgG1 | IgG1 | IgG3 | IgG1 | SEQ ID NO: 6 |

Figure 12:
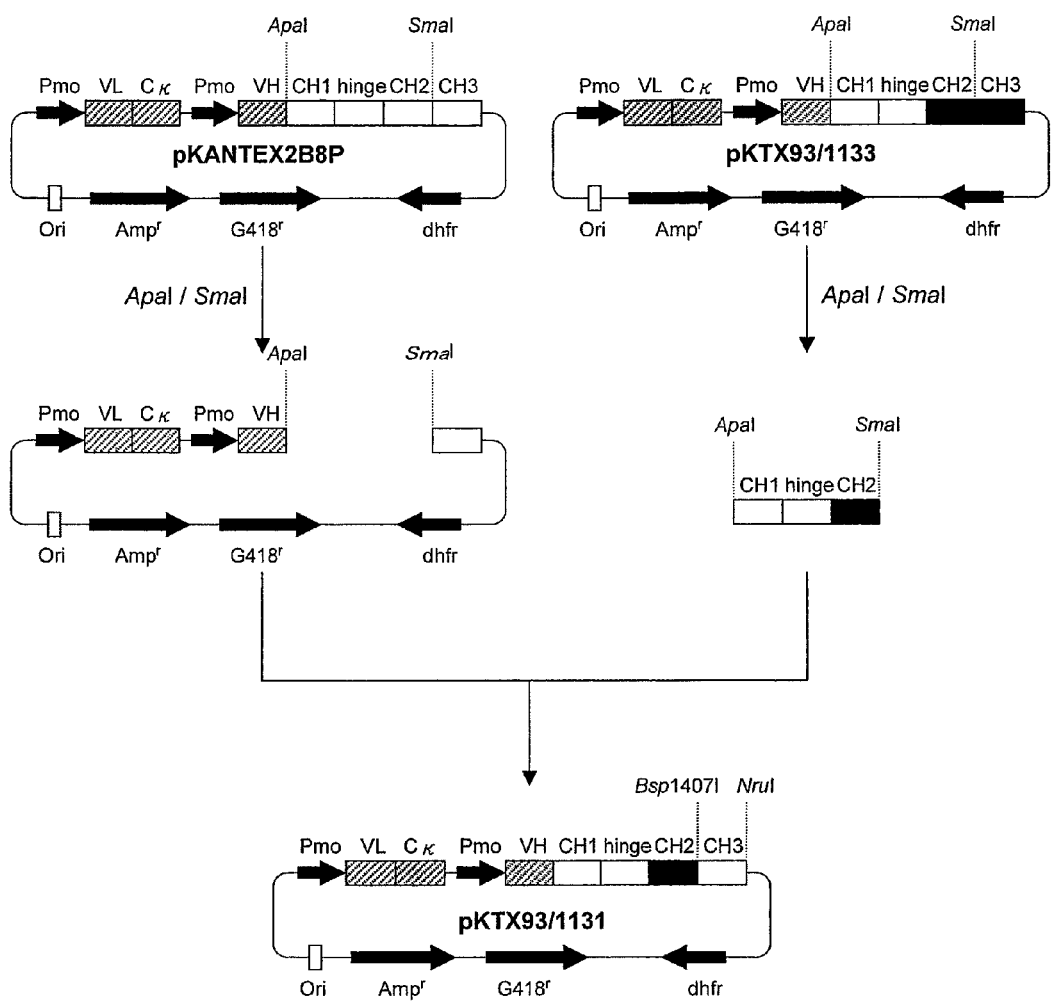
FIG. 12 shows construction steps of a plasmid pKTX93/1131.

(1) Construction of Expression Vector Encoding 1131-Type Anti-Cd20 Chimeric Isotype Antibody Expression vector pKTX93/1131 (FIG. 12) encoding a 1131-type anti-CD20 chimeric isotype antibody was constructed in accordance with the following procedure. First, a DNA fragment of about 700 bp encoding CH1, the hinge and CH2 was cleaved and purified from the expression vector for 1133-type anti-CD20 chimeric isotype antibody, pKTX93/1133, described in the item 1 of this Example using restriction enzymes ApaI (manufactured by Takara Shuzo) and SmaI (manufactured by Takara Shuzo). On the other hand, a DNA fragment of about 13 kbp was cleaved and purified by the same treatment with restriction enzymes on the expression vector for anti-CD20 human IgG1 antibody, pKANTEX2B8P. After mixing these purified DNA preparations, a ligation reaction was carried out using Ligation High solution (manufactured by TOYOBO), and *Escherichia coli* XL1-BLUE MRF' (manufactured by Stratagene) was transformed using the reaction solution. Each plasmid DNA was prepared from the thus obtained transformant clones and allowed to react using Big Dye Terminator Cycle Sequencing Kit v3.1 (manufactured by Applied Biosystems) in accordance with the instructions attached thereto, and then the nucleotide sequence of the DNA inserted into each plasmid was analyzed by a DNA sequencer ABI PRISM 3700 DNA Analyzer of the same company to confirm that the plasmid pKTX93/1131 shown in FIG. 12 was obtained.

Figure 13:
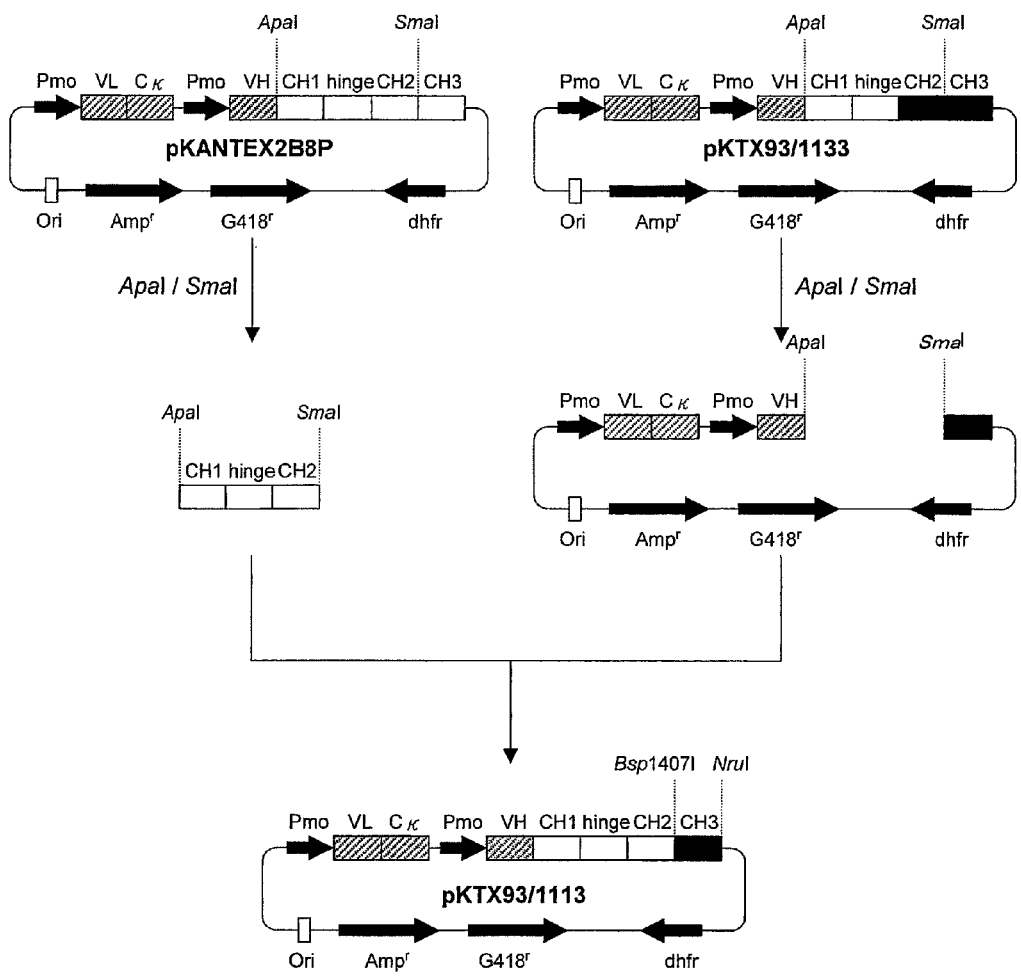
FIG. 13 shows construction steps of a plasmid pKTX93/1113.

(2) Construction of Expression Vector Encoding 1113-Type Anti-CD20 Chimeric Isotype Antibody Expression vector pKTX93/1113 (FIG. 13) encoding a 1113-type anti-CD20 chimeric isotype antibody was constructed in accordance with the following procedure. First, a DNA fragment of about 700 bp encoding CH1, the hinge and CH2 was cleaved and purified from the expression vector for anti-CD20 human IgG1 antibody, pKANTEX2B8P, described in the item 1 of this Example using restriction enzymes ApaI (manufactured by Takara Shuzo) and SmaI (manufactured by Takara Shuzo). On the other hand, a DNA fragment of about 13 kbp was cleaved and purified by carrying out the same restriction enzyme treatment on the expression vector for 1133-type anti-CD20 chimeric isotype antibody, pKTX93/1113, described in the item 1 of this Example. After mixing these purified DNA preparations, a ligation reaction was carried out using Ligation High solution (manufactured by TOYOBO), and *Escherichia coli* XL1-BLUE MRF' (manufactured by Stratagene) was transformed using the reaction solution. Each plasmid DNA was prepared from the thus obtained transformant clones and allowed to react using Big Dye Terminator Cycle Sequencing Kit v3.1 (manufactured by Applied Biosystems) in accordance with the instructions attached thereto, and then the nucleotide sequence of the DNA inserted into each plasmid was analyzed by a DNA sequencer ABI PRISM 3700 DNA Analyzer of the same company to confirm that the plasmid pKTX93/1113 shown in FIG. 13 was obtained.

2. Stable Expression of 1113-Type Anti-CD20 Chimeric Isotype Antibody and 1131-Type Anti-CD20 Chimeric Isotype Antibody in Animal Cell A cell which stably produces the anti-CD20 chimeric isotype antibody was prepared in the same manner as in the item 3 of Example 1 by introducing the expression vector for anti-CD20 chimeric isotype antibody prepared in the item 1 of this Example into the CHO/FUT8$^{-/-}$ described in the item 3 of Example 1 as the host cell.

3. Purification of 1113-Type Anti-CD20 Chimeric Isotype Antibody and 1131-Type Anti-CD20 Chimeric Isotype Antibody The transformant obtained in the item 2 of this Example capable of expressing the 1113-type anti-CD20 chimeric isotype antibody or 1131-type anti-CD20 chimeric isotype antibody was cultured and purified in the same manner as in the item 5 of Example 1. The 1113-type anti-CD20 chimeric isotype antibody and 1131-type anti-CD20 chimeric isotype antibody were purified using a column packed with Prosep-G (Protein-G binding resin: manufactured by Millipore). In addition, when the 1133-type anti-CD20 chimeric isotype antibody, 1113-type anti-CD20 chimeric isotype antibody and 1131-type anti-CD20 chimeric isotype antibody were purified using a column packed with Prosep-A (Protein-A binding resin: manufactured by Millipore), only the 1131-type anti-CD20 chimeric isotype antibody was capable of being purified. As host cells, CHO/FUT8$^{-/-}$ were used in each case.

The expression vector and name of the purified antibody for each chimeric isotype antibody are shown in Table 5.

TABLE 5

| Expression vector | Purified antibody (name) |
|---|---|
| pKTX93/1131 | 1131(–F) |
| pKTX93/1113 | 1113(–F) |

4. Evaluation of Purification Degree of 1113-Type Anti-CD20 Chimeric Isotype Antibody and 1131-Type Anti-CD20 Chimeric Isotype Antibody by SDS-Page In order to measure purification degree of the various anti-CD20 chimeric isotype antibodies obtained in the item 3 of this Example, SDS-PAGE was carried out in the same manner as in the item 6 of Example 1. As comparative controls of electrophoresis, the same operation was also carried out for the various CD20-IgG1(–F), CD20-IgG3(–F) and 1133(–F) prepared in the item 5 of Example 1.

Figure 14:
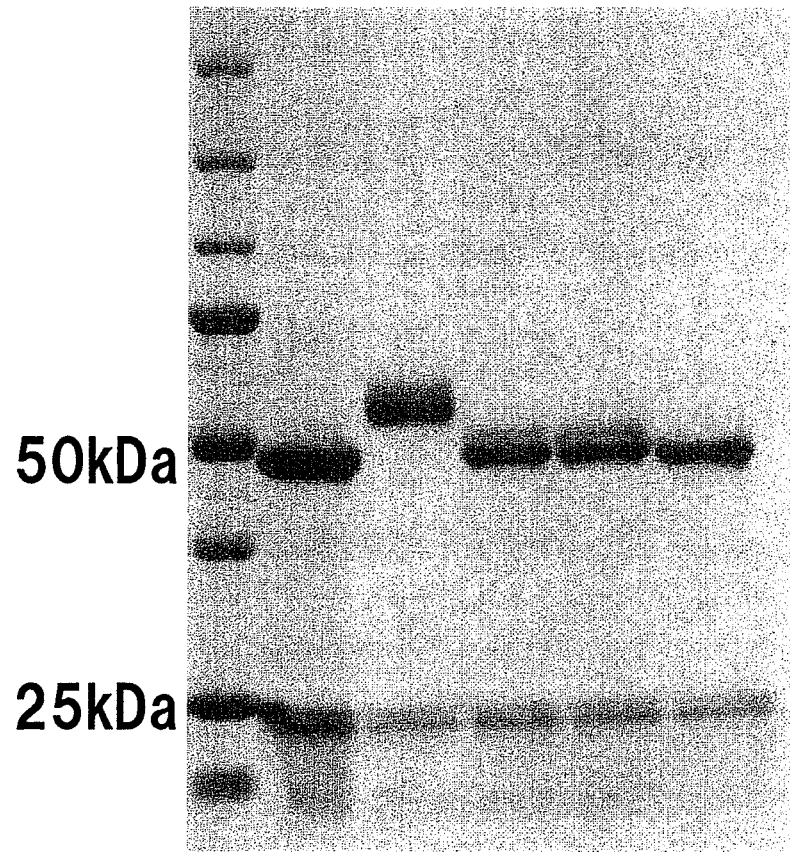
FIG. 14 shows SDS-PAGE electrophoresis patterns of anti-CD20 human IgG1 antibody, anti-CD20 human IgG3 antibody, 1133-type anti-CD20 chimeric isotype antibody, 1131 0type anti-CD20 chimeric isotype antibody and 1113-type anti-CD20 chimeric isotype antibody which were purified. Staining of proteins was carried out with Coomassie Brilliant Blue (CBB). Lane 1 corresponds to a molecular weight marker, lane 2 corresponds to CD20-IgG1(−F), lane 3 corresponds to CD20-IgG(−F), lane 4 corresponds to 1133(−F), lane 5 corresponds to 1113(−F) and lane 6 corresponds to 1131(−F).

The results are shown in FIG. 14. The 1113(–F) and 1131(–F) showed electrophoresis patterns similar to the CD20-IgG1(–F) and 1133(–F), respectively. The molecular weights deduced from the amino acid sequences of H chain and L chain constituting the 1113(–F) and 1131(–F) are similar to each other, and the H chain is about 50 kDa and the L chain is about 24 kDa. Since these molecular weights are similar to the H chain and L chain molecular weights of the CD20-IgG1(–F) and 1133(–F), and the electrophoresis patterns are also similar thereto, it was confirmed that the 1113(–F) and 1131(–F) are constituted by the desired H chain and L chain. In addition, the molecular weight deduced from the amino acid sequence of L chain constituting the CD20-IgG3(–F) was about 24 kDa which is similar to that of the CD20-IgG1(–F), but the H chain constituting the CD20-IgG3(–F) was about 54 kDa which is larger than that of the H chain of the CD20-IgG1(–F), so that L chain of the CD20-IgG3(–F) appeared at a position similar to that of the L chain of the CD20-IgG1(–F), but the bond of H chain of the CD20-IgG3(–F) was positioned at a high molecular weight side than that of H chain of the CD20-IgG1(–F). Based on the above results, it was confirmed that the desired IgG molecules respectively constituted by H chain and L chain are contained at a sufficient ratio in the various anti-CD20 chimeric isotype antibodies obtained in the item 3 of this Example.

EXAMPLE 4

Evaluation of Activities of 1113-Type Anti-CD20 Chimeric Isotype Antibody and 1131-Type anti-CD20 Chimeric Isotype Antibody Using the purified samples of various anti-CD20 chimeric isotype antibodies obtained in the item 3 of Example 3, various activities were compared in the following manners.

1. Measurement of CDC Activity of 1113-Type Anti-CD20 Chimeric Isotype Antibody and 1131-Type Anti-CD20 Chimeric Isotype Antibody By using anti-CD20 human IgG1 antibody CD20-IgG1(–F), anti-CD20 human IgG3 antibody CD20-IgG3(–F) and 1133-type anti-CD20 chimeric isotype antibody 1133(–F) obtained in the item 5 of Example 1, and 1131-type anti-CD20 chimeric isotype antibody 1131(–F) and 1113-type anti-CD20 chimeric isotype antibody 1113(–F) obtained in the item 3 of Example 3, the CDC activities on CD20-positive cell lines were evaluated according to the same procedure as in the item 2 of Example 2 by using CD20-positive ST486 cells or Raji cells.

Figure 15:
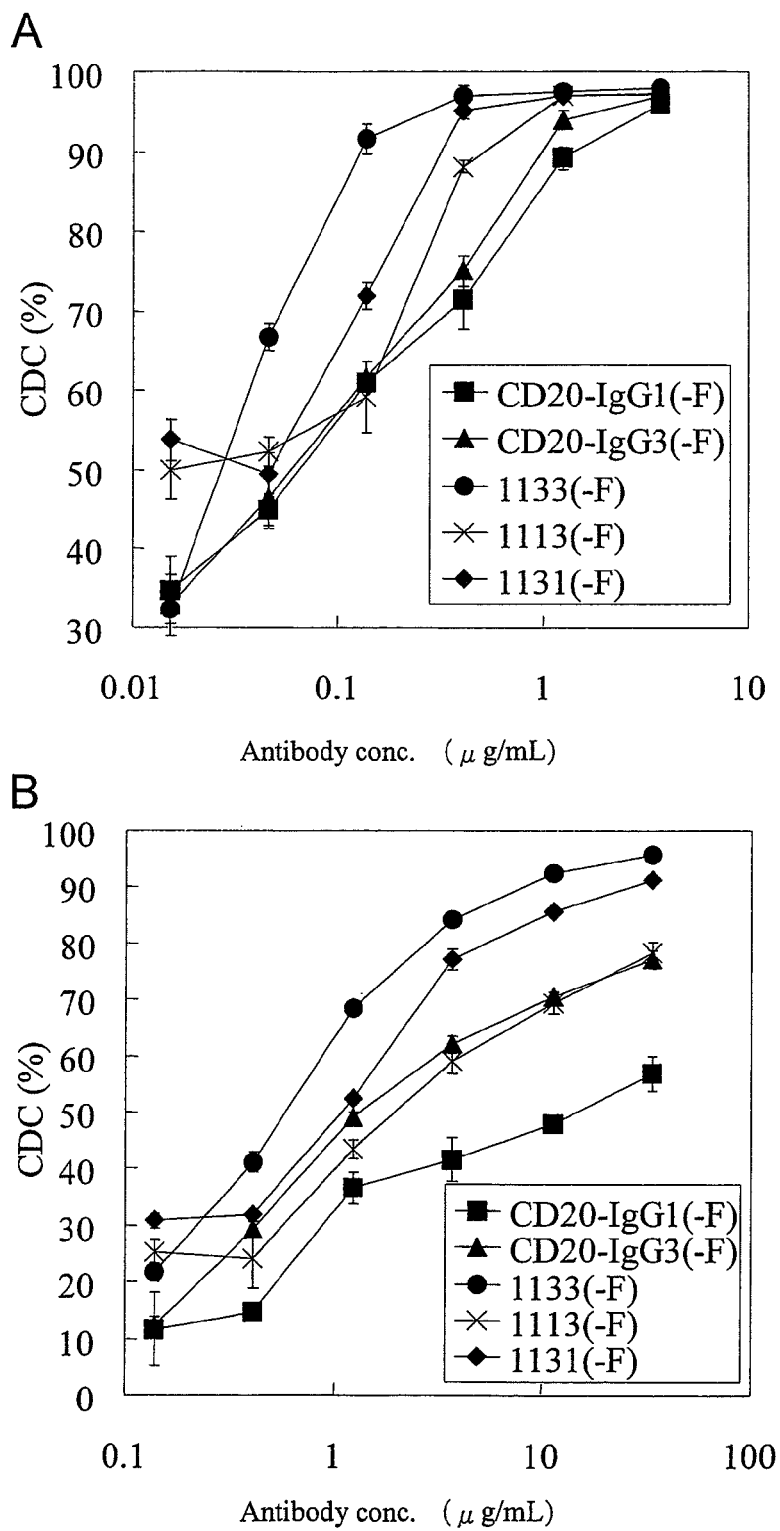
FIG. 15 shows the CDC activity of anti-CD20 human IgG1 antibody, anti-CD20 human IgG3 antibody, 1133-type anti-CD20 chimeric isotype antibody, 1131-type anti-CD20 chimeric isotype antibody and 1113-type anti-CD20 chimeric isotype antibody to ST 486 cell (A) or Raji cell (B). The abscissa shows an antibody concentration, and the ordinate shows the ratio of cytotoxicity at each antibody concentration. In the graph, ■ shows CD20-IgG1(−F), ▲ shows CD20-IgG3(−F), ● shows 1133(−F), × shows 1113(−F) and ♦ shows 1131(−F).

The results are shown in FIG. 15. As is shown in FIG. 15, 1133(–F) showed higher CDC activities on both of the ST486 cell line (FIG. 15A) and the Raji cell line (FIG. 15B) than CD20-IgG1(–F) and CD20-IgG3(–F). 1113(–F) and 1131(–F) showed higher CDC activity than CD20-IgG1(–F) and CD20-IgG3(–F) but lower than 1133(–F). In these antibodies, therefore, it is understood that the CDC activity strength decreases in the following order: 1133(–F)>1131(–F)>1113(–F)>IgG3(–F)>IgG1(–F).

Based on these results, it was found that the CDC activity of the 1133-type anti-CD20 chimeric isotype antibody, which has been enhanced by swapping the Fc of human IgG1 antibody with the Fc of human IgG3 antibody, is largely attenuated by replacing the CH2 domain in the Fc of human IgG3 antibody with the human IgG1 antibody.

The above results indicate how it is important to swap the amino acid sequence in the CH2 domain in the Fc of human IgG1 antibody with the amino acid sequence of the human IgG3 antibody in order to enhance the CDC activity.

2. Measurement of ADCC Activity of 1113-Type Anti-CD20 Chimeric Isotype Antibody and 1131-Type Anti-CD20 Chimeric Isotype Antibody on CD20-Positive Cell Line By using anti-CD20 human IgG1 antibody CD20-IgG1(–F), anti-CD20 human IgG3 antibody CD20-IgG3(–F) and 1133-type anti-CD20 chimeric isotype antibody 1133 (–F) obtained in the item 5 of Example 1, and 1131-type anti-CD20 chimeric isotype antibody 1131(–F) and 1113-type anti-CD20 chimeric isotype antibody 1113(–F) obtained in the item 3 of Example 3, in vitro ADCC activities were measured according to the same procedure as in the item 5 of Example 2 by using CD20-positive Daudi cells as the target cells. Cytotox 96 kit (Promega) was employed in the measurement.

Figure 16:
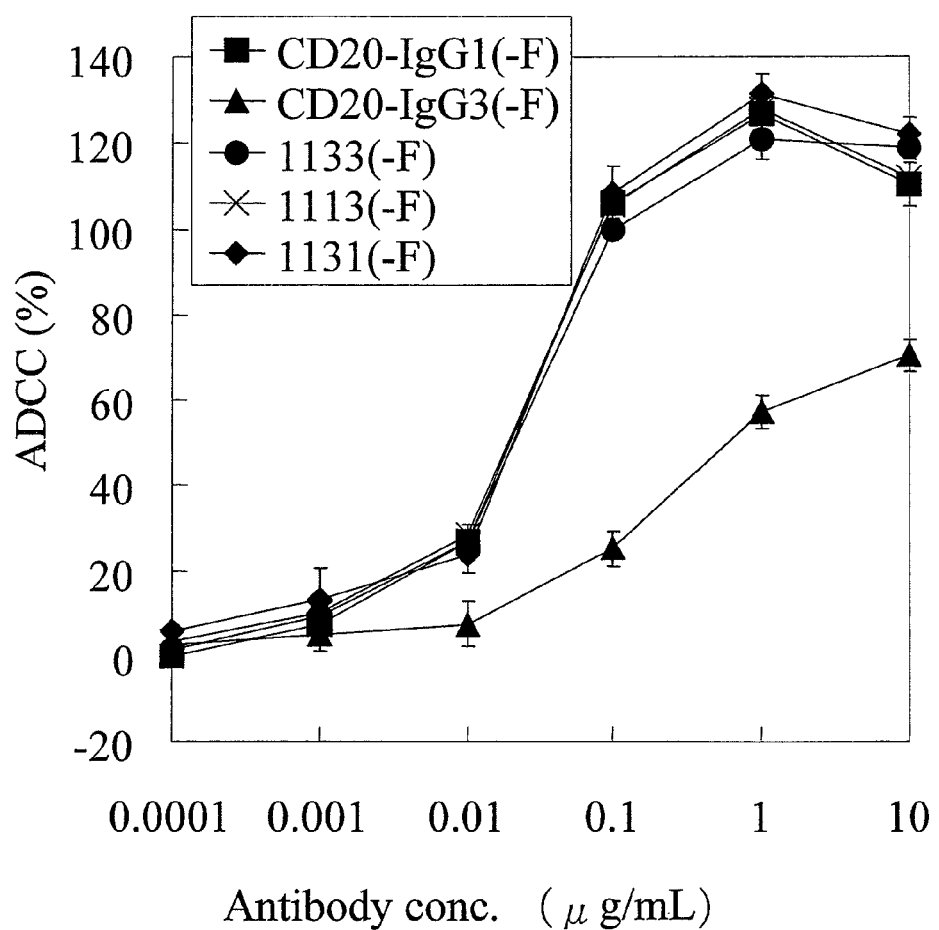
FIG. 16 shows the ADCC activity of anti-CD20 human IgG1 antibody, anti-CD20 human IgG3 antibody, 1133-type anti-CD20 chimeric isotype antibody, 1131-type anti-CD20 chimeric isotype antibody and 1113-type anti-CD20 chimeric isotype antibody to Daudi cell. The abscissa shows an antibody concentration, and the ordinate shows the ratio of cytotoxicity at each antibody concentration. In the graph, ■ shows CD20-IgG1(−F), ▲ shows CD20-IgG3(−F), ● shows 1133(−F), × shows 1113(−F) and ♦ shows 1131(−F).

The results are shown in FIG. 16. Thus, 1113(-F) and 1131(-F) showed ADCC activities similar to CD20-IgG1(-F) and 1133(-F).

3. Measurement of Protein A-Binding Activity of 1113-Type Anti-CD20 Chimeric Isotype Antibody and 1131-Type Anti-CD20 Chimeric Isotype Antibody By using anti-CD20 human IgG1 antibody CD20-IgG1(-F), anti-CD20 human IgG3 antibody CD20-IgG3(-F) and 1133-type anti-CD20 chimeric isotype antibody 1133 (-F) obtained in the item 5 of Example 1, and 1131-type anti-CD20 chimeric isotype antibody 1131(-F) and 1113-type anti-CD20 chimeric isotype antibody 1113(-F) obtained in the item 3 of Example 3, the protein A-binding activities were measured in accordance with the following procedures.

Anti-human kappa chain antibody (manufactured by Sigma) was diluted with PBS to 5 µg/mL, was dispensed into a 96-well ELISA plate (manufactured by Grainer) at 50 µl/well, and was allowed to stand for adsorption at room temperature overnight. After the reaction, the plate was washed with PBS and 100 µL/well of 1% BSA-PBS was added and reaction was carried out at room temperature for 1 hour to block the remaining active groups. Then, 1% BSA-PBS was removed and each anti-CD20 antibody to be measured was added at 50 µL/well and reaction was carried out at room temperature for 2 hours. After the completion of the reaction, the wells were washed with Tween-PBS and peroxidase-labeled Protein A (manufactured by Amersham Bioscience) diluted 5000-fold with PBS was added at 50 µL/well and reaction was carried out at 37° C. for 2 hours. After the reaction, the wells were washed with Tween-PBS and an ABTS substrate solution was added at 50 µL/well for color development. Next, the absorbance at 415 nm (hereinafter referred to as OD415) was measured.

Figure 17:
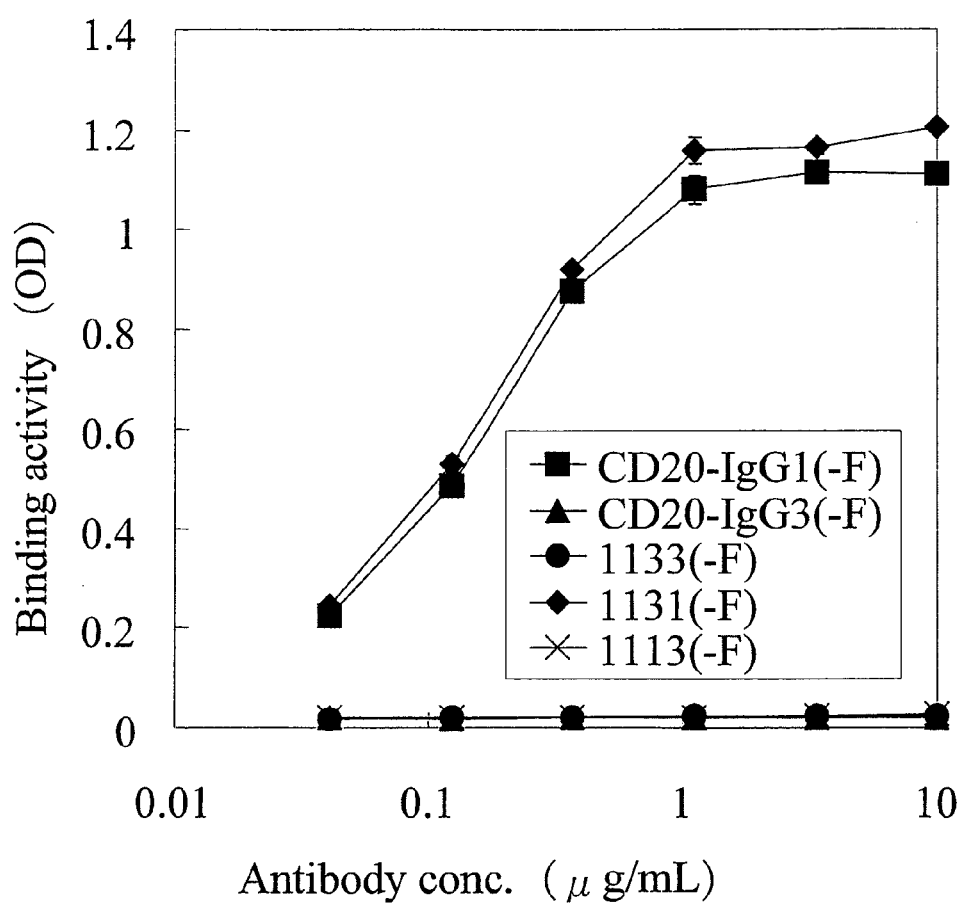
FIG. 17 shows a result of the measurement of the binding activity of anti-CD20 human IgG1 antibody, anti-CD20 human IgG3 antibody, 1133-type anti-CD20 chimeric isotype antibody, 1131-type anti-CD20 chimeric isotype antibody and 1113-type anti-CD20 chimeric isotype antibody to protein A measured by ELISA assay. In the graph, ■ shows CD20-IgG1(−F), ▲ shows CD20-IgG3(−F), ● shows 1133(−F), × shows 1113(−F) and ♦ shows 1131(−F).

The results are shown in FIG. 17. 1133(-F) and 1113(-F) showed no protein A-binding activity similar to CD20-IgG3(-F), while 1131(-F) showed a protein A-binding activity similar to CD20-IgG1(-F).

Table 6 shows the relationship between the structure and activity of each chimeric isotype antibody thus constructed clarified based on these results. In this table, ADCC activity and the CDC activity are expressed in descending order as +++++, ++++, +++, ++ and +. Concerning the protein A-binding activity, + means an antibody showing protein A-binding activity while – means one showing no protein A-binding activity.

TABLE 6

| Purified antibody (name) | CH1 | Hinge | CH2 | CH3 | ADCC | CDC | Protein A |
|---|---|---|---|---|---|---|---|
| CD20-IgG1(-F) | IgG1 | IgG1 | IgG1 | IgG1 | +++ | + | + |
| CD20-IgG3(-F) | IgG3 | IgG3 | IgG3 | IgG3 | ++ | ++ | – |
| 1133(+F) | IgG1 | IgG1 | IgG3 | IgG3 | ++ | +++++ | – |
| 1133(-F) | IgG1 | IgG1 | IgG3 | IgG3 | +++ | +++++ | – |
| 1131(-F) | IgG1 | IgG1 | IgG3 | IgG1 | +++ | ++++ | + |
| 1113(-F) | IgG1 | IgG1 | IgG1 | IgG3 | +++ | +++ | – |

In the item 1 of Example 4, it was found that the CDC activity of 1133-type anti-CD20 chimeric isotype antibody, which has been enhanced by swapping Fc of the human IgG1 antibody with Fc of the human IgG3 antibody, is largely attenuated by replacing the CH2 domain in Fc with the human IgG1 antibody. This result indicates how it is important to swap the amino acid sequence in the Fc in the CH2 domain by the amino acid sequence of the human IgG3 antibody in order to enhance the CDC activity.

It is also indicated that the ADCC activity of an antibody, in which CH1 and the hinge have the amino acid sequences of the human IgG1 antibody and the Fc is the chimeric isotype of the human IgG1 antibody and the human IgG3 antibody, is equivalent to human IgG1 antibody; and increase in the ADCC activity thereof caused by removing fucose bound to N-acetylglucosamine in the reducing terminal of the sugar chain linked to Fc is also equivalent to human IgG1 antibody.

EXAMPLE 5

1. Construction of Various Anti-CD20 Chimeric Isotype Antibodies Using Animal Cells (Analysis on the Amino Acid Sequence in the CH2 Domain and CDC Activity of 1133-Type Anti-CD20 Chimeric Isotype Antibody)

To analyze which region in the CH2 domain of human IgG3 antibody is important in enhancing the CDC activity, various antibodies having the CH2 domain of 1133-type partly replaced with human IgG1 antibody were constructed in the following manner.

First, the amino acid sequences of the CH2 domain in the human IgG1 antibody and the human IgG3 antibody were compared. In accordance with the EU index as in Kabat, et al., it was confirmed that the amino acid residues at positions 274, 276, 296, 300 and 339 were different (FIG. 18). Thus, antibodies wherein the amino acid residues at these five positions in the 1133-type anti-CD20 chimeric isotype antibody were respectively replaced with those in the amino acid sequence of human IgG1 were designed. An anti-CD20 chimeric isotype antibody in which the amino acid residue at position 274 has been replaced with human IgG1 antibody is referred to as 1133(274-IgG1)-type; an anti-CD20 chimeric isotype antibody in which the amino acid residue at position 276 was replaced with the human IgG1 antibody is referred to as 1133(276-IgG1)-type; an anti-CD20 chimeric isotype antibody in which the amino acid residue at position 296 was replaced with the human IgG1 antibody is referred to as 1133(296-IgG1)-type; an anti-CD20 chimeric isotype antibody in which the amino acid residue at position 300 was replaced with human IgG1 antibody is referred to as 1133 (300-IgG1)-type; and an anti-CD20 chimeric isotype antibody in which the amino acid residue at position 339 was replaced with human IgG1 antibody is referred to as 1133 (339-IgG1)-type. The CH3 domain of each of these antibodies is that of human IgG3 antibody. Table 7 shows the amino acid residues (i.e., whether human IgG1 antibody or human IgG3 antibody) at the above five positions in these antibodies.

TABLE 7

| Structural name | 274 | 276 | 296 | 300 | 339 | CH3 | Amino acid sequence |
|---|---|---|---|---|---|---|---|
| 1133 (274-IgG1) | IgG1 | IgG3 | IgG3 | IgG3 | IgG3 | IgG3 | SEQ ID NO: 7 |
| 1133 (276-IgG1) | IgG3 | IgG1 | IgG3 | IgG3 | IgG3 | IgG3 | SEQ ID NO: 8 |

TABLE 7 -continued

| Structural name | 274 | 276 | 296 | 300 | 339 | CH3 | Amino acid sequence |
|---|---|---|---|---|---|---|---|
| 1133 (296-IgG1) | IgG3 | IgG3 | IgG1 | IgG3 | IgG3 | IgG3 | SEQ ID NO: 9 |
| 1133 (300-IgG1) | IgG3 | IgG3 | IgG3 | IgG1 | IgG3 | IgG3 | SEQ ID NO: 10 |
| 1133 (339-IgG1) | IgG3 | IgG3 | IgG3 | IgG3 | IgG1 | IgG3 | SEQ ID NO: 11 |
| IgG1 | IgG1 | IgG1 | IgG1 | IgG1 | IgG1 | IgG1 | SEQ ID NO: 3 |
| 1133 | IgG3 | IgG3 | IgG3 | IgG3 | IgG3 | IgG3 | SEQ ID NO: 4 |
| 1131 | IgG3 | IgG3 | IgG3 | IgG3 | IgG3 | IgG1 | SEQ ID NO: 5 |
| 1113 | IgG1 | IgG1 | IgG1 | IgG1 | IgG1 | IgG3 | SEQ ID NO: 6 |

Figure 19:
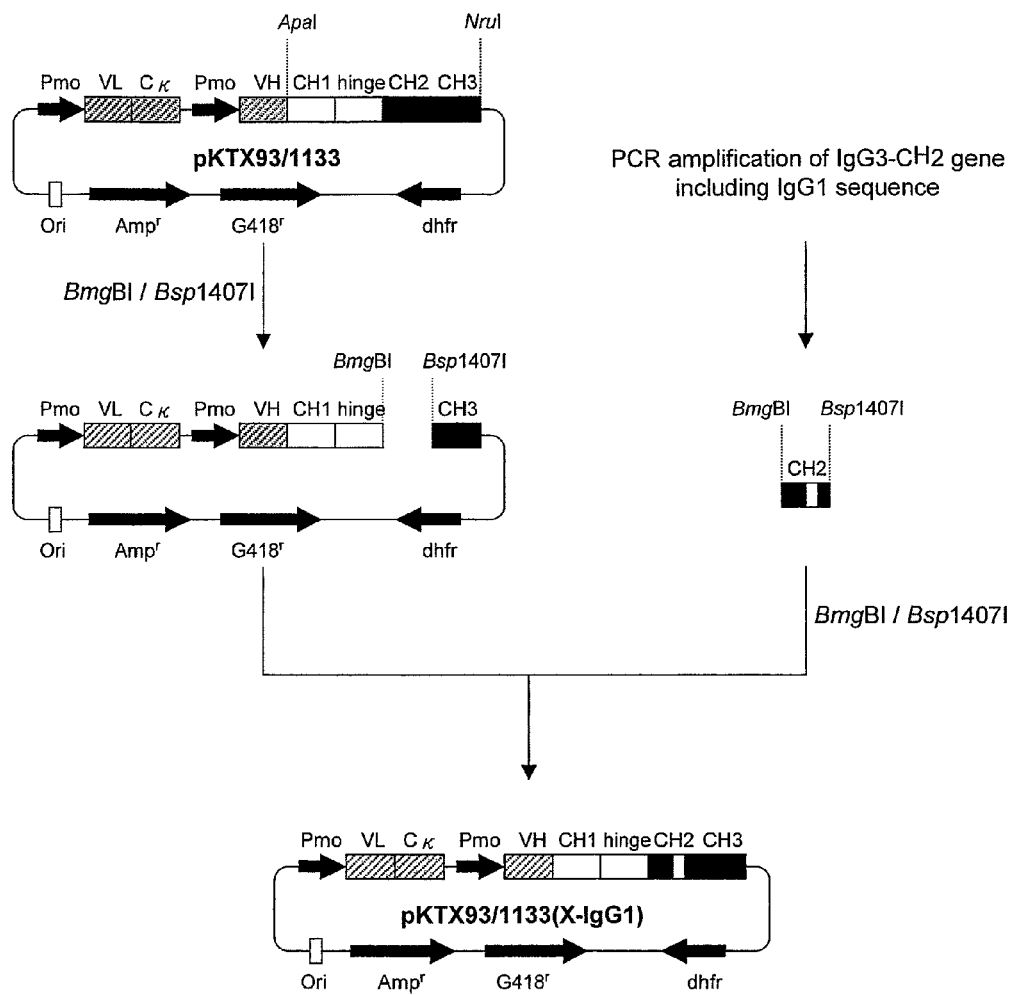
FIG. 19 shows construction steps of plasmids pKTX93/1133(274-IgG1), pKTX93/1133(276-IgG1), pKTX93/1133(296-IgG1), pKTX93/1133(300-IgG1) and pKTX93/1133(339-IgG1).

(1) Construction of Expression Vector Encoding 1133(274-IgG1)-Type Anti-CD20 Chimeric Isotype Antibody Expression vector pKTX93/1133(274-IgG1) (FIG. 19) encoding 1133(274-IgG1)-type anti-CD20 chimeric isotype antibody was constructed in accordance with the following procedures. First, using KOD plus (TOYOBO) and synthetic DNA primers having the nucleotide sequences represented by SEQ ID NOs:12 and 13 (manufactured by FASMAC), PCR was carried out by using the expression vector for 1133-type anti-CD20 chimeric isotype antibody, pKTX93/1133, as described in Example 1 as a template according to the instructions attached to KOD plus. By this PCR, a gene encoding the CH2 domain of the 1133(274-IgG1)-type chimeric isotype was synthesized. Using GeneAmp PCR System 9700 (Applied Biosystems), the PCR was carried out by thermally denaturing at 94° C. for 4 minutes, followed by 25 cycles with each cycle consisting of reactions at 94° C. for 30 seconds, at 55° C. for 30 seconds and at 68° C. for 60 seconds. After completion of the PCR, the reaction mixture was electrophoresed on 1% agarose gel and a DNA fragment of about 250 bp containing a gene encoding the CH2 domain was recovered by using QIAquick Gel Extraction Kit (manufactured by Qiagen). The recovered DNA fragment was digested with restriction enzymes BmgBI (manufactured by New England Biolabs) and Bsp1407I (manufactured by Takara Shuzo) and a DNA fragment of about 250 bp containing the CH2 domain-encoding gene was cleaved and purified. On the other hand, the expression vector for 1133-type anti-CD20 chimeric isotype antibody, pKTX93/1133, as described in Example 1 was subjected to the same restriction enzyme treatment and a DNA fragment of about 13 kbp was cleaved and purified. These purified DNAs were mixed together and subjected to ligation reaction using Ligation High Solution (manufactured by TOYOBO). By using the reaction mixture, Escherichia coli XL1-Blue MRF' (manufactured by Stratagene) was transformed. From clones of the thus obtained transformant, each plasmid DNA was prepared. After reaction by using Big Dye Terminator Cycle Sequencing Kit v3.1 (manufactured by Applied Biosystems) according to the attached instructions, the nucleotide sequence of the DNA inserted into each plasmid was analyzed by using DNA Sequencer ABI PRISM 3700 DNA Analyzer manufactured by the same company. Thus, it was confirmed that the plasmid pKTX93/1133(274-IgG1) shown in FIG. 19 was obtained.

(2) Construction of Expression Vector Encoding 1133(276-IgG1)-Type Anti-CD20 Chimeric Isotype Antibody Expression vector pKTX93/1133(276-IgG1) (FIG. 19) encoding 1133(276-IgG1)-type anti-CD20 chimeric isotype antibody was constructed in accordance with the following procedures. First, using KOD plus (TOYOBO) and synthetic DNA primers having the nucleotide sequences represented by SEQ ID NOs:13 and 14 (manufactured by FASMAC), PCR was carried out by using the expression vector for 1133-type anti-CD20 chimeric isotype antibody, pKTX93/1133, as described in Example 1 as a template according to the instructions attached to KOD plus. By this PCR, a gene encoding the CH2 domain of the 1133(276-IgG1)-type chimeric isotype was synthesized. Using GeneAmp PCR System 9700 (Applied Biosystems), the PCR was carried out by thermally denaturing at 94° C. for 4 minutes, followed by 25 cycles with each cycle consisting of reactions at 94° C. for 30 seconds, at 55° C. for 30 seconds and 68° C. for 60 seconds. After completion of the PCR, the reaction mixture was electrophoresed on 1% agarose gel and a DNA fragment of about 250 bp containing a gene encoding the CH2 domain was recovered by using QIAquick Gel Extraction Kit (manufactured by Qiagen). The recovered DNA fragment was digested with restriction enzymes BmgBI (manufactured by New England Biolabs) and Bsp1407I (manufactured by Takara Shuzo) and a DNA fragment of about 250 bp containing the CH2 domain-encoding gene was cleaved and purified. On the other hand, the expression vector for 1133-type anti-CD20 chimeric isotype antibody, pKTX93/1133, as described in Example 1 was subjected to the same restriction enzyme treatment and a DNA fragment of about 13 kbp was cleaved and purified. These purified DNAs were mixed together and subjected to ligation reaction using Ligation High Solution (manufactured by TOYOBO). By using the reaction mixture, Escherichia coli XL1-Blue MRF' (manufactured by Stratagene) was transformed. From clones of the thus obtained transformant, each plasmid DNA was prepared. After reaction by using Big Dye Terminator Cycle Sequencing Kit v3.1 (manufactured by Applied Biosystems) according to the attached instructions, the nucleotide sequence of the DNA inserted into each plasmid was analyzed by using DNA Sequencer ABI PRISM 3700 DNA Analyzer manufactured by the same company. Thus, it was confirmed that the plasmid pKTX93/1133(276-IgG1) shown in FIG. 19 was obtained.

(3) Construction of Expression Vector Encoding 1133(296-IgG1)-Type Anti-CD20 Chimeric Isotype Antibody Expression vector pKTX93/1133(296-IgG1) (FIG. 19) encoding 1133(296-IgG1)-type anti-CD20 chimeric isotype antibody was constructed in accordance with the following procedures. First, PCR was carried out by using KOD (TOYOBO) and synthetic DNA primers having the nucleotide sequences represented by SEQ ID NOs:15 and 16 (manufactured by FASMAC) according to the instructions attached to KOD. By this PCR, a gene encoding the CH2 domain of the 1133(296-IgG1)-type chimeric isotype was synthesized. Using GeneAmp PCR System 9700 (Applied Biosystems), the PCR was carried out by thermally denaturing at 96° C. for 5 minutes, followed by 25 cycles with each cycle consisting of reactions at 96° C. for 30 seconds, at 55° C. for 10 seconds and at 74° C. for 15 seconds. After completion of the PCR, the reaction mixture was electrophoresed on 1% agarose gel and a DNA fragment of about 250 bp containing a gene encoding the CH2 domain was recovered by using QIAquick Gel Extraction Kit (manufactured by Qiagen). The recovered DNA fragment was digested with restriction enzymes BmgBI (manufactured by New England Biolabs) and Bsp1407I (manufactured by Takara Shuzo) and a DNA fragment of about 250 bp containing the CH2 domain-encoding gene was cleaved and purified. On the other hand, the expression vector for 1133-type anti-CD20 chimeric isotype antibody, pKTX93/1133, as described in Example 1 was subjected to the same restriction enzyme treatment and a DNA fragment of about 13 kbp was cleaved and purified. These purified DNAs were mixed together and subjected to ligation reaction using Ligation High Solution (manufactured by TOYOBO). By using the reaction mixture, *Escherichia coli* XL1-Blue MRF' (manufactured by Stratagene) was transformed. From clones of the thus obtained transformant, each plasmid DNA was prepared. After reaction by using Big Dye Terminator Cycle Sequencing Kit v3.1 (manufactured by Applied Biosystems) according to the attached instructions, the nucleotide sequence of the DNA inserted into each plasmid was analyzed by using DNA Sequencer ABI PRISM 3700 DNA Analyzer manufactured by the same company. Thus, it was confirmed that the plasmid pKTX93/1133(296-IgG1) shown in FIG. 19 was obtained.

(4) Construction of Expression Vector Encoding 1133(300-IgG1)-Type Anti-CD20 Chimeric Isotype Antibody Expression vector pKTX93/1133(300-IgG1) (FIG. 19) encoding 1133(300-IgG1)-type anti-CD20 chimeric isotype antibody was constructed in accordance with the following procedures. First, PCR was carried out by using KOD (TOYOBO) and synthetic DNA primers having the nucleotide sequences represented by SEQ ID NOs:16 and 17 (manufactured by FASMAC) according to the instructions attached to KOD. By this PCR, a gene encoding the CH2 domain of the 1133(300-IgG1)-type chimeric isotype was synthesized. Using GeneAmp PCR System 9700 (Applied Biosystems), the PCR was carried out by thermally denaturing at 96° C. for 5 minutes, followed by 25 cycles with each cycle consisting of reactions at 96° C. for 30 seconds, at 55° C. for 10 seconds and at 74° C. for 15 seconds. After completion of the PCR, the reaction mixture was electrophoresed on 1% agarose gel and a DNA fragment of about 250 bp containing a gene encoding the CH2 domain was recovered by using QIAquick Gel Extraction Kit (manufactured by Qiagen). The recovered DNA fragment was digested with restriction enzymes BmgBI (manufactured by New England Biolabs) and Bsp1407I (manufactured by Takara Shuzo) and a DNA fragment of about 250 bp containing the CH2 domain-encoding gene was cleaved and purified. On the other hand, the expression vector for 1133-type anti-CD20 chimeric isotype antibody, pKTX93/1133, as described in Example 1 was subjected to the same restriction enzyme treatment and a DNA fragment of about 13 kbp was cleaved and purified. These purified DNAs were mixed together and subjected to ligation reaction using Ligation High Solution (manufactured by TOYOBO). By using the reaction mixture, *Escherichia coli* XL1-Blue MRF' (manufactured by Stratagene) was transformed. From clones of the thus obtained transformant, each plasmid DNA was prepared. After reaction by using Big Dye Terminator Cycle Sequencing Kit v3.1 (manufactured by Applied Biosystems) according to the attached instructions, the nucleotide sequence of the DNA inserted into each plasmid was analyzed by using DNA Sequencer ABI PRISM 3700 DNA Analyzer manufactured by the same company. Thus, it was confirmed that the plasmid pKTX93/1133(300-IgG1) shown in FIG. 19 was obtained.

(5) Construction of Expression Vector Encoding 1133(339-Igg1)-Type Anti-Cd20 Chimeric Isotype Antibody Expression vector pKTX93/1133(339-IgG1) (FIG. 19) encoding 1133(339-IgG1)-type anti-CD20 chimeric isotype antibody was constructed in accordance with the following procedures. First, using KOD plus (TOYOBO) and synthetic DNA primers having the nucleotide sequences represented by SEQ ID NOs:31 and 32 (manufactured by FASMAC), PCR was carried out by using the expression vector for 1133-type anti-CD20 chimeric isotype antibody, pKTX93/1133, as described in Example 1 as a template according to the instructions attached to KOD plus. By this PCR, a gene encoding the CH2 domain of the 1133(339-IgG1)-type chimeric isotype was synthesized. Using GeneAmp PCR System 9700 (Applied Biosystems), the PCR was carried out by thermally denaturing at 94° C. for 4 minutes, followed by 25 cycles with each cycle consisting of reactions at 94° C. for 30 seconds, at 55° C. for 30 seconds and 68° C. for 60 seconds. After completion of the PCR, the reaction mixture was electrophoresed on 1% agarose gel and a DNA fragment of about 250 bp containing a gene encoding the CH2 domain was recovered by using QIAquick Gel Extraction Kit (manufactured by Qiagen). The recovered DNA fragment was digested with restriction enzymes BmgBI (manufactured by New England Biolabs) and Bsp1407I (manufactured by Takara Shuzo) and a DNA fragment of about 250 bp containing the CH2 domain-encoding gene was cleaved and purified. On the other hand, the expression vector for 1133-type anti-CD20 chimeric isotype antibody, pKTX93/1133, as described in Example 1 was subjected to the same restriction enzyme treatment and a DNA fragment of about 13 kbp was cleaved and purified. These purified DNAs were mixed together and subjected to ligation reaction using Ligation High Solution (manufactured by TOYOBO). By using the reaction mixture, *Escherichia coli* XL1-Blue MRF' (manufactured by Stratagene) was transformed. From clones of the thus obtained transformant, each plasmid DNA was prepared. After reaction by using Big Dye Terminator Cycle Sequencing Kit v3.1 (manufactured by Applied Biosystems) according to the attached instructions, the nucleotide sequence of the DNA inserted into each plasmid was analyzed by using DNA Sequencer ABI PRISM 3700 DNA Analyzer manufactured by the same company. Thus, it was confirmed that the plasmid pKTX93/1133(339-IgG1) shown in FIG. 19 was obtained.

2. Stable Expression of Various Anti-CD20 Chimeric Isotype Antibodies in Animal Cells Each of the expression vectors for anti-CD20 chimeric isotype antibody constructed in the item 1 of this Example was transferred into host cells CHO/FUT8$^{-/-}$ as described in the item 3 of Example 1 and thus cells capable of stably producing the anti-CD20 chimeric isotype antibody were prepared by the same procedures as in the item 3 of Example 1.

3. Purification of Various Anti-CD20 Chimeric Isotype Antibodies

Each of the transformants expressing the respective anti-CD20 chimeric isotype antibodies obtained in the item 2 of this Example was cultured and purified by the same procedures as in the item 5 of Example 1. Each anti-CD20 chimeric isotype antibody was purified by using a column packed with Prosep-G (protein G-binding resin: manufactured by Millipore).

Table 8 shows the names of the expression vectors and purified antibodies corresponding to each of the chimeric isotype antibodies. As host cells, CHO/FUT8$^{-/-}$ were used in each case.

TABLE 8

| Expression vector | Purified antibody (name) |
|---|---|
| pKTX93/1133(274-IgG1) | 1133(274-IgG1)(–F) |
| pKTX93/1133(276-IgG1) | 1133(276-IgG1)(–F) |
| pKTX93/1133(296-IgG1) | 1133(296-IgG1)(–F) |
| pKTX93/1133(300-IgG1) | 1133(300-IgG1)(–F) |
| pKTX93/1133(339-IgG1) | 1133(339-IgG1)(–F) |

4. Evaluation of Purification Degrees of Various Purified Anti-Cd20 Chimeric Isotype Antibody Samples by SDS-PAGE To evaluate the purification degrees of the purified anti-CD20 chimeric isotype antibody samples obtained in the item 3 in this Example, SDS-PAGE was carried out by the same procedures as in the item 6 of Example 1. For electrophoretic comparisons, the purified CD20-IgG1(–F) and 1133(–F) samples prepared in Example 1-5 and the purified 1131(–F) and 1113(–F) samples prepared in Example 3 were treated in the same manner.

Figure 20:
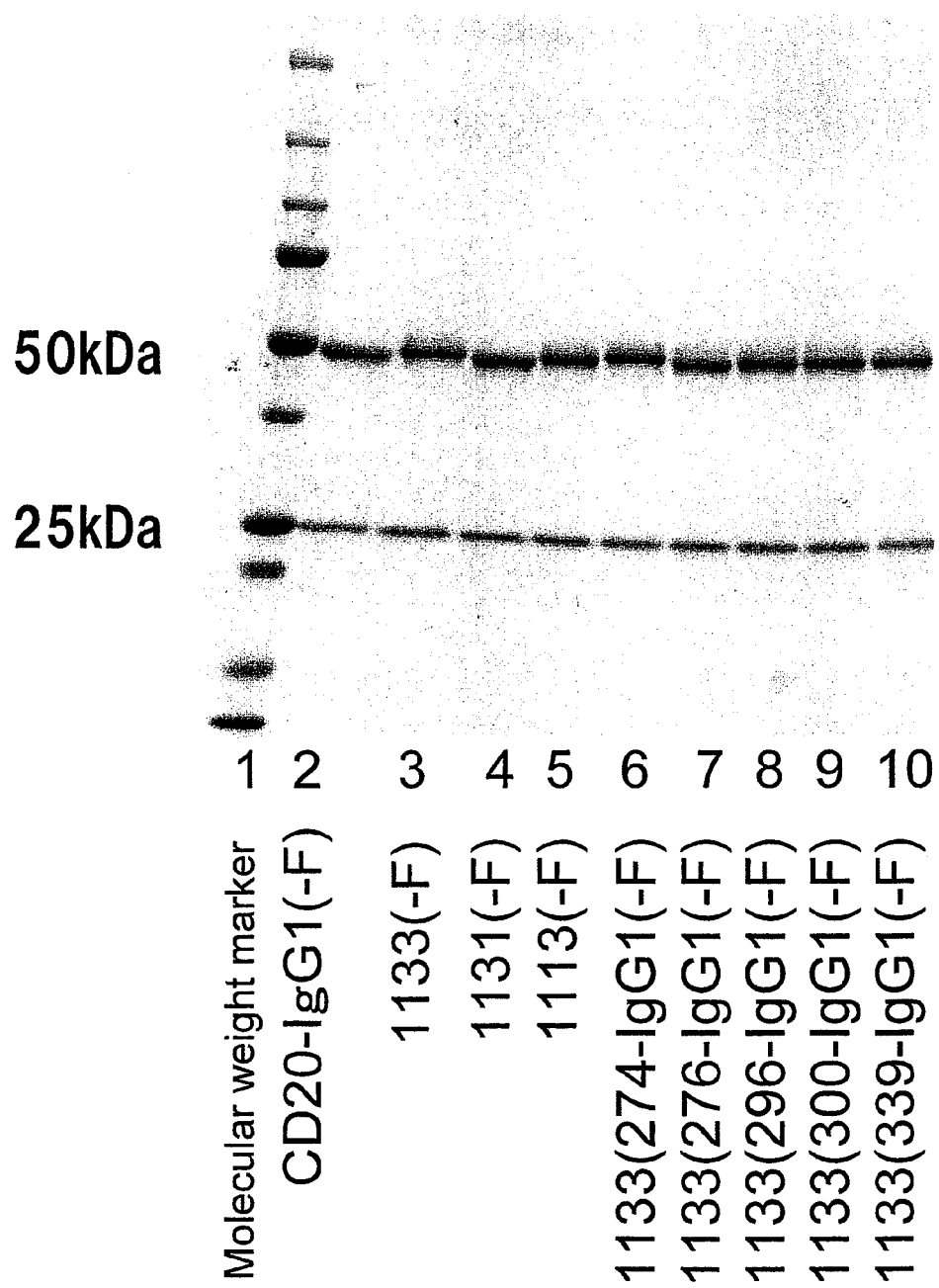
FIG. 20 shows SDS-PAGE electrophoresis patterns of various purified antibodies. Staining of proteins was carried out with Coomassie Brilliant Blue (CBB). Lane 1 corresponds to a molecular weight marker, lane 2 corresponds to CD20-IgG1(−F), lane 3 corresponds to 1133(−F), lane 4 corresponds to 1131(−F), lane 5 corresponds to 1113(−F), lane 6 corresponds to 1133(274-IgG1)(−F), lane 7 corresponds to 1133(276-IgG1)(−F), lane 8 corresponds to 1133(296-IgG1)(−F), lane 9 corresponds to 1133(300-IgG1)(−F) and lane 10 corresponds to 1133(339-IgG1)(−F).

The results are shown in FIG. 20. 1133(274-IgG1)(–F), 1133(276-IgG1)(–F), 1133(296-IgG1)(–F), 1133(300-IgG1)(–F) and 1133(339-IgG1)(–F) obtained in the item 3 of this Example showed electrophoretic patterns similar to CD20-IgG1(–F), 1133(–F), 1131(–F) and 1113(–F). The molecular weights of H chains and L chains constituting the anti-CD20 chimeric isotype antibodies obtained in the item 3 of this Example estimated from the amino acid sequences are similar to each other. That is, the molecular weights of the H chains and L chains are about 50 kDa and about 24 kDa, respectively. Namely, these molecular weights are similar to the molecular weights of the H chains and L chains of CD20-IgG1(–F), 1133(–F), 1131(–F) and 1113(–F) and the electrophoretic patterns are also similar to them. From these facts, it was confirmed that the anti-CD20 chimeric isotype antibodies obtained in the item 3 of this Example were constituted by the H chain and L chain.

Based on these results, it was confirmed that the desired IgG molecules constituted by the H and L chains are contained at a sufficient ratio in the purified sample of anti-CD20 chimeric isotype antibody obtained in the item 3 of this Example.

Example 6

Measurement of CDC Activities of Various Anti-CD20 Chimeric Isotype Antibodies (Analysis on the Amino Acid Sequence in the CH2 Domain and CDC Activity of 1133-Type Anti-CD20 Chimeric Isotype Antibody)

In order to evaluate the CDC activities on a CD20-positive cell line of the various anti-CD20 chimeric isotype antibodies obtained in the item 3 of Example 5, the procedures of the item 2 of Example 2 were followed by using Raji cells, CD20-positive cell line.

Figure 21:
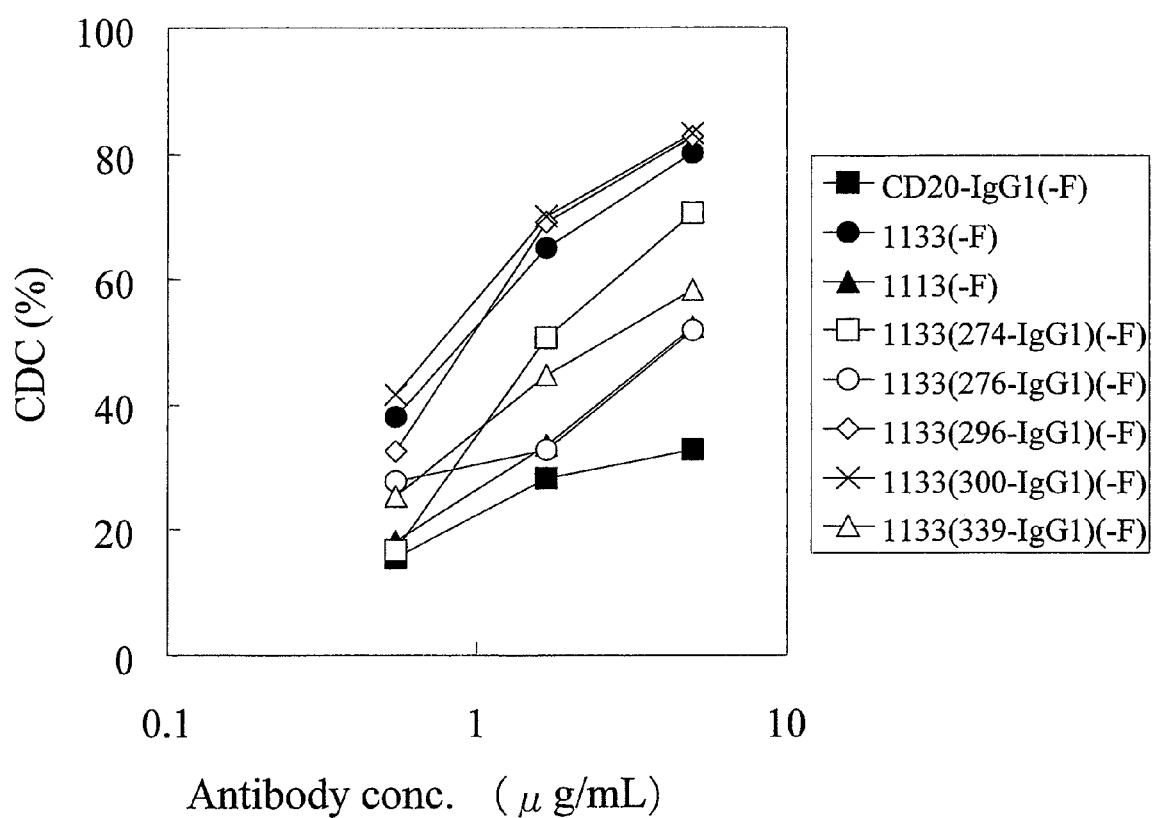
FIG. 21 shows the CDC activity of various anti-CD20 antibodies to Raji cell. The abscissa shows an antibody concentration, and the ordinate shows the ratio of cytotoxicity in each antibody concentration. In the graph, ■ shows CD20-IgG1(−F), ● shows 1133(−F), ▲ shows 1131(−F), □ shows 1133(274-IgG1)(−F), ○ shows 1133(276-IgG1)(−F), ◊ shows 1133(296-IgG1)(−F), × shows 1133(300-IgG1)(−F) and Δ shows 1133(339-IgG1)(−F).

The results are shown in FIG. 21. As is shown in FIG. 21, 1133(–F) showed the highest CDC activity, CD20-IgG1(–F) showed the lowest CDC activity, and the activity of 1113(–F) was intermediate between them. These results indicate that the CDC activity, which was enhanced by swapping the amino acid sequences in the CH2 and CH3 domains of anti-CD20 human IgG1 antibody with the amino acid sequences of human IgG3 antibody, was largely attenuated by replacing all of the IgG3-type amino acid sequences at the five positions in the CH2 domain with the IgG1-type amino acid sequences. Although 1133(296-IgG1)(–F) and 1133(300-IgG1)(–F) showed CDC activities equivalent to 1133(–F), the CDC activities of 1133(274-IgG1)(–F), 1133(276-IgG1)(–F) and 1133(339-IgG1)(–F) were lower than 1133(–F). In particular, the CDC activity of 1133(276-IgG1)(–F) was equivalent to 1113(–F). Table 9 shows the relationship between the amino acid sequence and activity of each antibody wherein the CDC activities are expressed in descending order as +++++, ++++, +++, ++ and +

TABLE 9

| Purified antibody (name) | 274 | 276 | 296 | 300 | 339 | CH3 | CDC |
|---|---|---|---|---|---|---|---|
| CD20-IgG1(–F) | IgG1 | IgG1 | IgG1 | IgG1 | IgG1 | IgG1 | + |
| 1133(–F) | IgG3 | IgG3 | IgG3 | IgG3 | IgG3 | IgG3 | +++++ |
| 1113(+F) | IgG1 | IgG1 | IgG1 | IgG1 | IgG1 | IgG3 | ++ |
| 1133(274-IgG1)(–F) | IgG1 | IgG3 | IgG3 | IgG3 | IgG3 | IgG3 | ++++ |
| 1133(276-IgG1)(–F) | IgG3 | IgG1 | IgG3 | IgG3 | IgG3 | IgG3 | ++ |
| 1133(296-IgG1)(–F) | IgG3 | IgG3 | IgG1 | IgG3 | IgG3 | IgG3 | +++++ |
| 1133(300-IgG1)(–F) | IgG3 | IgG3 | IgG3 | IgG1 | IgG3 | IgG3 | +++++ |
| 1133(339-IgG1)(–F) | IgG3 | IgG3 | IgG3 | IgG3 | IgG1 | IgG3 | +++ |

The above results indicate that, in antibodies which are composed of CH1 and the hinge of human IgG1 antibody and Fc of a chimeric isotype of human IgG1 antibody and human IgG3 antibody, in order to enhance the CDC activity, the amino acid residues at positions 274, 276 and 339 are preferably replaced with IgG3, and most preferably, the amino acid residues at positions 276 and 339 are replaced with IgG3.

Example 7

1. Construction of Various Anti-CD20 Chimeric Isotype Antibodies Using Animal Cells (Analysis on the Amino Acid Sequence in the CH2 Domain and CDC Activity of 1131-Type Anti-CD20 Chimeric Isotype Antibody)

In order to analyze the relationship between the amino acid sequence in the CH2 domain and CDC activity in greater detail, various antibodies as shown below were designed by partly replacing the CH2 domain of 1131-type anti-CD20 chimeric isotype antibody, having the CH2 domain alone of human IgG3 antibody, with the CH2 domain of human IgG1 antibody.

First, the 1131(296/300-IgG1)-type anti-CD20 chimeric isotype antibody, wherein the amino acid sequences at positions 296 and 300 of the 1131-type chimeric isotype antibody, at which no lowering in CDC activity was observed in the 1133-type, were returned to the amino acid sequences of human IgG1-type, was designed. Then, the various chimeric isotype antibodies, wherein the amino acid sequences at positions 274, 276 and 339, at each of which lowering in CDC activity was observed in the 1133-type, were returned to the amino acid sequences of human IgG1-type, were designed. These antibodies include 1131(274/296/300-IgG1)-type anti-CD20 chimeric isotype antibody in which the amino acid sequence at position 274 was returned to the human IgG1-type in addition to positions 296 and 300; 1131(274/276/296/300-IgG1)-type anti-CD20 chimeric isotype antibody in which the amino acid sequences at positions 274 and 276 were returned to the human IgG1-type in addition to positions 296 and 300; 1131(274/296/300/339-IgG1)-type anti-CD20 chimeric isotype antibody in which the amino acid sequences at positions 274 and 339 were returned to the human IgG1- type in addition to positions 296 and 300; and 1131(276/296/300/339-IgG1)-type anti-CD20 chimeric isotype antibody in which the amino acid sequences at positions 276 and 339 were returned to the human IgG1-type in addition to positions 296 and 300.

Table 10 shows the amino acid residues (i.e., whether human IgG1 antibody or human IgG3 antibody) at the above five positions in these antibodies.

TABLE 10

| Structural name | 274 | 276 | 296 | 300 | 339 | Amino acid sequence |
|---|---|---|---|---|---|---|
| 1131 | IgG3 | IgG3 | IgG3 | IgG3 | IgG3 | SEQ ID NO: 5 |
| 1131(296/300-IgG1) | IgG3 | IgG3 | IgG1 | IgG1 | IgG3 | SEQ ID NO: 33 |
| 1131(274/296/300-IgG1) | IgG1 | IgG3 | IgG1 | IgG1 | IgG3 | SEQ ID NO: 34 |
| 1131(274/276/296/300-IgG1) | IgG1 | IgG1 | IgG1 | IgG1 | IgG3 | SEQ ID NO: 35 |
| 1131(274/296/300/339-IgG1) | IgG1 | IgG3 | IgG1 | IgG1 | IgG1 | SEQ ID NO: 36 |
| 1131(276/296/300/339-IgG1) | IgG3 | IgG1 | IgG1 | IgG1 | IgG1 | SEQ ID NO: 37 |

Figure 22:
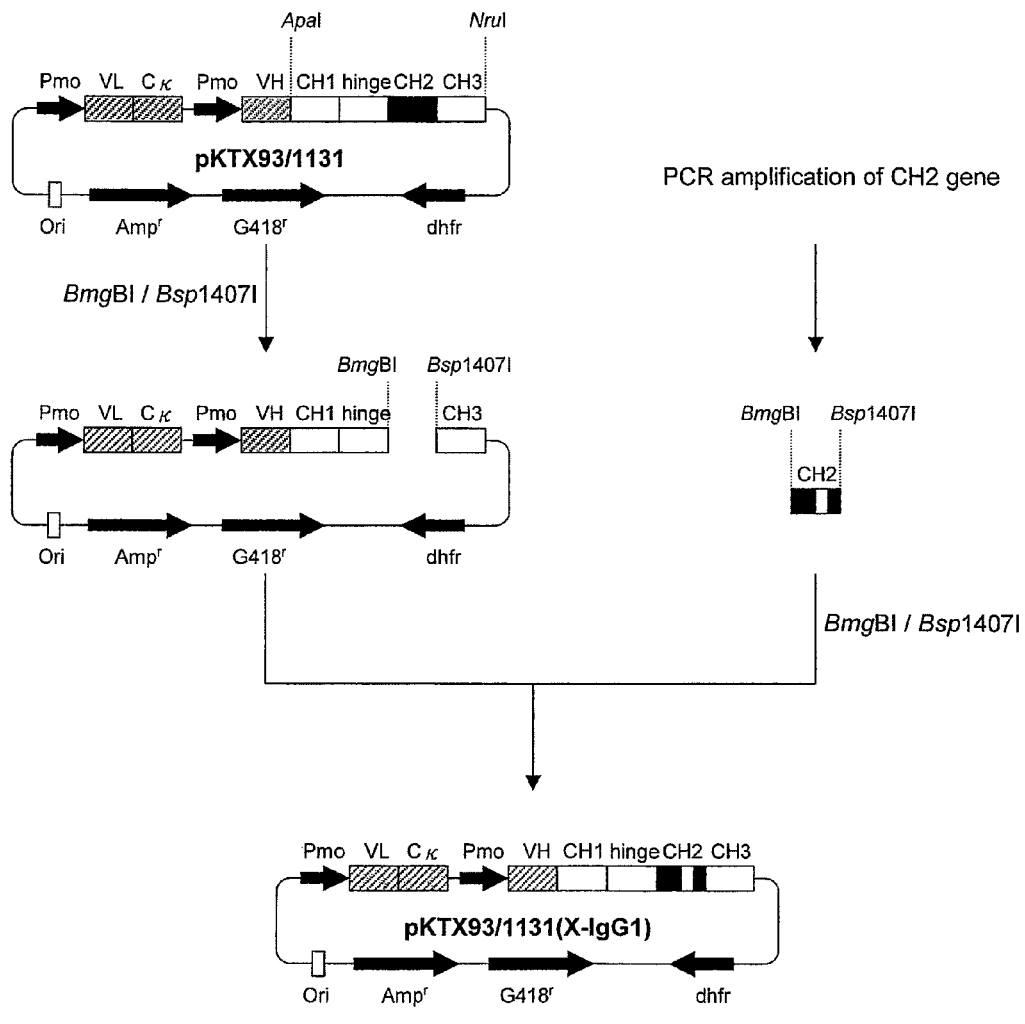
FIG. 22 shows construction steps of plasmids pKTX93/1131(296/300-IgG1), pKTX93/1131(274/296/300-IgG1), pKTX93/1131(274/276/296/300-IgG1), pKTX93/1131(274/296/300/339-IgG1) and pKTX93/1131(276/296/300/339-IgG1).

The various anti-CD20 chimeric isotype antibodies designed above were constructed by the following procedures.
(1) Construction of Expression Vector Encoding 1131(296/300-IgG1)-Type Anti-CD20 Chimeric Isotype Antibody Expression vector pKTX93/1131(296/300-IgG1) (FIG. 22) encoding 1131(296/300-IgG1)-type anti-CD20 chimeric isotype antibody was constructed in accordance with the following procedures. First, using KOD plus (TOYOBO) and synthetic DNA primers having the nucleotide sequences represented by SEQ ID NOs:13 and 31 (manufactured by FASMAC), PCR was carried out by using pKANTEX2B8P as a template according to the instructions attached to KOD plus. By this PCR, a gene encoding the CH2 domain of the 1131 (296/300-IgG1)-type chimeric isotype was synthesized. Using GeneAmp PCR System 9700 (Applied Biosystems), the PCR was carried out by thermally denaturing at 94° C. for 4 minutes, followed by 25 cycles with each cycle consisting of reactions at 94° C. for 30 seconds, at 55° C. for 30 seconds and at 68° C. for 60 seconds. After completion of the PCR, the reaction mixture was electrophoresed on 1% agarose gel and a DNA fragment of about 250 bp containing a gene encoding the CH2 domain was recovered by using QIAquick Gel Extraction Kit (manufactured by Qiagen). The recovered DNA fragment was digested with restriction enzymes BmgBI (manufactured by New England Biolabs) and Bsp1407I (manufactured by Takara Shuzo) and a DNA fragment of about 250 bp containing the CH2 domain-encoding gene was cleaved and purified. On the other hand, the expression vector for 1131-type anti-CD20 chimeric isotype antibody, pKTX93/1131, as described in Example 3 was subjected to the same restriction enzyme treatment and a DNA fragment of about 13 kbp was cleaved and purified. These purified DNAs were mixed together and subjected to ligation reaction using Ligation High Solution (manufactured by TOYOBO). By using the reaction mixture, *Escherichia coli* XL1-Blue MRF' (manufactured by Stratagene) was transformed. From clones of the thus obtained transformant, each plasmid DNA was prepared. After reaction by using Big Dye Terminator Cycle Sequencing Kit v3.1 (manufactured by Applied Biosystems) according to the attached instructions, the nucleotide sequence of the DNA inserted into each plasmid was analyzed by using DNA Sequencer ABI PRISM 3700 DNA Analyzer manufactured by the same company. Thus, it was confirmed that the plasmid pKTX93/1131(296/300-IgG1) shown in FIG. 22 was obtained.
(2) Construction of Expression Vector Encoding 1131(274/296/300-IgG1)-Type Anti-CD20 Chimeric Isotype Antibody Expression vector pKTX93/1131(274/296/300-IgG1) (FIG. 22) encoding 1131(274/296/300-IgG1)-type anti-CD20 chimeric isotype antibody was constructed in accordance with the following procedures. First, using KOD plus (TOYOBO) and synthetic DNA primers having the nucleotide sequences represented by SEQ ID NOs:12 and 13 (manufactured by FASMAC), PCR was carried out by using pKANTEX2B8P as a template according to the instructions attached to KOD plus. By this PCR, a gene encoding the CH2 domain of the 1131(274/296/300-IgG1)-type chimeric isotype was synthesized. Using GeneAmp PCR System 9700 (Applied Biosystems), the PCR was carried out by thermally denaturing at 94° C. for 4 minutes, followed by 25 cycles with each cycle consisting of reactions at 94° C. for 30 seconds, at 55° C. for 30 seconds and at 68° C. for 60 seconds. After completion of the PCR, the reaction mixture was electrophoresed on 1% agarose gel and a DNA fragment of about 250 bp containing a gene encoding the CH2 domain was recovered by using QIAquick Gel Extraction Kit (manufactured by Qiagen). The recovered DNA fragment was digested with restriction enzymes BmgBI (manufactured by New England Biolabs) and Bsp1407I (manufactured by Takara Shuzo) and a DNA fragment of about 250 bp containing the CH2 domain-encoding gene was cleaved and purified. On the other hand, the expression vector for 1131-type anti-CD20 chimeric isotype antibody, pKTX93/1131, as described in Example 3 was subjected to the same restriction enzyme treatment and a DNA fragment of about 13 kbp was cleaved and purified. These purified DNAs were mixed together and subjected to ligation reaction using Ligation High Solution (manufactured by TOYOBO). By using the reaction mixture, *Escherichia coli* XL1-Blue MRF' (manufactured by Stratagene) was transformed. From clones of the thus obtained transformant, each plasmid DNA was prepared. After reaction by using Big Dye Terminator Cycle Sequencing Kit v3.1 (manufactured by Applied Biosystems) according to the attached instructions, the nucleotide sequence of the DNA inserted into each plasmid was analyzed by using DNA Sequencer ABI PRISM 3700 DNA Analyzer manufactured by the same company. Thus, it was confirmed that the plasmid pKTX93/1131(274/296/300-IgG1) shown in FIG. 22 was obtained.
(3) Construction of Expression Vector Encoding 1131(274/276/296/300-IgG1)-type anti-CD20 Chimeric Isotype Antibody Expression vector pKTX93/1131(274/276/296/300-IgG1) (FIG. 22) encoding 1131(274/276/296/300-IgG1)-type anti- CD20 chimeric isotype antibody was constructed in accordance with the following procedures. First, using KOD plus (TOYOBO) and synthetic DNA primers having the nucleotide sequences represented by SEQ ID NOs:13 and 38 (manufactured by FASMAC), PCR was carried out by using pKANTEX2B8P as a template according to the instructions attached to KOD plus. By this PCR, a gene encoding the CH2 domain of the 1131(274/276/296/300-IgG1)-type chimeric isotype was synthesized. Using GeneAmp PCR System 9700 (Applied Biosystems), the PCR was carried out by thermally denaturing at 94° C. for 4 minutes, followed by 25 cycles with each cycle consisting of reactions at 94° C. for 30 seconds, at 55° C. for 30 seconds and at 68° C. for 60 seconds. After completion of the PCR, the reaction mixture was electrophoresed on 1% agarose gel and a DNA fragment of about 250 bp containing a gene encoding the CH2 domain was recovered by using QIAquick Gel Extraction Kit (manufactured by Qiagen). The recovered DNA fragment was digested with restriction enzymes BmgBI (manufactured by New England Biolabs) and Bsp1407I (manufactured by Takara Shuzo) and a DNA fragment of about 250 bp containing the CH2 domain-encoding gene was cleaved and purified. On the other hand, the expression vector for 1131-type anti-CD20 chimeric isotype antibody, pKTX93/1131, as described in Example 3 was subjected to the same restriction enzyme treatment and a DNA fragment of about 13 kbp was cleaved and purified. These purified DNAs were mixed together and subjected to ligation reaction using Ligation High Solution (manufactured by TOYOBO). By using the reaction mixture, *Escherichia coli* XL1-Blue MRF' (manufactured by Stratagene) was transformed. From clones of the thus obtained transformant, each plasmid DNA was prepared. After reaction by using Big Dye Terminator Cycle Sequencing Kit v3.1 (manufactured by Applied Biosystems) according to the attached instructions, the nucleotide sequence of the DNA inserted into each plasmid was analyzed by using DNA Sequencer ABI PRISM 3700 DNA Analyzer manufactured by the same company. Thus, it was confirmed that the plasmid pKTX93/1131(274/276/296/300-IgG1) shown in FIG. 22 was obtained.

(4) Construction of Expression Vector Encoding 1131(274/296/300/339-IgG1)-type anti-CD20 Chimeric Isotype Antibody Expression vector pKTX93/1131(274/296/300/339-IgG1) (FIG. 22) encoding 1131(274/296/300/339-IgG1)-type anti-CD20 chimeric isotype antibody was constructed in accordance with the following procedures. First, using KOD plus (TOYOBO) and synthetic DNA primers having the nucleotide sequences represented by SEQ ID NOs:12 and 32 (manufactured by FASMAC), PCR was carried out by using pKANTEX2B8P as a template according to the instructions attached to KOD plus. By this PCR, a gene encoding the CH2 domain of the 1131(274/296/300/339-IgG1)-type chimeric isotype was synthesized. Using GeneAmp PCR System 9700 (Applied Biosystems), the PCR was carried out by thermally denaturing at 94° C. for 4 minutes, followed by 25 cycles with each cycle consisting of reactions at 94° C. for 30 seconds, at 55° C. for 30 seconds and at 68° C. for 60 seconds. After completion of the PCR, the reaction mixture was electrophoresed on 1% agarose gel and a DNA fragment of about 250 bp containing a gene encoding the CH2 domain was recovered by using QIAquick Gel Extraction Kit (manufactured by Qiagen). The recovered DNA fragment was digested with restriction enzymes BmgBI (manufactured by New England Biolabs) and Bsp1407I (manufactured by Takara Shuzo) and a DNA fragment of about 250 bp containing the CH2 domain-encoding gene was cleaved and purified. On the other hand, the expression vector for 1131-type anti-CD20 chimeric isotype antibody, pKTX93/1131, as described in Example 3 was subjected to the same restriction enzyme treatment and a DNA fragment of about 13 kbp was cleaved and purified. These purified DNAs were mixed together and subjected to ligation reaction using Ligation High Solution (manufactured by TOYOBO). By using the reaction mixture, *Escherichia coli* XL1-Blue MRF' (manufactured by Stratagene) was transformed. From clones of the thus obtained transformant, each plasmid DNA was prepared. After reaction by using Big Dye Terminator Cycle Sequencing Kit v3.1 (manufactured by Applied Biosystems) according to the attached instructions, the nucleotide sequence of the DNA inserted into each plasmid was analyzed by using DNA Sequencer ABI PRISM 3700 DNA Analyzer manufactured by the same company. Thus, it was confirmed that the plasmid pKTX93/1131(274/296/300/339-IgG1) shown in FIG. 22 was obtained.

(5) Construction of Expression Vector Encoding 1131(276/296/300/339-IgG1)-Type Anti-CD20 chimeric isotype antibody Expression vector pKTX93/1131(276/296/300/339-IgG1) (FIG. 22) encoding 1131(276/296/300/339-IgG1)-type anti-CD20 chimeric isotype antibody was constructed in accordance with the following procedures. First, using KOD plus (TOYOBO) and synthetic DNA primers having the nucleotide sequences represented by SEQ ID NOs:14 and 32 (manufactured by FASMAC), PCR was carried out by using pKANTEX2B8P as a template according to the instructions attached to KOD plus. By this PCR, a gene encoding the CH2 domain of the 1131(276/296/300/339-IgG1)-type chimeric isotype was synthesized. Using GeneAmp PCR System 9700 (Applied Biosystems), the PCR was carried out by thermally denaturing at 94° C. for 4 minutes, followed by 25 cycles with each cycle consisting of reactions at 94° C. for 30 seconds, at 55° C. for 30 seconds and at 68° C. for 60 seconds. After completion of the PCR, the reaction mixture was electrophoresed on 1% agarose gel and a DNA fragment of about 250 bp containing a gene encoding the CH2 domain was recovered by using QIAquick Gel Extraction Kit (manufactured by Qiagen). The recovered DNA fragment was digested with restriction enzymes BmgBI (manufactured by New England Biolabs) and Bsp1407I (manufactured by Takara Shuzo) and a DNA fragment of about 250 bp containing the CH2 domain-encoding gene was cleaved and purified. On the other hand, the expression vector for 1131-type anti-CD20 chimeric isotype antibody, pKTX93/1131, as described in Example 3 was subjected to the same restriction enzyme treatment and a DNA fragment of about 13 kbp was cleaved and purified. These purified DNAs were mixed together and subjected to ligation reaction using Ligation High Solution (manufactured by TOYOBO). By using the reaction mixture, *Escherichia coli* XL1-Blue MRF' (manufactured by Stratagene) was transformed. From clones of the thus obtained transformant, each plasmid DNA was prepared. After reaction by using Big Dye Terminator Cycle Sequencing Kit v3.1 (manufactured by Applied Biosystems) according to the attached instructions, the nucleotide sequence of the DNA inserted into each plasmid was analyzed by using DNA Sequencer ABI PRISM 3700 DNA Analyzer manufactured by the same company. Thus, it was confirmed that the plasmid pKTX93/1131(276/296/300/339-IgG1) shown in FIG. 22 was obtained.

2. Stable Expression of Various Anti-Cd20 Chimeric Isotype Antibodies in Animal Cells Each of the expression vectors for anti-CD20 chimeric isotype antibody constructed in the item 1 of this Example was transferred into host cells CHO/FUT8$^{-/-}$ as described in the item 3 of Example 1 and thus cells capable of stably producing the anti-CD20 chimeric isotype antibody were prepared by the same procedures as in the item 3 of Example 1.

3. Purification of Various Anti-Cd20 Chimeric Isotype Antibodies

Each of the transformants expressing the respective anti-CD20 chimeric isotype antibodies obtained in the item 2 of this Example was cultured and purified by the same procedures as in the item 5 of Example 1. Each anti-CD20 chimeric isotype antibody was purified by using a column packed with Prosep-A (protein A-binding resin: manufactured by Millipore).

Table 11 shows the names of the expression vectors and purified antibodies corresponding to the chimeric isotype antibodies. As host cells, CHO/FUT8$^{-/-}$ were used in each case.

TABLE 11

| Expression vector | Purified antibody (name) |
|---|---|
| pKTX93/1131(296/300-IgG1) | 1131(296/300-IgG1)(–F) |
| pKTX93/1131(274/296/300-IgG1) | 1131(274/296/300-IgG1)(–F) |
| pKTX93/1131(274/276/296/300-IgG1) | 1131(274/276/296/300-IgG1)(–F) |
| pKTX93/1131(274/296/300/339-IgG1) | 1131(274/296/300/339-IgG1)(–F) |
| pKTX93/1131(276/296/300/339-IgG1) | 1131(276/296/300/339-IgG1)(–F) |

4. Evaluation of Purification Degrees of Various Purified Anti-CD20 Chimeric Isotype Antibody Samples by SDS-PAGE In order to evaluate the purification degrees of the purified anti-CD20 chimeric isotype antibody samples obtained in the item 3 in this Example, SDS-PAGE was carried out by the same procedures as in the item 6 of Example 1.

Figure 23:
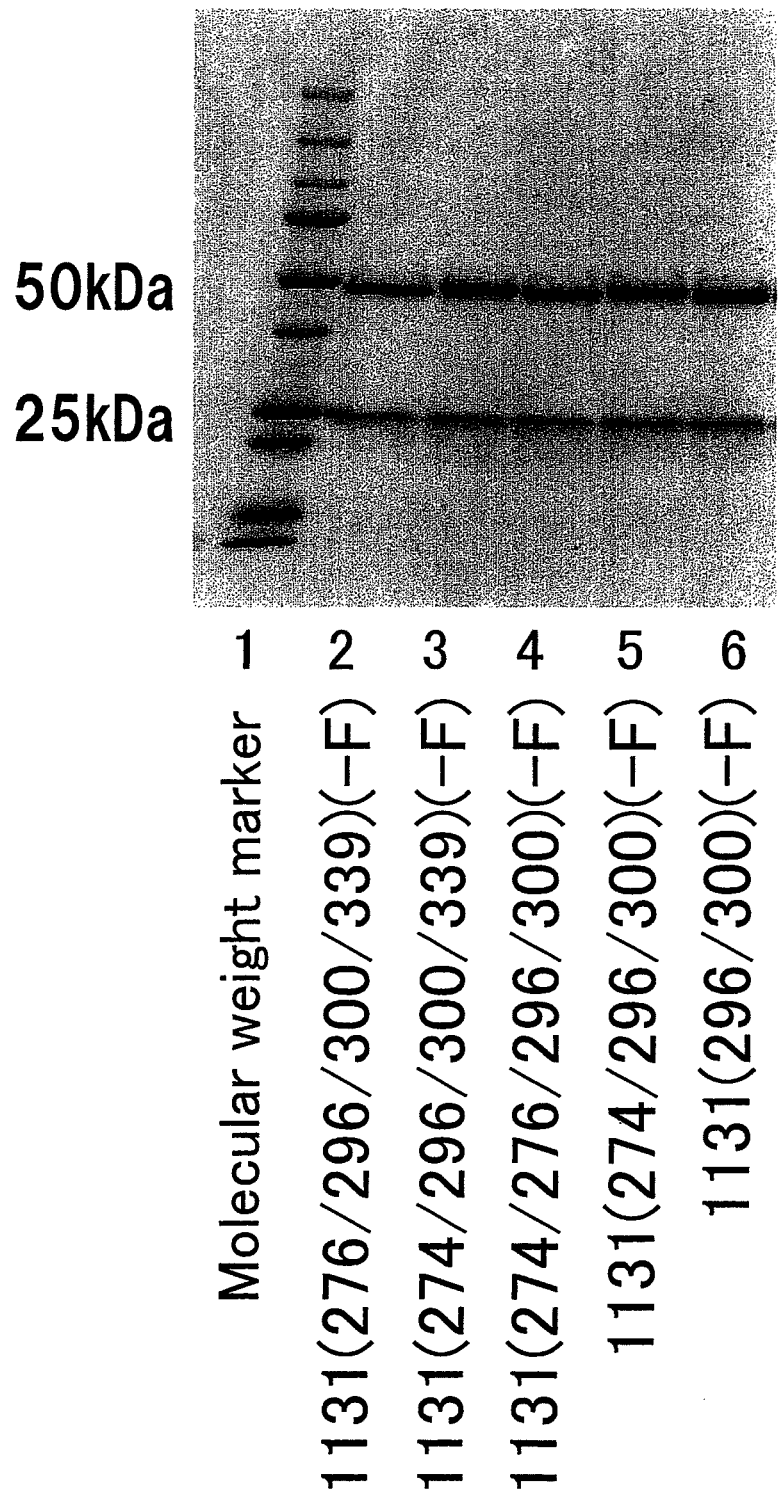
FIG. 23 shows SDS-PAGE electrophoresis patterns of various purified antibodies. Staining of proteins was carried out with Coomassie Brilliant Blue (CBB). Lane 1 corresponds to a molecular weight marker, lane 2 corresponds to 1131(296/300-IgG1)(−F), lane 3 corresponds to 1131(274/296/300-IgG1)(−F), lane 4 corresponds to 1131(274/276/296/300-IgG1)(−F), lane 5 corresponds to 1131(274/296/300/339-IgG1)(−F) and lane 6 corresponds to 1131(276/296/300/339-IgG1)(−F).

The results are shown in FIG. 23. The molecular weights of the H chains and the L chains constituting the respective anti-CD20 chimeric isotype antibodies obtained in the item 3 in this Example estimated from the amino acid sequences are close to each other. That is, the molecular weights of the H chain and the L chain are about 50 kDa and about 24 kDa, respectively. Namely, these molecular weights are close to the molecular weights of the H chains and the L chains of CD20-IgG1(–F) and 1131(–F) and the electrophoretic patterns are also similar to those obtained in Examples 4 and 6. From these facts, it was confirmed that the anti-CD20 chimeric isotype antibodies obtained in the item 3 in this Example were composed of the desired H chains and L chains.

Based on these results, it was confirmed that the desired IgG molecules constituted by the H and L chains are contained at a sufficient ratio in the purified sample of anti-CD20 chimeric isotype antibody obtained in the item 3 of this Example.

Example 8

Measurement of Various Activities of Various Anti-CD20 Chimeric Isotype Antibodies (Analysis on the Amino Acid Sequence in the CH2 Domain and CDC Activity of 1131-Type Anti-Cd20 Chimeric Isotype Antibody)

The anti-CD20 chimeric isotype antibodies obtained in the item 3 of Example 7 were compared in various activities as follows.

1. Measurement of CDC Activities of Various Anti-CD20 Chimeric Isotype Antibodies In order to evaluate the CDC activities on a CD20-positive cell line of the anti-CD20 chimeric isotype antibodies obtained in the item 3 of Example 7, the procedures of the item 2 of Example 2 were followed by using CD20-positive cell line, Raji cells.

Figure 24:
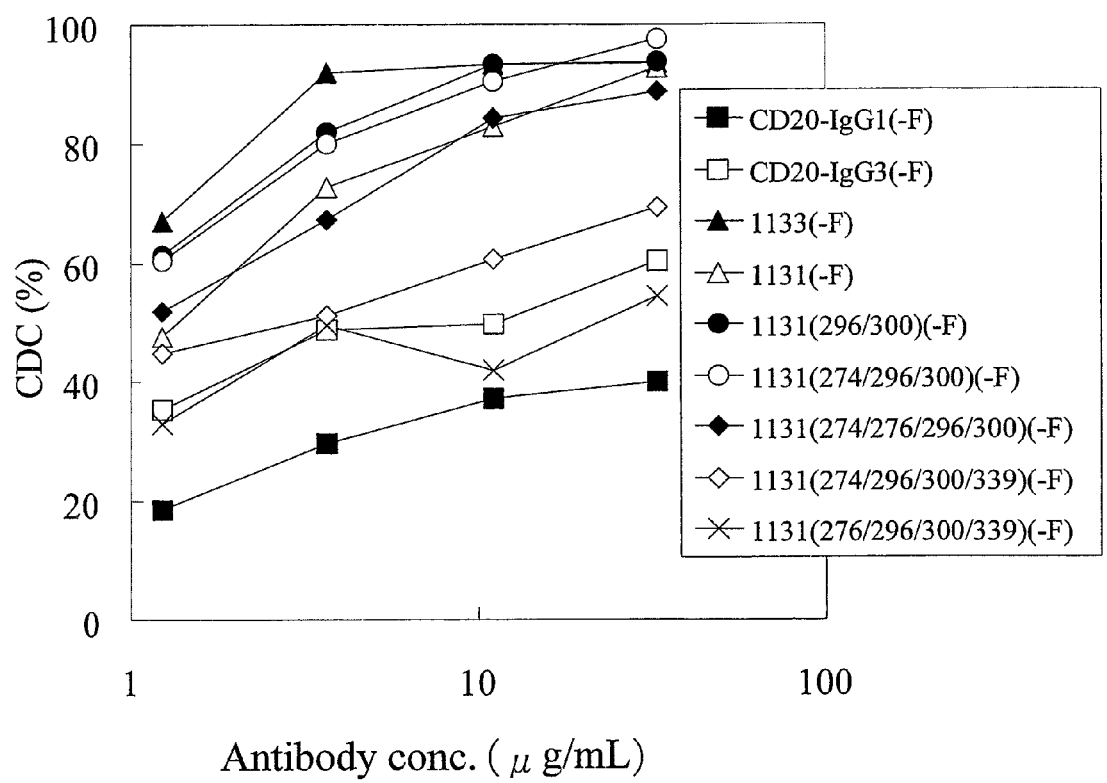
FIG. 24 shows the CDC activity of various anti-CD20 antibodies to Raji cell. The abscissa shows an antibody concentration, and the ordinate shows the CDC activity in each antibody concentration. In the graph, ■ shows CD20-IgG1(−F), □ shows CD20-IgG3(−F), ▲ shows 1133(−F), Δ shows 1131(−F), ● shows 1131(296/300-IgG1)(−F), ○ shows 1131(274/296/300-IgG1)(−F), ♦ shows 1131(274/276/296/300-IgG1)(−F), ◊ shows 1131(274/296/300/339-IgG1)(−F) and × shows 1131(276/296/300/339-IgG1)(−F).

The results are shown in FIG. 24. As is shown in FIG. 24, 1133(–F) showed the highest CDC activity, CD20-IgG1(–F) showed the lowest CDC activity, and the activity of 1131(–F) was slightly lower than 1133(–F). Although 1131(296/300-IgG1)(–F), 1131(274/296/300-IgG1)(–F) and 1131(274/276/296/300-IgG1)(–F) showed CDC activities similar to or even higher than 1131(–F), 1131(274/296/300/339-IgG1)(–F) and 1131(276/296/300/339-IgG1)(–F) showed CDC activities lower than 1131(–F). In particular, the CDC activity of 1131(276/296/300/399-IgG1)(–F) was low and similar to IgG3(–F). Table 12 shows the relationship between the amino acid sequence and the CDC activity strength of each antibody wherein the CDC activities are expressed in descending order as ++++++, +++++, ++++, +++, ++ and +.

TABLE 12

| Purified antibody (name) | 274 | 276 | 296 | 300 | 339 | CDC |
|---|---|---|---|---|---|---|
| CD20-IgG1(–F) | IgG1 | IgG1 | IgG1 | IgG1 | IgG1 | + |
| CD20-IgG3(–F) | IgG3 | IgG3 | IgG3 | IgG3 | IgG3 | ++ |
| 1133(–F) | IgG3 | IgG3 | IgG3 | IgG3 | IgG3 | ++++++ |
| 1131(–F) | IgG3 | IgG3 | IgG3 | IgG3 | IgG3 | ++++ |
| 1131(296/300-IgG1)(–F) | IgG3 | IgG3 | IgG1 | IgG1 | IgG3 | +++++ |
| 1131(274/296/300-IgG1)(–F) | IgG1 | IgG3 | IgG1 | IgG1 | IgG3 | +++++ |
| 1131(274/276/296/300-IgG1)(–F) | IgG1 | IgG1 | IgG1 | IgG1 | IgG3 | +++ |
| 1131(274/296/300/339-IgG1)(–F) | IgG1 | IgG3 | IgG1 | IgG1 | IgG1 | +++ |
| 1131(276/296/300/339-IgG1)(–F) | IgG3 | IgG1 | IgG1 | IgG1 | IgG1 | ++ |

These results indicate that, in antibodies which are composed of CH1 and the hinge of the amino acid sequences of human IgG1 antibody and Fc of a chimeric isotype of human IgG1 antibody and human IgG3 antibody, in order to enhance the CDC activity, the amino acid residues at least at positions 276 and 339 are preferably amino acid residues of human IgG3.

2. Measurement of Protein A-Binding Activities of Various Anti-CD20 Chimeric Isotype Antibodies The protein A-binding activities of 1131(296/300-IgG1)(–F), 1131(274/296/300-IgG1)(–F) and 1131(274/276/296/300-IgG1)(–F), each showing a particularly high CDC activity in the item 1 in this Example, were measured as in the item 3 of Example 4.

Figure 25:
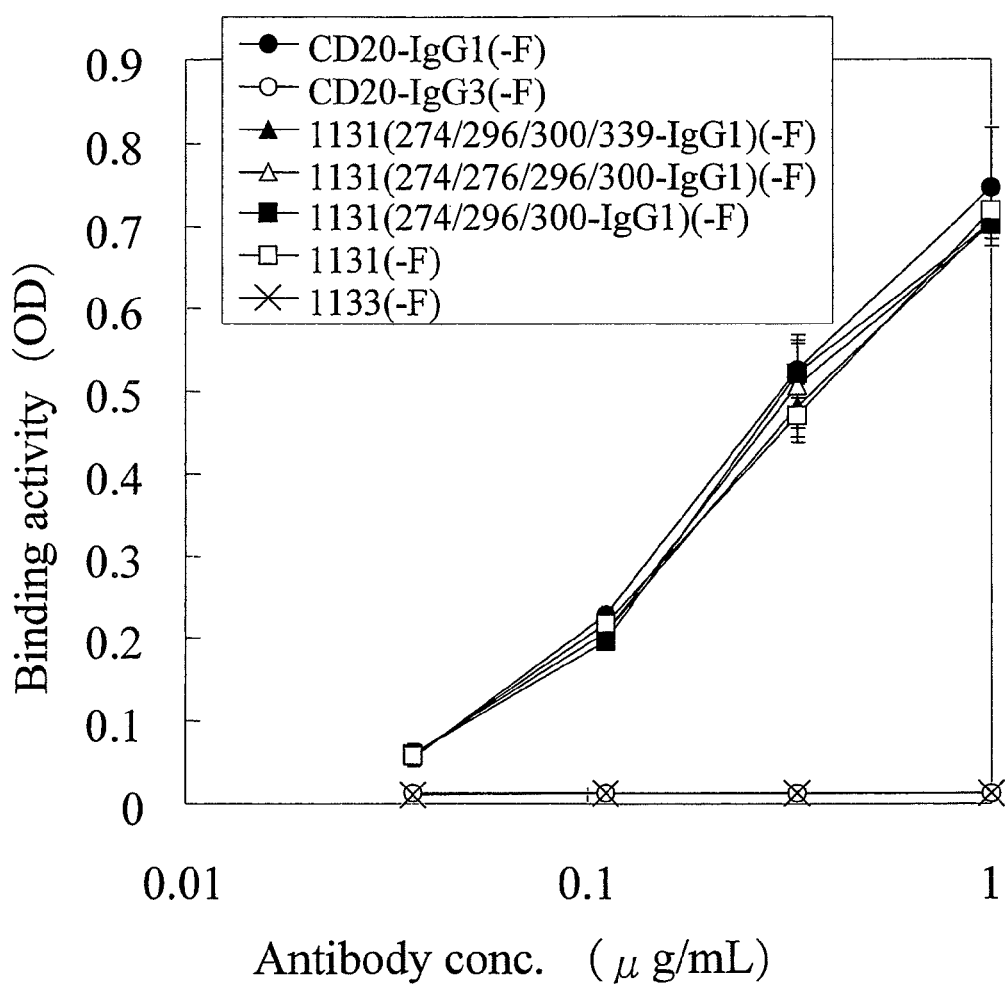
FIG. 25 shows a result of the measurement of the binding activity of various anti-CD20 antibodies to protein A measured by ELISA assay. The abscissa shows an antibody concentration, and the ordinate shows the binding activity (absorbance) to protein A in each antibody concentration. In the graph, ● shows CD20-IgG1(−F), ○ shows CD20-IgG3(−F), ▲ shows 1131(274/296/300/339-IgG1)(−F), Δ shows 1131(274/276/296/300-IgG1)(−F), ■ shows 1131(274/296/300-IgG1)(−F), □ shows 1131(−F) and × shows 1133(−F).

The results are shown in FIG. 25. As is shown in FIG. 25, 1131 (296/300-IgG1)(–F), 1131(274/296/300-IgG1)(–F) and 1131(274/276/296/300-IgG1)(–F) showed protein A-binding activities similar to CD20-IgG1(–F) and 1131(–

F). These results indicate that the protein A-binding activity of chimeric isotype antibodies is not affected by the amino acid sequences at positions 276 and/or 339 of the IgG3-type isotype antibodies.

Based on these results, it was found that, in antibodies having protein A-binding activity, which are composed of CH1 and the hinge of the amino acid sequences of human IgG1 antibody and Fc of a chimeric isotype of human IgG1 antibody and human IgG3 antibody, in order to enhance the CDC activity, the amino acid residues at positions 276 and 339 are preferably lysine and threonine, respectively, which are the amino acid residues of the human IgG3-type.

Example 9

Construction of Anti-Campath Human IgG1 Antibody, 1133-Type Anti-Campath Chimeric Isotype Antibody and 1131-Type Anti-Campath Chimeric Isotype Antibody Using Animal Cells 1. Construction of Various Vectors Based on the results of Examples 2 and 4, it was found that CDC activity is enhanced by swapping CH2 or Fc of anti-CD20 human IgG1 antibody with the amino acid sequence of human IgG3. In order to confirm the enhancement of CDC activity in an antibody against another antigen, human IgG1, 1133-type and 1131-type antibodies of a humanized anti-Campath antibody, Campath-1H, were constructed and compared in CDC activity.

Figure 26:
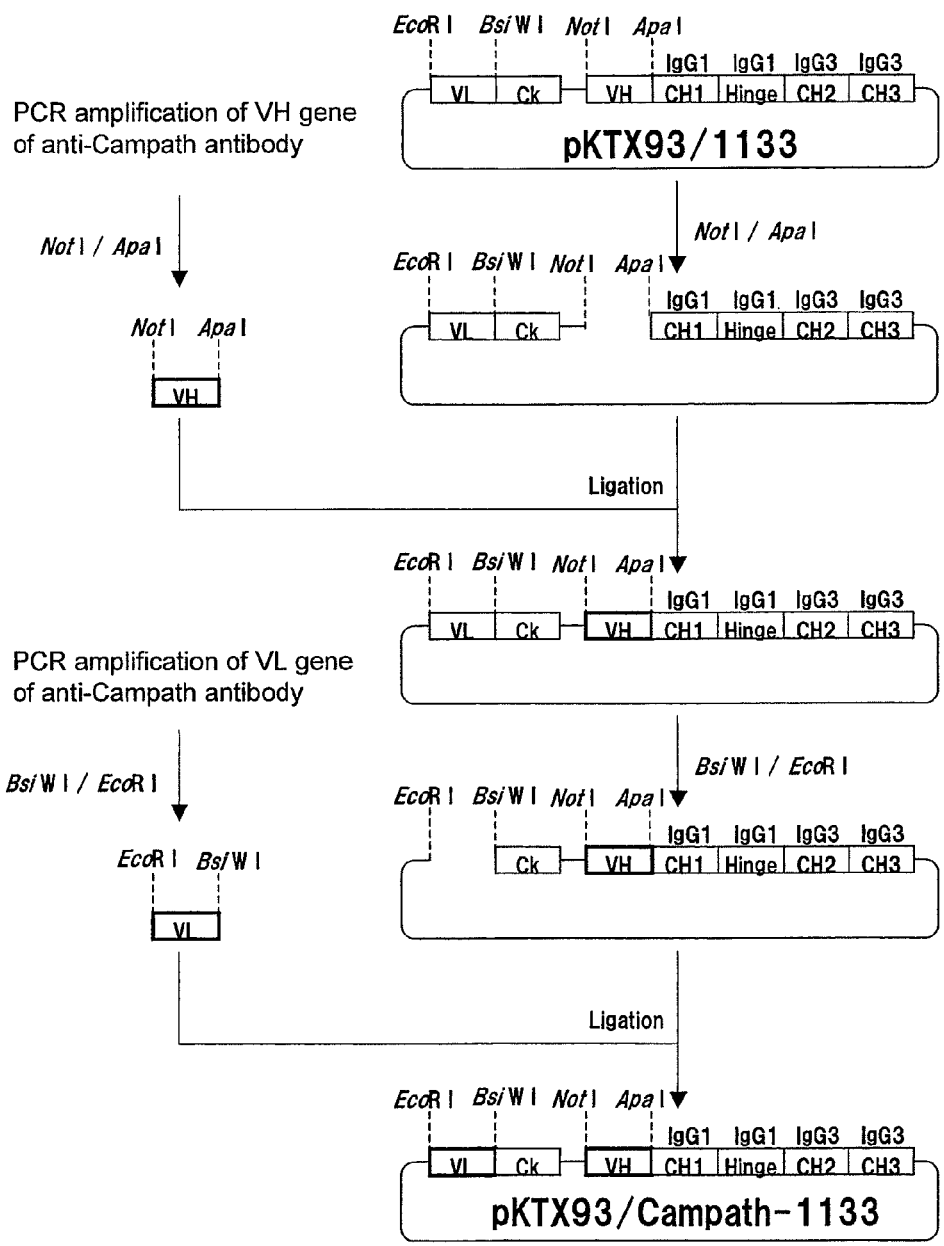
FIG. 26 shows construction steps of a plasmid pKTX93/Campath-1133.

(1) Construction of Expression Vector Encoding the Gene Sequence of 1133-Type Anti-Campath Chimeric Isotype Antibody Expression vector encoding a 1133-type anti-Campath chimeric isotype antibody, which specifically recognizes human Campath antigen (CD52) and has human IgG1 amino acid sequences in the CH1 and hinge and human IgG3 amino acid sequences in the CH2 and CH3, was constructed in accordance with the following procedures (FIG. 26).

First, the amino acid sequences and gene sequences of the heavy chain variable region (Accession: S79311) and light chain variable region (Accession: S79307) of humanized anti-Campath antibody Campath-1H were obtained from National Center of Biotechnology Information (NCBI) database. The amino acid sequence and gene sequence of the heavy chain variable region of humanized anti-Campath antibody Campath-1H are represented respectively by SEQ ID NOs:39 and 40, and the amino acid sequence and gene sequence of the light chain variable region of humanized anti-Campath antibody Campath-1H are represented respectively by SEQ ID NOs:41 and 42. Based on these sequential data, the amino acid sequence of the heavy chain of 1133-type anti-Campath chimeric isotype antibody represented by SEQ ID NO:43, containing the heavy chain variable region of humanized anti-Campath antibody Campath-1H and the 1133-type chimeric isotype heavy chain constant region, and the amino acid sequence of the light chain of an anti-Campath antibody represented by SEQ ID NO:44, containing the light chain variable region of humanized anti-Campath antibody Campath-1H and the human antibody light chain constant region sequence, were designed.

Next, the nucleotide sequence represented by SEQ ID NO:45 was designed. In this nucleotide sequence, a restriction enzyme NotI recognition was added to the 5'-terminal side of the gene sequence of the humanized anti-Campath antibody Campath-1H heavy chain variable region represented by SEQ ID NO:40 while another restriction enzyme ApaI recognition sequence was added to the 3'-terminal side thereof. Based on the nucleotide sequence represented by SEQ ID NO:45, the nucleotide sequences represented by SEQ ID NOs:46, 47, 48 and 49 were respectively designed. These nucleotide sequences are designed by dividing the nucleotide sequence represented by SEQ ID NO:45 into four parts, in such a manner that mutually adjoining sequences have an overlapping sequence of approximately 20 bp and the sense strands and antisense strands designed in reciprocal orders.

In practice, synthetic oligo DNAs having the nucleotide sequences represented by SEQ ID NOs:46, 47, 48 and 49 were prepared (manufactured by FASMAC) and PCR was carried out using the same. In order to adjust the final concentration of each of the two synthetic oligo DNAs located at both terminals to 0.5 µM and the final concentration of each of the two synthetic oligo DNAs located inside to 0.1 µM, a PCR solution [0.02 U/µl KOD+DNA Polymerase (manufactured by TOYOBO), 0.2 mM dNTPs, 1 mM magnesium sulfate, 1/10 by volume 10-fold diluted PCR buffer (manufactured by TOYOBO; attached to KOD DNA Polymerase)] was prepared. Using a DNA thermal cycler GeneAmp PCR System 9700 (manufactured by Applied Biosystems), the PCR was carried out by thermally denaturing at 94° C. for 4 minutes, followed by 25 cycles with each cycle consisting of reactions at 94° C. for 30 seconds, at 50° C. for 30 seconds and at 68° C. for 60 seconds. After completion of the PCR, the reaction mixture was electrophoresed on agarose gel and a PCR product of about 480 bp was recovered by using QIAquick Gel Extraction Kit (manufactured by Qiagen). The PCR product thus recovered was digested with restriction enzymes NotI (manufactured by Takara Shuzo) and ApaI (manufactured by Takara Shuzo) and the reaction mixture was electrophoresed on agarose gel. Using QIAquick Gel Extraction Kit (manufactured by Qiagen), a DNA fragment of about 450 bp was cleaved and purified. On the other hand, the expression vector for 1133-type anti-CD20 chimeric isotype antibody, pKTX93/1133, constructed in Example 1 was subjected to the same restriction enzyme treatment and a DNA fragment of about 13 kbp was cleaved and purified. These purified DNA fragments were mixed together and subjected to ligation reaction by adding Ligation High Solution (manufactured by TOYOBO). By using the reaction mixture, *Escherichia coli* XL1-Blue MRF' (manufactured by Stratagene) was transformed. From clones of the thus obtained transformant, each plasmid DNA was prepared. After reaction by using Big Dye Terminator Cycle Sequencing Kit v3.1 (manufactured by Applied Biosystems) according to the attached instructions, the nucleotide sequence of the DNA inserted into each plasmid was analyzed by using DNA Sequencer ABI PRISM 3700 DNA Analyzer manufactured by the same company. Thus, it was confirmed that the expression vector for 1133-type chimeric isotype, in which the heavy chain variable region was replaced with the nucleotide sequence encoding the heavy chain variable region of the anti-Campath humanized antibody Campath-1H, was obtained.

Next, the nucleotide sequence represented by SEQ ID NO:50 was designed. In this nucleotide sequence, a restriction enzyme EcoRI recognition was added to the 5'-terminal side of the gene sequence of the humanized anti-Campath antibody Campath-1H light chain variable region represented by SEQ ID NO:42, and another restriction enzyme BsiWI recognition sequence was added to the 3'-terminal side thereof. Based on the nucleotide sequence represented by SEQ ID NO:50, the nucleotide sequences represented by SEQ ID NOs:51, 52, 53 and 54 were respectively designed. These nucleotide sequences are designed by dividing the nucleotide sequence represented by SEQ ID NO:50 into four parts, in such a manner that mutually adjoining sequences have an overlapping sequence of approximately 20 bp and the sense strands and antisense strands designed in reciprocal orders. Using these four synthetic oligo DNAs, PCR was carried out to amplify the DNA fragment having the nucleotide sequence represented by SEQ ID NO:50.

In practice, synthetic oligo DNAs having the nucleotide sequences represented by SEQ ID NOs: 51, 52, 53 and 54 were prepared (manufactured by FASMAC) and PCR was conducted using the same. In order to adjust the final concentration of each of the two synthetic oligo DNAs located at both terminals to 0.5 µM and the final concentration of each of the two synthetic oligo DNAs located inside to 0.1 µM, a PCR solution [0.02 U/µl KOD+ DNA Polymerase (manufactured by TOYOBO), 0.2 mM dNTPs, 1 mM magnesium sulfate, 1/10 by volume 10-fold diluted PCR buffer (manufactured by TOYOBO; attached to KOD DNA Polymerase)] was prepared. Using a DNA thermal cycler GeneAmp PCR System 9700 (manufactured by Applied Biosystems), the PCR was performed by thermally denaturing at 94° C. for 4 minutes, followed by 25 cycles with each cycle consisting of reactions at 94° C. for 30 seconds, at 50° C. for 30 seconds and at 68° C. for 60 seconds. After completion of the PCR, the reaction mixture was electrophoresed on agarose gel and a PCR product of about 420 bp was recovered by using QIAquick Gel Extraction Kit (manufactured by Qiagen). The PCR product thus recovered was digested with restriction enzymes EcoRI (manufactured by Takara Shuzo) and BsiWII (manufactured by TOYOBO) and the reaction mixture was electrophoresed on agarose gel. Using QIAquick Gel Extraction Kit (manufactured by Qiagen), a DNA fragment of about 400 bp was cleaved and purified. On the other hand, the expression vector for 1133-type chimeric isotype constructed herein, in which the heavy chain variable region was replaced with the nucleotide sequence encoding the humanized anti-Campath antibody Campath-1H heavy chain variable region, was subjected to the same restriction enzyme treatment and a DNA fragment of about 13 kbp was cleaved and purified. These purified DNA fragments were mixed together and subjected to ligation reaction by adding Ligation High Solution (manufactured by TOYOBO). By using the reaction mixture, Escherichia coli XL1-Blue MRF' (manufactured by Stratagene) was transformed. From clones of the thus obtained transformant, each plasmid DNA was prepared. After reaction by using Big Dye Terminator Cycle Sequencing Kit v3.1 (manufactured by Applied Biosystems) according to the attached instructions, the nucleotide sequence of the DNA inserted into each plasmid was analyzed by using DNA Sequencer ABI PRISM 3700 DNA Analyzer manufactured by the same company. Thus, it was confirmed that the expression vector for 1133-type anti-Campath chimeric isotype antibody, pKTX93/Campath1H-1133, was obtained.

Figure 27:
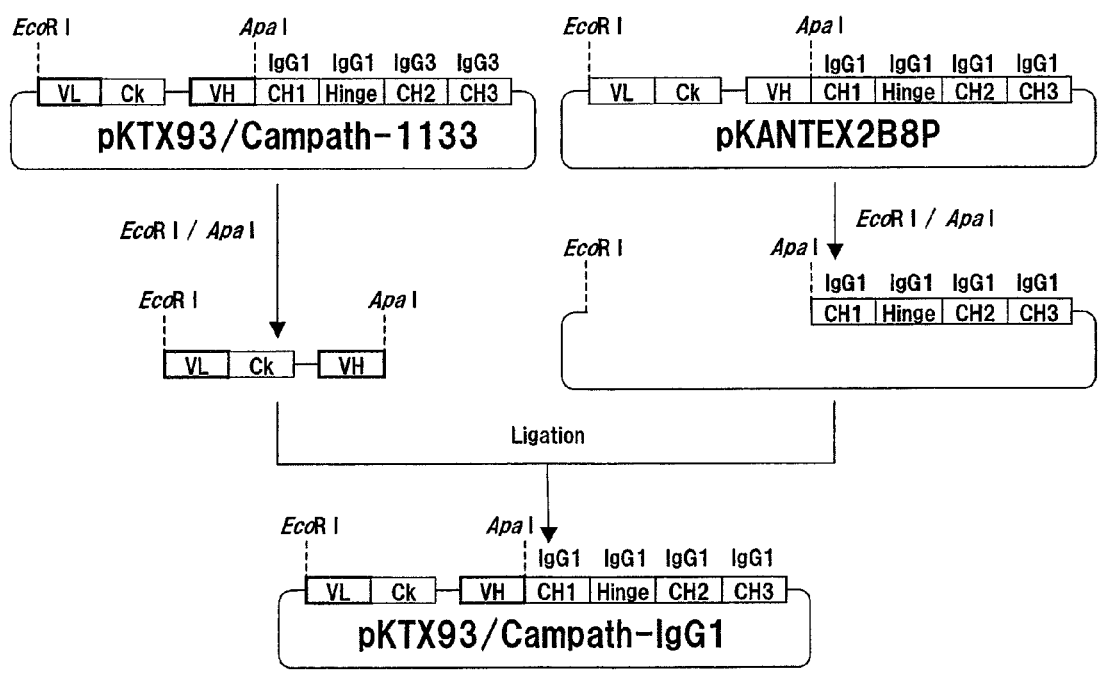
FIG. 27 shows construction steps of a plasmid pKTX93/Campath-IgG1.

(2) Construction of Expression Vector Encoding the Gene Sequence of Anti-Campath Human IgG1 Antibody Expression vector encoding an anti-Campath human IgG1 antibody which specifically recognizes human Campath antigen (CD52), in which the heavy chain constant region has the amino acid sequence of human IgG1, was constructed by the following procedures (FIG. 27).

The expression vector for 1133-type anti-Campath antibody, pKTX93/Campath1H-1133, constructed herein was digested with EcoRI (manufactured by Takara Shuzo) and another restriction enzyme ApaI (manufactured by Takara Shuzo) and the reaction mixture was electrophoresed on agarose gel. Using QIAquick Gel Extraction Kit (manufactured by Qiagen), a DNA fragment of about 3300 bp was cleaved and purified. On the other hand, expression vector for anti-CD20 humanized chimeric antibody, pKANTEX2B8P, was subjected to the same restriction enzyme treatment and a DNA fragment of about 10 kbp was cleaved and purified. These purified DNA fragments were mixed together and subjected to ligation reaction by adding Ligation High Solution (manufactured by TOYOBO). By using the reaction mixture, Escherichia coli XL1-Blue MRF' (manufactured by Stratagene) was transformed. From clones of the thus obtained transformant, each plasmid DNA was prepared. After reaction by using Big Dye Terminator Cycle Sequencing Kit v3.1 (manufactured by Applied Biosystems) according to the attached instructions, the nucleotide sequence of the DNA inserted into each plasmid was analyzed by using DNA Sequencer ABI PRISM 3700 DNA Analyzer manufactured by the same company. Thus, it was confirmed that the expression vector for anti-Campath human IgG1 antibody, pKTX93/Campath1H-IgG1, was obtained.

Figure 28:
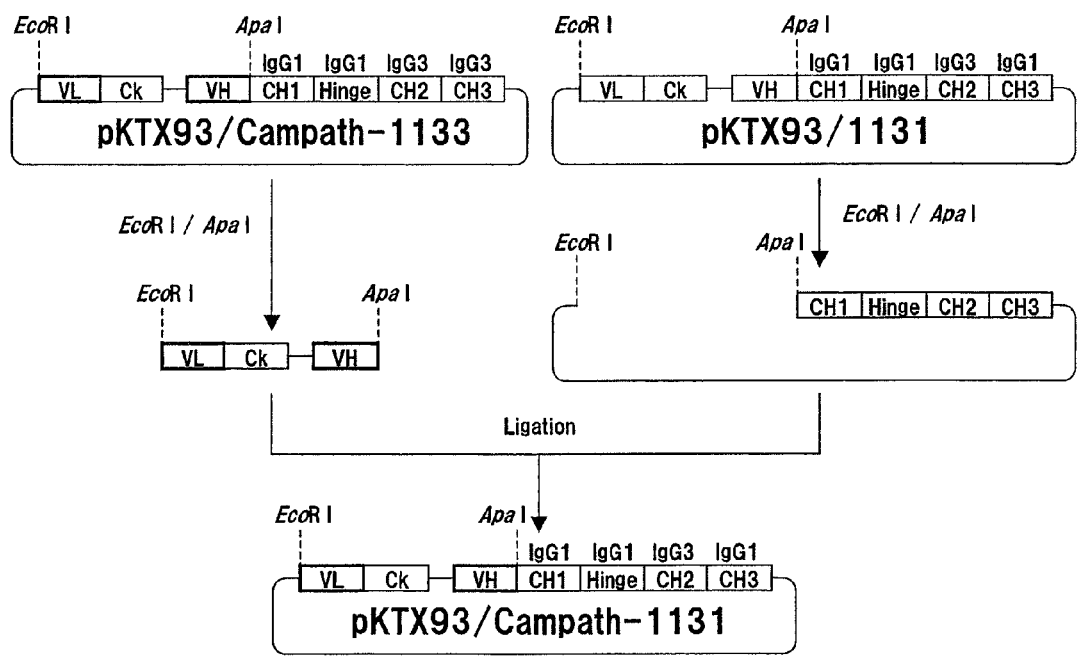
FIG. 28 shows construction steps of a plasmid pKTX93/Campath-1131.

(3) Construction of Expression Vector Encoding the Gene Sequence of 1131-Type Anti-Campath Antibody An expression vector encoding a 1131-type anti-Campath chimeric isotype antibody which specifically recognizes human Campath antigen (CD52), in which, in the amino acid sequence of the heavy chain constant region, CH1 and the hinge have the amino acid sequence of human IgG1, the CH2 has the amino acid sequence of human IgG3 and the CH3 has the amino acid sequence of human IgG1, was constructed by the following procedures (FIG. 28).

The expression vector for 1133-type anti-Campath antibody, pKTX93/Campath1H-1133, constructed in the item 1 in this Example was digested with EcoRI (manufactured by Takara Shuzo) and another restriction enzyme ApaI (manufactured by Takara Shuzo) and the reaction mixture was electrophoresed on agarose gel. Using QIAquick Gel Extraction Kit (manufactured by Qiagen), a DNA fragment of about 3300 bp was cleaved and purified. On the other hand, the expression vector for 1131-type anti-CD20 chimeric isotype antibody, pKTX93/1131, constructed in Example 3 was subjected to the same restriction enzyme treatment and a DNA fragment of about 10 kbp was cleaved and purified. These purified DNA fragments were mixed together and subjected to ligation reaction by adding Ligation High Solution (manufactured by TOYOBO). By using the reaction mixture, Escherichia coli XL1-Blue MRF' (manufactured by Stratagene) was transformed. From clones of the thus obtained transformant, each plasmid DNA was prepared. After reaction by using Big Dye Terminator Cycle Sequencing Kit v3.1 (manufactured by Applied Biosystems) according to the attached instructions, the nucleotide sequence of the DNA inserted into each plasmid was analyzed by using DNA Sequencer ABI PRISM 3700 DNA Analyzer manufactured by the same company. Thus, it was confirmed that the expression vector for 1131-type anti-Campath chimeric isotype antibody, pKTX93/Campath1H-1131, was obtained.

2. Stable Expression of Various Anti-Campath Antibodies in Animal Cells

Each of the expression vectors for anti-Campath antibody constructed in the item 1 of this Example was transferred into host cells CHO/FUT8$^{-/-}$ as described in the item 3 of Example 1 and thus cells capable of stably producing the anti-Campath antibody were prepared by the same procedures as in the item 3 of Example 1.

3. Purification of Various Anti-Campath Antibodies

Each of the transformants expressing the respective anti-Campath chimeric isotype antibodies obtained in 2 of this Example was cultured and purified by the same procedures as in the item 5 of Example 1. The anti-Campath human IgG1 antibody and the 1131-type anti-Campath chimeric isotype antibody were purified by using a column packed with Prosep-A (protein A-binding resin: manufactured by Millipore). The 1133-type anti-Campath chimeric isotype antibody was purified by using a column packed with Prosep-G (protein G-binding resin: manufactured by Millipore).

Table 8 shows the names of the expression vectors and purified antibodies corresponding to the chimeric isotype antibodies. As host cells, CHO/FUT8−/− were used in each case.

TABLE 13

| Expression vector | Purified antibody (name) |
| --- | --- |
| pKTX93/Campath1H-IgG1 | Campath1H-IgG1(−F) |
| pKTX93/Campath1H-1133 | Campath1H-1133(−F) |
| pKTX93/Campath1H-1131 | Campath1H-1131(−F) |

4. Evaluation of Purification Degrees of Various Purified Anti-Campath Antibody Samples by SDS-PAGE In order to evaluate the purification degrees of the purified samples of the modified antibodies obtained in the item 3 in this Example, SDS-PAGE was carried out by the same procedures as in the item 6 of Example 1. As a result, it was confirmed that the desired IgG molecules constituted by the H and L chains are contained at a sufficient ratio in the purified sample of anti-CD20 chimeric isotype antibody obtained in the item 3 of this Example.

Example 10

Measurement of CDC Activities of Various Anti-Campath Antibodies

Figure 29:
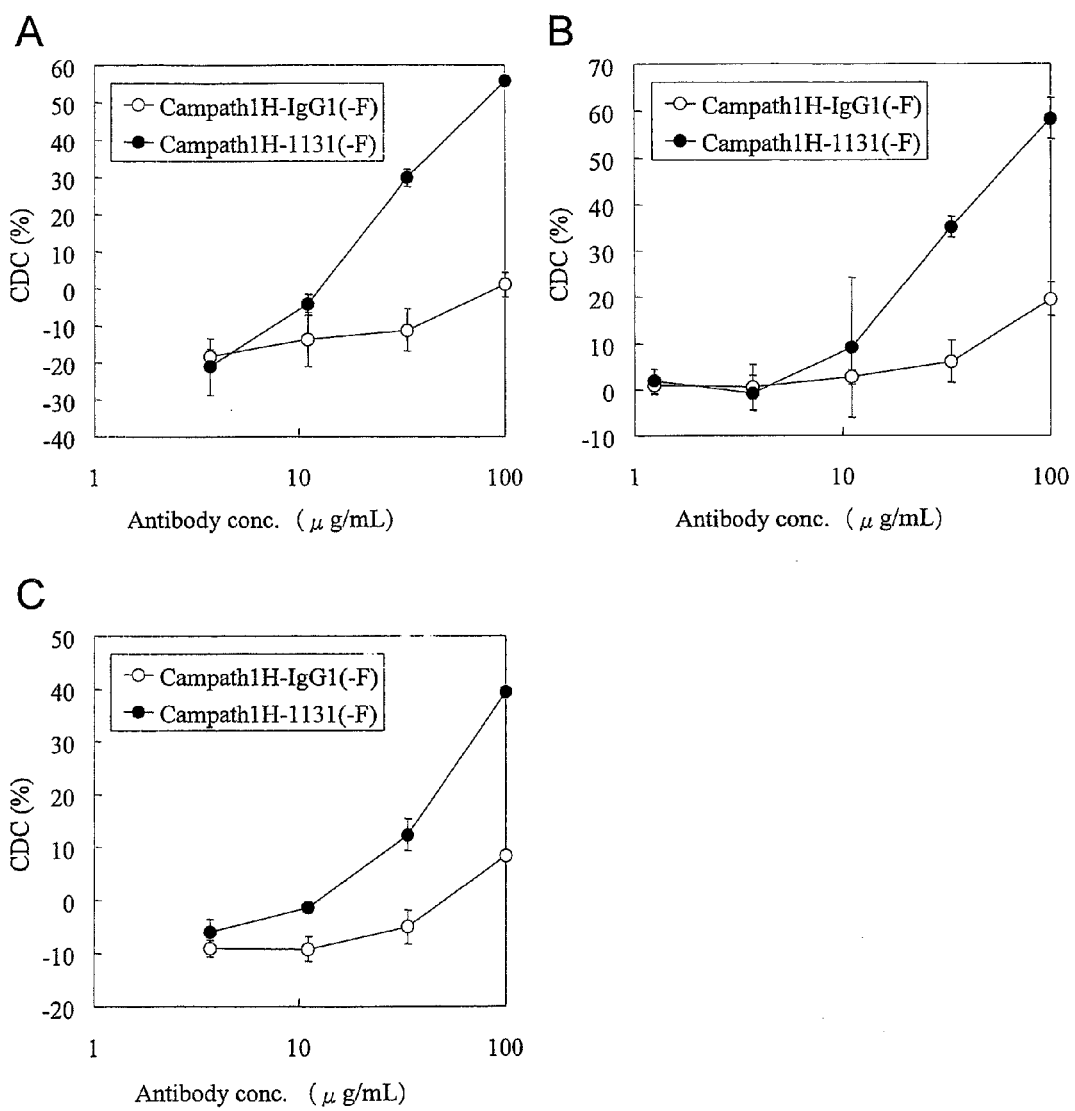
FIG. 29 shows the CDC activity of anti-Campath human IgG1 antibody and 1131-type anti-Campath chimeric isotype antibody to MEC-1 cell (A), MEC-2 cell (B) or EHEB cell (C). The abscissa shows an antibody concentration, and the ordinate shows the ratio of cytotoxicity in each antibody concentration. In the graph, ● shows Campath1H-1131(−F) and ○ shows Campath1H-IgG1(−F).

In order to evaluate the CDC activities on Campath antigen-positive human chronic B cell leukemia cell lines MEC-1 (DSMZ: ACC497), MEC-2 (DSMZ: ACC500) and EHEB (DSMZ: ACC67) of the purified samples of the anti-Campath human IgG1 antibody and 1131-type anti-Campath chimeric isotype antibody obtained in the item 3 of Example 9, the procedures of the item 2 of Example 2 were carried out. The results are shown in FIG. 29. On each of the cell lines MEC-1, MEC-2 and EHEB, Campath1H-1131(−F) showed higher CDC activity than Campath1H-IgG(−F). When the purified sample of the 1133-type anti-Campath chimeric isotype antibody was tested in the same manner, Campath1H-1133(−F) showed higher CDC activity than Campath1H-IgG(−F) on each of the cell lines MEC-1, MEC-2 and EHEB.

These results indicate that, similar to the anti-CD20 antibodies, in anti-Campath antibodies which are composed of CH1 and the hinge of the amino acid sequences of human IgG1 antibody and Fc of a chimeric isotype of human IgG1 antibody and human IgG3 antibody, the part wherein the swapping of the amino acid sequence in the Fc region with the amino acid sequence of human IgG3 antibody is important for enhancing the CDC activity resides in the CH2 domain.

While the invention has been described in detail and with reference to specific embodiments thereof, it will be apparent to one skill in the art that various changes and modifications can be made therein without departing from the spirit and scope thereof.

This application is based on Japanese application No. 2007-013640 filed on Jan. 24, 2007, the entire contents of which are incorporated hereinto by reference. All references cited herein are incorporated in their entirety.

The invention claimed is:

1. A recombinant antibody composition comprising a human IgG1 antibody, wherein said antibody comprises a CH2 domain in which the amino acids at positions 276 and 339, as indicated by the EU index as in Kabat, et al., are substituted with different amino acids;
   wherein the substitution at position 276 is with an amino acid selected from the group consisting of aspartic acid, leucine, serine and lysine;
   wherein the substitution at position 339 is with an amino acid selected from the group consisting of aspartic acid, phenylalanine, isoleucine, lysine, asparagine, serine, tryptophan, tyrosine and threonine;
   and wherein said antibody exhibits improved complement-dependent cytotoxic activity over the IgG1 antibody prior to said substitutions.

2. The recombinant antibody composition according to claim 1, wherein the amino acid substitutions at positions 276 and 339, as indicated by the EU index as in Kabat, et al., are with lysine and threonine, respectively.

3. The recombinant antibody composition according to claim 1, wherein the CH3 domain in the Fc region of said antibody has the same amino acid sequence as the CH3 domain of human IgG3.

4. The recombinant antibody composition according to claim 1, wherein said antibody comprises complex-type N-glycoside-linked sugar chains in the Fc region, and wherein the ratio of sugar chains in which fucose is not bound to N-acetylglucosamine in the reducing terminal of the sugar chains among the total complex-type N-glycoside-linked sugar chains which bind to the Fc region contained in the composition is 20% or more.

5. The recombinant antibody composition according to claim 1, wherein said antibody comprises complex-type N-glycoside-linked sugar chains in the Fc region, wherein the complex-type N-glycoside-linked sugar chains bound to the Fc region of the antibody are sugar chains in which fucose is not bound to N-acetylglucosamine in the reducing terminal in the sugar chains.

6. A pharmaceutical composition comprising the recombinant antibody composition described in claim 1 as an active ingredient.

7. A process for producing the recombinant antibody composition of claim 1, comprising culturing a transformant in a medium to form and accumulate the antibody composition in the culture; and recovering and purifying the antibody composition from the culture, said transformant containing a DNA encoding the human IgG1 antibody contained in the recombinant antibody composition.

* * * * *

SEQUENCE LISTING

<160> NUMBER OF SEQ ID NOS: 56

<210> SEQ ID NO 1
<211> LENGTH: 30
<212> TYPE: DNA
<213> ORGANISM: Artificial Sequence
<220> FEATURE:
<223> OTHER INFORMATION: Synthetic DNA

<400> SEQUENCE: 1
caaaggtacc caagggccca tcggtcttcc         30

<210> SEQ ID NO 2
<211> LENGTH: 45
<212> TYPE: DNA
<213> ORGANISM: Artificial Sequence
<220> FEATURE:
<223> OTHER INFORMATION: Synthetic DNA

<400> SEQUENCE: 2
gtttggatcc tcgcgagtcg cactcattta cccggagaca gggag         45

<210> SEQ ID NO 3
<211> LENGTH: 330
<212> TYPE: PRT
<213> ORGANISM: Artificial Sequence
<220> FEATURE:
<223> OTHER INFORMATION: Synthetic Peptide

<400> SEQUENCE: 3

Ala Ser Thr Lys Gly Pro Ser Val Phe Pro Leu Ala Pro Ser Ser Lys
 1               5                   10                  15

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Asn Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Ile Phe Ser Cys Ser Val Met His Glu Ala Leu His Asn Arg Phe Thr
305                 310                 315                 320

Gln Lys Ser Leu Ser Leu Ser Pro Gly Lys
                325                 330

<210> SEQ ID NO 4
<211> LENGTH: 377
<212> TYPE: PRT
<213> ORGANISM: Artificial Sequence
<220> FEATURE:
<223> OTHER INFORMATION: Synthetic Peptide

<400> SEQUENCE: 4

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
            50                  55                  60
Leu Ser Ser Val Val Thr Val Pro Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Lys Phe Asn Trp Tyr
            195                 200                 205

Val Asp Gly Val Glu Val His Asn Ala Lys Thr Lys Pro Arg Glu Glu
210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Asp Glu Leu
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Val
            340                 345                 350

Phe Ser Cys Ser Val Met His Glu Ala Leu His Asn His Tyr Thr Gln
            355                 360                 365

Lys Ser Leu Ser Leu Ser Pro Gly Lys
            370                 375

<210> SEQ ID NO 5
<211> LENGTH: 330
<212> TYPE: PRT
<213> ORGANISM: Artificial Sequence
<220> FEATURE:
<223> OTHER INFORMATION: Synthetic Peptide

<400> SEQUENCE: 5

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45
```

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 6
<211> LENGTH: 330
<212> TYPE: PRT
<213> ORGANISM: Artificial Sequence
<220> FEATURE:
<223> OTHER INFORMATION: Synthetic Peptide

<400> SEQUENCE: 6

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Asn Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Ile Phe Ser Cys Ser Val Met His Glu Ala Leu His Asn Arg Phe Thr
305                 310                 315                 320

Gln Lys Ser Leu Ser Leu Ser Pro Gly Lys
                325                 330

<210> SEQ ID NO 7
<211> LENGTH: 330
<212> TYPE: PRT
<213> ORGANISM: Artificial Sequence
<220> FEATURE:
<223> OTHER INFORMATION: Synthetic Peptide

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro

```
                   115                 120                 125
Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Lys Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Asn Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Ile Phe Ser Cys Ser Val Met His Glu Ala Leu His Asn Arg Phe Thr
305                 310                 315                 320

Gln Lys Ser Leu Ser Leu Ser Pro Gly Lys
                325                 330

<210> SEQ ID NO 8
<211> LENGTH: 330
<212> TYPE: PRT
<213> ORGANISM: Artificial Sequence
<220> FEATURE:
<223> OTHER INFORMATION: Synthetic Peptide

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Asn Trp
145                 150                 155                 160
```

```
Tyr Val Asp Gly Val Glu Val His Asn Ala Lys Thr Lys Pro Arg Glu
            165                 170                 175

Glu Gln Phe Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Thr Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Ser Gly Gln Pro Glu Asn
            260                 265                 270

Asn Tyr Asn Thr Thr Pro Pro Met Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Ile Phe Ser Cys Ser Val Met His Glu Ala Leu His Asn Arg Phe Thr
305                 310                 315                 320

Gln Lys Ser Leu Ser Leu Ser Pro Gly Lys
            325                 330

<210> SEQ ID NO 9
<211> LENGTH: 330
<212> TYPE: PRT
<213> ORGANISM: Artificial Sequence
<220> FEATURE:
<223> OTHER INFORMATION: Synthetic Peptide

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
            165                 170                 175

Glu Gln Tyr Asn Ser Thr Phe Arg Val Val Ser Val Leu Thr Val Leu
            180                 185                 190
```

His Gln Asp Trp Leu Asn Gly Lys Glu Tyr Lys Cys Lys Val Ser Asn
           195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Asn Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Ile Phe Ser Cys Ser Val Met His Glu Ala Leu His Asn Arg Phe Thr
305                 310                 315                 320

Gln Lys Ser Leu Ser Leu Ser Pro Gly Lys
                325                 330

<210> SEQ ID NO 10
<211> LENGTH: 330
<212> TYPE: PRT
<213> ORGANISM: Artificial Sequence
<220> FEATURE:
<223> OTHER INFORMATION: Synthetic Peptide

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Phe Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Glu Glu

```
                       225                 230                 235                 240
Met Thr Lys Asn Gln Val Ser Leu Thr Cys Leu Val Lys Gly Phe Tyr
                    245                 250                 255

Pro Ser Asp Ile Ala Val Glu Trp Glu Ser Ser Gly Gln Pro Glu Asn
                260                 265                 270

Asn Tyr Asn Thr Thr Pro Pro Met Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Ile Phe Ser Cys Ser Val Met His Glu Ala Leu His Asn Arg Phe Thr
305                 310                 315                 320

Gln Lys Ser Leu Ser Leu Ser Pro Gly Lys
                325                 330

<210> SEQ ID NO 11
<211> LENGTH: 330
<212> TYPE: PRT
<213> ORGANISM: Artificial Sequence
<220> FEATURE:
<223> OTHER INFORMATION: Synthetic Peptide

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270
```

```
Asn Tyr Asn Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Ile Phe Ser Cys Ser Val Met His Glu Ala Leu His Asn Arg Phe Thr
305                 310                 315                 320

Gln Lys Ser Leu Ser Leu Ser Pro Gly Lys
                325                 330

<210> SEQ ID NO 12
<211> LENGTH: 56
<212> TYPE: DNA
<213> ORGANISM: Artificial Sequence
<220> FEATURE:
<223> OTHER INFORMATION: Synthetic DNA

<400> SEQUENCE: 12
cgtggtggtg gacgtgagcc acgaagaccc cgaggtcaag ttcaagtggt acgtgg      56

<210> SEQ ID NO 13
<211> LENGTH: 71
<212> TYPE: DNA
<213> ORGANISM: Artificial Sequence
<220> FEATURE:
<223> OTHER INFORMATION: Synthetic DNA

<400> SEQUENCE: 13
catctcctcc cgggatgggg gcagggtgta cacctgtggt tctcggggct gtcctttggt    60
tttggagatg g                                                         71

<210> SEQ ID NO 14
<211> LENGTH: 56
<212> TYPE: DNA
<213> ORGANISM: Artificial Sequence
<220> FEATURE:
<223> OTHER INFORMATION: Synthetic DNA

<400> SEQUENCE: 14
cgtggtggtg gacgtgagcc acgaagaccc cgaggtccag ttcaactggt acgtgg       56

<210> SEQ ID NO 15
<211> LENGTH: 158
<212> TYPE: DNA
<213> ORGANISM: Artificial Sequence
<220> FEATURE:
<223> OTHER INFORMATION: Synthetic DNA

<400> SEQUENCE: 15
cgtggtggtg gacgtgagcc acgaagaccc cgaggtccag ttcaagtggt acgtggacgg    60
cgtggaggtg cataatgcca agacaaagcc gcgggaggag cagtacaaca gcacgttccg   120
tgtggtcagc gtcctcaccg tcctgcacca ggactggc                           158

<210> SEQ ID NO 16
<211> LENGTH: 155
<212> TYPE: DNA
<213> ORGANISM: Artificial Sequence
<220> FEATURE:
<223> OTHER INFORMATION: Synthetic DNA

<400> SEQUENCE: 16
catctcctcc cgggatgggg gcagggtgta cacctgtggt tctcggggct gtcctttggt    60
tttggagatg gttttctcga tgggggctgg gagggctttg ttggagacct tgcacttgta   120
```

-continued ctccttgccg ttcagccagt cctggtgcag gacgg                                155

<210> SEQ ID NO 17
<211> LENGTH: 158
<212> TYPE: DNA
<213> ORGANISM: Artificial Sequence
<220> FEATURE:
<223> OTHER INFORMATION: Synthetic DNA

<400> SEQUENCE: 17
cgtggtggtg acgtgagcc acgaagaccc cgaggtccag ttcaagtggt acgtggacgg     60
cgtggaggtg cataatgcca agacaaagcc gcgggaggag cagttcaaca gcacgtaccg    120
tgtggtcagc gtcctcaccg tcctgcacca ggactggc                            158

<210> SEQ ID NO 18
<211> LENGTH: 1504
<212> TYPE: DNA
<213> ORGANISM: Cricetulus griseus
<220> FEATURE:
<221> NAME/KEY: CDS
<222> LOCATION: (1)..(1119)

<400> SEQUENCE: 18

```
atg gct cac gct ccc gct agc tgc ccg agc tcc agg aac tct ggg gac      48
Met Ala His Ala Pro Ala Ser Cys Pro Ser Ser Arg Asn Ser Gly Asp
 1               5                  10                  15 ggc gat aag ggc aag ccc agg aag gtg gcg ctc atc acg ggc atc acc      96
Gly Asp Lys Gly Lys Pro Arg Lys Val Ala Leu Ile Thr Gly Ile Thr
             20                  25                  30 ggc cag gat ggc tca tac ttg gca gaa ttc ctg ctg gag aaa gga tac     144
Gly Gln Asp Gly Ser Tyr Leu Ala Glu Phe Leu Leu Glu Lys Gly Tyr
         35                  40                  45 gag gtt cat gga att gta cgg cga tcc agt tca ttt aat aca ggt cga     192
Glu Val His Gly Ile Val Arg Arg Ser Ser Ser Phe Asn Thr Gly Arg
     50                  55                  60 att gaa cat tta tat aag aat cca cag gct cat att gaa gga aac atg     240
Ile Glu His Leu Tyr Lys Asn Pro Gln Ala His Ile Glu Gly Asn Met
 65                  70                  75                  80 aag ttg cac tat ggt gac ctc acc gac agc acc tgc cta gta aaa atc     288
Lys Leu His Tyr Gly Asp Leu Thr Asp Ser Thr Cys Leu Val Lys Ile
                 85                  90                  95 atc aat gaa gtc aaa cct aca gag atc tac aat ctt ggt gcc cag agc     336
Ile Asn Glu Val Lys Pro Thr Glu Ile Tyr Asn Leu Gly Ala Gln Ser
            100                 105                 110 cat gtc aag att tcc ttt gac tta gca gag tac act gca gat gtt gat     384
His Val Lys Ile Ser Phe Asp Leu Ala Glu Tyr Thr Ala Asp Val Asp
        115                 120                 125 gga gtt ggc acc ttg cgg ctt ctg gat gca att aag act tgt ggc ctt     432
Gly Val Gly Thr Leu Arg Leu Leu Asp Ala Ile Lys Thr Cys Gly Leu
    130                 135                 140 ata aat tct gtg aag ttc tac cag gcc tca act agt gaa ctg tat gga     480
Ile Asn Ser Val Lys Phe Tyr Gln Ala Ser Thr Ser Glu Leu Tyr Gly
145                 150                 155                 160 aaa gtg caa gaa ata ccc cag aaa gag acc acc cct ttc tat cca agg     528
Lys Val Gln Glu Ile Pro Gln Lys Glu Thr Thr Pro Phe Tyr Pro Arg
                165                 170                 175 tcg ccc tat gga gca gcc aaa ctt tat gcc tat tgg att gta gtg aac     576
Ser Pro Tyr Gly Ala Ala Lys Leu Tyr Ala Tyr Trp Ile Val Val Asn
            180                 185                 190 ttt cga gag gct tat aat ctc ttt gcg gtg aac ggc att ctc ttc aat     624
Phe Arg Glu Ala Tyr Asn Leu Phe Ala Val Asn Gly Ile Leu Phe Asn
```

```
                    195                 200                 205
cat gag agt cct aga aga gga gct aat ttt gtt act cga aaa att agc         672
His Glu Ser Pro Arg Arg Gly Ala Asn Phe Val Thr Arg Lys Ile Ser
    210                 215                 220 cgg tca gta gct aag att tac ctt gga caa ctg gaa tgt ttc agt ttg         720
Arg Ser Val Ala Lys Ile Tyr Leu Gly Gln Leu Glu Cys Phe Ser Leu
225                 230                 235                 240 gga aat ctg gac gcc aaa cga gac tgg ggc cat gcc aag gac tat gtc         768
Gly Asn Leu Asp Ala Lys Arg Asp Trp Gly His Ala Lys Asp Tyr Val
                245                 250                 255 gag gct atg tgg ctg atg tta caa aat gat gaa cca gag gac ttt gtc         816
Glu Ala Met Trp Leu Met Leu Gln Asn Asp Glu Pro Glu Asp Phe Val
            260                 265                 270 ata gct act ggg gaa gtt cat agt gtc cgt gaa ttt gtt gag aaa tca         864
Ile Ala Thr Gly Glu Val His Ser Val Arg Glu Phe Val Glu Lys Ser
        275                 280                 285 ttc atg cac att gga aag acc att gtg tgg gaa gga aag aat gaa aat         912
Phe Met His Ile Gly Lys Thr Ile Val Trp Glu Gly Lys Asn Glu Asn
    290                 295                 300 gaa gtg ggc aga tgt aaa gag acc ggc aaa att cat gtg act gtg gat         960
Glu Val Gly Arg Cys Lys Glu Thr Gly Lys Ile His Val Thr Val Asp
305                 310                 315                 320 ctg aaa tac tac cga cca act gaa gtg gac ttc ctg cag gga gac tgc        1008
Leu Lys Tyr Tyr Arg Pro Thr Glu Val Asp Phe Leu Gln Gly Asp Cys
                325                 330                 335 tcc aag gcg cag cag aaa ctg aac tgg aag ccc cgc gtt gcc ttt gac        1056
Ser Lys Ala Gln Gln Lys Leu Asn Trp Lys Pro Arg Val Ala Phe Asp
            340                 345                 350 gag ctg gtg agg gag atg gtg caa gcc gat gtg gag ctc atg aga acc        1104
Glu Leu Val Arg Glu Met Val Gln Ala Asp Val Glu Leu Met Arg Thr
        355                 360                 365 aac ccc aac gcc tga gcacctctac aaaaaaattc gcgagacatg gactatggtg        1159
Asn Pro Asn Ala
    370 cagagccagc caaccagagt ccagccactc ctgagaccat cgaccataaa ccctcgactg      1219 cctgtgtcgt cccacacagct aagagctggg ccacaggttt gtgggcacca ggacggggac    1279 actccagagc taaggccact tcgcttttgt caaaggctcc tctcaatgat tttgggaaat     1339 caagaagttt aaaatcacat actcatttta cttgaaatta tgtcactaga caacttaaat    1399 ttttgagtct tgagattgtt tttctctttt cttattaaat gatctttcta tgacccagca    1459 aaaaaaaaaa aaaaaaggga tataaaaaaa aaaaaaaaaa aaaaa                    1504

<210> SEQ ID NO 19
<211> LENGTH: 372
<212> TYPE: PRT
<213> ORGANISM: Cricetulus griseus

<400> SEQUENCE: 19

Met Ala His Ala Pro Ala Ser Cys Pro Ser Ser Arg Asn Ser Gly Asp
1               5                   10                  15

Gly Asp Lys Gly Lys Pro Arg Lys Val Ala Leu Ile Thr Gly Ile Thr
            20                  25                  30

Gly Gln Asp Gly Ser Tyr Leu Ala Glu Phe Leu Leu Glu Lys Gly Tyr
        35                  40                  45

Glu Val His Gly Ile Val Arg Arg Ser Ser Ser Phe Asn Thr Gly Arg
    50                  55                  60

Ile Glu His Leu Tyr Lys Asn Pro Gln Ala His Ile Glu Gly Asn Met
65                  70                  75                  80
```

Lys Leu His Tyr Gly Asp Leu Thr Asp Ser Thr Cys Leu Val Lys Ile
                85                  90                  95

Ile Asn Glu Val Lys Pro Thr Glu Ile Tyr Asn Leu Gly Ala Gln Ser
            100                 105                 110

His Val Lys Ile Ser Phe Asp Leu Ala Glu Tyr Thr Ala Asp Val Asp
        115                 120                 125

Gly Val Gly Thr Leu Arg Leu Leu Asp Ala Ile Lys Thr Cys Gly Leu
    130                 135                 140

Ile Asn Ser Val Lys Phe Tyr Gln Ala Ser Thr Ser Glu Leu Tyr Gly
145                 150                 155                 160

Lys Val Gln Glu Ile Pro Gln Lys Glu Thr Thr Pro Phe Tyr Pro Arg
                165                 170                 175

Ser Pro Tyr Gly Ala Ala Lys Leu Tyr Ala Tyr Trp Ile Val Val Asn
            180                 185                 190

Phe Arg Glu Ala Tyr Asn Leu Phe Ala Val Asn Gly Ile Leu Phe Asn
        195                 200                 205

His Glu Ser Pro Arg Arg Gly Ala Asn Phe Val Thr Arg Lys Ile Ser
    210                 215                 220

Arg Ser Val Ala Lys Ile Tyr Leu Gly Gln Leu Glu Cys Phe Ser Leu
225                 230                 235                 240

Gly Asn Leu Asp Ala Lys Arg Asp Trp Gly His Ala Lys Asp Tyr Val
                245                 250                 255

Glu Ala Met Trp Leu Met Leu Gln Asn Asp Glu Pro Glu Asp Phe Val
            260                 265                 270

Ile Ala Thr Gly Glu Val His Ser Val Arg Glu Phe Val Glu Lys Ser
        275                 280                 285

Phe Met His Ile Gly Lys Thr Ile Val Trp Glu Gly Lys Asn Glu Asn
    290                 295                 300

Glu Val Gly Arg Cys Lys Glu Thr Gly Lys Ile His Val Thr Val Asp
305                 310                 315                 320

Leu Lys Tyr Tyr Arg Pro Thr Glu Val Asp Phe Leu Gln Gly Asp Cys
                325                 330                 335

Ser Lys Ala Gln Gln Lys Leu Asn Trp Lys Pro Arg Val Ala Phe Asp
            340                 345                 350

Glu Leu Val Arg Glu Met Val Gln Ala Asp Val Glu Leu Met Arg Thr
        355                 360                 365

Asn Pro Asn Ala
    370

<210> SEQ ID NO 20
<211> LENGTH: 1316
<212> TYPE: DNA
<213> ORGANISM: Cricetulus griseus

<400> SEQUENCE: 20
gccccgcccc ctccacctgg accgagagta gctggagaat tgtgcaccgg aagtagctct    60
tggactggtg aaccctgcg caggtgcagc aacaatgggt gagccccagg gatccaggag   120
gatcctagtg acagggggct ctggactggt gggcagagct atccagaagg tggtcgcaga   180
tggcgctggc ttaccggag aggaatgggt gtttgtctcc tccaaagatg cagatctgac   240
ggatgcagca caaacccaag ccctgttcca gaaggtacag cccacccatg tcatccatct   300
tgctgcaatg gtaggaggcc ttttccggaa tatcaaatac aacttggatt tctggaggaa   360
gaatgtgcac atcaatgaca acgtcctgca ctcagctttc gaggtgggca ctcgcaaggt   420

-continued

```
ggtctcctgc ctgtccacct gtatcttccc tgacaagacc acctatccta ttgatgaaac    480
aatgatccac aatggtccac cccacagcag caattttggg tactcgtatg ccaagaggat    540
gattgacgtg cagaacaggg cctacttcca gcagcatggc tgcaccttca ctgctgtcat    600
ccctaccaat gtctttggac ctcatgacaa cttcaacatt gaagatggcc atgtgctgcc    660
tggcctcatc cataaggtgc atctggccaa gagtaatggt tcagccttga ctgtttgggg    720
tacagggaaa ccacggaggc agttcatcta ctcactggac ctagcccggc tcttcatctg    780
ggtcctgcgg gagtacaatg aagttgagcc catcatcctc tcagtgggcg aggaagatga    840
agtctccatt aaggaggcag ctgaggctgt agtggaggcc atggacttct gtggggaagt    900 cactttttgat tcaacaaagt cagatgggca gtataagaag acagccagca atggcaagct    960
tcgggcctac ttgcctgatt ccgtttcac acccttcaag caggctgtga aggagacctg   1020
tgcctggttc accgacaact atgagcaggc ccggaagtga agcatgggac aagcgggtgc   1080
tcagctggca atgcccagtc agtaggctgc agtctcatca tttgcttgtc aagaactgag   1140
gacagtatcc agcaacctga ccacatgct ggtctctctg ccaggggggct tcatgcagcc   1200 atccagtagg gccatgtttt gtccatcctc gggggaaggc cagaccaaca ccttgtttgt   1260
ctgcttctgc cccaacctca gtgcatccat gctggtcctg ctgtcccttg tctaga        1316
```

<210> SEQ ID NO 21
<211> LENGTH: 321
<212> TYPE: PRT
<213> ORGANISM: Cricetulus griseus

<400> SEQUENCE: 21

```
Met Gly Glu Pro Gln Gly Ser Arg Arg Ile Leu Val Thr Gly Gly Ser
 1               5                  10                  15

Gly Leu Val Gly Arg Ala Ile Gln Lys Val Val Ala Asp Gly Ala Gly
             20                  25                  30

Leu Pro Gly Glu Glu Trp Val Phe Val Ser Ser Lys Asp Ala Asp Leu
         35                  40                  45

Thr Asp Ala Ala Gln Thr Gln Ala Leu Phe Gln Lys Val Gln Pro Thr
     50                  55                  60

His Val Ile His Leu Ala Ala Met Val Gly Gly Leu Phe Arg Asn Ile
 65                  70                  75                  80

Lys Tyr Asn Leu Asp Phe Trp Arg Lys Asn Val His Ile Asn Asp Asn
                 85                  90                  95

Val Leu His Ser Ala Phe Glu Val Gly Thr Arg Lys Val Val Ser Cys
            100                 105                 110

Leu Ser Thr Cys Ile Phe Pro Asp Lys Thr Thr Tyr Pro Ile Asp Glu
        115                 120                 125

Thr Met Ile His Asn Gly Pro Pro His Ser Ser Asn Phe Gly Tyr Ser
    130                 135                 140

Tyr Ala Lys Arg Met Ile Asp Val Gln Asn Arg Ala Tyr Phe Gln Gln
145                 150                 155                 160

His Gly Cys Thr Phe Thr Ala Val Ile Pro Thr Asn Val Phe Gly Pro
                165                 170                 175

His Asp Asn Phe Asn Ile Glu Asp Gly His Val Leu Pro Gly Leu Ile
            180                 185                 190

His Lys Val His Leu Ala Lys Ser Asn Gly Ser Ala Leu Thr Val Trp
        195                 200                 205

Gly Thr Gly Lys Pro Arg Arg Gln Phe Ile Tyr Ser Leu Asp Leu Ala
    210                 215                 220
```

```
Arg Leu Phe Ile Trp Val Leu Arg Glu Tyr Asn Glu Val Glu Pro Ile
225                 230                 235                 240

Ile Leu Ser Val Gly Glu Glu Asp Glu Val Ser Ile Lys Glu Ala Ala
            245                 250                 255

Glu Ala Val Val Glu Ala Met Asp Phe Cys Gly Glu Val Thr Phe Asp
        260                 265                 270

Ser Thr Lys Ser Asp Gly Gln Tyr Lys Lys Thr Ala Ser Asn Gly Lys
    275                 280                 285

Leu Arg Ala Tyr Leu Pro Asp Phe Arg Phe Thr Pro Phe Lys Gln Ala
    290                 295                 300

Val Lys Glu Thr Cys Ala Trp Phe Thr Asp Asn Tyr Glu Gln Ala Arg
305                 310                 315                 320

Lys

<210> SEQ ID NO 22
<211> LENGTH: 2008
<212> TYPE: DNA
<213> ORGANISM: Cricetulus griseus

<400> SEQUENCE: 22
aacagaaact tattttcctg tgtggctaac tagaaccaga gtacaatgtt tccaattctt      60
tgagctccga gaagacagaa gggagttgaa actctgaaaa tgcgggcatg gactggttcc     120
tggcgttgga ttatgctcat tcttttgcc tgggggacct tattgtttta tataggtggt      180
catttggttc gagataatga ccaccctgac cattctagca gagaactctc caagattctt     240
gcaaagctgg agcgcttaaa acaacaaaat gaagacttga ggagaatggc tgagtctctc     300
cgaataccag aaggccctat tgatcagggg acagctacag aagagtccg tgttttagaa      360 gaacagcttg ttaaggccaa agaacagatt gaaaattaca agaaacaagc taggaatgat     420
ctgggaaagg atcatgaaat cttaaggagg aggattgaaa atggagctaa agagctctgg     480 tttttttctac aaagtgaatt gaagaaatta agaaaattag aaggaaacga actccaaaga   540
catgcagatg aaattctttt ggatttagga catcatgaaa ggtctatcat gacagatcta     600
tactacctca gtcaaacaga tggagcaggt gagtggcggg aaaaagaagc caaagatctg     660
acagagctgg tccagcggag aataacatat ctgcagaatc ccaaggactg cagcaaagcc     720
agaaagctgg tatgtaatat caacaaaggc tgtggctatg atgtcaact ccatcatgtg      780 gtttactgct tcatgattgc ttatggcacc cagcgaacac tcatcttgga atctcagaat     840
tggcgctatg ctactggagg atgggagact gtgtttagac tgtaagtga cactgcaca     900 gacaggtctg gcctctccac tggacactgg tcaggtgaag tgaaggacaa aaatgttcaa     960
gtggtcgagc tccccattgt agacagcctc catcctcgtc ctccttactt acccttggct    1020
gtaccagaag accttgcaga tcgactcctg agagtccatg gtgatcctgc agtgtggtgg    1080
gtatcccagt ttgtcaaata cttgatccgt ccacaacctt ggctgaaaag ggaaatagaa    1140
gaaaccacca agaagcttgg cttcaaacat ccagttattg gagtccatgt cagacgcact    1200
gacaaagtgg gaacagaagc agccttccat cccattgagg aatacatggt acacgttgaa    1260
gaacattttc agcttctcga acgcagaatg aaagtggata aaaaaagagt gtatctggcc    1320
actgatgacc cttctttgtt aaaggaggca aagacaaagt actccaatta tgaatttatt    1380
agtgataact ctatttcttg gtcagctgga ctacacaacc gatacacaga aaattcactt    1440
cggggcgtga tcctggatat acactttctc tcccaggctg acttcctgt gtgtactttt    1500 tcatcccagg tctgtagggt tgcttatgaa atcatgcaaa cactgcatcc tgatgcctct    1560
```

```
gcaaacttcc attctttaga tgacatctac tattttggag gccaaaatgc ccacaaccag    1620
attgcagttt atcctcacca acctcgaact aaagaggaaa tccccatgga acctggagat    1680
atcattggtg tggctggaaa ccattggaat ggttactcta aaggtgtcaa cagaaaacta    1740
ggaaaaacag gcctgtaccc ttcctacaaa gtccgagaga agatagaaac agtcaaatac    1800
cctacatatc ctgaagctga aaaatagaga tggagtgtaa gagattaaca acagaattta    1860
gttcagacca tctcagccaa gcagaagacc cagactaaca tatggttcat tgacagacat    1920
gctccgcacc aagagcaagt gggaaccctc agatgctgca ctggtggaac gcctctttgt    1980
gaagggctgc tgtgccctca agcccatg                                       2008

<210> SEQ ID NO 23
<211> LENGTH: 1728
<212> TYPE: DNA
<213> ORGANISM: Mus musculus

<400> SEQUENCE: 23
atgcgggcat ggactggttc ctggcgttgg attatgctca ttcttttgc ctgggggacc      60 ttgttatttt ataggtgg tcatttggtt cgagataatg accaccctga tcactccagc      120
agagaactct ccaagattct tgcaaagctt gaacgcttaa acagcaaaa tgaagacttg      180 aggcgaatgg ctgagtctct ccgaatacca gaaggcccca ttgaccaggg gacagctaca      240
ggaagagtcc gtgttttaga agaacagctt gttaaggcca agaacagat tgaaaattac      300 aagaaacaag ctagaaatgg tctggggaag gatcatgaaa tcttaagaag gaggattgaa      360
aatggagcta aagagctctg gttttttcta caaagcgaac tgaagaaatt aaagcattta      420
gaaggaaatg aactccaaag acatgcagat gaaattcttt tggatttagg acaccatgaa      480
aggtctatca tgacagatct atactacctc agtcaaacag atggagcagg ggattggcgt      540
gaaaaagagg ccaaagatct gacagagctg gtccagcgga gaataacata tctccagaat      600
cctaaggact gcagcaaagc caggaagctg gtgtgtaaca tcaataaagg ctgtggctat      660
ggttgtcaac tccatcacgt ggtctactgt ttcatgattg cttatggcac ccagcgaaca      720
ctcatcttgg aatctcagaa ttggcgctat gctactggtg gatgggagac tgtgtttaga      780
cctgtaagtg agacatgtac agacagatct ggcctctcca ctggacactg gtcaggtgaa      840
gtaaatgaca aaaacattca agtggtcgag ctccccattg tagacagcct ccatcctcgg      900
cctccttact taccactggc tgttccagaa gaccttgcag accgactcct aagagtccat      960
ggtgaccctg cagtgtggtg ggtgtcccag tttgtcaaat acttgattcg tccacaacct     1020
tggctggaaa aggaaataga agaagccacc aagaagcttg cttcaaaaca tccagttatt     1080
ggagtccatg tcagacgcac agacaaagtg gaacagaag cagccttcca ccccatcgag     1140
gagtacatgg tacacgttga agaacatttt cagcttctcg cacgcagaat gcaagtggat     1200
aaaaaaagag tatatctggc tactgatgat cctactttgt taaggaggc aaagacaaag     1260 tactccaatt atgaatttat tagtgataac tctatttctt ggtcagctgg actacacaat     1320
cggtacacag aaaattcact tcggggtgtg atcctggata tacactttct ctcacaggct     1380
gactttctag tgtgtactt ttcatcccag gtctgtcggg ttgcttatga aatcatgcaa     1440
accctgcatc ctgatgcctc tgcgaacttc cattctttgg atgacatcta ctattttgga    1500
ggccaaaatg cccacaatca gattgctgtt tatcctcaca aacctcgaac tgaagaggaa    1560
attccaatgg aacctggaga tatcattggt gtggctggaa accattggga tggttattct    1620
aaaggtatca acagaaaact tggaaaaaca ggcttatatc cctcctacaa agtccgagag    1680
```
aagatagaaa cagtcaagta tcccacatat cctgaagctg aaaaatag    1728

<210> SEQ ID NO 24
<211> LENGTH: 575
<212> TYPE: PRT
<213> ORGANISM: Cricetulus griseus

<400> SEQUENCE: 24

```
Met Arg Ala Trp Thr Gly Ser Trp Arg Trp Ile Met Leu Ile Leu Phe
 1               5                  10                  15

Ala Trp Gly Thr Leu Leu Phe Tyr Ile Gly Gly His Leu Val Arg Asp
                20                  25                  30

Asn Asp His Pro Asp His Ser Ser Arg Glu Leu Ser Lys Ile Leu Ala
            35                  40                  45

Lys Leu Glu Arg Leu Lys Gln Gln Asn Glu Asp Leu Arg Arg Met Ala
        50                  55                  60

Glu Ser Leu Arg Ile Pro Glu Gly Pro Ile Asp Gln Gly Thr Ala Thr
 65                 70                  75                  80

Gly Arg Val Arg Val Leu Glu Glu Gln Leu Val Lys Ala Lys Glu Gln
                85                  90                  95

Ile Glu Asn Tyr Lys Lys Gln Ala Arg Asn Asp Leu Gly Lys Asp His
            100                 105                 110

Glu Ile Leu Arg Arg Ile Glu Asn Gly Ala Lys Glu Leu Trp Phe
        115                 120                 125

Phe Leu Gln Ser Glu Leu Lys Lys Leu Lys Lys Leu Glu Gly Asn Glu
        130                 135                 140

Leu Gln Arg His Ala Asp Glu Ile Leu Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Glu Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Arg
        195                 200                 205

Lys Leu Val Cys Asn Ile Asn Lys Gly Cys Gly Tyr Gly Cys Gln Leu
        210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Leu
            260                 265                 270

Ser Thr Gly His Trp Ser Gly Glu Val Lys Asp Lys Asn Val Gln Val
        275                 280                 285

Val Glu Leu Pro Ile Val Asp Ser Leu His Pro Arg Pro Pro Tyr Leu
    290                 295                 300

Pro Leu Ala Val Pro Glu Asp Leu Ala Asp Arg Leu Leu Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Arg Glu Ile Glu Thr Thr Lys Lys
            340                 345                 350

Leu Gly Phe Lys His Pro Val Ile Gly Val His Val Arg Arg Thr Asp
        355                 360                 365

Lys Val Gly Thr Glu Ala Ala Phe His Pro Ile Glu Glu Tyr Met Val
```

```
                    370                 375                 380
His Val Glu Glu His Phe Gln Leu Leu Glu Arg Arg Met Lys Val Asp
385                 390                 395                 400

Lys Lys Arg Val Tyr Leu Ala Thr Asp Asp Pro Ser Leu Leu Lys Glu
                    405                 410                 415

Ala Lys Thr Lys Tyr Ser Asn Tyr Glu Phe Ile Ser Asp Asn Ser Ile
                    420                 425                 430

Ser Trp Ser Ala Gly Leu His Asn Arg Tyr Thr Glu Asn Ser Leu Arg
                    435                 440                 445

Gly Val Ile Leu Asp Ile His Phe Leu Ser Gln Ala Asp Phe Leu Val
                    450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
                    485                 490                 495

Tyr Tyr Phe Gly Gly Gln Asn Ala His Asn Gln Ile Ala Val Tyr Pro
                    500                 505                 510

His Gln Pro Arg Thr Lys Glu Glu Ile Pro Met Glu Pro Gly Asp Ile
                    515                 520                 525

Ile Gly Val Ala Gly Asn His Trp Asn Gly Tyr Ser Lys Gly Val Asn
530                 535                 540

Arg Lys Leu Gly Lys Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                    565                 570                 575

<210> SEQ ID NO 25
<211> LENGTH: 575
<212> TYPE: PRT
<213> ORGANISM: Mus musculus

<400> SEQUENCE: 25

Met Arg Ala Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
                    20                  25                  30

Asn Asp His Pro Asp His Ser Ser Arg Glu Leu Ser Lys Ile Leu Ala
                    35                  40                  45

Lys Leu Glu Arg Leu Lys Gln Gln Asn Glu Asp Leu Arg Arg Met Ala
                    50                  55                  60

Glu Ser Leu Arg Ile Pro Glu Gly Pro Ile Asp Gln Gly Thr Ala Thr
65                  70                  75                  80

Gly Arg Val Arg Val Leu Glu Glu Gln Leu Val Lys Ala Lys Glu Gln
                    85                  90                  95

Ile Glu Asn Tyr Lys Lys Gln Ala Arg Asn Gly Leu Gly Lys Asp His
                    100                 105                 110

Glu Ile Leu Arg Arg Arg Ile Glu Asn Gly Ala Lys Glu Leu Trp Phe
                    115                 120                 125

Phe Leu Gln Ser Glu Leu Lys Lys Leu Lys His Leu Glu Gly Asn Glu
                    130                 135                 140

Leu Gln Arg His Ala Asp Glu Ile Leu Leu Asp Leu Gly His His Glu
145                 150                 155                 160

Arg Ser Ile Met Thr Asp Leu Tyr Tyr Leu Ser Gln Thr Asp Gly Ala
                    165                 170                 175

Gly Asp Trp Arg Glu Lys Glu Ala Lys Asp Leu Thr Glu Leu Val Gln
```

```
                    180                 185                 190
Arg Arg Ile Thr Tyr Leu Gln Asn Pro Lys Asp Cys Ser Lys Ala Arg
                195                 200                 205
Lys Leu Val Cys Asn Ile Asn Lys Gly Cys Gly Tyr Gly Cys Gln Leu
            210                 215                 220
His His Val Val Tyr Cys Phe Met Ile Ala Tyr Gly Thr Gln Arg Thr
225                 230                 235                 240
Leu Ile Leu Glu Ser Gln Asn Trp Arg Tyr Ala Thr Gly Gly Trp Glu
                245                 250                 255
Thr Val Phe Arg Pro Val Ser Glu Thr Cys Thr Asp Arg Ser Gly Leu
            260                 265                 270
Ser Thr Gly His Trp Ser Gly Glu Val Asn Asp Lys Asn Ile Gln Val
        275                 280                 285
Val Glu Leu Pro Ile Val Asp Ser Leu His Pro Arg Pro Tyr Leu
    290                 295                 300
Pro Leu Ala Val Pro Glu Asp Leu Ala Asp Arg Leu Arg Val His
305                 310                 315                 320
Gly Asp Pro Ala Val Trp Trp Val Ser Gln Phe Val Lys Tyr Leu Ile
                325                 330                 335
Arg Pro Gln Pro Trp Leu Glu Lys Glu Ile Glu Ala Thr Lys Lys
            340                 345                 350
Leu Gly Phe Lys His Pro Val Ile Gly Val His Val Arg Arg Thr Asp
                355                 360                 365
Lys Val Gly Thr Glu Ala Ala Phe His Pro Ile Glu Glu Tyr Met Val
            370                 375                 380
His Val Glu Glu His Phe Gln Leu Leu Ala Arg Arg Met Gln Val Asp
385                 390                 395                 400
Lys Lys Arg Val Tyr Leu Ala Thr Asp Asp Pro Thr Leu Leu Lys Glu
                405                 410                 415
Ala Lys Thr Lys Tyr Ser Asn Tyr Glu Phe Ile Ser Asp Asn Ser Ile
            420                 425                 430
Ser Trp Ser Ala Gly Leu His Asn Arg Tyr Thr Glu Asn Ser Leu Arg
        435                 440                 445
Gly Val Ile Leu Asp Ile His Phe Leu Ser Gln Ala Asp Phe Leu Val
    450                 455                 460
Cys Thr Phe Ser Ser Gln Val Cys Arg Val Ala Tyr Glu Ile Met Gln
465                 470                 475                 480
Thr Leu His Pro Asp Ala Ser Ala Asn Phe His Ser Leu Asp Asp Ile
                485                 490                 495
Tyr Tyr Phe Gly Gly Gln Asn Ala His Asn Gln Ile Ala Val Tyr Pro
            500                 505                 510
His Lys Pro Arg Thr Glu Glu Glu Ile Pro Met Glu Pro Gly Asp Ile
        515                 520                 525
Ile Gly Val Ala Gly Asn His Trp Asp Gly Tyr Ser Lys Gly Ile Asn
    530                 535                 540
Arg Lys Leu Gly Lys Thr Gly Leu Tyr Pro Ser Tyr Lys Val Arg Glu
545                 550                 555                 560
Lys Ile Glu Thr Val Lys Tyr Pro Thr Tyr Pro Glu Ala Glu Lys
                565                 570                 575

<210> SEQ ID NO 26
<211> LENGTH: 383
<212> TYPE: DNA
<213> ORGANISM: Cricetulus griseus
```

```
<400> SEQUENCE: 26
gttaactggg gctctttaa accctgaatt tttctaaatc cccacctcca agagtttggt      60
ttaaactgat tttttaatg aataccttt gaagaataga gcattgtctc atcatgcaaa     120
gcttctcagg gattcagcta gcatgttgaa gaaacataag ggtgttaaat tgtttgtcac    180
aagtgctgaa taaatattga cgtagtcttc agctattcta tactggaagt agatgatatt    240
ctcattggaa attctgttag gaagtaaccc ttcttgtctt cttacctgca tagaatccca    300
ggatataaaa cttgtgcttg tcgcccttgc cattgtctct cactggtggc ctttattgca    360
tctcatatct gccttctctt tcc                                            383

<210> SEQ ID NO 27
<211> LENGTH: 564
<212> TYPE: DNA
<213> ORGANISM: Cricetulus griseus

<400> SEQUENCE: 27
taagaattcc tgtgcccagc tgtatgtgag gctctctgca ggtgtaggga tgtttctgct     60
ttctttctgc acatgcttca cagctgaagt ccttttgggtg tgagattgac attcagatag   120
actaaagtga ctggacttgt tgggaaacat actgtatgca ttattgccgt tgcctccagg    180
tgaaattaac acctcattca ccaatccctg ttcatccaaa ctttctaccc acatcacttt    240
aaatagaaat tagacccaat atgactcctt ttttcctaag ctgtttatag agattgtgct    300
ggagcagtga gcttttgtgt ttgtttgttt gttttgtaat tttccccatg aaaatttctc    360
taaactcaaa cctaagaggg aaaaaaaaaa aacagactta tatgtgccac acttgtaaaa    420
aaaaatcatg aaagatgtat atgatattt taaacagttt gaatattaag atcacaattt     480
ctattttaaa aacaatcttg ttttacatat caatcaccca attcccttgc cttcccatcc    540
tcccattccc cccactgatc cccc                                           564

<210> SEQ ID NO 28
<211> LENGTH: 120
<212> TYPE: DNA
<213> ORGANISM: Cricetulus griseus

<400> SEQUENCE: 28
atgaatgttc attctttggg tatatgccca agagtagaat tgctaaatat tgaggtagac     60
tgattcccat tttcttgagg agtcgccata ttgatttcca aagtgactgt acaagttaac    120

<210> SEQ ID NO 29
<211> LENGTH: 274
<212> TYPE: DNA
<213> ORGANISM: Cricetulus griseus

<400> SEQUENCE: 29
aggcactagg taaatatttt tgaagaaaga atgagtatct cctatttcag aaaaactttt      60
attgacttaa atttaggata tcagaattag aaaacagtaa aaatttatag gagagttttt    120
aatgaatgtt atttttaaggt tccatacaaa tagtaattaa aacttacaca aactatttgt    180
agtaatgatt cagtctggta taccctgatg agcattatac acttttaaat tctttttgta    240
aattttttta ttagttcaaa ttaggaacaa gctt                                274

<210> SEQ ID NO 30
<211> LENGTH: 9196
<212> TYPE: DNA
<213> ORGANISM: Cricetulus griseus
```

<400> SEQUENCE: 30

```
tctagaccag gctggtctcg aactcacaga gaaccacctg cctctgccac ctgagtgctg      60
ggattaaagg tgtgcaccac caccgcccgg cgtaaaatca tattttttgaa tattgtgata    120
atttacatta taattgtaag taaaaatttt cagcctattt tgttatacat ttttgcgtaa    180
attattcttt tttgaaagtt ttgttgtcca taatagtcta gggaaacata agttataat    240
ttttgtctat gtatttgcat atatatctat ttaatctcct aatgtccagg aaataaatag    300
ggtatgtaat agcttcaaca tgtggtatga tagaattttt cagtgctata aagttgtta    360
cagcaaagtg ttattaattc atatgtccat atttcaattt tttatgaatt attaaattga    420
atccttaagc tgccagaact agaattttat tttaatcagg aagccccaaa tctgttcatt    480
ctttctatat atgtggaaag gtaggcctca ctaactgatt cttcacctgt tttagaacat    540
ggtccaagaa tggagttatg taaggggaat tacaagtgtg agaaaactcc tagaaaacaa    600
gatgagtctt gtgaccttag tttctttaaa aacacaaaat tcttggaatg tgttttcatg    660
ttcctcccag gtggatagga gtgagtttat ttcagattat ttattacaac tggctgttgt    720
tacttgtttc tatgtctttta tagaaaaaca tattttttttt gccacatgca gcttgtcctt    780
atgattttat acttgtgtga ctcttaactc tcagagtata aattgtctga tgctatgaat    840
aaagttggct attgtatgag acttcagccc acttcaatta ttggcttcat tctctcagat    900
cccaccacct ccagagtggt aaacaacttg aaccattaaa cagactttag tctttatttg    960
aatgatagat ggggatatca gatttatagg cacagggttt tgagaaaggg agaaggtaaa   1020
cagtagagtt taacaacaac aaaaagtata ctttgtaaac gtaaaactat ttattaaagt   1080
agtagacaag acattaaata ttccttggga ttagtgcttt ttgaatttg ctttcaaata    1140
atagtcagtg agtataccccc tcccccattc tatattttag cagaaatcag aataaatggt   1200
gtttctggta cattctttg tagagaattt attttctttg ggttttttgtg catttaaagt    1260
caataaaaat taaggttcag taatagaaaa aaaactctga ttttttggaat cccctttctt   1320
cagcttttct atttaatctc ttaatgataa tttaatttgt ggccatgtgg tcaaagtata    1380
tagccttgta tatgtaaatg ttttaaccaa cctgcctta cagtaactat ataattttat    1440
tctataatat atgactttc ttccatagct ttagagttgc ccagtcactt aagttacat    1500
tttcatatat gttctttgtg ggaggagata atttttatttc taagagaatc ctaagcatac   1560
tgattgagaa atggcaaaca aaacacataa ttaaagctga taaagaacga acatttggag   1620
tttaaaatac atagccaccc taagggttta actgttgtta gccttctttt ggaattttta   1680
ttagttcata tagaaaaatg gattttatcg tgacatttcc atatatgtat ataatatat    1740
tacatcatat ccacctgtaa ttattagtgt ttttaaatat atttgaaaaa ataatggtct   1800
ggtttgatcc atttgaacct tttgatgttt ggtgtggttg ccaattggtt gatggttatg   1860
ataacctttg cttctctaag gttcaagtca gtttgagaat atgtcctcta aaaatgacag    1920
gttgcaagtt aagtagtgag atgacagcga gatggagtga tgagaatttg tagaaatgaa    1980
ttcacttata ctgagaactt gttttgctt tagataatga acatattagc ctgaagtaca    2040
tagccgaatt gattaattat tcaaagatat aatctttta tccctataaa agaggtatta    2100
cacaacaatt caagaaagat agaattagac ttccagtatt ggagtgaacc atttgttatc    2160
aggtagaacc ctaacgtgtg tggttgactt aaagtgttta ctttttacct gatactgggt    2220
agctaattgt ctttcagcct cctggccaaa gataccatga aagtcaactt acgttgtatt    2280
ctatatctca aacaactcag ggtgtttctt actctttcca cagcatgtag agcccaggaa    2340
```

```
gcacaggaca agaaagctgc ctccttgtat caccaggaag atcttttgt aagagtcatc   2400 acagtatacc agagagacta attttgtctg aagcatcatg tgttgaaaca acagaaactt   2460
attttcctgt gtggctaact agaaccagag tacaatgttt ccaattcttt gagctccgag   2520
aagacagaag ggagttgaaa ctctgaaaat gcgggcatgg actggttcct ggcgttggat   2580
tatgctcatt cttttgcct gggggacctt attgttttat ataggtggtc atttggttcg   2640
agataatgac caccctgacc attctagcag agaactctcc aagattcttg caaagctgga   2700
gcgcttaaaa caacaaaatg aagacttgag gagaatggct gagtctctcc ggtaggtttg   2760
aaatactcaa ggatttgatg aaatactgtg cttgaccttt aggtataggg tctcagtctg   2820
ctgttgaaaa atataatttc tacaaaccgt ctttgtaaaa ttttaagtat tgtagcagac   2880
tttttaaaag tcagtgatac atctatatag tcaatatagg tttacatagt tgcaatctta   2940
ttttgcatat gaatcagtat atagaagcag tggcatttat atgcttatgt tgcatttaca   3000
attatgttta gacgaacaca aactttatgt gatttggatt agtgctcatt aaattttttt   3060
attctatgga ctacaacaga gacataaatt ttgaaaggct tagttactct taaattctta   3120
tgatgaaaag caaaaattca ttgttaaata gaacagtgca tccggaatgt gggtaattat   3180
tgccatattt ctagtctact aaaaattgtg gcataactgt tcaaagtcat cagttgtttg   3240
gaaagccaaa gtctgattta aatggaaaac ataaacaatg atatctattt ctagatacct   3300
ttaacttgca gttactgagt ttacaagttg tctgacaact ttggattctc ttacttcata   3360
tctaagaatg atcatgtgta cagtgcttac tgtcacttta aaaaactgca gggctagaca   3420
tgcagatatg aagactttga cattagatgt ggtaattggc actaccagca agtggtatta   3480
agatacagct gaatatatta cttttgagg aacataattc atgaatggaa agtggagcat   3540
tagagaggat gccttctggc tctcccacac cactgtttgc atccattgca tttcacactg   3600
cttttagaac tcagatgttt catatggtat attgtgtaac tcaccatcag tttatctttt   3660
aaatgtctat ggatgataat gttgtatgtt aacactttta caaaacaaa tgaagccata   3720 tcctcggtgt gagttgtgat ggtggtaatt gtcacaatag gattattcag caaggaacta   3780
agtcagggac aagaagtggg cgatactttg ttggattaaa tcattttact ggaagttcat   3840
cagggagggt tatgaaagtt gtggtctttg aactgaaatt atatgtgatt cattattctt   3900
gatttaggcc ttgctaatag taactatcat ttattgggaa tttgtcatat gtgccaatt   3960 gtcatgggcc agacagcgtg ttttactgaa tttctagata tctttatgag attctagtac   4020
tgttttcagc cattttacag atgaagaatc ttaaaaaatg ttaaataatt tagttttgccc   4080 aagattatac gttaacaaat ggtagaacct tctttgaatt ctggcagtat ggctacacag   4140
tccgaactct tatcttccta agctgaaaac agaaaaagca atgacccaga aaattttat   4200 taaaagtctc aggagagact tcccatcctg agaagatctc ttttcccttt tataaattag   4260
gctcctgaat aatcactgaa ttttctccat gttccatcta tagtactgtt atttctgttt   4320 tcctttttc ttaccacaaa gtatcttgtt tttgctgtat gaagaaaat gtgttattgt   4380 aatgtgaaat tctctgtccc tgcagggtcc cacatccgcc tcaatcccaa ataaacacac   4440
agaggctgta ttaattatga aactgttggt cagttggcta gggcttctta ttggctagct   4500
ctgtcttaat tattaaacca taactactat tgtaagtatt ccatgtggt cttatcttac   4560 caaggaaagg gtccagggac ctcttactcc tctggcgtgt tggcagtgaa gaggagagag   4620
cgatttccta tttgtctctg cttattttct gattctgctc agctatgtca cttcctgcct   4680
ggccaatcag ccaatcagtg ttttattcat tagccaataa aagaaacatt tacacagaag   4740
```

```
gacttccccc atcatgttat ttgtatgagt tcttcagaaa atcatagtat cttttaatac      4800
taatttttat aaaaaattaa ttgtattgaa aattatgtgt atatgtgtct gtgtgtcgat      4860
ttgtgctcat aagtagcatg gagtgcagaa gagggaatca gatcttttttt taagggacaa    4920 agagtttatt cagattacat tttaaggtga taatgtatga ttgcaaggtt atcaacatgg      4980
cagaaatgtg aagaagctgg tcacattaca tccagagtca agagtagaga gcaatgaatt      5040
gatgcatgca ttcctgtgct cagctcactt ttcctggagc tgagctgatt gtaagccatc      5100
tgatgtcttt gctgggaact aactcaaagg caagttcaaa acctgttctt aagtataagc      5160
catctctcca gtccctcata tggtctctta agacactttc tttatattct tgtacataga      5220
aattgaattc ctaacaactg cattcaaatt acaaatagt ttttaaaagc tgatataata       5280
aatgtaaata caatctagaa cattttata aataagcata ttaactcagt aaaaataaat       5340
gcatggttat tttccttcat tagggaagta tgtctcccca ggctgttctc tagattctac      5400
tagtaatgct gtttgtacac catccacagg ggttttattt taaagctaag acatgaatga     5460
tggacatgct tgttagcatt tagacttttt tccttactat aattgagcta gtattttgt       5520 gctcagtttg atatctgtta attcagataa atgtaatagt aggtaatttc tttgtgataa      5580
aggcatataa attgaagttg gaaaacaaaa gcctgaaatg acagttttta agattcagaa      5640
caataatttt caaaagcagt tacccaactt tccaaataca atctgcagtt ttcttgatat      5700
gtgataaatt tagacaaaga aatagcacat tttaaaatag ctatttactc ttgattttt       5760 tttcaaattt aggctagttc actagttgtg tgtaaggtta tggctgcaaa catcttgac      5820 tcttggttag ggaatccagg atgatttacg tgtttggcca aaatcttgtt ccattctggg      5880
tttcttctct atctaggtag ctagcacaag ttaaaggtgt ggtagtattg gaaggctctc     5940
aggtatatat ttctatattc tgtatttttt tcctctgtca tatatttgct ttctgtttta     6000
ttgatttcta ctgttagttt gatacttact ttcttacact ttctttggga tttattttgc     6060
tgttctaaga tttcttagca agttcatatc actgattta acagttgctt cttttgtaat     6120
atagactgaa tgccccttat ttgaaatgct tgggatcaga aactcagatt tgaacttttc      6180
ttttttaata ttttccatcaa gtttaccagc tgaatgtcct gatccaagaa tatgaaatct    6240
gaaatgcttt gaaatctgaa acttttagag tgataaagct tcccttttaaa ttaatttgtg    6300 ttctatattt tttgacaatg tcaacctttc attgttatcc aatgagtgaa catatttca      6360 attttttgt ttgatctgtt atattttgat ctgaccatat ttataaaatt ttatttaatt      6420
tgaatgttgc gctgttactt atctttatta ttatttttgc ttatttttcta gccaaatgaa   6480 attatattct gtattatttt agtttgaatt ttactttgtg gcttagtaac tgccttttgt     6540
tggtgaatgc ttaagaaaaa cgtgtggtct actgatattg gttctaatct tatatagcat     6600
gttgtttgtt aggtagttga ttatgctggt cagattgtct tgagtttatg caaatgtaaa     6660
atatttagat gcttgttttg ttgtctaaga acaaagtatg cttgctgtct cctatcggtt      6720
ctggtttttc cattcatctc ttcaagctgt tttgtgtgtt gaatactaac tccgtactat     6780
cttgttttct gtgaattaac ccctttttcaa aggtttcttt tctttttttt tttaagggac   6840
aacaagttta ttcagattac attttaagct gataatgtat gattgcaagg ttatcaacat    6900
ggcagaaatg tgaagaagct aggcacatta catccacatg gagtcaagag cagagagcag    6960
tgaattaatg catgcattcc tgtggtcagc tcacttttcc tattcttaga tagtctagga    7020
tcataaacct gggggaatagt gctaccacaa tgggcatatc cacttacttc agttcatgca    7080
atcaaccaag gcacatccac aggaaaaact gatttagaca acctctcatt gagactcttc    7140
```

```
ccagatgatt agactgtgtc aagttgacaa ttaaaactat cacacctgaa gccatcacta      7200
gtaaatataa tgaaaatgtt gattatcacc ataattcatc tgtatccctt tgttattgta      7260
gattttgtga agttcctatt caagtccctg ttccttcctt aaaaacctgt tttttagtta      7320
aataggtttt ttagtgttcc tgtctgtaaa tactttttta aagttagata ttattttcaa      7380
gtatgttctc ccagtctttg gcttgtattt tcatcccttc aatacatata tttttgtaat      7440
ttattttttt tatttaaatt agaaacaaag ctgcttttac atgtcagtct cagttccctc      7500
tccctcccct cctcccctgc tccccaccta agccccaatt ccaactcctt tcttctcccc      7560
aggaagggtg aggccctcca tgggggaaat cttcaatgtc tgtcatatca tttggagcag      7620
ggcctagacc ctccccagtg tgtctaggct gagagagtat ccctctatgt ggagagggct      7680
cccaaagttc atttgtgtac taggggtaaa tactgatcca ctatcagtgg ccccatagat      7740
tgtccggacc tccaaactga cttcctcctt cagggagtct ggaacagttc tatgctggtt      7800
tcccagatat cagtctgggg tccatgagca accccttgtt caggtcagtt gtttctgtag      7860
gtttccccag cccggtcttg accccttttgc tcatcacttc tccctctctg caactggatt      7920
ccagagttca gctcagtgtt tagctgtggg tgtctgcatc tgcttccatc agctactgga      7980
tgagggctct aggatggcat ataaggtagt catcagtctc attatcagag aagggctttt      8040
aaggtagcct cttgattatt gcttagattg ttagttgggg tcaaccttgt aggtctctgg      8100
acagtgacag aattctcttt aaacctataa tggctccctc tgtggtggta tccctttttct     8160 tgctctcatc cgttcctccc ctgactagat cttcctgctc cctcatgtcc tcctctcccc      8220
tccccttctc cccttctctt tcttctaact ccctctcccc tccacccacg atccccatta      8280
gcttatgaga tcttgtcctt attttagcaa aaccttttg gctataaaat taattaatt t       8340 aatatgctta tatcaggttt attttggcta gtatttgtat gtgtttggtt agtgttttta      8400
accttaattg acatgtatcc ttatatttag acacagattt aaatatttga agttttttt t       8460 tttttttttt ttaaagattt atttattttt tatgtcttct gcctgcatgc cagaagaggg      8520
caccagatct cattcaaggt ggttgtgagc caccatgtgg ttgctgggaa ttgaactcag      8580
gacctctgga agaacagtca gtgctcttaa ccgctgagcc atctctccag cccctgaagt      8640
gtttctttta aagaggatag cagtgcatca tttttccctt tgaccaatga ctcctacctt      8700
actgaattgt tttagccatt tatatgtaat gctgttacca ggtttacatt ttctttatc       8760 ttgctaaatt tcttccctgt ttgtctcatc tcttattttt gtctgttgga ttatataggc      8820
ttttattttt ctgtttttac agtaagttat atcaaattaa aattatttta tggaatgggt      8880
gtgttgacta catgtatgtc tgtgcaccat gtgctgacct ggtcttggcc agaagaaggt      8940
gtcatattct ctgaaactgg tattgtggat gttacgaact gccataggt gctaggaatc       9000 aaacccccagc tcctctggaa aagcagccac tgctctgagc cactgagtcc tctcttcaag      9060
caggtgatgc caacttttaa tggttaccag tggataagag tgcttgtatc tctagcaccc      9120
atgaaaattt atgcattgct atatgggctt gtcacttcag cattgtgtga cagagacagg      9180
aggatcccaa gagctc                                                     9196
```

<210> SEQ ID NO 31
<211> LENGTH: 56
<212> TYPE: DNA
<213> ORGANISM: Artificial Sequence
<220> FEATURE:
<223> OTHER INFORMATION: Synthetic DNA

<400> SEQUENCE: 31

```
cgtggtggtg gacgtgagcc acgaagaccc cgaggtccag ttcaagtggt acgtgg        56
```

<210> SEQ ID NO 32
<211> LENGTH: 59
<212> TYPE: DNA
<213> ORGANISM: Artificial Sequence
<220> FEATURE:
<223> OTHER INFORMATION: Synthetic DNA

<400> SEQUENCE: 32

```
catctcctat gggggcaggg cctgtggttc tcggggctgt cctttggctt tggagatgg    59
```

<210> SEQ ID NO 33
<211> LENGTH: 330
<212> TYPE: PRT
<213> ORGANISM: Artificial Sequence
<220> FEATURE:
<223> OTHER INFORMATION: Synthetic peptide

<400> SEQUENCE: 33

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 34
<211> LENGTH: 330
<212> TYPE: PRT
<213> ORGANISM: Artificial Sequence
<220> FEATURE:
<223> OTHER INFORMATION: Synthetic peptide

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Lys Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

<210> SEQ ID NO 35
<211> LENGTH: 330
<212> TYPE: PRT
<213> ORGANISM: Artificial Sequence
<220> FEATURE:
<223> OTHER INFORMATION: Synthetic peptide

<400> SEQUENCE: 35

```
Ala Ser Thr Lys Gly Pro Ser Val Phe Pro Leu Ala Pro Ser Ser Lys
 1               5                  10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Thr Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 36
<211> LENGTH: 330
<212> TYPE: PRT
<213> ORGANISM: Artificial Sequence
<220> FEATURE:
<223> OTHER INFORMATION: Synthetic peptide

```
<400> SEQUENCE: 36

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Lys Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 37
<211> LENGTH: 330
<212> TYPE: PRT
<213> ORGANISM: Artificial Sequence
<220> FEATURE:
<223> OTHER INFORMATION: Synthetic peptide

<400> SEQUENCE: 37

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
```

-continued

```
                    20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
             50                  55                  60
Leu Ser Ser Val Val Thr Val Pro Ser Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Gln Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 38
<211> LENGTH: 50
<212> TYPE: DNA
<213> ORGANISM: Artificial Sequence
<220> FEATURE:
<223> OTHER INFORMATION: Synthetic DNA

<400> SEQUENCE: 38
cgtggtggtg agccacgaag accccgaggt caagttcaac tggtacgtgg              50

<210> SEQ ID NO 39
<211> LENGTH: 121
<212> TYPE: PRT
<213> ORGANISM: Artificial Sequence
<220> FEATURE:
<223> OTHER INFORMATION: Synthetic peptide

<400> SEQUENCE: 39
```

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Asp Phe
            20                  25                  30

Tyr Met Asn Trp Val Arg Gln Pro Pro Gly Arg Gly Leu Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Val Thr Met Leu Val Asp Thr Ser Lys Asn Gln
65                  70                  75                  80

Phe Ser Leu Arg Leu Ser Ser Val Thr Ala Ala Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ser
        115                 120

<210> SEQ ID NO 40
<211> LENGTH: 363
<212> TYPE: DNA
<213> ORGANISM: Artificial Sequence
<220> FEATURE:
<223> OTHER INFORMATION: Synthetic DNA

<400> SEQUENCE: 40
caggtccaac tgcaggagag cggtccaggt cttgtgagac ctagccagac cctgagcctg    60
acctgcaccg tgtctggctt caccttcacc gatttctaca tgaactgggt gagacagcca    120
cctggacgag gtcttgagtg gattggattt attagagaca aagctaaagg ttacacaaca    180
gagtacaatc catctgtgaa ggggagagtg acaatgctgg tagacaccag caagaaccag    240
ttcagcctga gactcagcag cgtgacagcc gccgacaccg cggtctatta ttgtgcaaga    300
gagggccaca ctgctgctcc ttttgattac tggggtcaag gcagcctcgt cacagtctcc    360
tca    363

<210> SEQ ID NO 41
<211> LENGTH: 107
<212> TYPE: PRT
<213> ORGANISM: Artificial Sequence
<220> FEATURE:
<223> OTHER INFORMATION: Synthetic peptide

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Gln Gly Thr Lys Val Glu Ile Lys
            100                 105

<210> SEQ ID NO 42
<211> LENGTH: 321
<212> TYPE: DNA
<213> ORGANISM: Artificial Sequence
<220> FEATURE:
<223> OTHER INFORMATION: Synthetic DNA

<400> SEQUENCE: 42

```
gacatccaga tgacccagag cccaagcagc ctgagcgcca gcgtgggtga cagagtgacc      60
atcacctgta aagcaagtca gaatattgac aaatacttaa actggtacca gcagaagcca     120
ggtaaggctc caaagctgct gatctacaat acaaacaatt tgcaaacggg tgtgccaagc     180
agattcagcg gtagcggtag cggtaccgac ttcaccttca ccatcagcag cctccagcca     240
gaggacatcg ccacctacta ctgcttgcag catataagta ggccgcgcac gttcggccaa     300
gggaccaagg tggaaatcaa a                                              321
```

<210> SEQ ID NO 43
<211> LENGTH: 451
<212> TYPE: PRT
<213> ORGANISM: Artificial Sequence
<220> FEATURE:
<223> OTHER INFORMATION: Synthetic peptide

<400> SEQUENCE: 43

```
Gln Val Gln Leu Gln Glu Ser Gly Pro Gly Leu Val Arg Pro Ser Gln
  1               5                  10                  15

Thr Leu Ser Leu Thr Cys Thr Val Ser Gly Phe Thr Phe Thr Asp Phe
             20                  25                  30

Tyr Met Asn Trp Val Arg Gln Pro Pro Gly Arg Gly Leu Glu Trp Ile
         35                  40                  45

Gly Phe Ile Arg Asp Lys Ala Lys Gly Tyr Thr Thr Glu Tyr Asn Pro
     50                  55                  60

Ser Val Lys Gly Arg Val Thr Met Leu Val Asp Thr Ser Lys Asn Gln
 65                  70                  75                  80

Phe Ser Leu Arg Leu Ser Ser Val Thr Ala Ala Asp Thr Ala Val Tyr
                 85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Val Asp Val Ser His
            260                 265                 270

Glu Asp Pro Glu Val Gln Phe Lys Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Ser Gly Gln Pro Glu Asn Asn Tyr Asn Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Ile Phe Ser Cys Ser Val Met
            420                 425                 430

His Glu Ala Leu His Asn Arg Phe Thr Gln Lys Ser Leu Ser Leu Ser
        435                 440                 445

Pro Gly Lys
    450

<210> SEQ ID NO 44
<211> LENGTH: 214
<212> TYPE: PRT
<213> ORGANISM: Artificial Sequence
<220> FEATURE:
<223> OTHER INFORMATION: Synthetic peptide

<400> SEQUENCE: 44

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
 50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 45
<211> LENGTH: 476
<212> TYPE: DNA
<213> ORGANISM: Artificial Sequence
<220> FEATURE:
<223> OTHER INFORMATION: Synthetic DNA

<400> SEQUENCE: 45
cccacaagct gcggccgcga cccctcacca tgggatggag ctgtatcatc ctcttcttgg     60
tagcaacagc tacaggtgtc cactcccagg tccaactgca ggagagcggt ccaggtcttg    120
tgagacctag ccagaccctg agcctgacct gcaccgtgtc tggcttcacc ttcaccgatt    180
tctacatgaa ctgggtgaga cagccacctg gacgaggtct tgagtggatt ggatttatta    240
gagacaaagc taaaggttac acaacagagt acaatccatc tgtgaagggg agagtgacaa    300
tgctggtaga caccagcaag aaccagttca gcctgagact cagcagcgtg acagccgccg    360
acaccgcggt ctattattgt gcaagagagg ccacactgc tgctccttttt gattactggg    420 gtcaaggcag cctcgtcaca gtctcctcag cctccaccaa gggcccatcg gtcttc        476

<210> SEQ ID NO 46
<211> LENGTH: 131
<212> TYPE: DNA
<213> ORGANISM: Artificial Sequence
<220> FEATURE:
<223> OTHER INFORMATION: Synthetic DNA

<400> SEQUENCE: 46
cccacaagct gcggccgcga cccctcacca tgggatggag ctgtatcatc ctcttcttgg     60
tagcaacagc tacaggtgtc cactcccagg tccaactgca ggagagcggt ccaggtcttg    120
tgagacctag c                                                         131

<210> SEQ ID NO 47
<211> LENGTH: 140
<212> TYPE: DNA
<213> ORGANISM: Artificial Sequence
<220> FEATURE:
<223> OTHER INFORMATION: Synthetic DNA

<400> SEQUENCE: 47
gctttgtctc taataaatcc aatccactca agacctcgtc caggtggctg tctcacccag     60
ttcatgtaga aatcggtgaa ggtgaagcca gacacggtgc aggtcaggct cagggtctgg    120
ctaggtctca caagacctgg                                                140

<210> SEQ ID NO 48
<211> LENGTH: 140
<212> TYPE: DNA
<213> ORGANISM: Artificial Sequence
<220> FEATURE:
<223> OTHER INFORMATION: Synthetic DNA

<400> SEQUENCE: 48
ggattggatt tattagagac aaagctaaag gttacacaac agagtacaat ccatctgtga     60

```
aggggagagt gacaatgctg gtagacacca gcaagaacca gttcagcctg agactcagca    120
gcgtgacagc cgccgacacc                                                140

<210> SEQ ID NO 49
<211> LENGTH: 131
<212> TYPE: DNA
<213> ORGANISM: Artificial Sequence
<220> FEATURE:
<223> OTHER INFORMATION: Synthetic DNA

<400> SEQUENCE: 49
gaagaccgat gggcccttgg tggaggctga ggagactgtg acgaggctgc cttgacccca    60
gtaatcaaaa ggagcagcag tgtggccctc tcttgcacaa taatagaccg cggtgtcggc   120
ggctgtcacg c                                                        131

<210> SEQ ID NO 50
<211> LENGTH: 421
<212> TYPE: DNA
<213> ORGANISM: Artificial Sequence
<220> FEATURE:
<223> OTHER INFORMATION: Synthetic DNA

<400> SEQUENCE: 50
cccacaagct gaattcgcct cctcaaaatg ggatggagct gtatcatcct cttcttggta    60
gcaacagcta caggtgtcca ctccgacatc cagatgaccc agagcccaag cagcctgagc   120
gccagcgtgg gtgacagagt gaccatcacc tgtaaagcaa gtcagaatat tgacaaatac   180
ttaaactggt accagcagaa gccaggtaag gctccaaagc tgctgatcta caatacaaac   240
aatttgcaaa cgggtgtgcc aagcagattc agcggtagcg gtagcggtac cgacttcacc   300
ttcaccatca gcagcctcca gccagaggac atcgccacct actactgctt gcagcatata   360
agtaggccgc gcacgttcgg ccaagggacc aaggtggaaa tcaaacgtac ggtggctgca   420
c                                                                   421

<210> SEQ ID NO 51
<211> LENGTH: 120
<212> TYPE: DNA
<213> ORGANISM: Artificial Sequence
<220> FEATURE:
<223> OTHER INFORMATION: Synthetic DNA

<400> SEQUENCE: 51
cccacaagct gaattcgcct cctcaaaatg ggatggagct gtatcatcct cttcttggta    60
gcaacagcta caggtgtcca ctccgacatc cagatgaccc agagcccaag cagcctgagc   120

<210> SEQ ID NO 52
<211> LENGTH: 117
<212> TYPE: DNA
<213> ORGANISM: Artificial Sequence
<220> FEATURE:
<223> OTHER INFORMATION: Synthetic DNA

<400> SEQUENCE: 52
ggagccttac ctggcttctg ctggtaccag tttaagtatt tgtcaatatt ctgacttgct    60
ttacaggtga tggtcactct gtcacccacg ctggcgctca ggctgcttgg gctctgg     117

<210> SEQ ID NO 53
<211> LENGTH: 125
<212> TYPE: DNA
<213> ORGANISM: Artificial Sequence
```

<220> FEATURE:
<223> OTHER INFORMATION: Synthetic DNA

<400> SEQUENCE: 53
gcagaagcca ggtaaggctc caaagctgct gatctacaat acaaacaatt tgcaaacggg     60
tgtgccaagc agattcagcg gtagcggtag cggtaccgac ttcaccttca ccatcagcag    120
cctcc                                                                125

<210> SEQ ID NO 54
<211> LENGTH: 123
<212> TYPE: DNA
<213> ORGANISM: Artificial Sequence
<220> FEATURE:
<223> OTHER INFORMATION: Synthetic DNA

<400> SEQUENCE: 54
gtgcagccac cgtacgtttg atttccacct tggtcccttg gccgaacgtg cgcggcctac     60
ttatatgctg caagcagtag taggtggcga tgtcctctgg ctggaggctg ctgatggtga    120
agg                                                                  123

<210> SEQ ID NO 55
<211> LENGTH: 110
<212> TYPE: PRT
<213> ORGANISM: Homo sapiens

<400> SEQUENCE: 55

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 56
<211> LENGTH: 110
<212> TYPE: PRT
<213> ORGANISM: Homo sapiens

<400> SEQUENCE: 56

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser His Glu Asp Pro Glu Val Gln Phe Lys Trp Tyr
            35                  40                  45

Val Asp Gly Val Glu Val His Asn Ala Lys Thr Lys Pro Arg Glu Glu
        50                  55                  60

Gln Phe Asn Ser Thr Phe Arg Val Val Ser Val Leu Thr Val Leu His
 65                  70                  75                  80

Gln Asp Trp Leu Asn Gly Lys Glu Tyr Lys Cys Lys Val Ser Asn Lys

-continued

```
                                85                     90                       95
        Ala Leu Pro Ala Pro Ile Glu Lys Thr Ile Ser Lys Thr Lys
                    100                    105                    110
```